US 9,044,564 B2

(12) United States Patent
Dravitzki et al.

(10) Patent No.: US 9,044,564 B2
(45) Date of Patent: Jun. 2, 2015

(54) NASAL MASK SYSTEM

(71) Applicant: ResMed Limited, Bella Vista, New South Wales (AU)

(72) Inventors: Brent James Dravitzki, Sydney (AU); Enrico Brambilla, Irvine, CA (US); Lemmy Nga, Sydney (AU); Nigel Quarmby, Sydney (AU); Aaron Samuel Davidson, Sydney (AU); Joel Edward Gibson, Sydney (AU); Anthony Paul Barbara, Sydney (AU); Justin John Formica, Sydney (AU); Angelene Marie Ozolins, Sydney (AU); Robert Thomas Burnham, Sydney (AU); Lachlan Richard Goldspink, Sydney (AU)

(73) Assignee: ResMed Limited, Bella Vista (AU)

( * ) Notice: Subject to any disclaimer, the term of this patent is extended or adjusted under 35 U.S.C. 154(b) by 0 days.

(21) Appl. No.: 14/096,470

(22) Filed: Dec. 4, 2013

(65) Prior Publication Data
US 2014/0174448 A1 Jun. 26, 2014

Related U.S. Application Data

(62) Division of application No. 13/375,021, filed as application No. PCT/AU2010/000657 on May 28, 2010.

(60) Provisional application No. 61/213,326, filed on May
(Continued)

(30) Foreign Application Priority Data

Jun. 2, 2009 (AU) ................................ 2009902524
Dec. 15, 2009 (AU) ................................ 2009906101

(51) Int. Cl.
*A61M 16/06* (2006.01)
*A61M 16/08* (2006.01)

(52) U.S. Cl.
CPC ........... *A61M 16/0644* (2014.02); *A61M 16/06* (2013.01); *A61M 16/0683* (2013.01);
(Continued)

(58) Field of Classification Search
CPC ............ A61M 16/0622; A61M 16/06; A61M 2016/06; A61M 2016/0605; A61M 2016/0611; A61M 2016/0616; A61M 2016/0622; A61M 2016/0661; A62B 18/00; A62B 18/02; A62B 18/025; A62B 18/06
USPC .......................... 128/205.25, 206.12–206.18, 128/206.21–207.13
See application file for complete search history.

(56) References Cited

U.S. PATENT DOCUMENTS 2,875,757 A 3/1959 Galleher, Jr.
6,374,826 B1 4/2002 Gunaratnam et al.
(Continued)

FOREIGN PATENT DOCUMENTS

JP H06-510444 11/1994
JP 2006-518230 8/2006
(Continued)

OTHER PUBLICATIONS

Office Action issued in corresponding Japanese Appln. No. 2012-512169 dated Apr. 7, 2014, with English language translation thereof.
(Continued)

*Primary Examiner* — Valerie L Skorupa
(74) *Attorney, Agent, or Firm* — Nixon & Vanderhye P.C.

(57) ABSTRACT

A nasal cushion for a mask system includes a side wall defining a breathing chamber, an undercushion extending from the side wall, and a membrane that at least partially covers the undercushion. The membrane is adapted to seal along the nasal bridge, sides of nose, corners of nose, and upper lip of the patient's face in use. The undercushion is only provided along the side of nose, corner of nose, and upper lip regions of the cushion. The undercushion includes a flap or extending portion in each side of nose region that is wider than the other regions thereof and adapted to engage and provide a force into the sides of the patient's nose in use.

32 Claims, 150 Drawing Sheets

Related U.S. Application Data 29, 2009, provisional application No. 61/222,711, filed on Jul. 2, 2009, provisional application No. 61/272,162, filed on Aug. 25, 2009, provisional application No. 61/272,250, filed on Sep. 4, 2009, provisional application No. 61/263,175, filed on Nov. 20, 2009, provisional application No. 61/282,693, filed on Mar. 18, 2010.

(52) U.S. Cl.
CPC ........ *A61M16/0816* (2013.01); *A61M 2205/42* (2013.01); *A61M 2210/0618* (2013.01); *A61M 16/0622* (2014.02); *A61M 16/0633* (2014.02)

(56) References Cited

U.S. PATENT DOCUMENTS

| | | | |
|---|---|---|---|
| 6,467,483 | B1 | 10/2002 | Kopacko et al. |
| 7,000,614 | B2 | 2/2006 | Lang et al. |
| 7,509,958 | B2 | 3/2009 | Amarasinghe et al. |
| 2002/0005198 | A1 | 1/2002 | Kwok et al. |
| 2003/0019495 | A1 | 1/2003 | Palkon et al. |
| 2003/0196656 | A1 | 10/2003 | Moore et al. |
| 2003/0196658 | A1* | 10/2003 | Ging et al. ............... 128/201.22 |
| 2004/0094159 | A1* | 5/2004 | Kwok et al. ............. 128/206.24 |
| 2004/0221850 | A1* | 11/2004 | Ging et al. ............... 128/206.27 |
| 2005/0098183 | A1 | 5/2005 | Nash et al. |
| 2005/0155605 | A1 | 7/2005 | Lithgow et al. |
| 2006/0032504 | A1 | 2/2006 | Burton et al. |
| 2006/0076019 | A1 | 4/2006 | Ho |
| 2006/0201515 | A1* | 9/2006 | Kwok et al. ............. 128/206.24 |
| 2007/0215161 | A1 | 9/2007 | Frater et al. |
| 2007/0277828 | A1 | 12/2007 | Ho et al. |
| 2008/0110464 | A1* | 5/2008 | Davidson et al. ........ 128/206.26 |
| 2008/0276937 | A1* | 11/2008 | Davidson et al. ........ 128/204.18 |
| 2008/0314389 | A1 | 12/2008 | Thomas et al. |
| 2009/0050156 | A1 | 2/2009 | Ng et al. |
| 2009/0114230 | A1 | 5/2009 | Hernandez et al. |
| 2009/0120442 | A1 | 5/2009 | Ho |
| 2009/0139526 | A1* | 6/2009 | Melidis et al. ........... 128/206.26 |
| 2009/0223521 | A1 | 9/2009 | Howard et al. |
| 2012/0138061 | A1 | 6/2012 | Dravitzki et al. |

FOREIGN PATENT DOCUMENTS

| | | |
|---|---|---|
| JP | 2004-570 | 1/2007 |
| WO | WO 01/62326 | 8/2001 |
| WO | WO 2004/022146 | 3/2004 |
| WO | WO 2005/002656 | 1/2005 |
| WO | WO 2005/094928 | 10/2005 |
| WO | WO 2005/118040 | 12/2005 |
| WO | WO 2006/074513 | 7/2006 |
| WO | WO 2006/074516 | 7/2006 |
| WO | WO 2007/143792 | 12/2007 |
| WO | WO 2009/026627 | 3/2009 |
| WO | WO 2009/052560 | 4/2009 |
| WO | WO 2009/062265 | 5/2009 |
| WO | WO 2009/108995 | 9/2009 |
| WO | WO 2010/066004 | 6/2010 |

OTHER PUBLICATIONS

Final Office Action issued in corresponding U.S. Appl. No. 13/375,021 dated May 6, 2014.
International Search Report issued in PCT/AU2010/000657, mailed Sep. 9, 2010.
Patent Examination Report issued in a related Australian Patent Application No. 2010251884, dated Jul. 27, 2012.
Further Examination Report issued in a corresponding New Zealand Application No. 612693 dated Dec. 13, 2013.
U.S. Appl. No. 14/184,068, filed Feb. 19, 2014.
First Examination Report issued in a corresponding New Zealand Application No. 617661, dated Nov. 22, 2013.
Office Action issued in a corresponding U.S. Appl. No. 13/375,021, dated Jan. 3, 2014, including PTO-892 listing US 2003/0196658, US 2009/0139526, US 2009/0120442, US 2008/0276937, and US 2007/0215161.
Office Action issued in a corresponding Chinese Application No. 201080033786.7 dated Jan. 6, 2014, with English language translation thereof.
Patent Examination Report issued in corresponding Australian Appln. No. 2013257413 dated Aug. 4, 2014.
Patent Examination Report issued in corresponding Australian Appln. No. 2013257426 dated Aug. 4, 2014.
US Office Action issued in a related U.S. Appl. No. 13/375,021 dated Nov. 5, 2014, including PTO-892 listing US 2006/0032504 and US 2009/0114230.
Further Examination Report issued in corresponding New Zealand Appln. No. 612693, dated Sep. 8, 2014.
Office Action issued in corresponding Chinese Appln. No. 201080033786.7 dated Sep. 3, 2014, with English translation thereof.
Further Examination Report issued in corresponding New Zealand Appln. No. 617661 dated Jan. 6, 2015.
Final Office Action issued in a related U.S. Appl. No. 13/375,021 dated Mar. 11, 2015, including PTO-892 listing US 2008/011064.
Patent Examination Report issued in corresponding Australian Appln. No. 2013257426 dated Feb. 11, 2015.
Patent Examination Report issued in corresponding Australian Appln. No. 2013257413 dated Feb. 19, 2015.
Office Action issued in corresponding Japanese Appln. No. 2012-512169 dated Jan. 26, 2015, with English translation thereof.
Third Office Action issued in corresponding Chinese Appln. No. 201080033786.7 dated Mar. 23, 2015, with English translation thereof.

\* cited by examiner

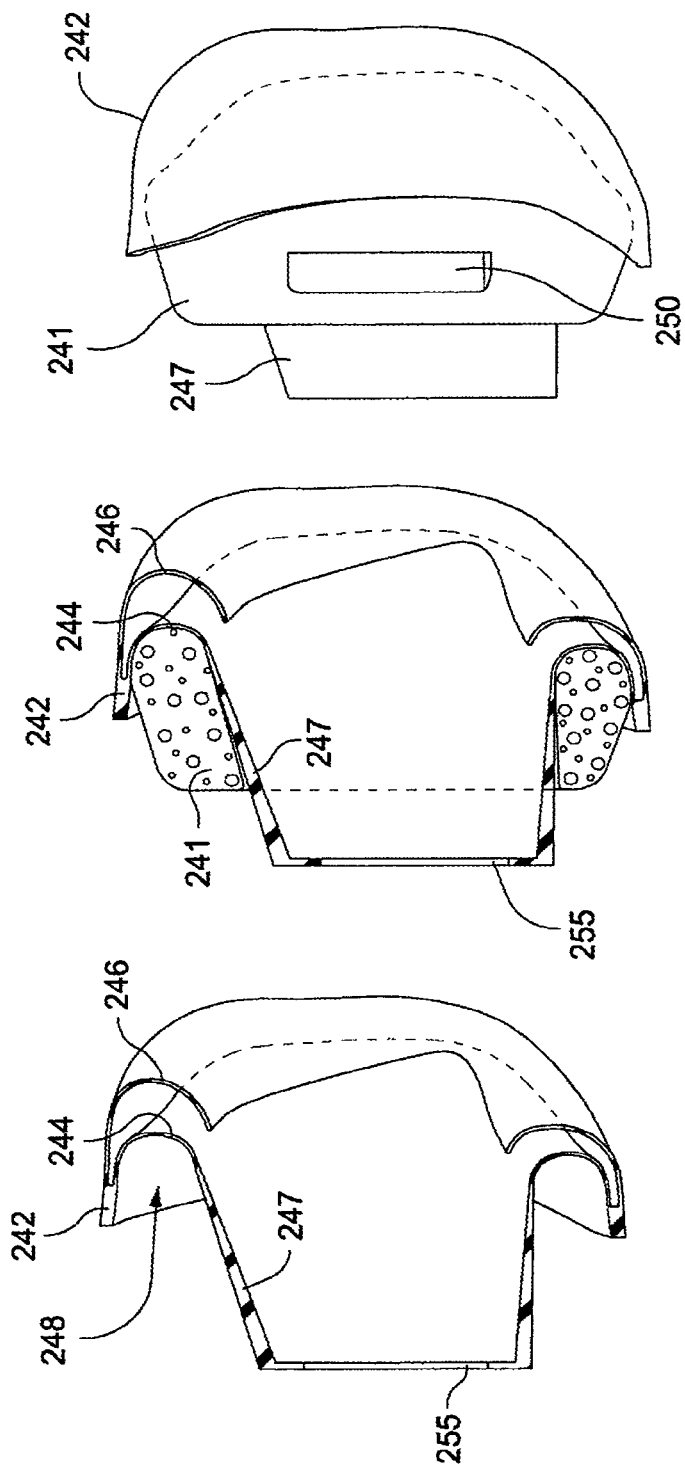

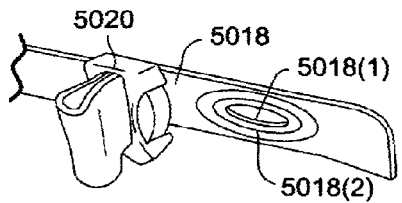
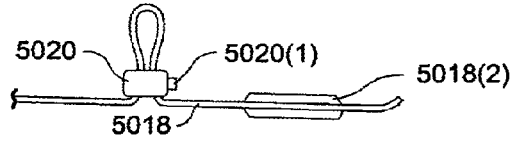
Fig. 3-13(a)   Fig. 3-13(b)
Fig. 3-14(a) 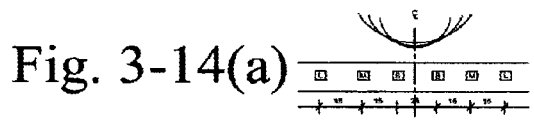 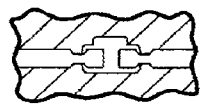 Fig. 3-14(e)
Fig. 3-14(b) 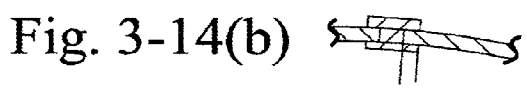 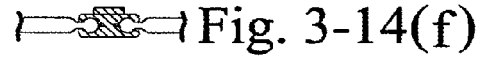 Fig. 3-14(f)
Fig. 3-14(c) 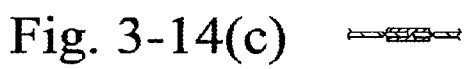 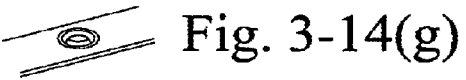 Fig. 3-14(g)
Fig. 3-14(d) 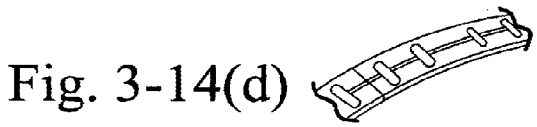  Fig. 3-14(h)
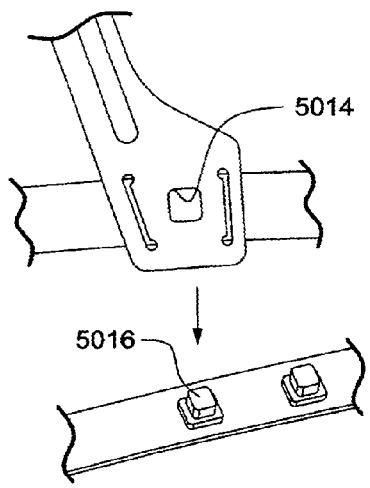
Fig. 3-15

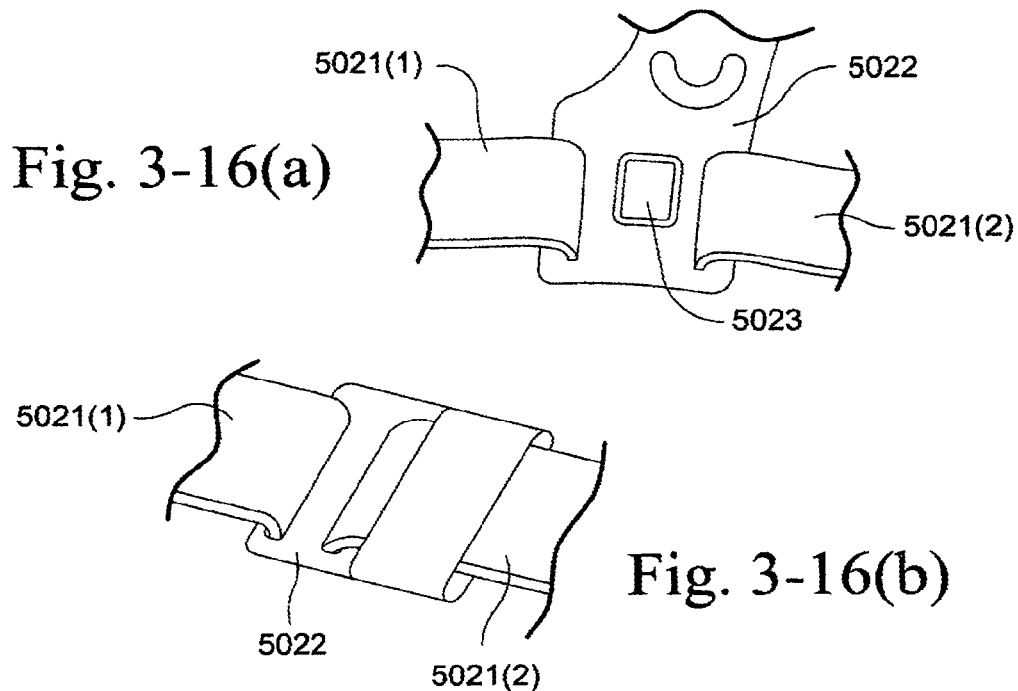
Fig. 3-16(a)
Fig. 3-16(b)
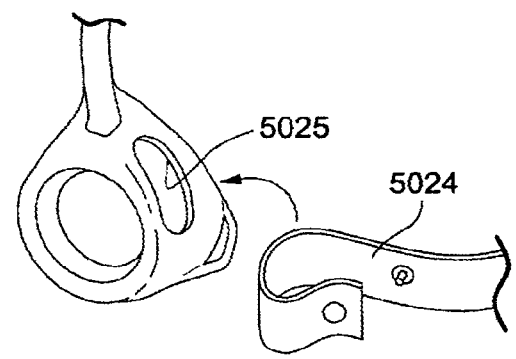
Fig. 3-17
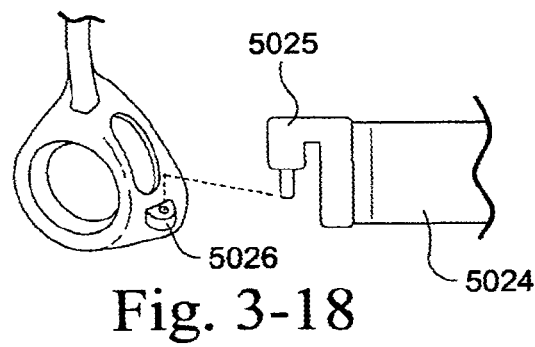
Fig. 3-18

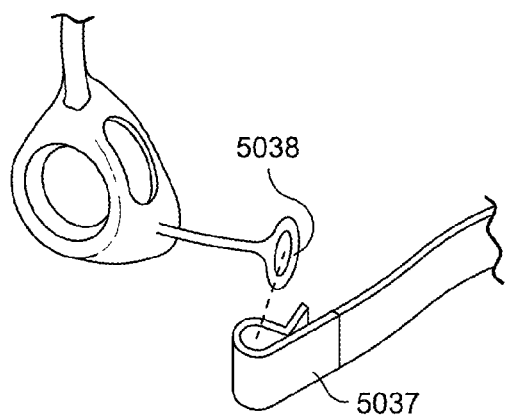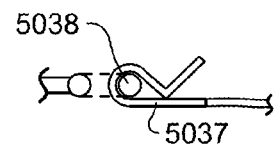
Fig. 3-25(b)
Fig. 3-25(a)
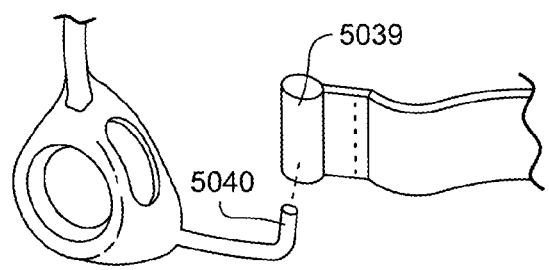
Fig. 3-26(a)
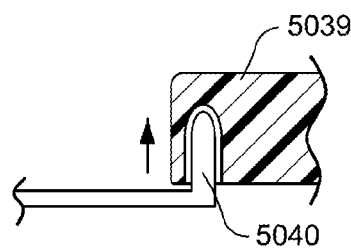
Fig. 3-26(b)
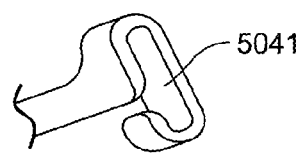
Fig. 3-27

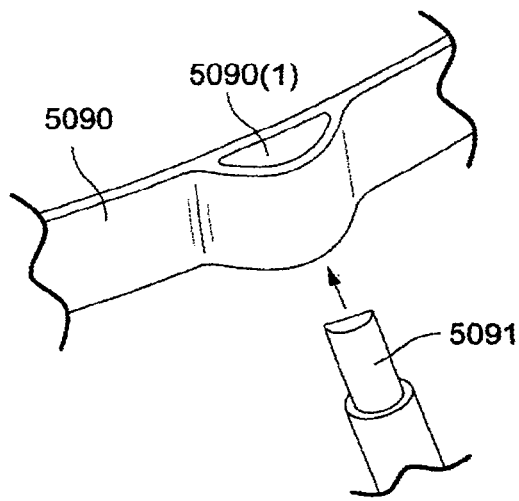
Fig. 3-57
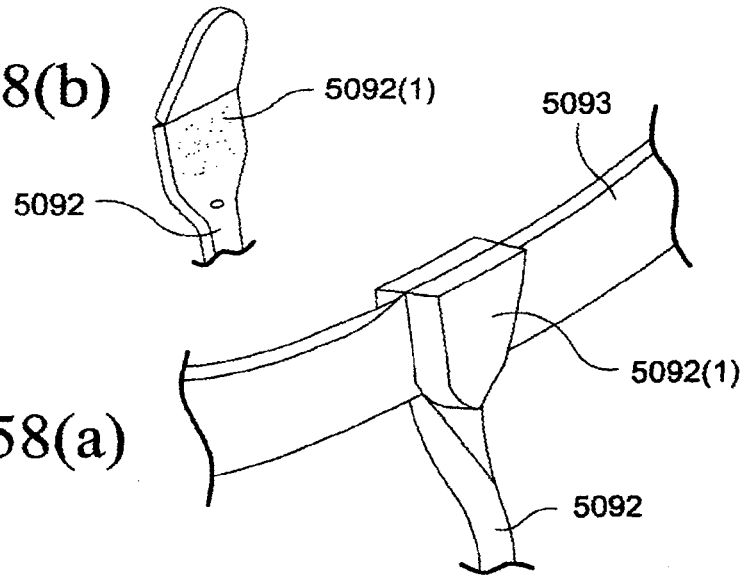
Fig. 3-58(b)
Fig. 3-58(a)
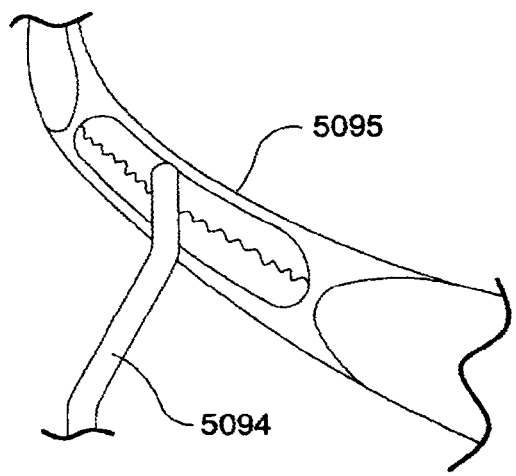
Fig. 3-59

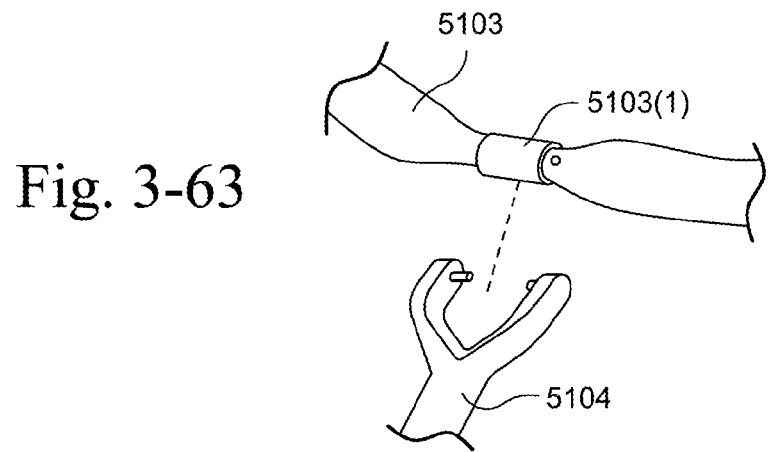
Fig. 3-63
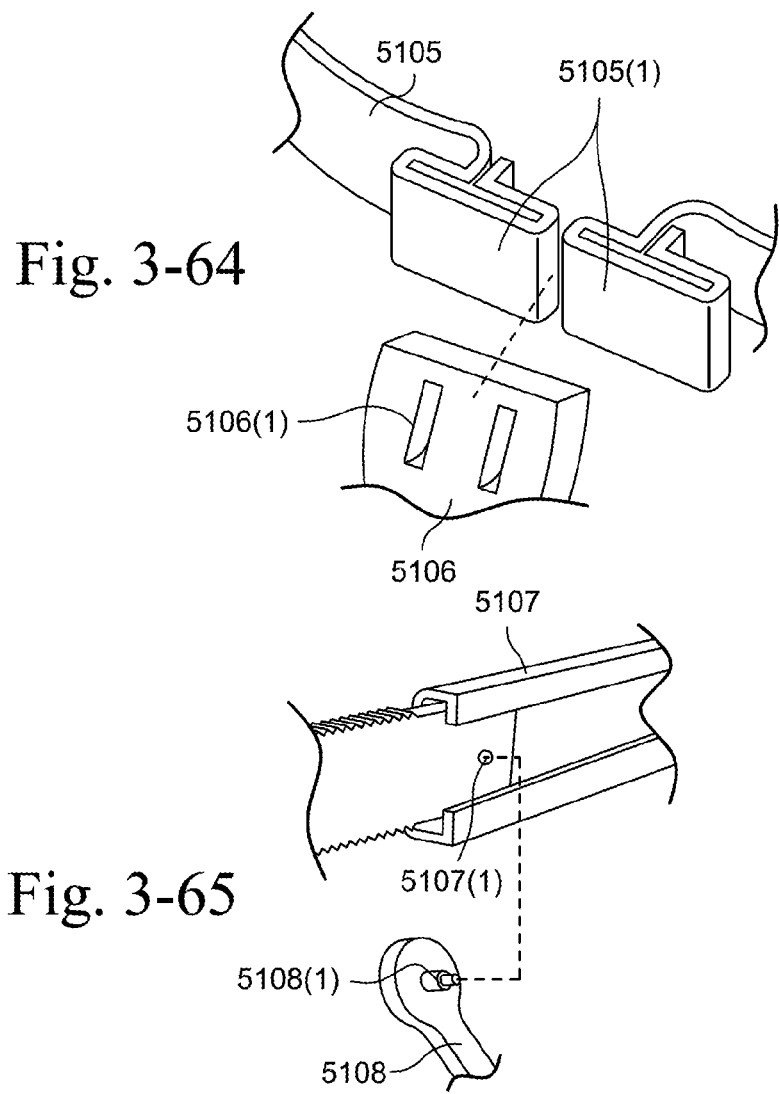
Fig. 3-64
Fig. 3-65

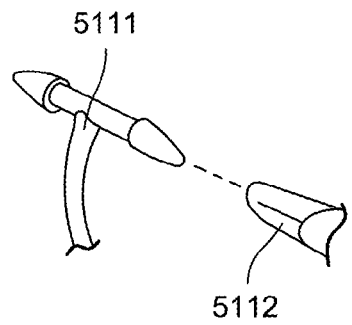
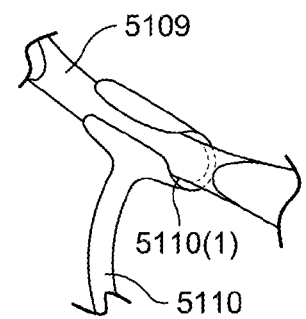
Fig. 3-66(a)   Fig. 3-66(b)
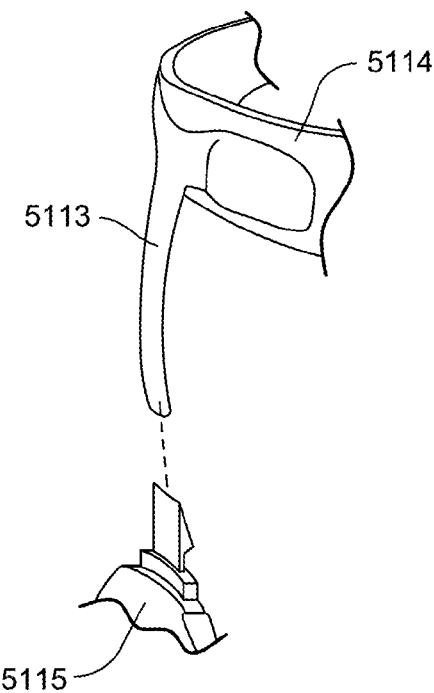
Fig. 3-67
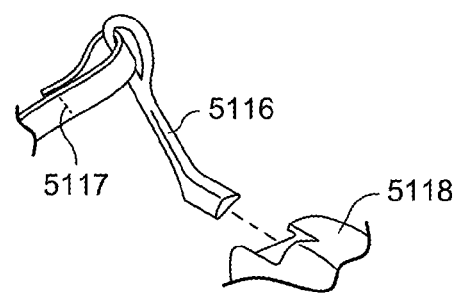
Fig. 3-68

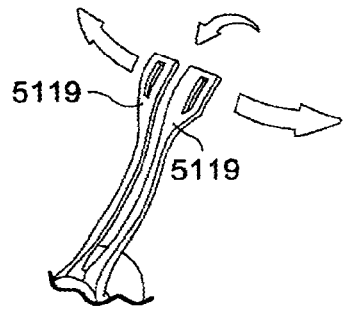
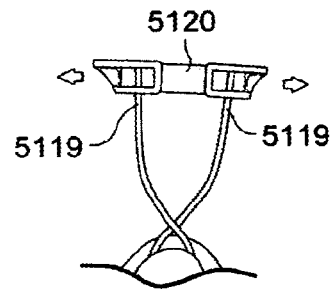
Fig. 3-69(a)    Fig. 3-69(b)
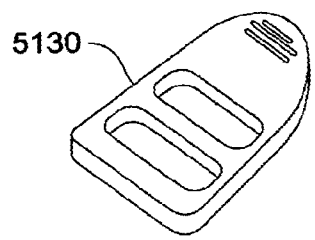
Fig. 3-70(a)
Fig. 3-70(b)
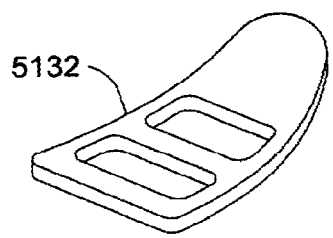
Fig. 3-71(a)
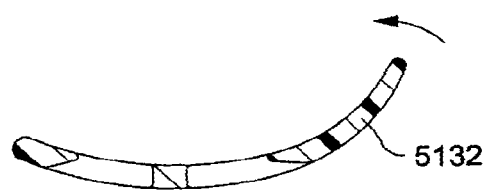
Fig. 3-71(b)

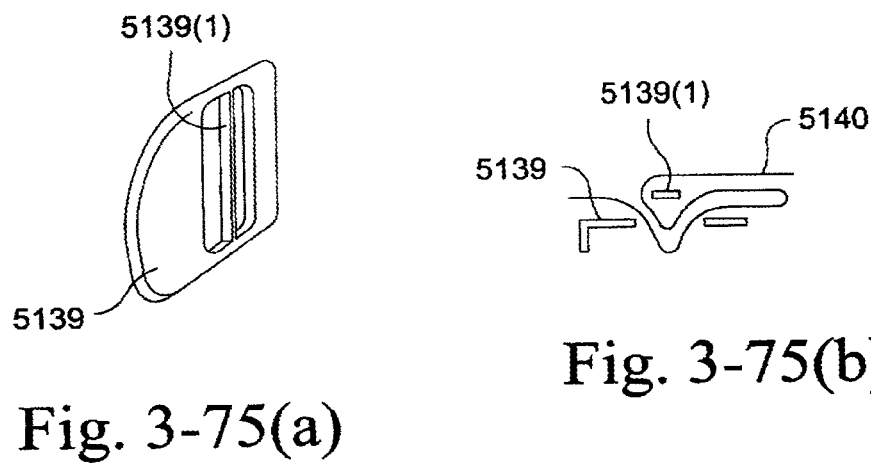
Fig. 3-75(a)
Fig. 3-75(b)
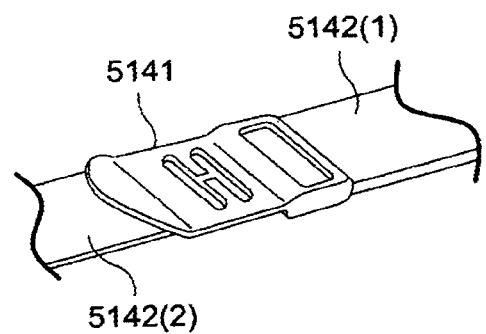
Fig. 3-76

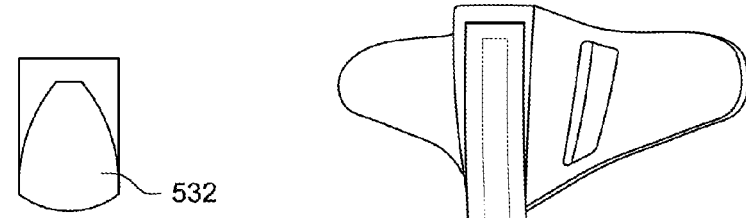
Fig. 9-3(b)
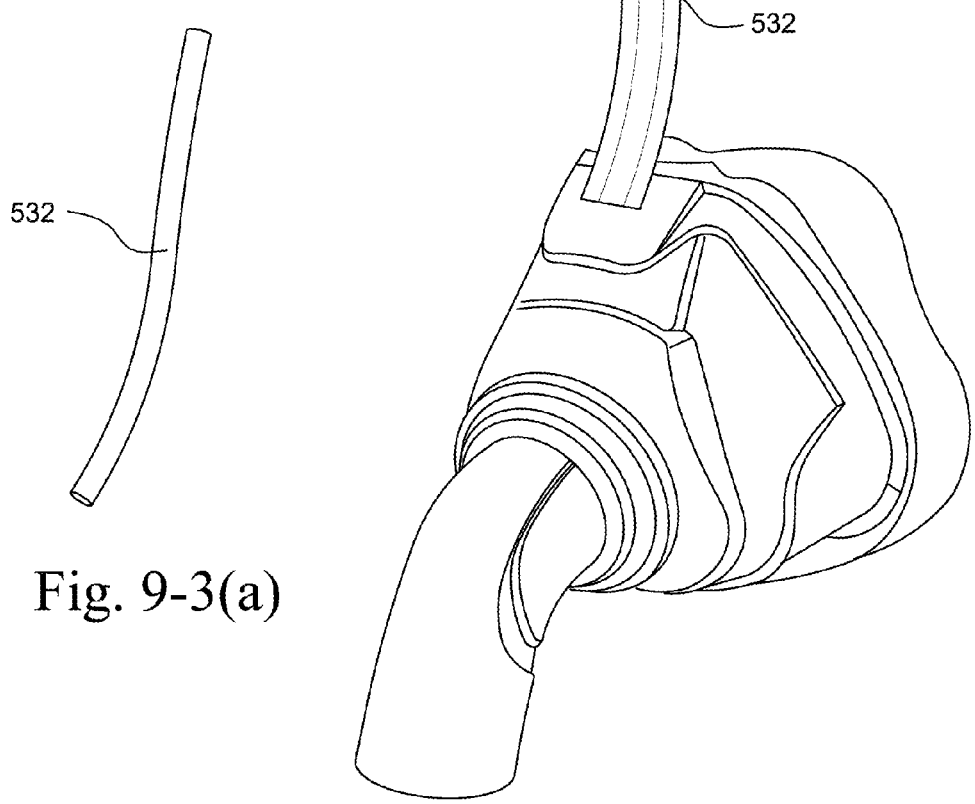
Fig. 9-3(a)
Fig. 9-4

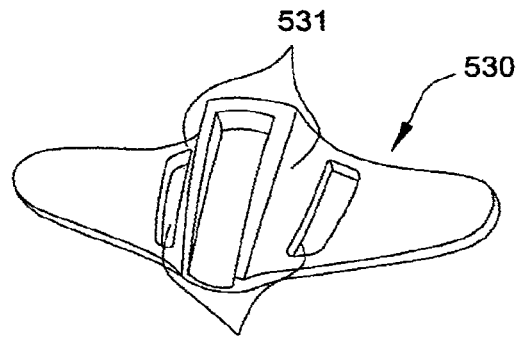
Fig. 10-1
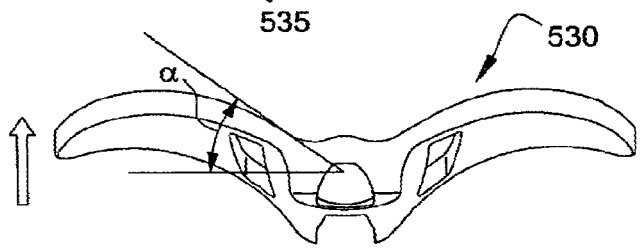
Fig. 10-2
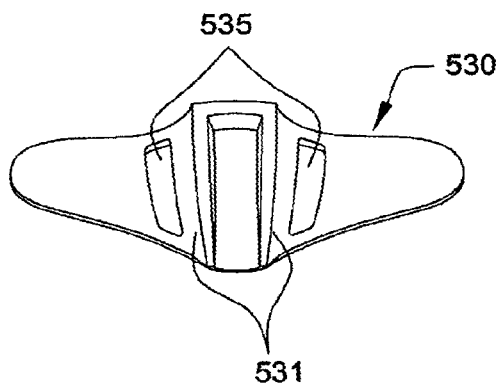
Fig. 10-3
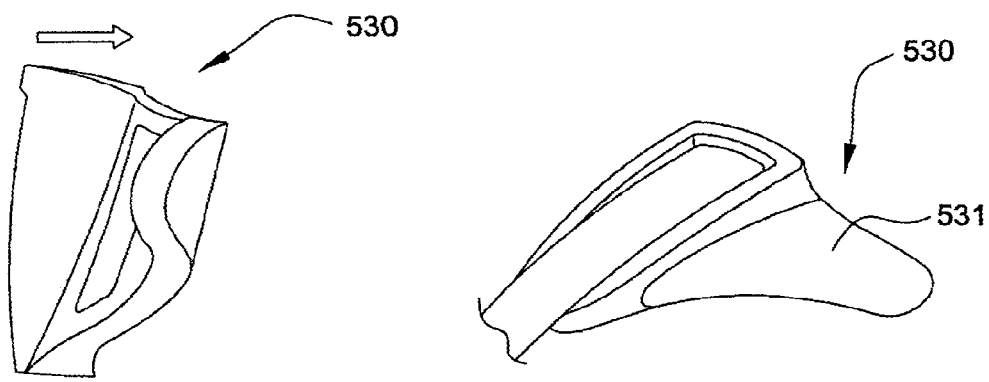
Fig. 10-4
Fig. 10-5

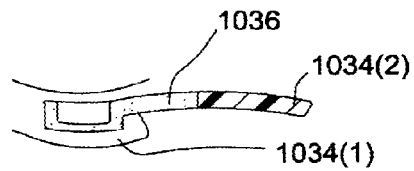
Fig. 22(a)
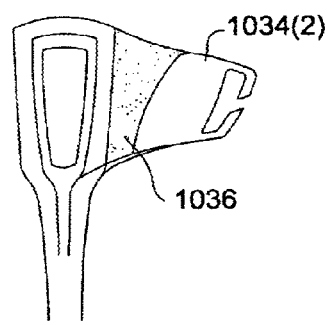
Fig. 22(b)
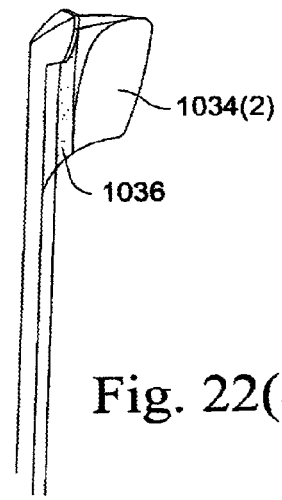
Fig. 22(c)
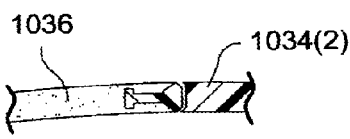
Fig. 22(d)
Fig. 22(e)
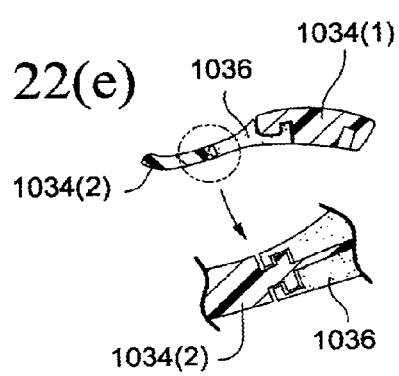
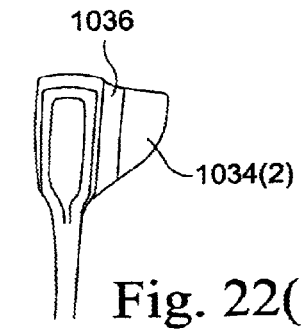
Fig. 22(f)
Fig. 22(g)
Fig. 22(h)

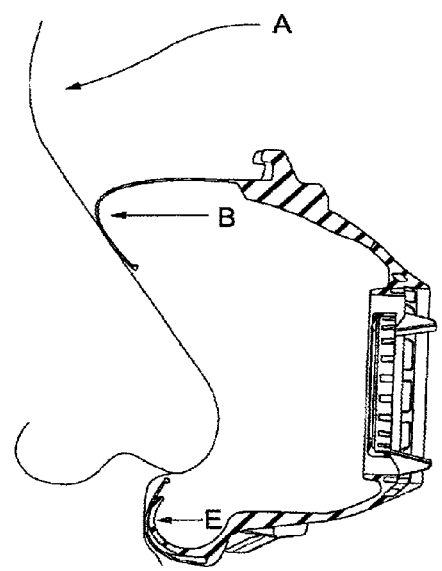
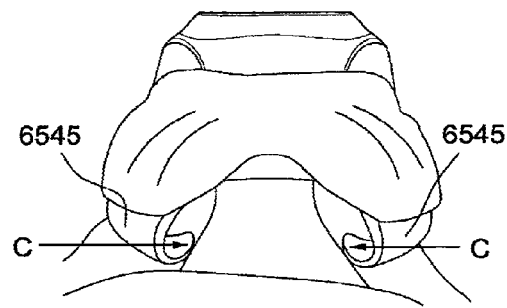
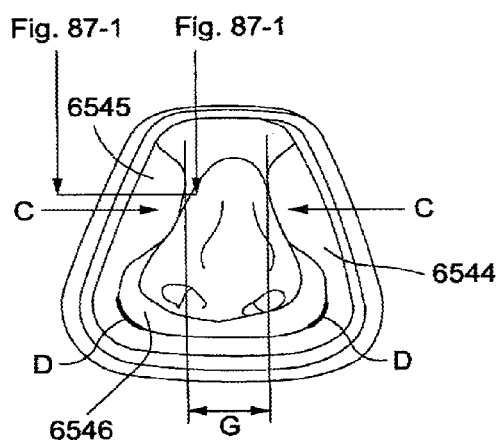
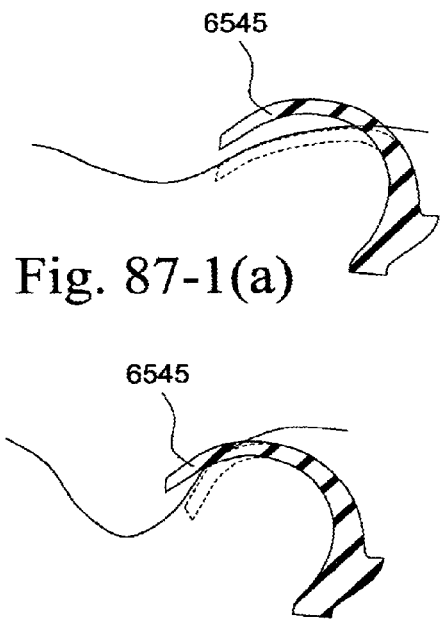
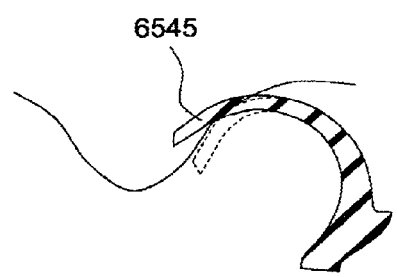
Fig. 86
Fig. 87-2
Fig. 87
Fig. 87-1(a)
Fig. 87-1(b)

NASAL MASK SYSTEM

CROSS-REFERENCE TO APPLICATION

This application is a divisional of U.S. application Ser. No. 13/375,021, filed Nov. 29, 2011, which is a U.S. National Phase of International Application No. PCT/AU2010/00065, filed May 28, 2010, which designated the U.S. and claims the benefit of U.S. Provisional Application Nos. 61/213,326, filed May 29, 2009, 61/222,711, filed Jul. 2, 2009, 61/272,162, filed Aug. 25, 2009, 61/272,250, filed Sep. 4, 2009, 61/263,175, filed Nov. 20, 2009, and 61/282,693, filed Mar. 18, 2010, and Australian Provisional Application Nos. 2009902524, filed 2 Jun. 2009, and 2009906101, filed 15 Dec. 2009; each of which is incorporated herein by reference in its entirety. Australian Provisional Application, filed 28 May 2010; is also incorporated herein by reference in its entirety.

FIELD OF THE INVENTION

The present invention relates to a nasal mask system used for treatment, e.g., of Sleep Disordered Breathing (SDB) with Continuous Positive Airway Pressure (CPAP) or Non-Invasive Positive Pressure Ventilation (NIPPV).

BACKGROUND OF THE INVENTION

Patient interfaces, such as a full-face or nasal mask systems, for use with blowers and flow generators in the treatment of Sleep Disordered Breathing (SDB), typically include a soft face-contacting portion, such as a cushion, and a rigid or semi-rigid shell or frame. In use, the interface is held in a sealing position by headgear so as to enable a supply of air at positive pressure (e.g., 2-30 cm $H_2O$) to be delivered to the patient's airways.

One factor in the efficacy of therapy and compliance of patients with therapy is the comfort and fit of the patient interface.

The present invention provides alternative arrangements of mask systems to enhance the efficacy of therapy and compliance of patients with therapy.

SUMMARY OF THE INVENTION

One aspect of the present technology is to provide a mask system that is simple and unobtrusive. Another aspect of the present technology is a mask system that can accommodate a wide range of different facial shapes including faces with high and low nasal bridge regions, and narrow and wide noses. Another aspect of the present technology is a mask system with a wide fit range.

A mask in accordance with the present technology is able to adapt the relative influence of different sealing forces dependent upon the size and shape of the face and nose of the wearer. In one form, an amount of tension force may be increased by splaying outwardly of an undercushion.

One aspect of the present technology is a cushion for a mask that seals at its upper extent in a region of the nose that is generally close to the junction between bone and cartilage on a range of people with larger noses, and which avoids impinging on the sight of people with smaller noses.

Another aspect of the present technology is a cushion for a mask that includes a thicker undercushion or backup band that supports a thinner membrane or facial flap. In one form the cushion has an undercushion or backup band that is relatively less stiff in an upper lip region than in a corner of the nose region, in a direction that is normal to the plane of the face of a person. In one form the cushion has no undercushion or backup band in a nasal bridge region of the cushion. In one form the undercushion or backup band directs a sealing force against the sides of the nose in a nasal bridge region. In one form the cushion is constructed and arranged so that when used by a person a relatively deep nasal bridge, the sides of the cushion in the region of the nasal bridge are drawn inwards and the force on the side of the nose increases. In one form, when used by a person with a relatively low nasal bridge, the sides of the cushion in the region of the nasal bridge splay outwards. In one form the undercushion is constructed and arranged to buckle. In one form the undercushion has a C-shaped or a sickle-shaped cross-section.

In one form, a seal forming surface of a cushion in accordance with the present technology has a non-tacky surface. In one form a seal forming surface of a cushion in accordance with the present technology has a non-polished surface. In one form, a seal forming surface of a cushion in accordance with the present technology has a frosted surface finish.

A cushion in accordance with the present technology is adapted to form a seal around a nose of a patient including a seal in a nasal bridge region of a patient. The nasal bridge region is a region of greater variability between different patients than other regions of a nose. Another region of potential variability between faces is an angle of the forehead with respect to a plane of the face.

In order to accommodate a wide range of face shapes, a series of masks of different sizes and shapes may be constructed. However this may be expensive. In accordance with the present technology, a cushion angle adjustment mechanism for a mask system may be provided to facilitate rotation or orientation of the cushion with respect to the plane of the face. In this way, a given mask system is able to accommodate a wider fit range of patients.

The cushion size and shape may be structured to accommodate a wide range of different facial shapes.

One aspect of the invention relates to a mask system including a frame adapted to attach headgear, a sealing arrangement releasably connectable to the frame, and an elbow provided to the sealing arrangement and adapted to be connected to an air delivery tube that delivers breathable gas to the patient. The sealing arrangement defines a breathing chamber and is adapted to form a seal with the patient's face. The sealing arrangement includes structure to establish a positive connection with the frame and with the elbow.

Another aspect of the invention relates to a mask system including a frame and a sealing arrangement provided to the frame. The sealing arrangement includes a silicone cushion and a foam cushion provided to the silicone cushion. The silicone cushion defines a breathing chamber and the foam cushion is supported by the silicone cushion such that the foam cushion is not in communication with the breathing chamber. The foam cushion supports the sealing arrangement on the frame.

Another aspect of the invention relates to a mask system including a frame adapted to attach headgear and a sealing arrangement releasably connectable to the frame. The sealing arrangement defines a breathing chamber and is adapted to form a seal with the patient's face. The sealing arrangement includes one or more protrusions adapted to interlock with respective openings provided to the frame and provide visual reinforcement that the connection has been established.

Another aspect of the invention relates to a sealing arrangement for a mask system including a side wall defining a breathing chamber, an undercushion curving outwards from the side wall and away from the breathing cavity, and a membrane that at least partially covers the undercushion. The membrane extends from the undercushion and curves inwards into the breathing cavity.

Another aspect of the invention relates to a mask system including a frame, a sealing arrangement releasably connectable to the frame, an elbow provided to the sealing arrangement and adapted to be connected to an air delivery tube that delivers breathable gas to the patient, and a forehead support provided to the frame. The sealing arrangement defines a breathing chamber and is adapted to form a seal with the patient's face. The forehead support includes an elongated arm adapted to extend from the frame and an upper headgear connector adapted to attach upper headgear straps. At least a portion of the arm may be constructed from metal.

Another aspect of the invention relates to a vent assembly for exhausting gases from a mask including at least two vent arrays and a connecting structure that joins the at least two vent arrays together. Each of the at least two vent arrays includes at least one vent hole structured to exhaust gas from the mask. The connecting structure has a first position and a second position in which the at least two vent arrays are arranged at an angle offset from the at least two vent arrays when the connecting structure is in the first position.

Another aspect of the invention relates to a method for making a mask including molding a vent structure, inserting the vent structure into a mold for a mask component, and molding the mask component over the vent structure, wherein molding the mask component aligns the vent structures to create air flow paths that reduce interference of exiting air streams in use.

Another aspect of the invention relates to a nasal mask defining a breathing chamber for the delivery of a supply of gas at positive pressure to the airways of a patient. The nasal mask includes a sidewall, and a cushion located adjacent the sidewall at a rear side of the nasal mask. A rearward sealing surface of the cushion has a contour in a top lip region that is formed with a concave curvature to have a shape that is complementary to a top lip region of a person. The contour of the rearward surface of the cushion is constructed and arranged to extend in use along respective left and right sides of the nose from a nasal bridge region of a person located adjacent the joint between the nasal bone and the cartilage to respective left and right nasal corner regions of a person adjacent the left and right naso-labial creases. The contour of the rearward sealing surface of the cushion is further adapted to extend along the top lip of a person from the left side of the nose to the right side of the nose. The cushion includes a relatively thick backup band formed from a resilient flexible material and extending from the sidewall to form respective cantilevers in a top lip region, a corner region and a side of nose region of the cushion. The cantilevers each have a length and a thickness and the cantilevers define respective lip region, corner region and side of nose region stiffnesses. The corner region cantilever is stiffer than the top lip region cantilever in a direction normal to the plane of the face. The cushion further includes a relatively thin facial flap. The facial flap is inwardly curving and extends around the perimeter of the cushion to define the rearward sealing surface of the cushion. An inner edge of the facial flap defines an orifice through which a portion of a nose of the patient passes in use.

Another aspect of the invention relates to a nasal mask defining a breathing chamber for the delivery of a supply of gas at positive pressure to the airways of a patient. The nasal mask includes a sidewall, and a cushion located adjacent the sidewall at a rear side of the nasal mask. A rearward sealing surface of the cushion has a contour in a top lip region that is formed with a concave curvature to have a shape that is complementary to a top lip region of a person. The contour of the rearward surface of the cushion is constructed and arranged to extend in use along respective left and right sides of the nose from a nasal bridge region of a person to respective left and right nasal corner regions of a person. The contour of the rearward sealing surface of the cushion is further adapted to extend along the top lip of a person from the left side of the nose to the right side of the nose. The cushion includes a relatively thick backup band formed from a resilient flexible material and extending from the sidewall to form respective cantilevers in a top lip region, a corner region and a side of nose region of the cushion. The top lip region cantilever has a C-shaped cross-section. The cushion further includes a relatively thin facial flap. The facial flap is inwardly curving and extends around the perimeter of the cushion to define the rearward sealing surface of the cushion. An inner edge of the facial flap defines an orifice through which a portion of a nose of the patient passes in use.

Another aspect of the invention relates to a nasal mask defining a breathing chamber for the delivery of a supply of gas at positive pressure to the airways of a patient. The nasal mask includes a sidewall, and a cushion located adjacent the sidewall at a rear side of the nasal mask. A rearward sealing surface of the cushion has a contour in a top lip region that is formed with a concave curvature to have a shape that is complementary to a top lip region of a person. The contour of the rearward surface of the cushion is constructed and arranged to extend in use along respective left and right sides of the nose from a nasal bridge region of a person to respective left and right nasal corner regions of a person. The contour of the rearward sealing surface of the cushion is further adapted to extend along the top lip of a person from the left side of the nose to the right side of the nose. The cushion includes a relatively thin facial flap. The facial flap is inwardly curving and extends around the perimeter of the cushion to define the rearward sealing surface of the cushion. An inner edge of the facial flap defines an orifice through which a portion of a nose of the patient passes in use. The cushion further includes a relatively thick backup band formed from a resilient flexible material and extending from the sidewall to form respective cantilevers in a top lip region, a corner region and a side of nose region of the cushion. A length of the side of nose region cantilever is longer than a length of the corner region cantilever, and the side of nose region cantilever is constructed and arranged to provide a force in a direction approximately normal to the side of the nose.

In one form the cushion and mask body are moulded in one piece. Preferably the cushion and adjacent sidewall are moulded in one piece. In this arrangement a more controlled and comfortable bending of the undercushion may be achieved.

Another aspect of the invention relates to a nasal cushion for a mask system. The nasal cushion includes a side wall defining a breathing chamber, an undercushion extending from the side wall, and a membrane that at least partially covers the undercushion. The membrane is adapted to seal along the nasal bridge, sides of nose, corners of nose, and upper lip of the patient's face in use. The undercushion is only provided along the side of nose, corner of nose, and upper lip regions of the cushion. The undercushion includes a flap or extending portion in each side of nose region that is wider than the other regions thereof and adapted to engage and provide a force into the sides of the patient's nose in use.

Another aspect of the invention relates to a nasal cushion for a mask system. The nasal cushion includes a cushion perimeter providing a plurality of regions. Each region is specifically configured to seal along or around the nose, and each region has characteristics that are at least partially determinative of the sealing force, stabilization, force distribution, comfort, and/or fit range provided by the cushion.

Another aspect of the invention relates to a forehead support for a respiratory mask including a forehead support arm structured to extend from a frame and a forehead support pad provided to the arm. The forehead support pad includes upper headgear connectors adapted to engage upper headgear straps and a flexible region. The upper headgear connectors are constructed of a first material and the flexible region is constructed of a second material that is more flexible than the first material to allow adjustment of the distance of the forehead support pad from the patient's forehead in use.

Another aspect of the invention relates to a headgear connector for a respiratory mask including a frame connection structured to extend from a frame and a connector provided to the frame connection. The frame connection is constructed of a more rigid material to hold the shape of the connector and transmit headgear forces to the mask and the connector is constructed of a more flexible material to facilitate engagement and disengagement of headgear straps with the connector.

Another aspect of the invention relates to a vent for a respiratory mask including a stem, at least one branch extending from the stem, and a vent array provided to the end of each branch. Each vent array includes a body and at least one vent hole through the body. The branches are spaced about the stem and/or the branches are angled with respect to stem to position the vent arrays such that they achieve diffuse exiting air flow streams.

Another aspect of the invention relates to an elbow for a respiratory mask including a mask connection end adapted to connect to the mask and a tube connection end adapted to connect to an air delivery tube. The mask connection end includes a first region constructed of a more rigid material and a second region constructed of a more flexible material. The second region provides flexibility to one or more portions of the mask connection end to enable engagement and disengagement of the elbow with the mask and/or sealing of the elbow with the mask.

Further aspects of the invention are as set out in the claims.

Other aspects, features, and advantages of this invention will become apparent from the following detailed description when taken in conjunction with the accompanying drawings, which are a part of this disclosure and which illustrate, by way of example, principles of this invention.

BRIEF DESCRIPTION OF THE DRAWINGS

The accompanying drawings facilitate an understanding of the various examples of this invention. In such drawings:

FIG. 1-2 is an exploded perspective view of the nasal mask system of FIG. 1-1 showing the frame, silicone cushion, elbow, and swivel ring;

FIG. 1-3 is a perspective view showing the cushion of the nasal mask system of FIG. 1-1;

FIG. 1-4 is a cross-sectional view of the cushion of FIG. 1-3;

FIG. 1-5 is a perspective view of a cushion according to an example of the present invention;

FIG. 1-6 is a side view of the cushion of FIG. 1-5;

FIG. 1-7 is bottom view of the cushion of FIG. 1-5;

FIG. 1-8 is a front view of the cushion of FIG. 1-5;

FIG. 1-9 is a cross-section view through line 1-9-1-9 of FIG. 1-8;

FIG. 1-10 is a cross-section view through line 1-10-1-10 of FIG. 1-8;

FIG. 1-11 is a cross-section view through line 1-11-1-11 of FIG. 1-8;

FIG. 1-12 is a cross-section view through line 1-12-1-12 of FIG. 1-8;

FIG. 2-1 is a perspective view of a nasal mask system according to another example of the present invention;

FIG. 2-2 is an exploded perspective view of the nasal mask system of FIG. 2-1 showing the frame, foam cushion, silicone cushion, elbow, and swivel ring;

FIG. 2-3 is a perspective view showing the frame of the nasal mask system of FIG. 2-1;

FIG. 2-4 is a perspective view showing the foam cushion, silicone cushion, elbow, and swivel ring of the nasal mask system of FIG. 2-1;

FIG. 2-5 is a cross-sectional view of the foam cushion, silicone cushion, elbow, and swivel ring of FIG. 2-4;

FIG. 2-6 is a cross-sectional view of the silicone cushion of the nasal mask system of FIG. 2-1;

FIG. 2-7 is a cross-sectional view of the silicone cushion and foam cushion of the nasal mask system of FIG. 2-1;

FIG. 2-8 is a side view of the silicone cushion and foam cushion of the nasal mask system of FIG. 2-1;

FIGS. 3-1 to 3-79 are schematic views of headgear strap arrangements and headgear connection arrangements according to alternative examples of the present invention;

FIGS. 4-1 to 4-4 are schematic views of elbow to cushion connection arrangements according to alternative examples of the present invention;

FIGS. 4-5 to 4-9 are schematic views of swivel to elbow connection arrangements according to alternative examples of the present invention;

FIGS. 5-1 and 5-2 are isometric views of an alternative embodiment of the present invention;

FIG. 5-3 is a front view of an alternative embodiment of the present invention;

FIG. 5-4 is a rear view of an alternative embodiment of the present invention;

FIG. 5-5 is an alternative embodiment of the present invention in use;

FIG. 5-6 is a side view of an alternative embodiment of the present invention;

FIGS. 6-1 to 6-12(*b*) are schematic views of headgear connection arrangements according to alternative examples of the present invention;

FIGS. 7-1 to 7-3 show various views of a mask system according to an embodiment of the present invention;

FIGS. 8-1 to 8-3 show various views of a lower headgear connector for a frame according to an embodiment of the invention;

FIGS. 8-4 and 8-5 show lower headgear connectors according to alternative embodiments;

FIGS. 9-1(*a*) and 9-1(*b*) show an elongated arm for a forehead support according to an embodiment of the invention;

FIGS. 9-2, 9-3(*a*), and 9-3(*b*) show a mask system with an elongated arm for a forehead support according to another embodiment of the invention;

FIG. 9-4 shows a mask system with an elongated arm for a forehead support according to another embodiment of the invention;

FIGS. 10-1 to 10-5 show various views of a forehead support according to an embodiment of the invention;

FIG. 10-6 shows a forehead support according to another embodiment of the invention;

FIG. 11-1 shows a cushion according to an embodiment of the invention;

FIGS. 11-2 to 11-9 show various views of a cushion according to another embodiment of the invention;

FIGS. 12-1 to 12-3 show various views of an elbow according to an embodiment of the invention;

FIGS. 12-4 to 12-8 show various views of an elbow according to another embodiment of the invention;

FIG. 12-9 is an end view of an elbow according to an embodiment of the invention;

FIG. 13-1 shows a swivel/vent ring according to an embodiment of the invention;

FIG. 13-2 shows a swivel/vent ring according to another embodiment of the invention;

FIGS. 14-1 and 14-2 show headgear according to an embodiment of the invention;

FIGS. 15-1 to 15-3 show various views of frame to cushion engagement according to an embodiment of the invention;

FIGS. 16-1 and 16-2 show a mask system according to an embodiment of the present invention;

FIGS. 17-1 and 17-2 show a mask system according to an embodiment of the present invention;

FIGS. 18-1 and 18-2 show headgear routing according to an embodiment of the invention;

FIGS. 19-1 and 19-2 show headgear routing according to an embodiment of the invention;

FIGS. 20-2(a), 20-2(b), and 20-2(c) are sequential perspective views of a bendable or flexible forehead support according to an embodiment of the invention;

FIGS. 22(a), 22(b), 22(c), 22(d), 22(e), 22(f), 22(g), and 22(h) are various views of a forehead support including flexible regions according to an embodiment of the invention;

FIG. 79 is a cross-sectional view through line 79-79 of FIG. 78;

FIG. 86 is a schematic view showing sealing forces of the cushion as viewed from the side of the patient's nose according to an embodiment of the invention;

FIG. 87 is a schematic view showing sealing forces of the cushion as viewed from the front of the patient's nose according to an embodiment of the invention;

FIGS. 87-1(a) and 87-1(b) are cross-sectional views through line 87-1-87-1 of FIG. 87 show deformation of the undercushion for low and high nose bridges;

FIG. 87-2 is a schematic view showing sealing forces of the cushion as viewed from the top of the patient's nose according to an embodiment of the invention, the membrane of the cushion being rolled back for the purposes of illustration to reveal the location of the undercushion in use;

FIGS. 116-1, 116-2, and 116-3 illustrate sealing of the cushion in the nasal bridge region according to an embodiment of the invention;

FIG. 119 shows a cross-section of an undercushion or backup band suitable for use along the side of a nose that can provide a sealing force into the plane of the face (arrow pointing up) and into the side of the nose (arrow pointing to the left).

DETAILED DESCRIPTION OF ILLUSTRATED EMBODIMENTS

The following description is provided in relation to several examples which may share common characteristics and features. It is to be understood that one or more features of any one example may be combinable with one or more features of the other examples. In addition, any single feature or combination of features in any of the examples may constitute additional examples.

In this specification, the word "comprising" is to be understood in its "open" sense, that is, in the sense of "including", and thus not limited to its "closed" sense, that is the sense of "consisting only of". A corresponding meaning is to be attributed to the corresponding words "comprise", "comprised" and "comprises" where they appear.

The term "air" will be taken to include breathable gases, for example air with supplemental oxygen.

1. Nasal Mask System

Examples of the invention are directed towards a nasal mask system that is easy and quick to fit (e.g., with little or no adjustment), enable reduced strap tension, is manufacturable in high volumes, provides high consumer appeal, provides comfort and seal, provides reliable quality, unobtrusive, and/or fits a large majority of the population.

As described in greater detail below, the nasal mask system includes a frame, a sealing arrangement (e.g., a cushion) provided to the frame and adapted to form a seal with the patient's nose, and an elbow, e.g., provided to the sealing arrangement, adapted to be connected to an air delivery tube that delivers breathable gas to the patient. A swivel ring may be optionally provided to couple the elbow to the sealing arrangement. Headgear may be removably attached to the frame to maintain the nasal mask system in a desired adjusted position on the patient's face. The nasal mask system is intended for use in positive pressure therapy for users with Obstructive Sleep Apnea (OSA) or another respiratory disorder.

While each example below is described as including a nasal interface type, aspects of the invention may be adapted for use with other suitable interface types, e.g., full-face interface, nasal prongs, etc.

2. Frame

Figure 1:
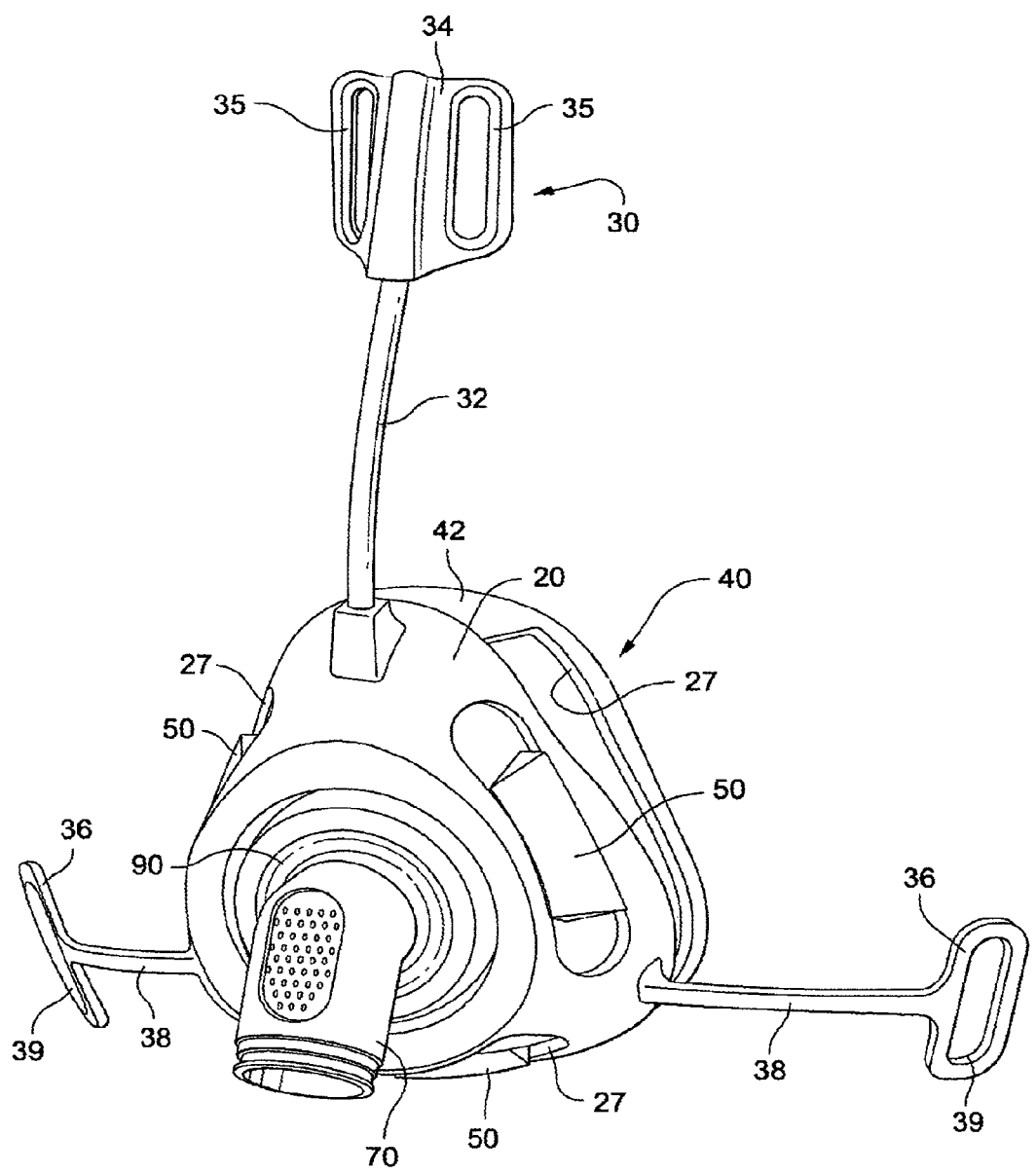
FIG. 1-1 is a perspective view of a nasal mask system according to an example of the present invention.
Figures 1, 2:
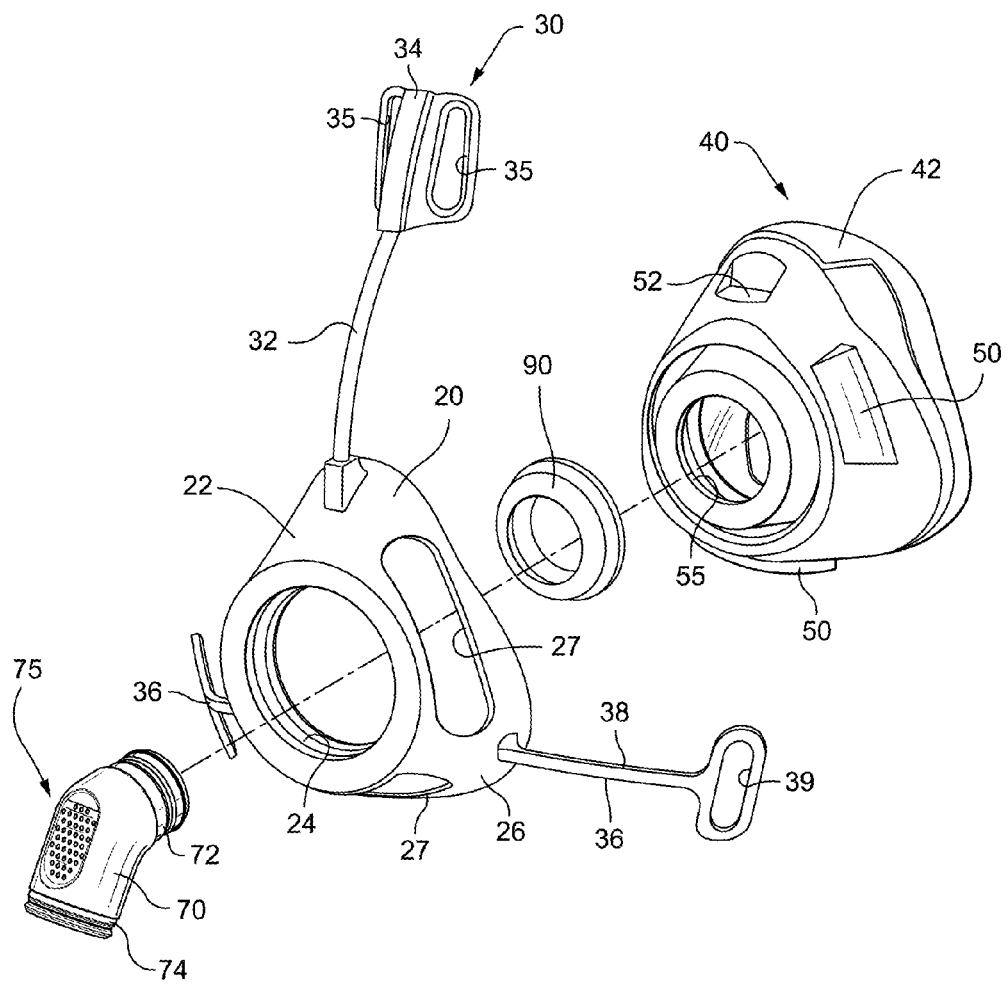
Figures 1, 2, 3:

As shown in FIGS. 1-1, 1-2, and 2-1 to 2-3, the frame 20 (also referred to an exoskeleton or skeleton) is structured to maintain, stabilize and/or support the sealing arrangement 40 (and also the elbow 70) in an operative position with respect to the patient's face. In addition, the frame 20 is structured to attach headgear to the nasal mask system.

As illustrated, the main body 22 (e.g., see FIGS. 1-2, 2-2, and 2-3) of the frame 20 includes an open construction with a central opening 24 to allow the sealing arrangement 40 to communicate with or receive the elbow 70 and a side wall 26 structured to retain or otherwise engage the sealing arrangement 40. In use, the frame 20 of this example is not in the air path, i.e., sealing arrangement 40 defines breathing cavity and is directly coupled to the elbow 70 as described below. The frame 20 may be semi-rigid or at least allow for some flexibility. The frame 20 may be made from a single material, a combination of materials, or a combination of the same material in varying hardnesses. The frame 20 may be made from polycarbonate, polypropylene, nylon, clear nylon, thermoplastic elastomer (TPE), silicone, or any other suitable material.

A forehead support 30 extends from the top end of the main body 22. The forehead support 30 may be fixed (i.e., unadjustable), adjustable (e.g., the height or length of elongated arm may be extendable, or the angle of the forehead support may be changeable), or interchangeable (e.g., various sizes of forehead supports for different sized patients or the elongated arm may be replaced with different various lengths of arm). The forehead support 30 includes an elongated arm 32 and an upper headgear connector 34 providing slots or receiving holes 35 at the free end of the arm adapted to receive respective headgear straps in use, thus using the padding of the headgear straps rather than requiring a separate pad. In an example, the headgear connector may be adjustable, e.g., with respect to the arm 32 (e.g., tilt or angle towards the patient's forehead). Lower headgear connectors 36 are provided to respective sides of the main body 22, each lower headgear connector 36 including an elongated arm 38 and a slot or receiving hole 39 at the free end of the arm adapted to receive a respective headgear strap in use. The elongated arm 38 may be bendable or selectively deformable so as to allow the arm to bend towards or away from the patient's face in use, thereby pulling the headgear onto the patient's face, e.g., enabling side sleeping. In an example, if the elongated arm 38 is bendable or deformable with hand pressure of the user, the elongated arm may be suitably malleable to hold the deformed shape. This feature of the elongated arm 38 may increase the comfort, fit and/or sealing of the embodiment. The forehead support and headgear connectors may provide an unobtrusive arrangement which extend out of the patient's line of sight. The generally thin and elongate configuration of the elongated arm 38 may at least partially prevent or limit obstruction to patient's line of sight, whilst wearing the embodiment. In an example, the elongated arm 38 may be constructed of wire or a metallic alloy. However, a person skilled in the art will appreciate that other materials may be used including but not limited to polymeric materials.

In an example, the arms 32, 38 may be suitably formed, shaped, or contoured to follow the contours of the patient's face whilst avoiding the patient's line of sight or impeding their vision. Also, the arms 32, 38 may include some inherent flexibility to allow a range of adjustment. The elongated arms

32, 38 may be made from a generally inextensible material such as aluminum, stainless steel, polycarbonate, polypropylene, TPE, or any other suitable material. Alternatively, the elongated arms 32, 38 may be continuous with the frame 20 and therefore made from the same material, or the elongated arms 32, 38 may be made from the same material as the frame 20 but not a single piece construction (i.e., the elongated arms 32, 38 may be attached to the frame 20). However, wherein the elongated arm 32, 38 is made of different material from the frame 20, the elongated arm 32, 38 may be secured onto frame 20 using an alternative fixing or securing method, e.g., such as gluing. The upper headgear connector 34 may be made from the same material as the elongated arm 32. Alternatively, the upper headgear connector 34 may be made from a more flexible material than the elongated arm 32 such as Hytrel™, silicone, nylon, or any other suitable material. The lower headgear connectors 36 may be continuous with the frame 20 and therefore made from the same material, or the lower headgear connectors 36 may be made from the same material as the frame 20 but not a single piece construction (i.e., elongated arm 38 may be attached to frame 20). Alternatively, the lower headgear connectors 36 may be made from a more flexible material than frame 20 such as Hytrel™, silicone, nylon, or any other suitable material.

The forehead support and headgear connectors may be integrally molded or otherwise attached to the main body of the frame 20. The frame 20 is constructed from a more rigid material than the sealing arrangement 40 (e.g., made of silicone, foam). For example, the frame may be constructed of plastic (e.g., polycarbonate) and/or metal materials, e.g., relatively thin metal material.

In an example, the arms 32 and/or 38 may be relatively thin or slender (e.g., 1-3 mm). In an example, the forehead support 30 and headgear connectors 36 may be formed of a material (e.g., metallic material) which is different than the material of the frame main body 22. In such example, the forehead support 30 and headgear connectors 36 may be attachable to the frame main body 22. The relatively thin or slender arms 32 and/or 38 may reduce the overall visual impact of the mask or embodiment.

In an example, upper headgear connector 34 provides a flattened area for the attachment of straps from the headgear. In an example, the straps attach to the upper headgear connector 34 through two apertures 35 mounted on opposed sides of the upper headgear connector 34 and the straps are adapted to extend through the apertures and elicit a force towards the patient's face and effectively pull the upper headgear connector 34 towards the patient's forehead, in this embodiment.

2.1 Alternative Frame

Figures 1, 2, 3, 4:
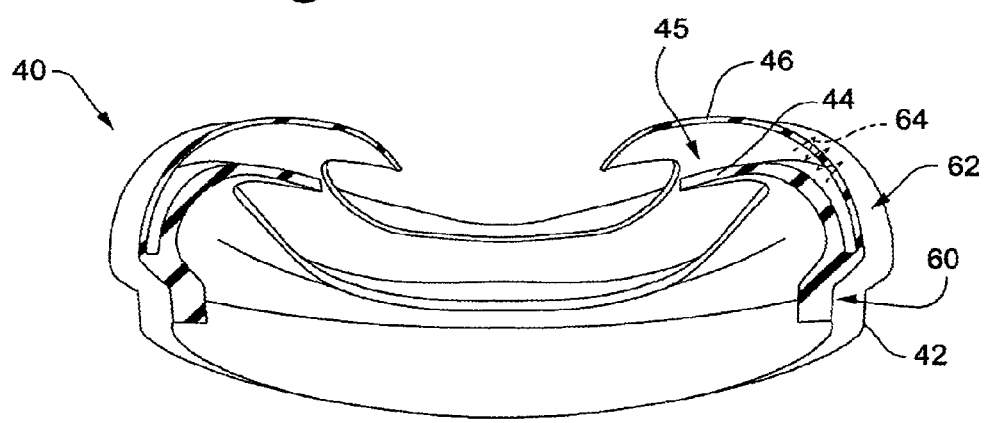
Figures 1, 2, 3, 4, 5:
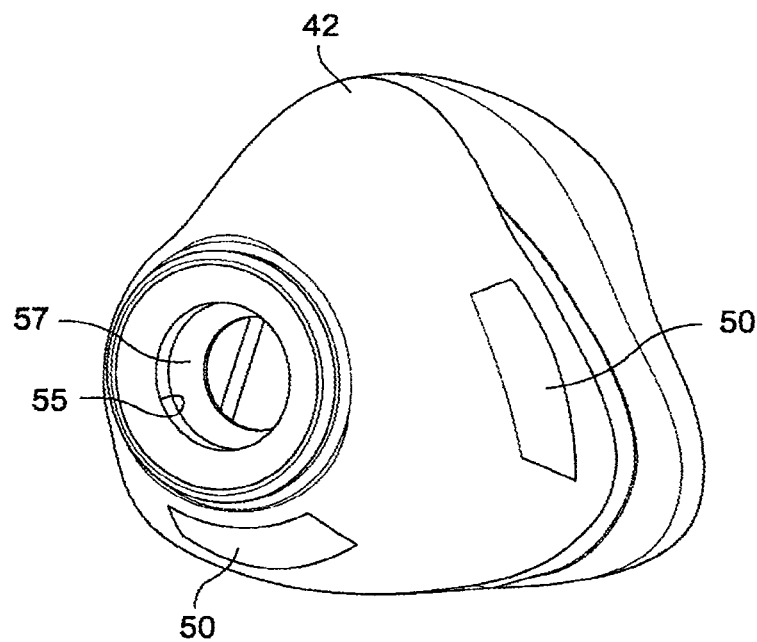
Figures 1, 2, 3, 4, 5, 6:
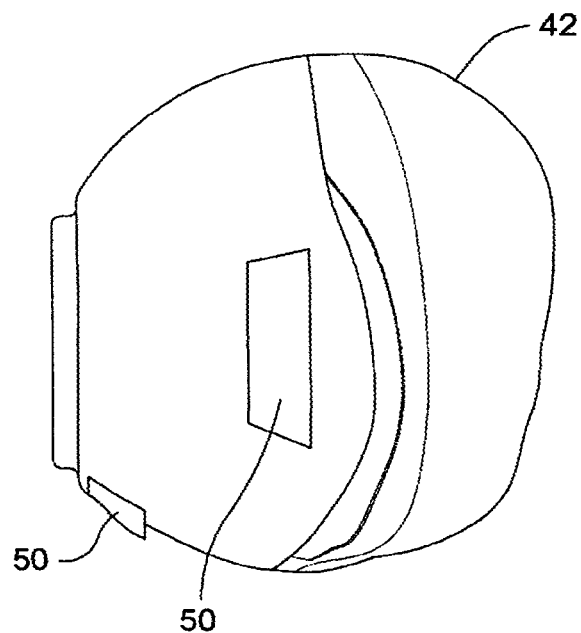

FIGS. 5-1 to 5-6 show an alternative embodiment of a frame 420 that is structured to maintain or otherwise support a sealing arrangement 440 (and an elbow 70) in an operative position with respect to the patient's face.

The frame 420 may be structured to attach a headgear to the nasal mask system. The frame 420 may be made from polycarbonate, polypropylene, nylon, or any other suitable material. A swivel ring 90 may connect the sealing arrangement 440 to an elbow 70. The swivel ring 90 may be any suitable polymer such as polycarbonate or polypropylene. The elbow 70 may be small and unobtrusive. The elbow may include a venting arrangement 75 comprising holes or apertures for venting. The elbow 70 may be made from polypropylene, polycarbonate or any other suitable material.

A forehead support 430 extends from a top end of the main body 422 of the frame 420. The forehead support 430 may be fixed (i.e., un-adjustable), adjustable (e.g., the height or length of elongated arm may be extendable, or the angle of the forehead support may be changeable), or interchangeable (e.g., various sizes of forehead supports for different sized patients or the elongated arm may be replaced with different various lengths of arm). The forehead support 430 includes an elongated arm 432 and an upper headgear connector 434 providing slots or receiving holes 435 at the free end of the arm 432 adapted to receive respective headgear straps in use, thus using the padding of the headgear straps rather than requiring a separate pad. In an example, the headgear connector 434 may be adjustable, e.g., with respect to the arm 432 (e.g., tilt or angle towards the patient's forehead).

Upper headgear connector, or forehead support pad, 434 may be made from silicone, nylon, polypropylene, TPE, polycarbonate, or any other suitable material. Elongated arm 432 may be made from a malleable metal. The frame 420 may be a connection point for the elongated arm 432 and the sealing arrangement 440.

Lower headgear connectors 436 are provided to respective sides of the main body 422 of the frame 420. The lower headgear connectors 436 may be hook shaped. The lower headgear connectors 436 may also be integrally formed with the main body 422 of the frame 420, or they may be formed separately from the main body and attached by, for example, adhesive or any form of mechanical fixation.

Each lower headgear connector 436 may include a gap 439 between an upper end of the connector 436 and the main body 422 of the frame to permit a headgear strap to be inserted therebetween. It should be appreciated that the headgear connectors 436 may also be connected at both the lower end and the upper end to the main body 422 of the frame 420. The connectors 436 may be bendable or selectively deformable so as to allow the connectors 436 to bend towards or away from the patient's face in use, thereby pulling the headgear onto the patient's face, e.g., enabling side sleeping. This may increase the comfort, fit and/or sealing of the nasal mask system. The forehead support 430 and the headgear connectors 434, 436 may provide an unobtrusive arrangement which extend out of the patient's line of sight. The placement of the lower headgear connectors 436 at lower corner positions on the main body 422 of the frame 420 may at least partially prevent or limit obstruction to patient's line of sight, whilst wearing the nasal mask system.

2.2 Alternative Frame

The following illustrates alternative embodiments of a frame, arm, and forehead support, for a mask system.

2.2.1 Frame

Figures 1, 2, 3, 4, 5, 6, 7:
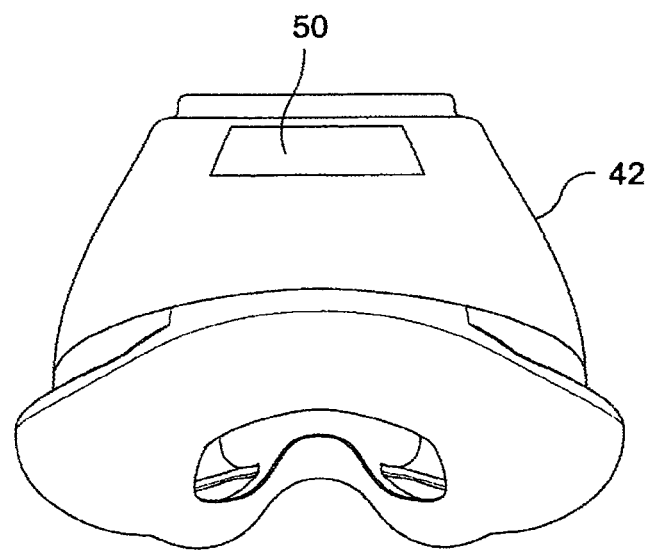

FIGS. 7-1 to 7-3 show a nasal mask system including a frame 520, sealing arrangement or cushion 540, elongated arm 532 and forehead support 530, elbow 570, and ring 590 to couple the elbow to the cushion.

Figures 1, 2, 3, 4, 5, 6, 7, 8:
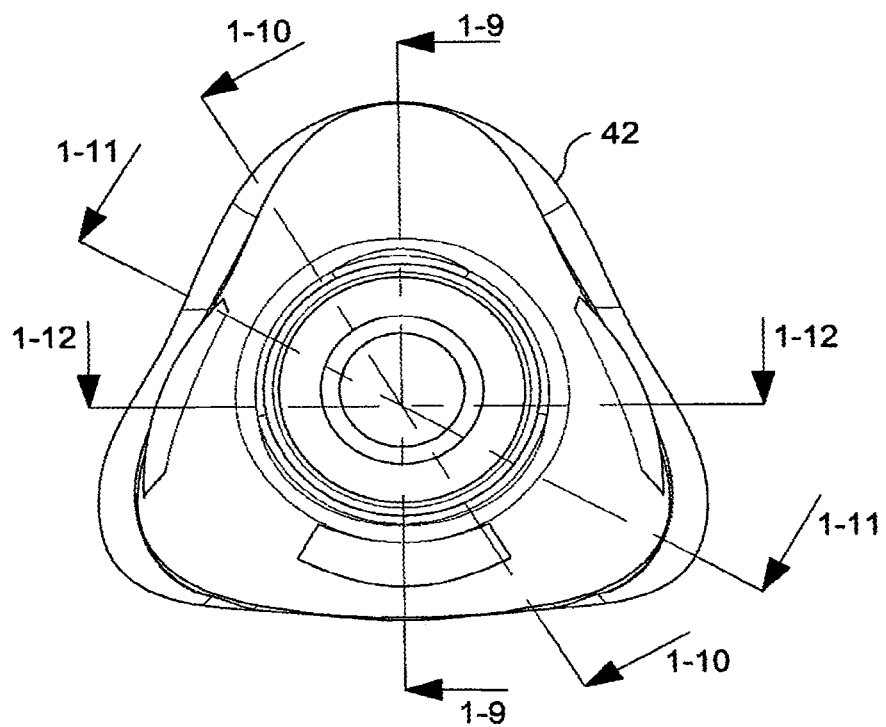

As best shown in FIGS. 8-1 to 8-3, each lower headgear connector 536 provided to the frame may be generally S-shaped. Each lower headgear connector includes a top portion 536(1), a middle portion 536(2), a lower portion 536(3), and a connecting portion 536(4) that attaches the connector to the frame. The top portion 536(1) may have a lead in adapted to guide the headgear strap into position. The middle portion 536(2) is adapted to abut or is close to the frame, so as to retain the strap within the connector once it is engaged. The lower portion 536(3) is adapted to receive the strap once it has been pushed through the middle portion. The connecting portion 536(4) allows the connector to hinge outwards or away from the frame to allow a headgear strap to pass between the middle portion of the connector and the frame.

The connectors 536 are aligned close to the frame to enable ease of use in sliding headgear along the side of the frame.

The self closing connector enables easy access while still acting as a retention feature for headgear.

In an embodiment, one or more portions of the connector may be constructed of TPE.

FIGS. 8-4 and 8-5 illustrate alternative lower headgear connectors, e.g., hook-shaped connector 536-1, and connector 536-2 with free end adapted to engage a connector base 520-1 on the frame. As shown in FIG. 8-5, the free end of the hook-shaped connector 536-1 includes a retaining hook to help retain the headgear strap. As shown in FIG. 8-4, the connector 536-2 may be biased into engagement with the base 520-1 to help retain the headgear strap.

Figures 1, 3:
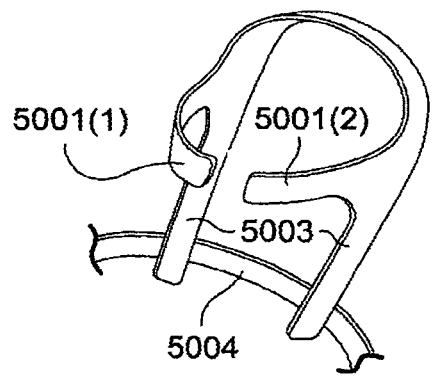
Figures 2, 3:
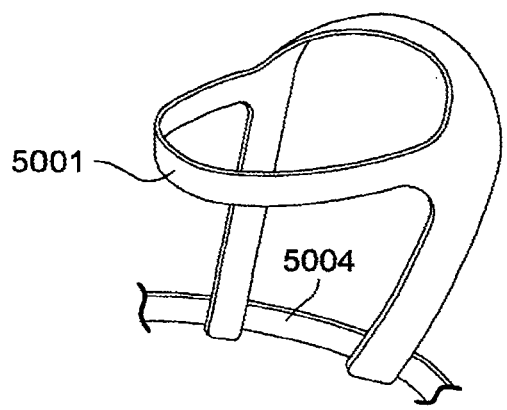
Figure 3:
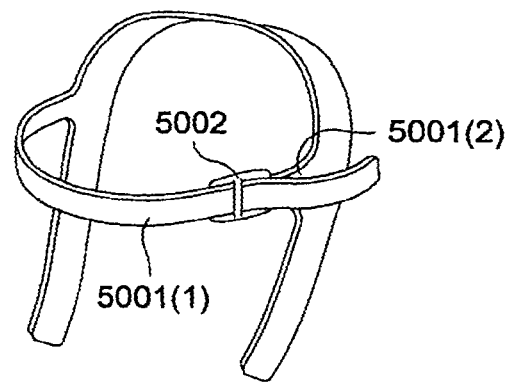
Figures 3, 4:
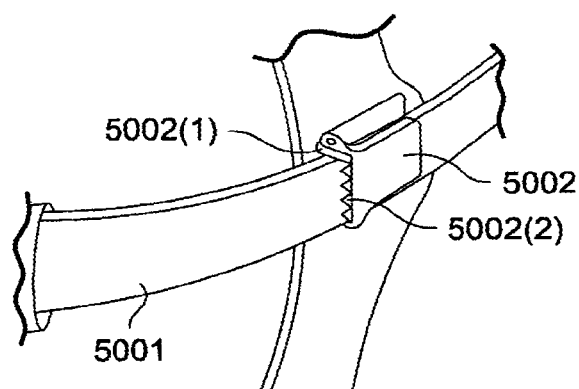
Figures 3, 4, 5:
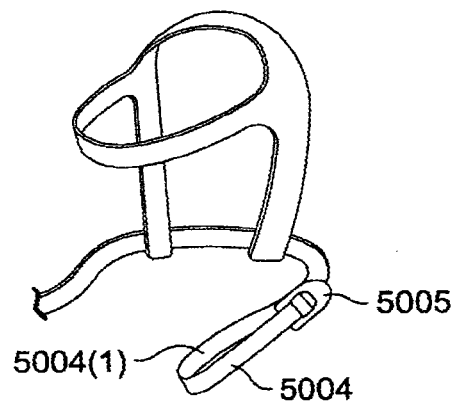
Figures 3, 4, 5, 6:
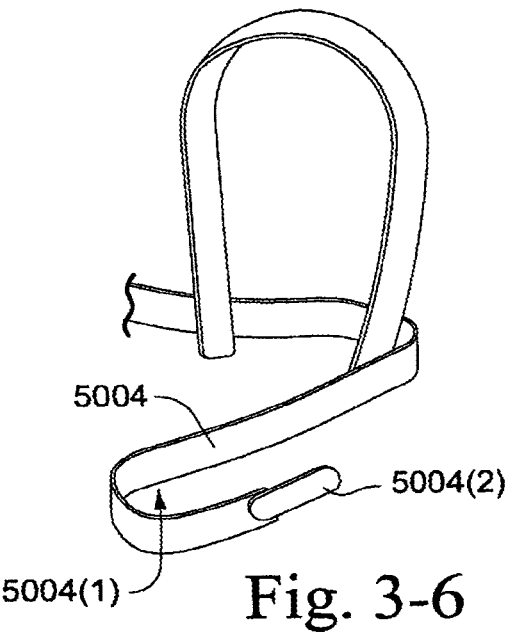
Figures 3, 4, 5, 6, 7, 7A:
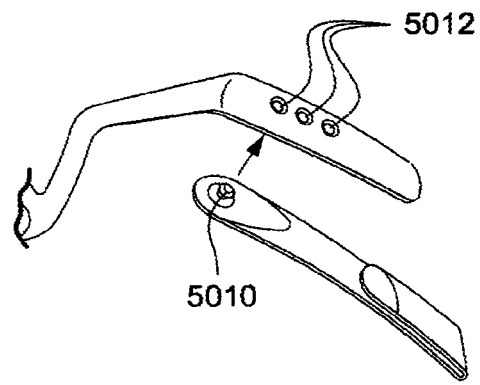
Figures 3, 4, 5, 6, 7, 7B:
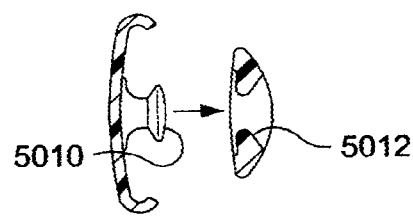
Figures 3, 4, 5, 6, 7, 8:
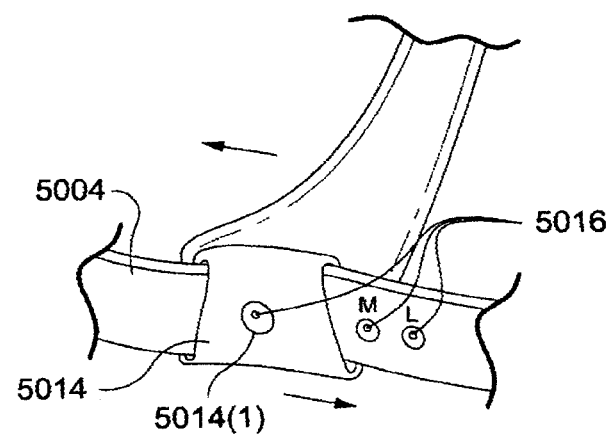
Figures 3, 4, 5, 6, 7, 8, 9:
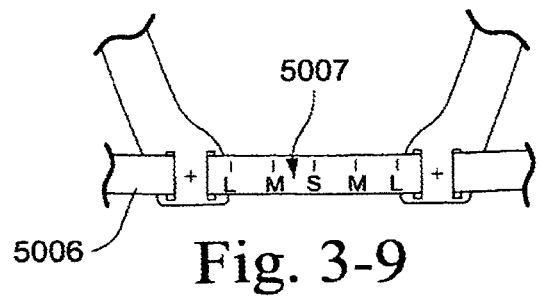
Figures 3, 4, 5, 6, 7, 8, 9, 10:
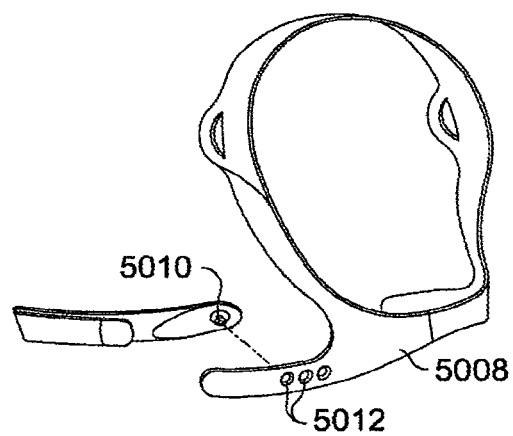
Figures 3, 4, 5, 6, 7, 8, 9, 10, 11:
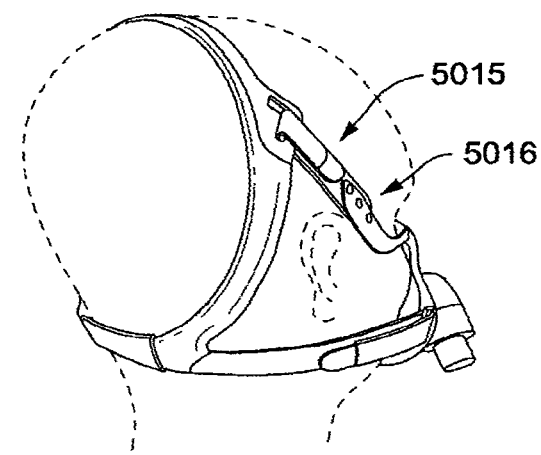
Figures 3, 4, 5, 6, 7, 8, 9, 10, 11, 12:
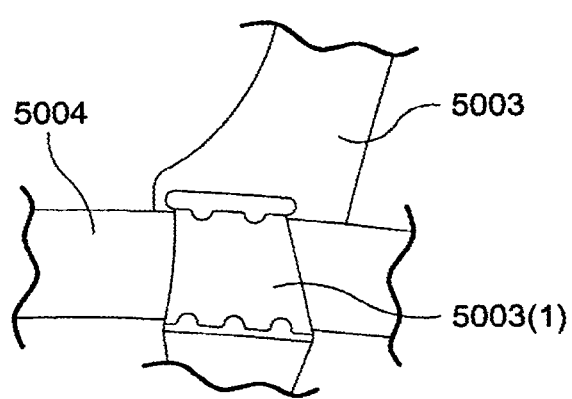
Figures 3, 4, 5, 6, 7, 8, 9, 10, 11, 12, 13, 14, 15, 16, 17, 18, 19:
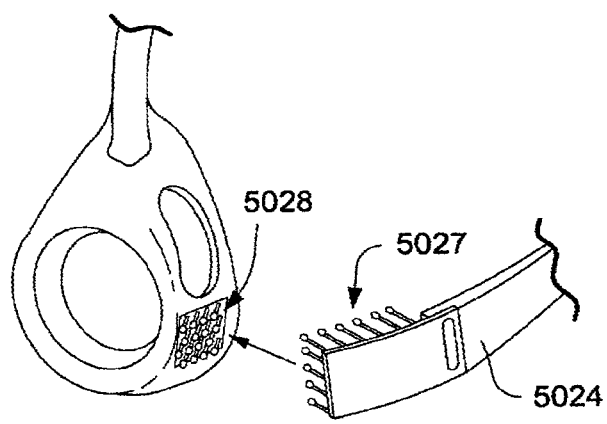

FIGS. 16-1 and 16-2 illustrate another embodiment of a frame 520-1 for supporting the cushion and headgear (e.g., open frame arrangement with lower cross-bars 5536 for lower headgear straps and a forehead support bar with an opening 5537 for upper headgear straps). FIGS. 17-1 and 17-2 illustrate another embodiment of a frame 520-2 for supporting the cushion and headgear (e.g., headgear clip 5540 includes opening 5440(1) adapted to engage a bar-like receptacle 5541 on frame). The frame 520-2 also includes a forehead support bar with an opening for upper headgear straps as in FIGS. 16-1 and 16-2 described above. In addition, the frame 520-2 includes upwardly extending cushion support bars 521 adapted to support and/or retain the cushion.

In an alternative embodiment, the frame may include clip receptacles adapted to removably interlock with respective headgear clips associated with lower headgear straps.

2.2.2 Elongated Arm

The frame supports the elongated arm (e.g., constructed of metal, malleable metal) that holds the forehead support.

Figures 1, 2, 3, 4, 5, 6, 7, 8, 9:
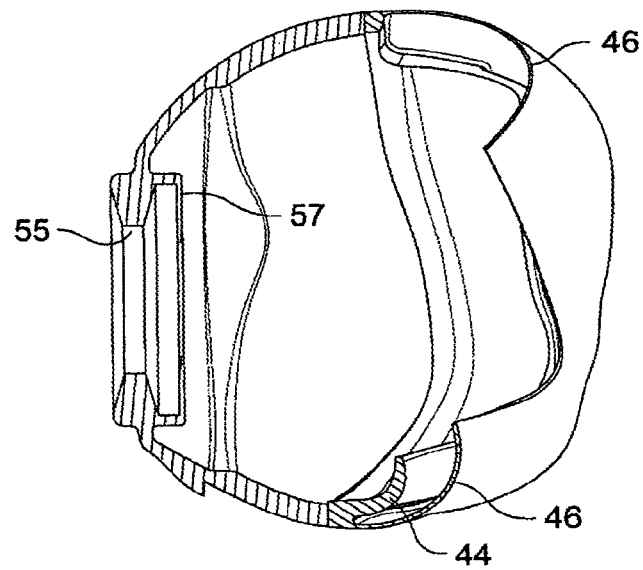
Figures 1B, 9:
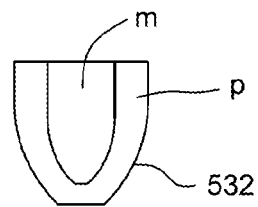
Figures 1A, 9:
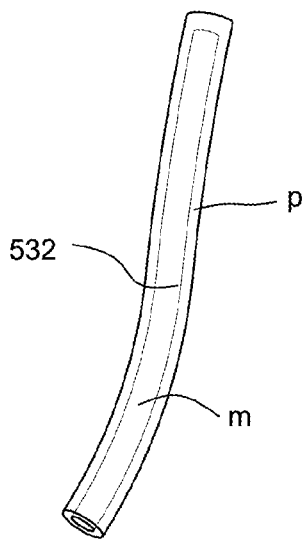
Figures 2, 9:
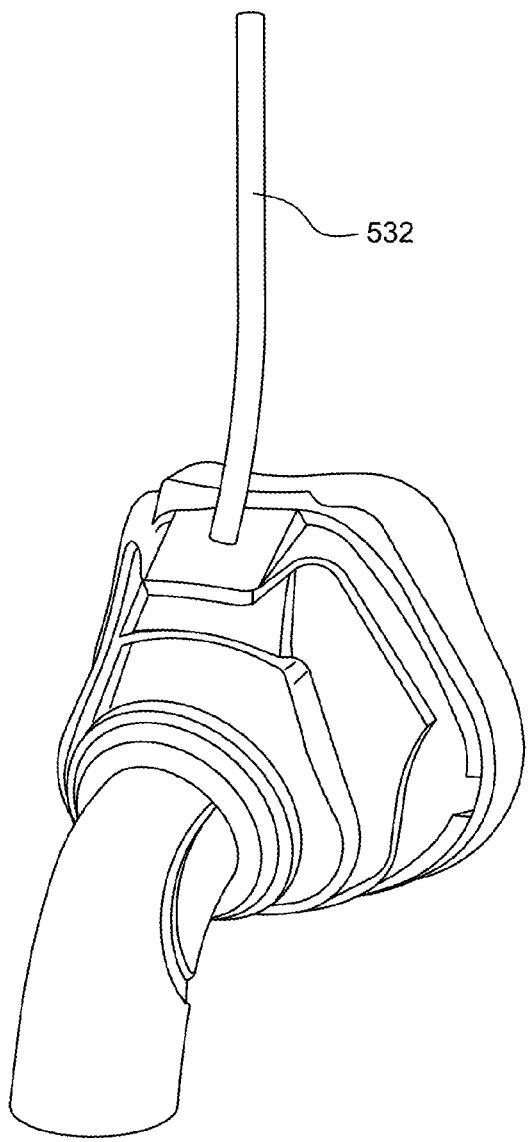
Figures 6, 10:
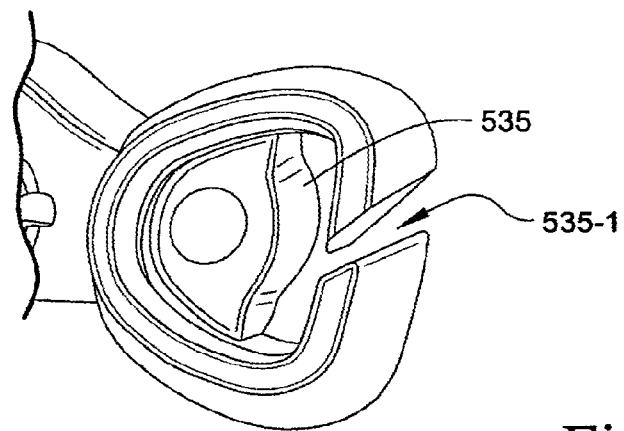
Figures 1, 11:
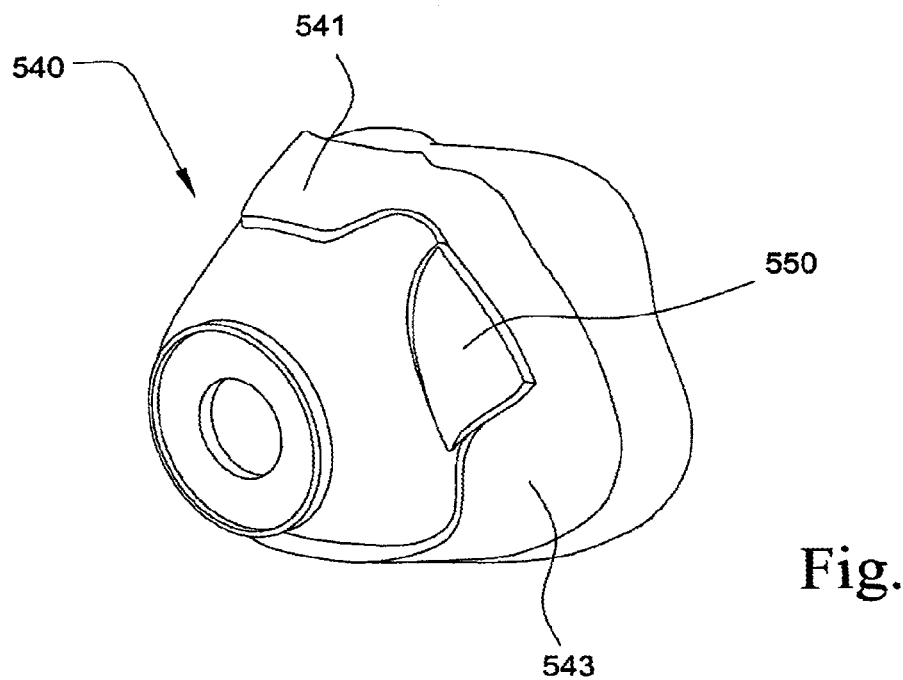
Figures 2, 11:
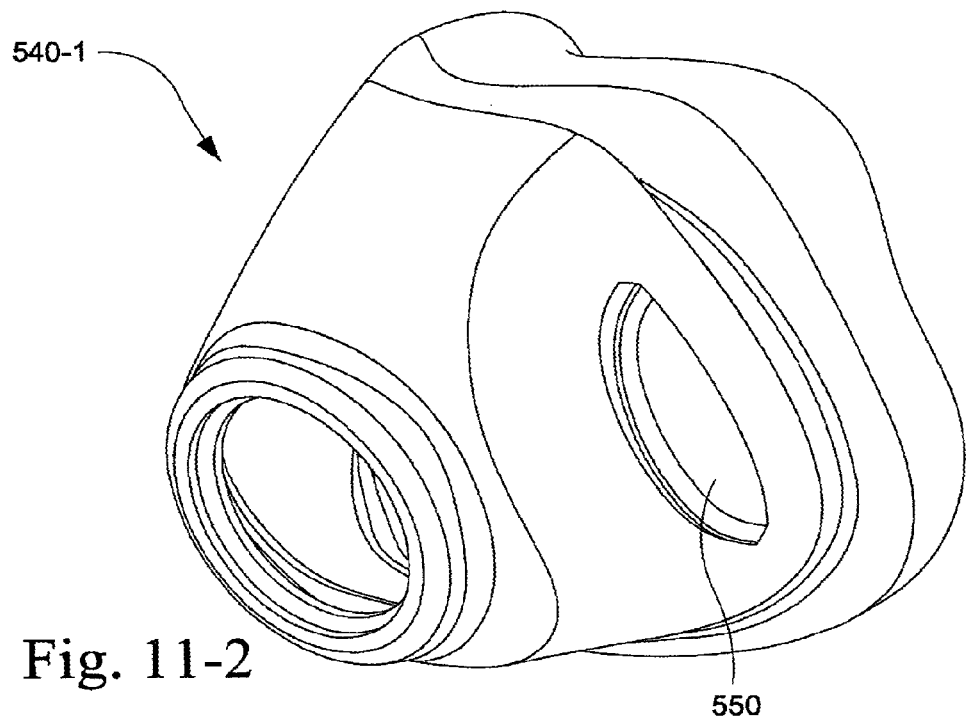
Figures 3, 11:
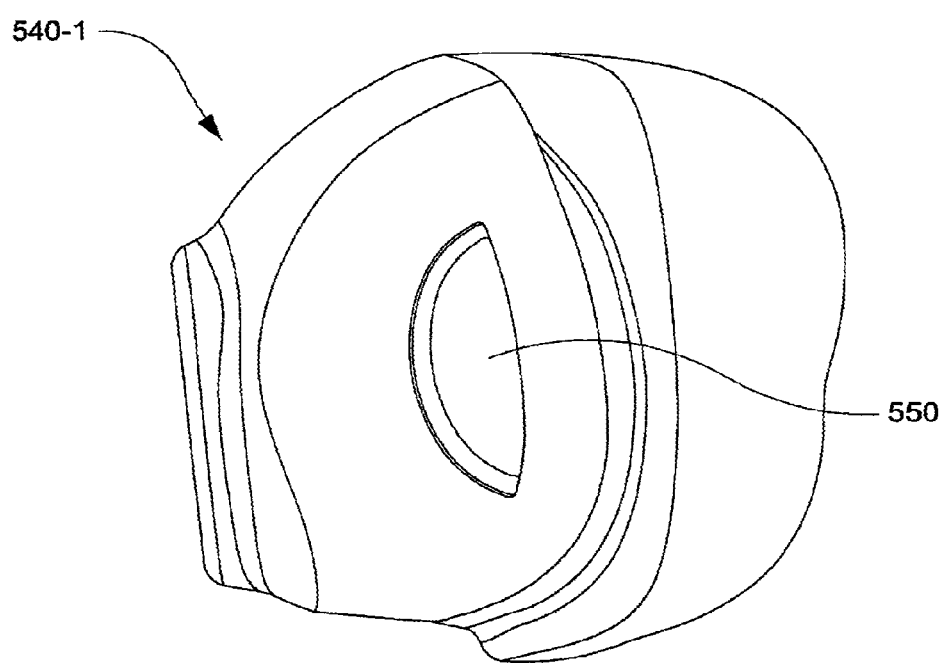
Figures 4, 11:
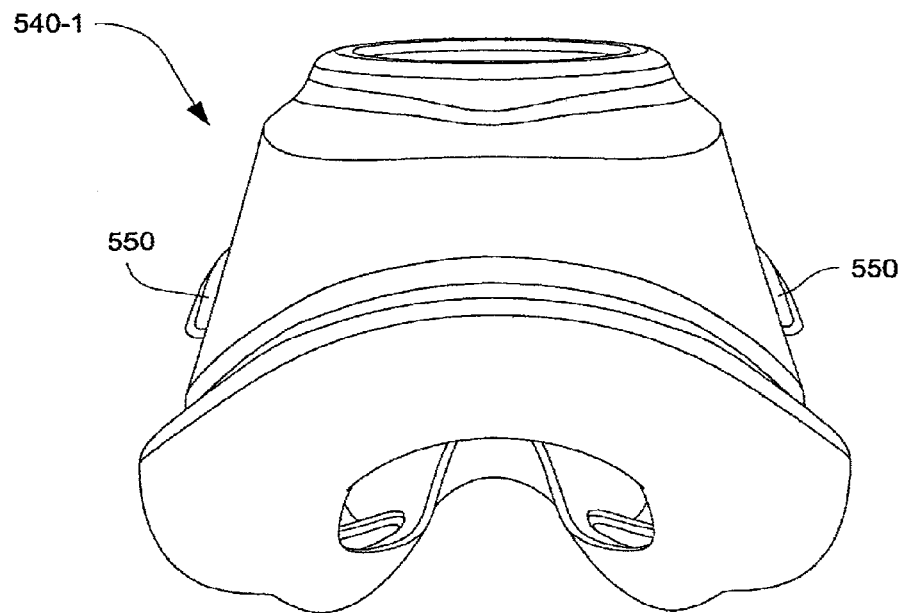
Figures 5, 11:
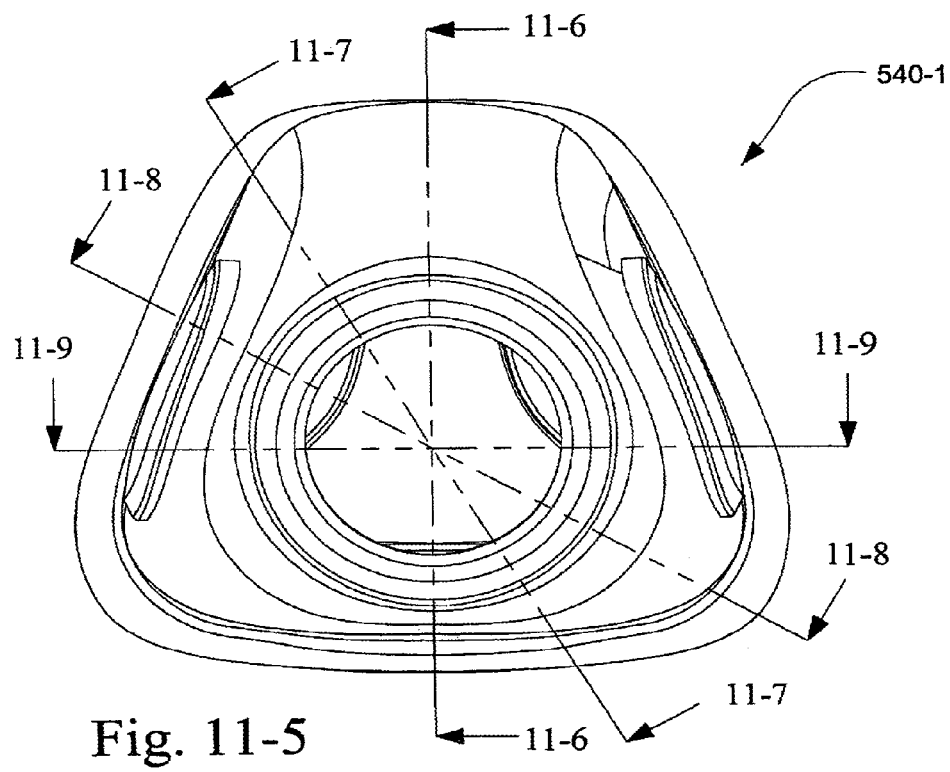
Figures 6, 11:
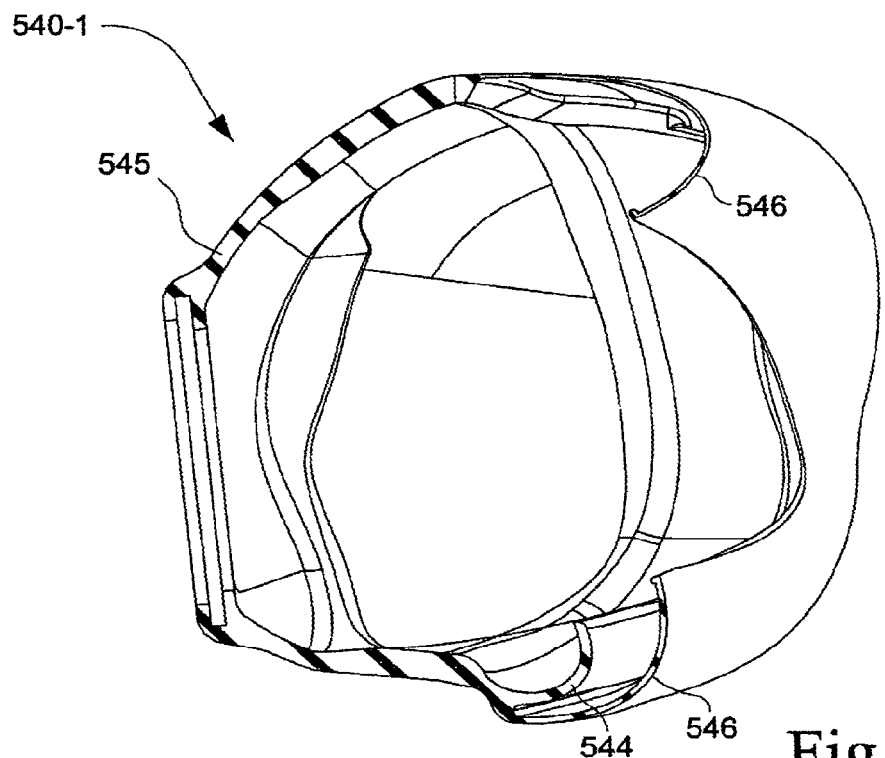
Figures 7, 11:
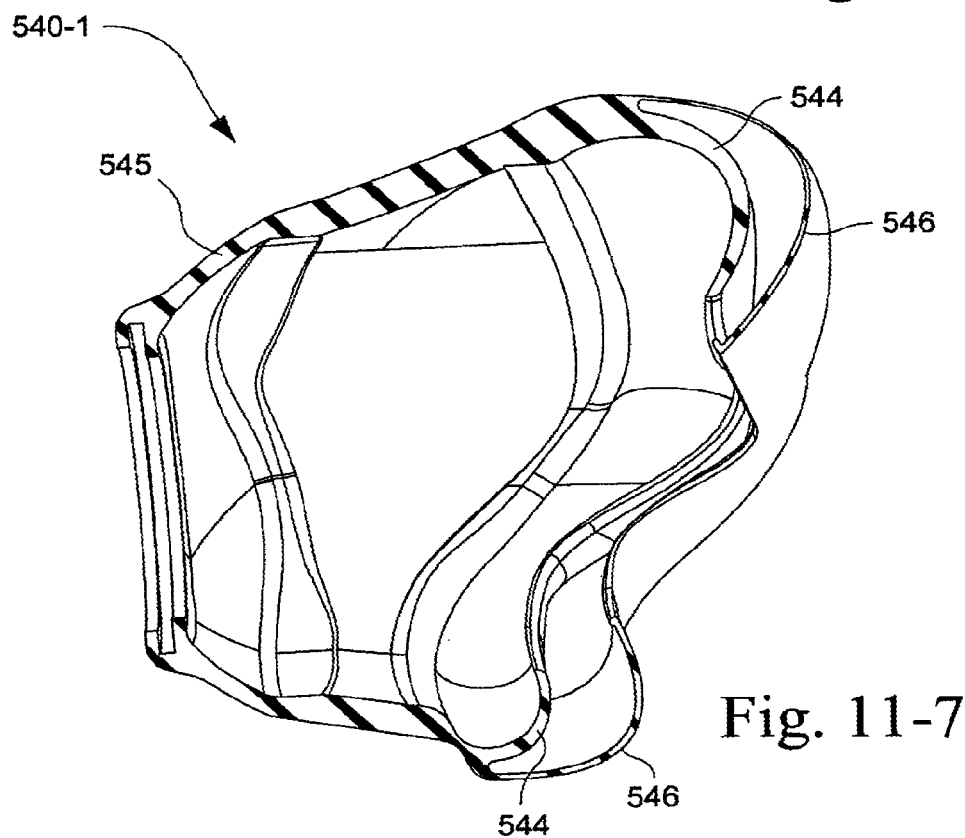
Figures 8, 11:
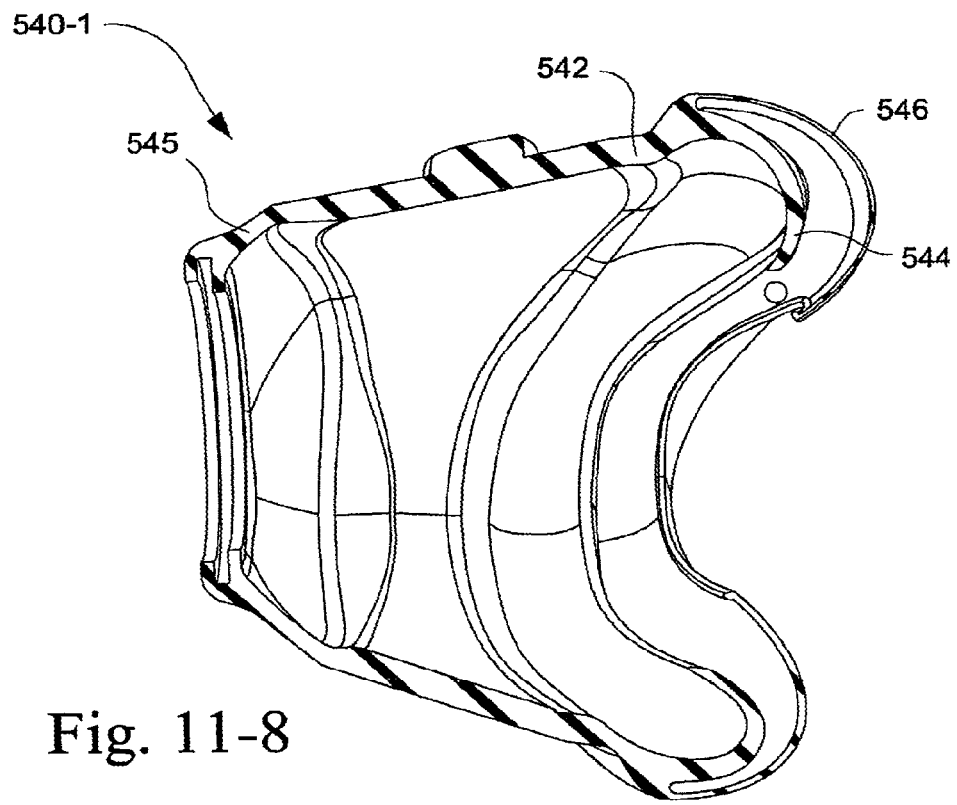
Figures 9, 11:
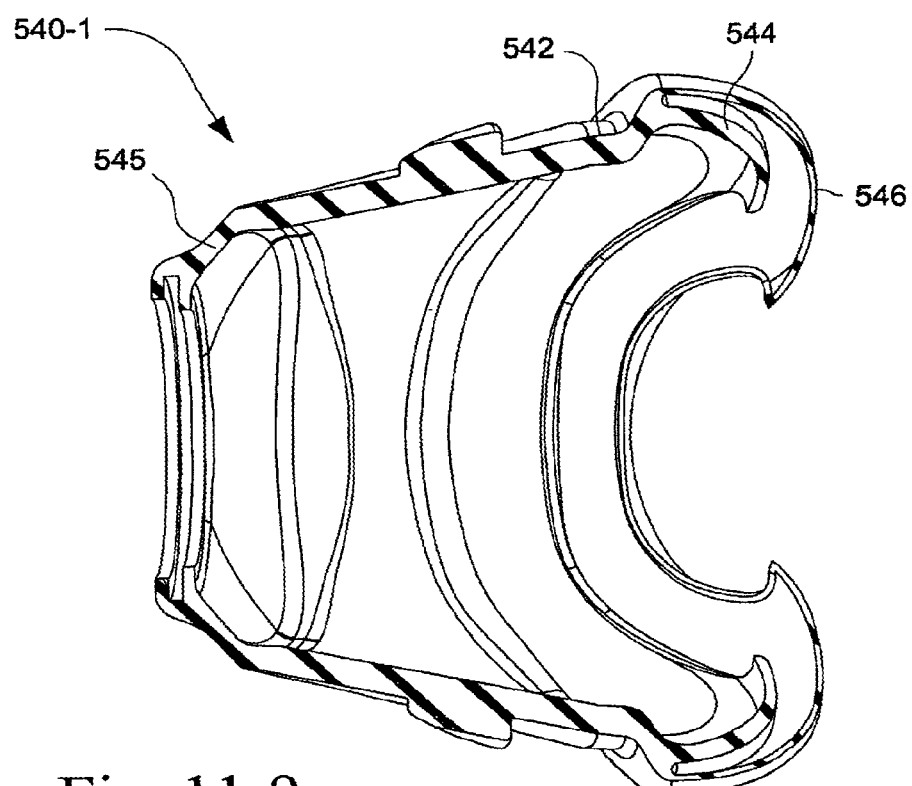
Figures 1, 12:
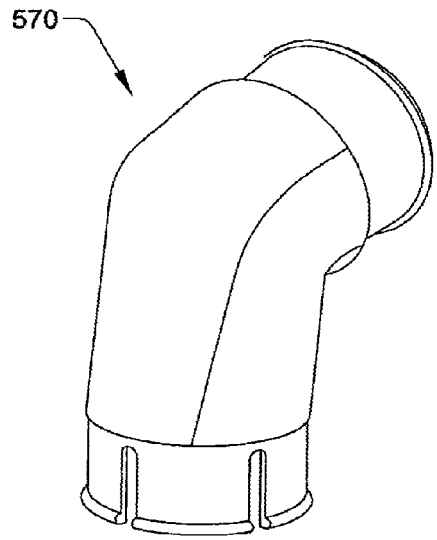
Figures 2, 12:
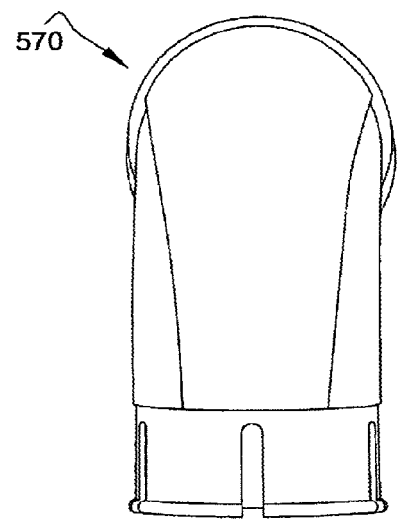
Figures 3, 12:
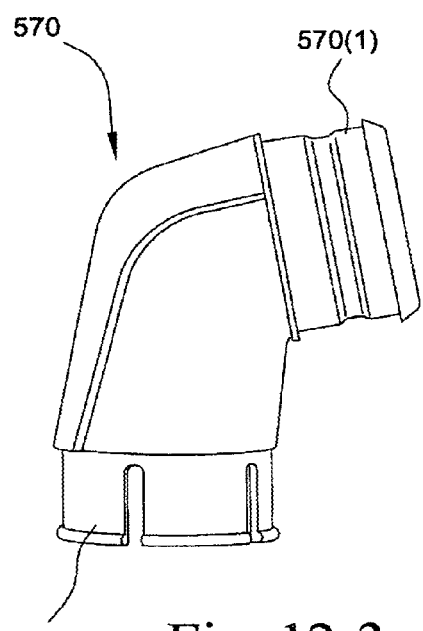
Figures 4, 12:
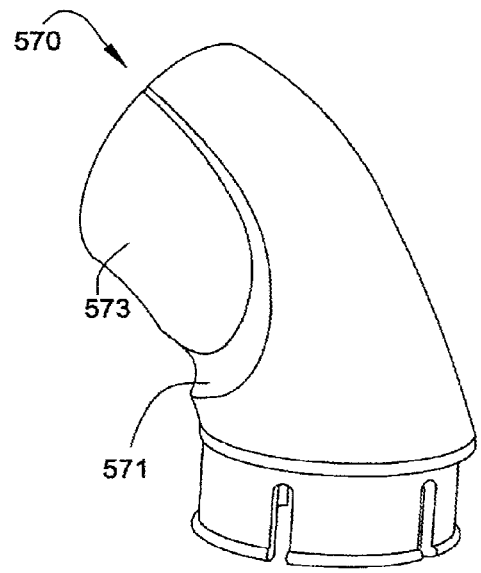
Figures 5, 12:
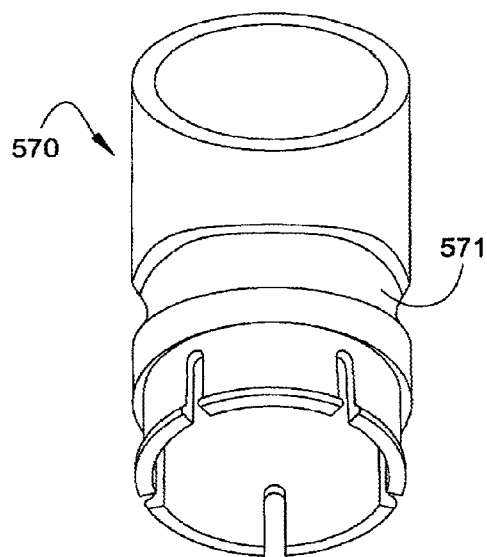
Figures 6, 12:
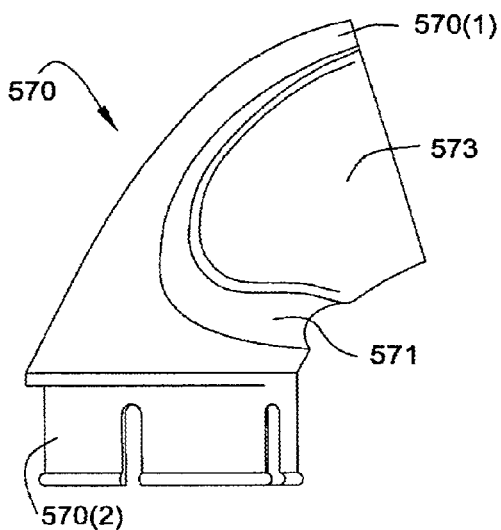
Figures 7, 12:
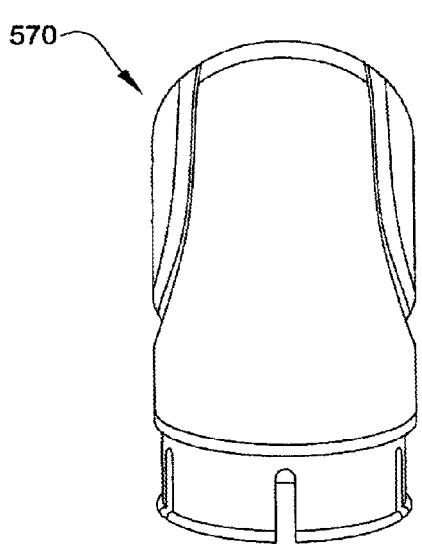
Figures 8, 12:
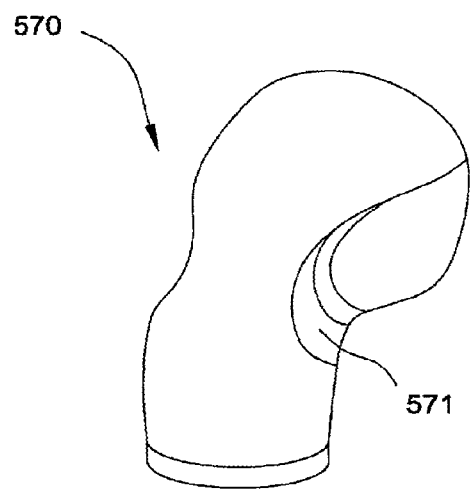
Figures 9, 12:
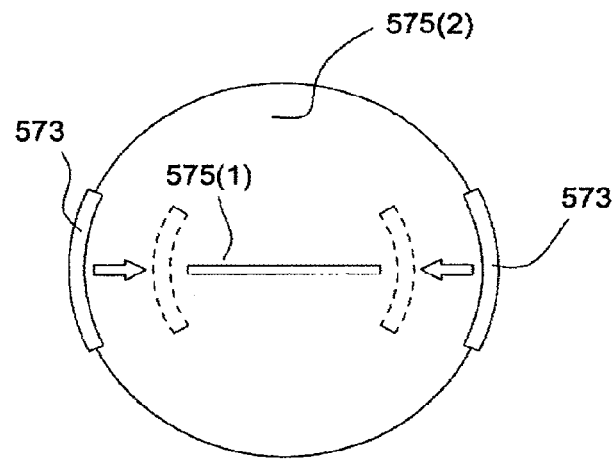
Figures 1, 13:
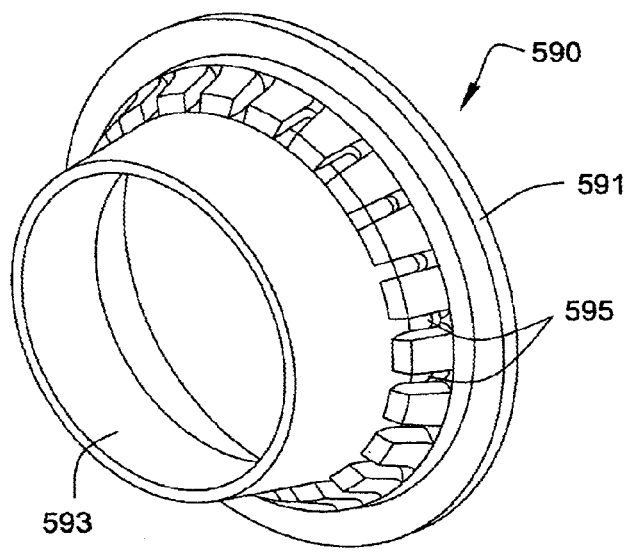
Figures 2, 13:
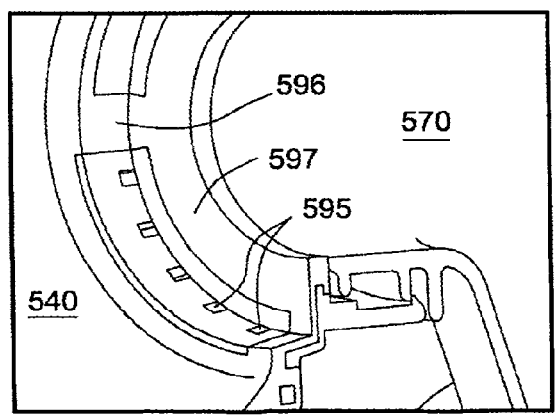
Figures 1, 14:
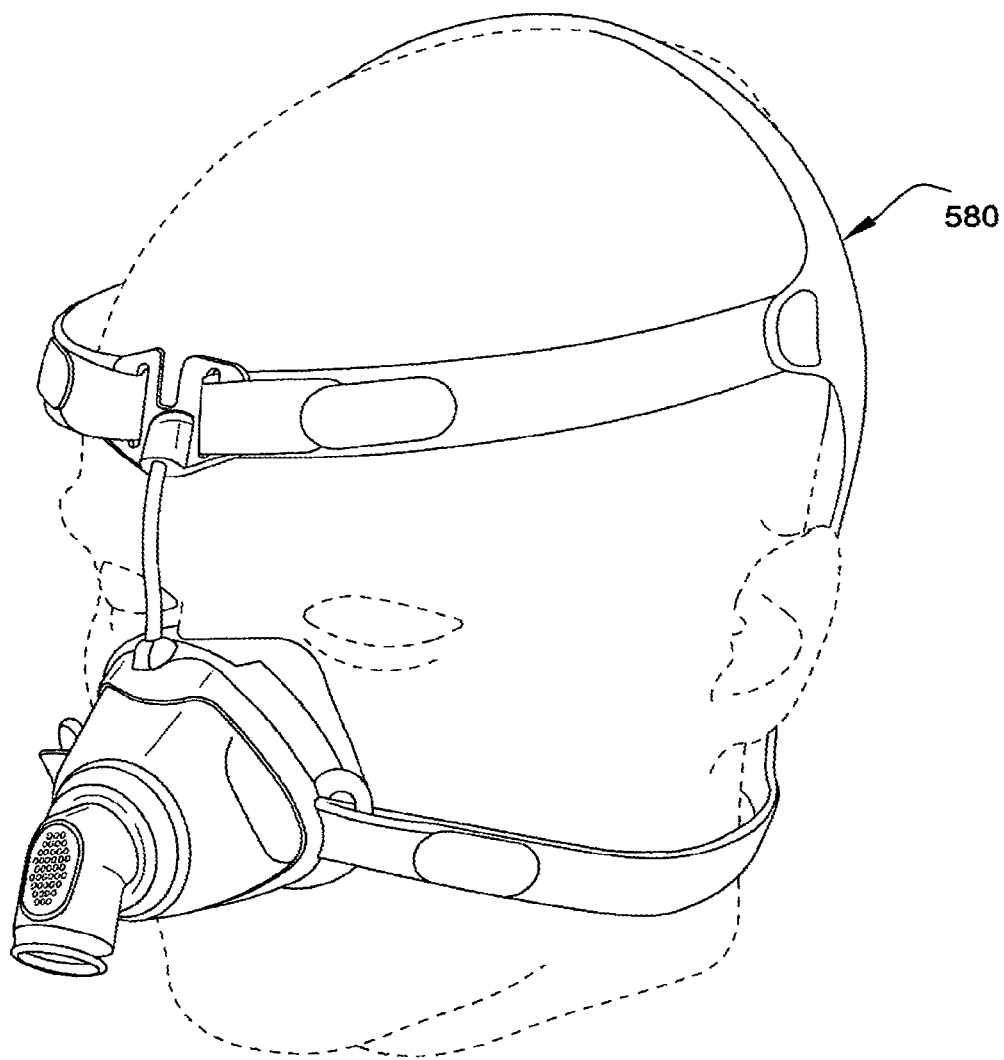
Figures 2, 14:
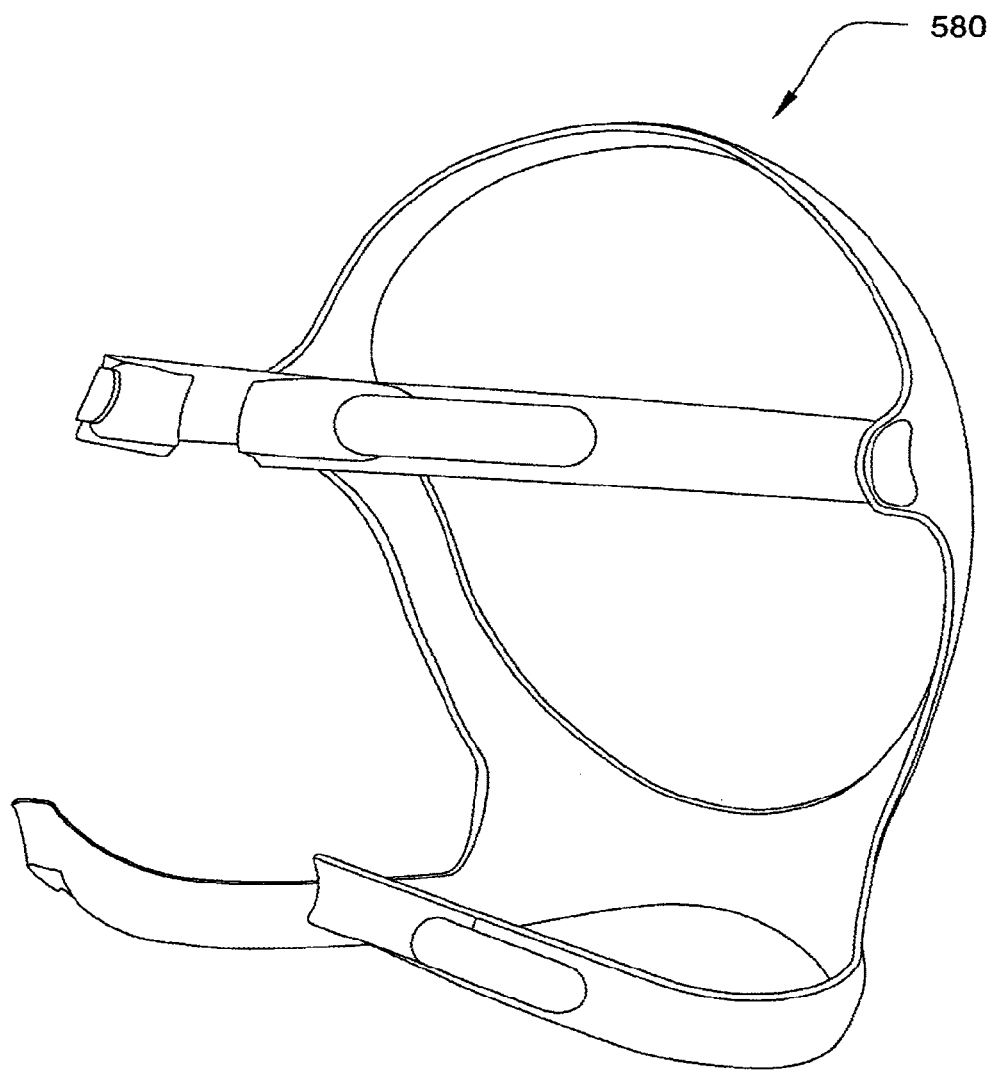
Figures 1, 15:
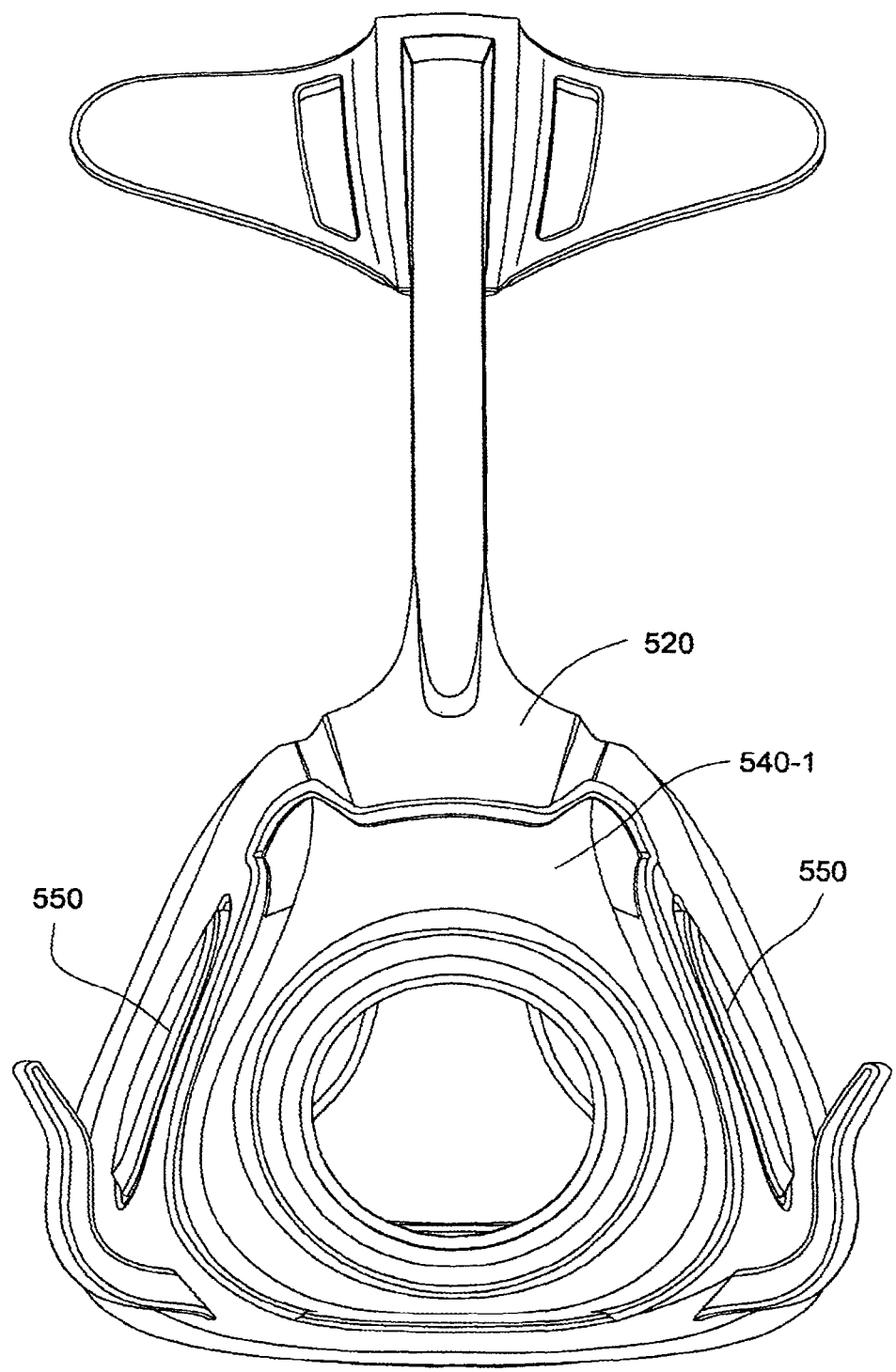
Figures 2, 15:
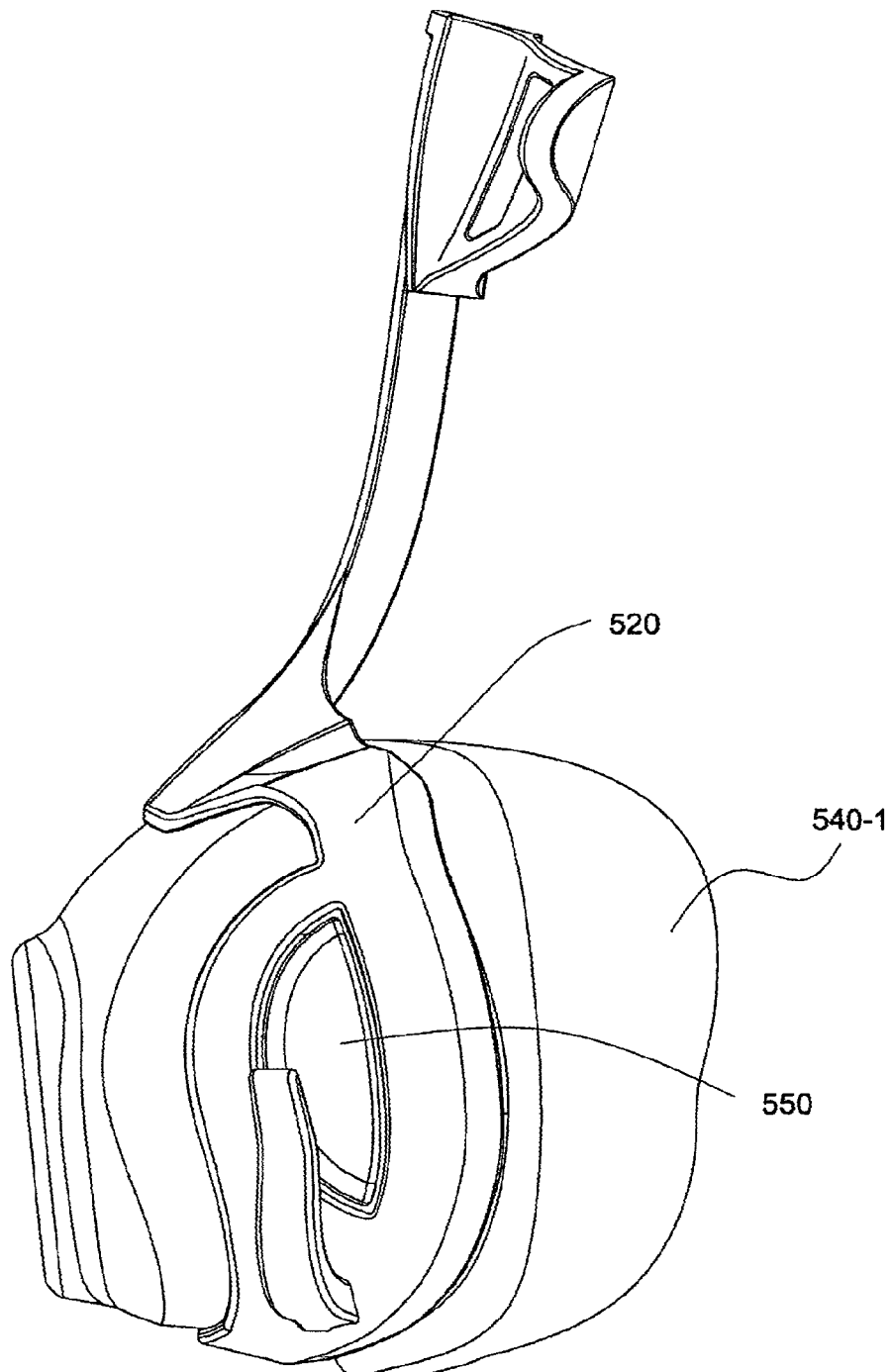
Figures 3, 15:
Figures 1, 16:
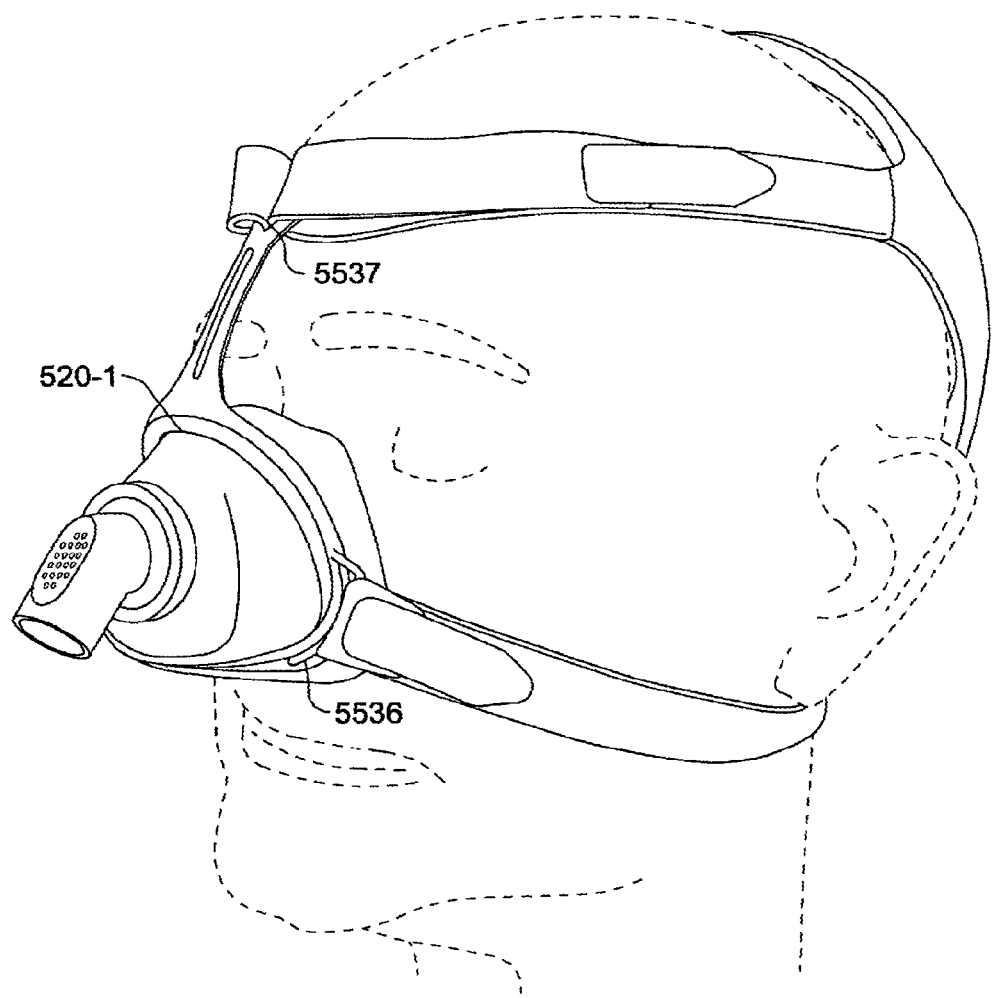
Figures 2, 16:
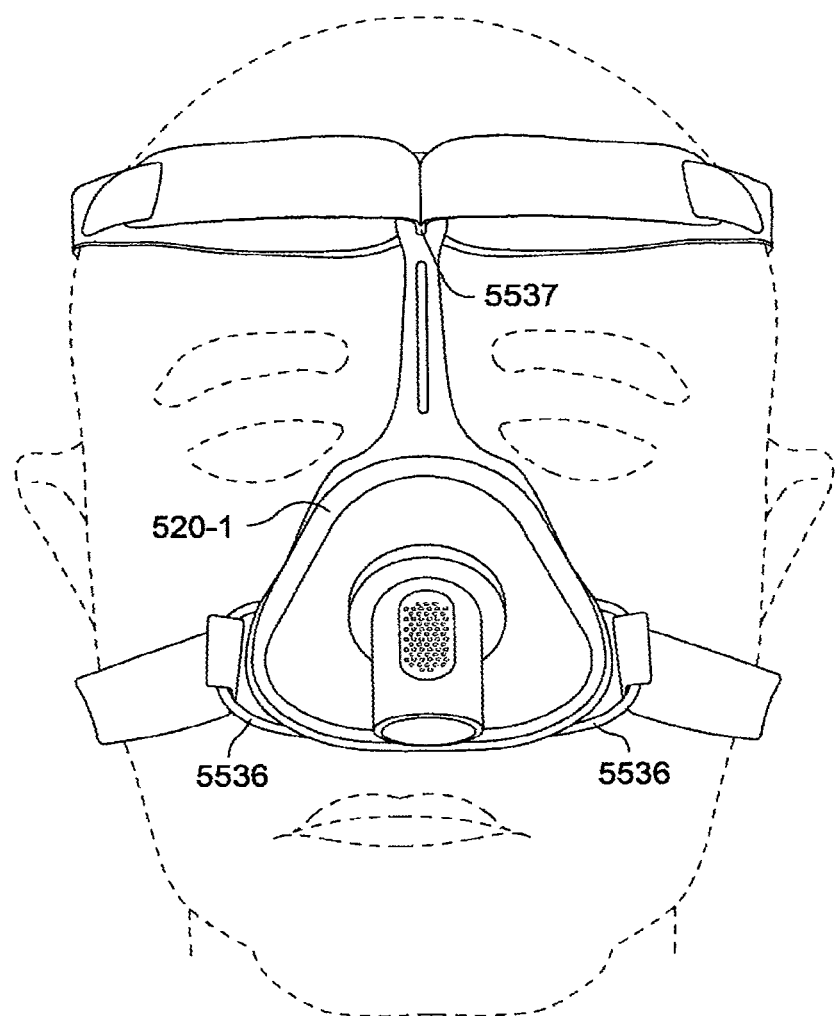
Figures 1, 17:
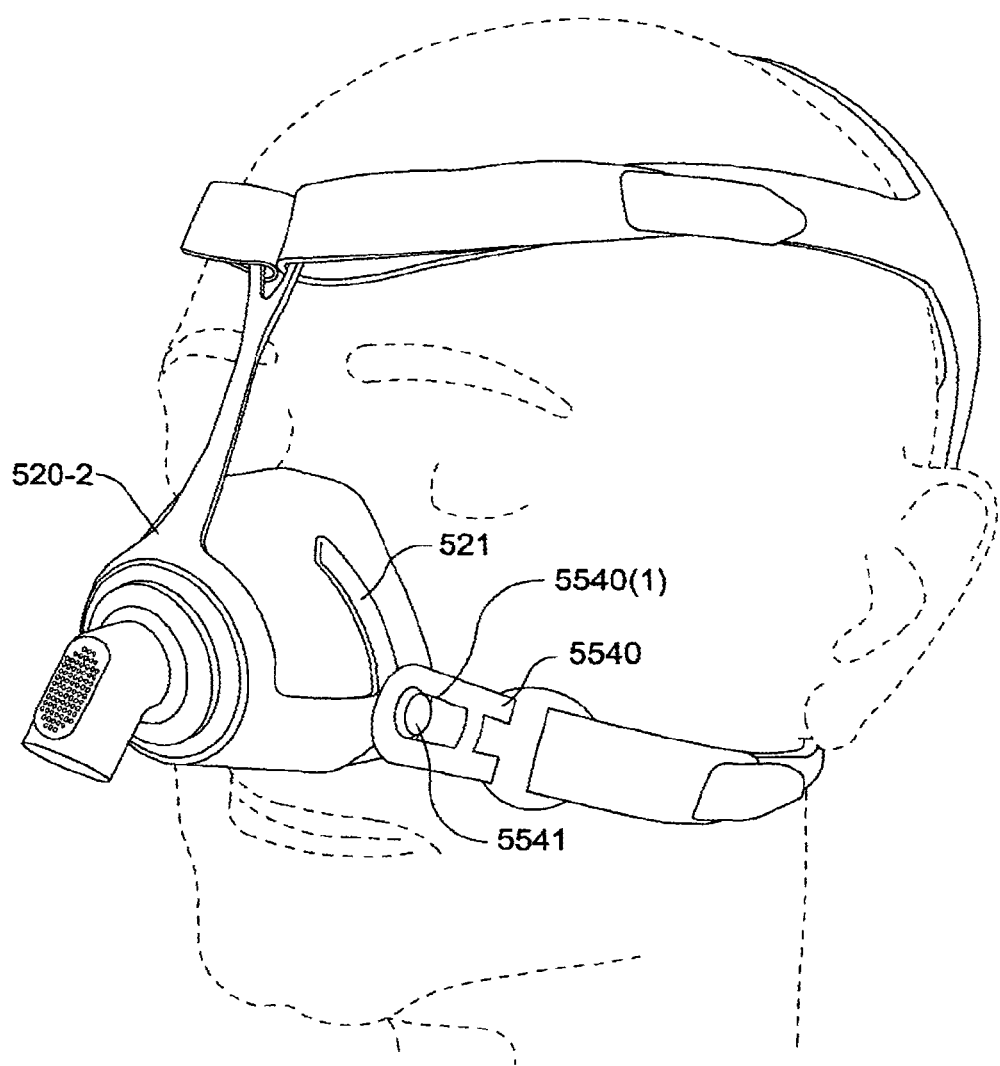
Figures 2, 17:
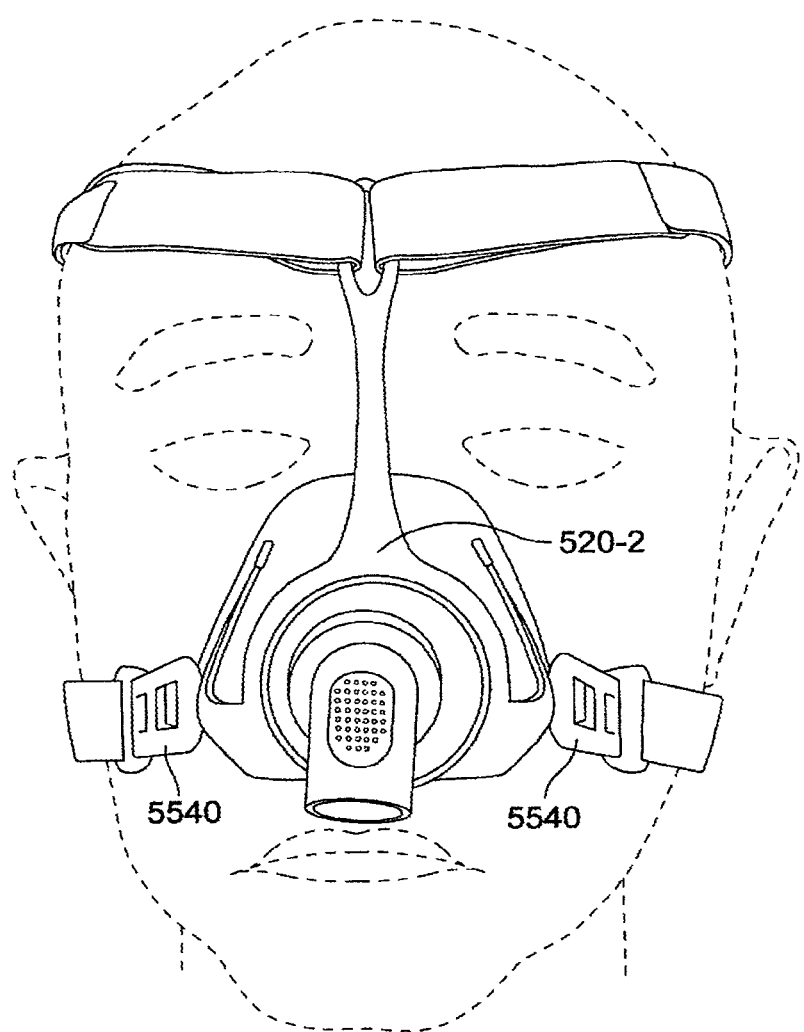
Figures 1, 18:
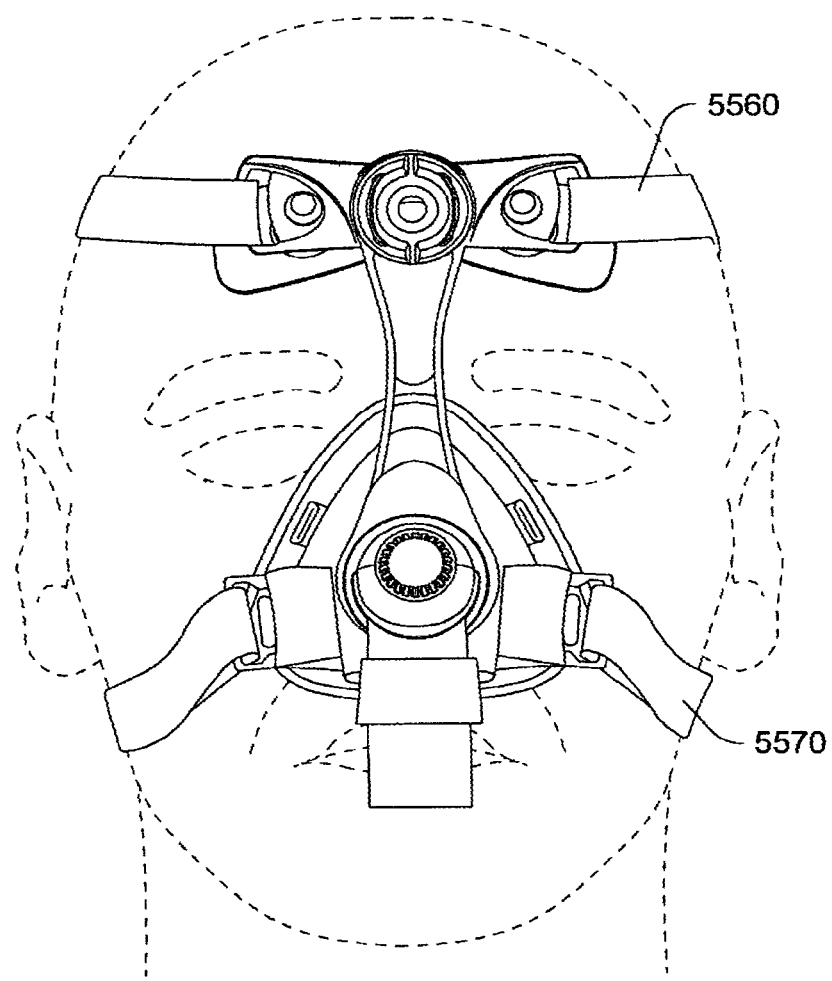
Figures 2, 18:
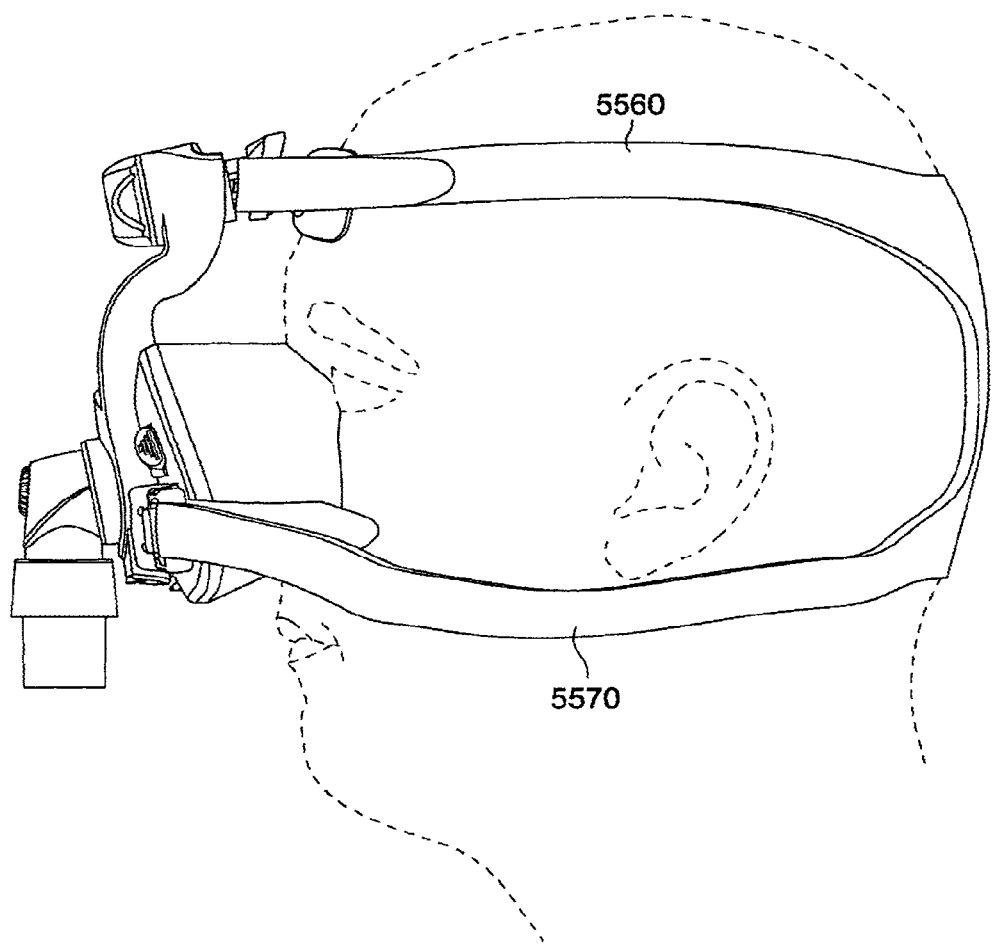
Figures 1, 19:
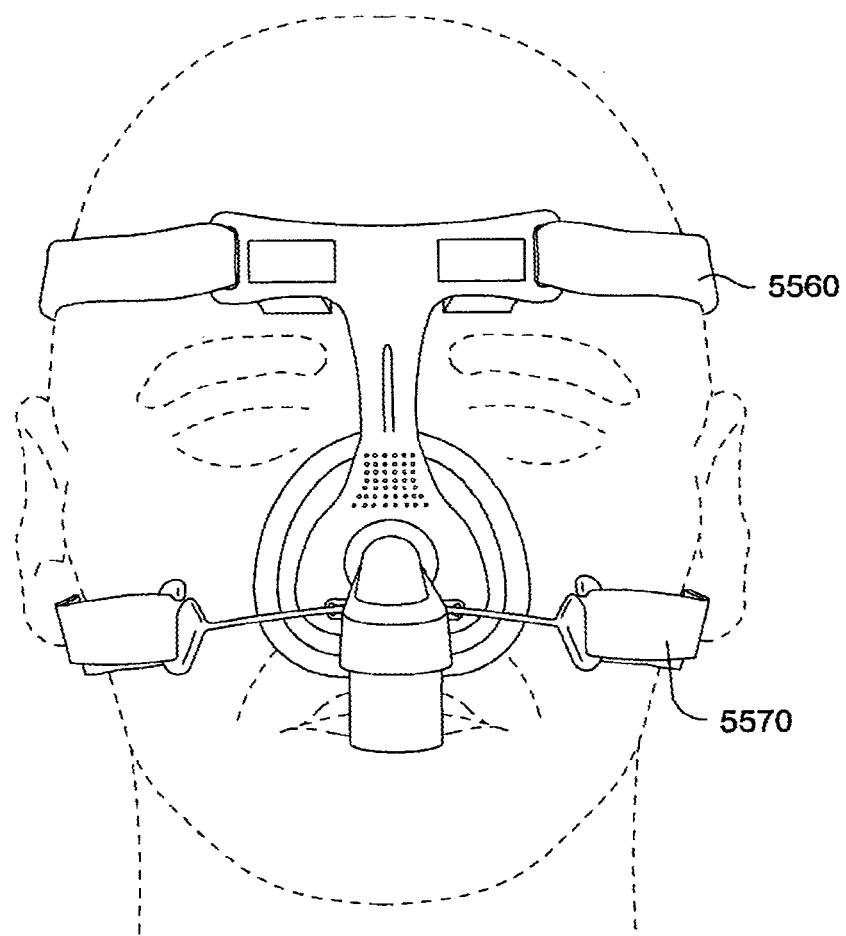
Figures 2, 19:
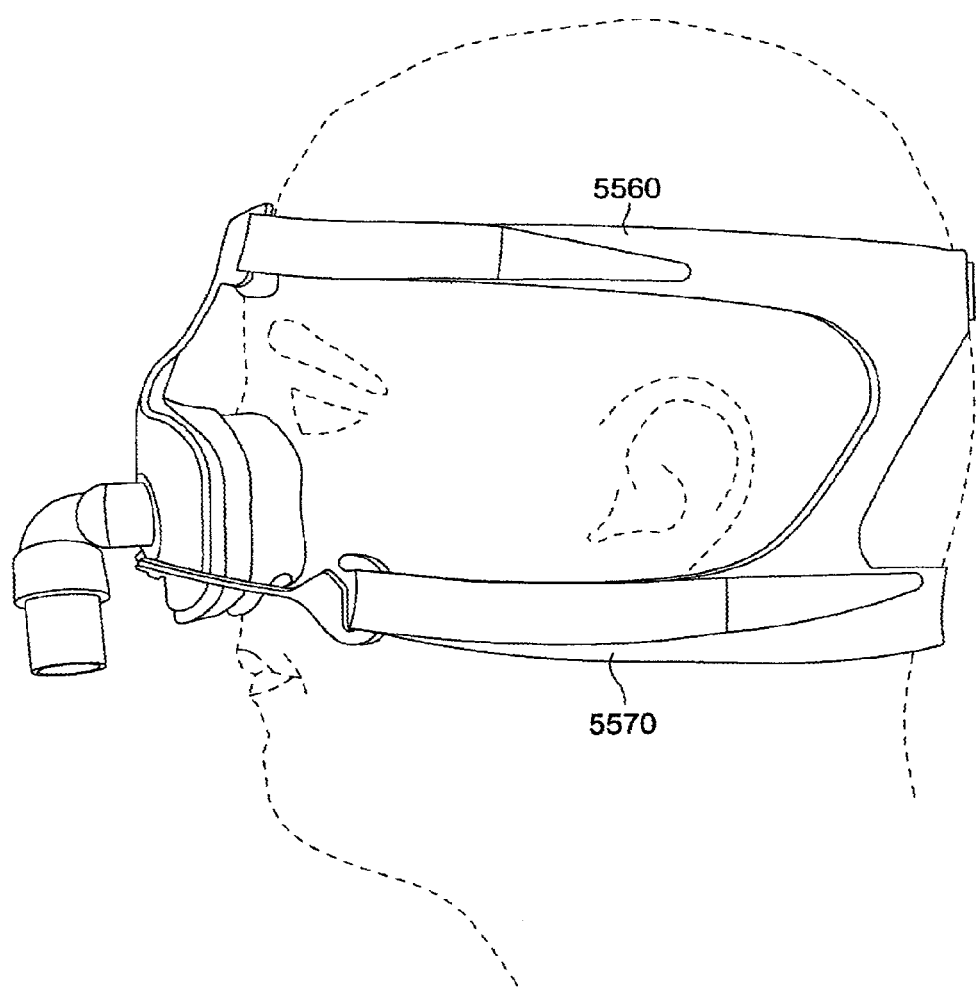

In an embodiment, as shown in FIGS. 7-1 to 7-3, the metal arm 532 may be an encapsulated extrusion. As shown in FIGS. 9-1(a) and 9-1(b), the metal m of the arm 532 may be wider at the front so the plastic encapsulation p does not overshadow the metal. Such encapsulated arrangement provides a soft tactile feature to soften and protect the metal.

In another embodiment, as shown in FIGS. 9-2, 9-3(a), and 9-3(b), the metal arm 532 may be an exposed extrusion (e.g., polished extruded aluminum). This arrangement highlights the metal feature and provides a streamlined, unobtrusive design.

FIG. 9-4 illustrates an arm 532 constructed of glass filled Nylon encapsulated in a polymer coating (such as silicone, TPE). The encapsulated metal design may be substituted with a reinforced plastic to provide strength in place of the metal and facilitate a thin unobtrusive arm. This arrangement also provides the opportunity to add color and finish details.

2.2.3 Forehead Support

Figures 1, 2, 3, 4, 5, 6, 7, 8, 9, 10:
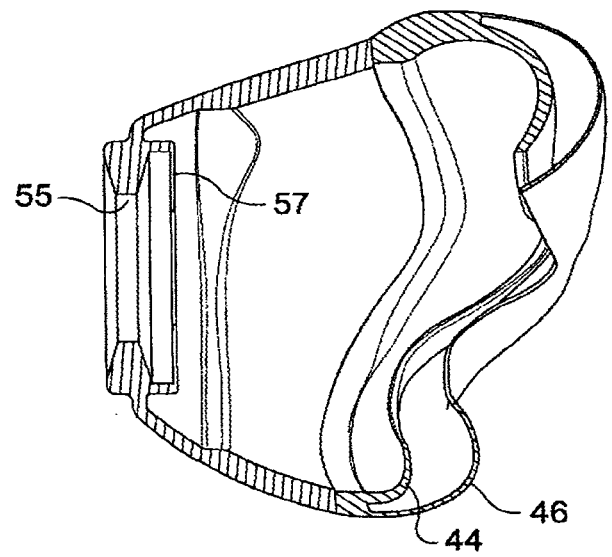

The forehead support is supported by the arm 532. As shown in FIGS. 10-1 to 10-5, the forehead support 530 may have flexible region 531 built into the forehead support to allow it to spring from its natural v-shaped position or shape to a more linear position or shape. The flexible region may be a thinned portion of material (i.e., same material as rest of forehead support, just thinner to allow flex), a softer, less stiff material or a combination of a softer material and a thinner section when compared to the remaining portions of the forehead support 530.

The flexible region may be a co-molded portion of flexible material, such as thermoplastic elastomer (may also be colored), silicone, or any other material that may flex. The remainder of the forehead support may be made from a less flexible material such as nylon, polycarbonate or polypropylene. Co-molding may be via a chemical and/or mechanical bond between the two materials. The separately formed/assembled flexible region reduces breakage risk and enables assembly offsite with the headgear. The forehead support may include a frosted finish.

In an embodiment, the forehead support 530 may first be molded flat. Then, the flexible region 531 may be molded over the forehead support 530, with the forehead support 530 positioned in its in use or flexed configuration. This may preload or provide a bias or spring to the forehead support.

The flexible region provides an auto-adjust flex feature that is adjusted with headgear tension enabling greater biasing of the cushion to assist fit. Preferably, the forehead support may flex so as to tilt or rotate the upper portion of the mask cushion inwards and outwards of the patient's nasal bridge region. In one form, when the headgear straps are tightened, the forehead support may splay outwards or flatten against the patient's forehead. This will tilt or rotate the mask cushion, with the lower portion of the mask cushion acting as a hinge point. The upper portion of the mask cushion may hence tilt or rotate inwards, in a direction generally normal to the plane of the patient's face, towards the patient's nose bridge. This may be useful to patients who have a higher nose bridge than other patients as this will urge the nasal bridge region of the mask cushion into sealing engagement with their nose.

Alternatively, the forehead support may be made from a thickened, compliant material, such as foam, that can be compressed thereby achieving a similar result.

As shown in FIG. 10-2, the position of the forehead support without any loading (i.e., natural state), may be demonstrated as angle α, e.g., angle α may be 5-90°, e.g., 15°.

In use, the forehead support may allow about 0-30 mm of adjustment in the anterior-posterior direction (as indicated by the arrow in FIGS. 10-2 and 10-4). In an exemplary embodiment, the forehead support may allow about 5-20 mm (e.g., about 10-20 mm, about 10-15 mm) of adjustment in the anterior-posterior direction. This may allow for a greater fit range of patients as it may accommodate a greater variety of anthropometrics, particularly at the nasal bridge region.

Headgear may attach to the forehead support through loop holes 535 (e.g., see FIGS. 10-1 and 10-3) or may attach through a loop through arrangement in which a slot 535-1 extends into the hole 535 (see FIG. 10-6).

2.3 Alternative Embodiments of the Forehead Support

Figures 3, 4, 5, 6, 7, 8, 9, 10, 11, 12, 13, 14, 15, 16, 17, 18, 19, 20, 20A:
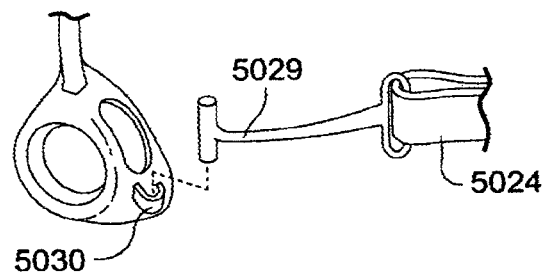
Figures 3, 4, 5, 6, 7, 8, 9, 10, 11, 12, 13, 14, 15, 16, 17, 18, 19, 20, 20B:
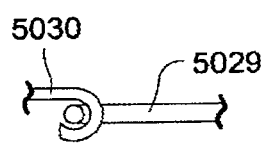
Figures 3, 4, 5, 6, 7, 8, 9, 10, 11, 12, 13, 14, 15, 16, 17, 18, 19, 20, 21:
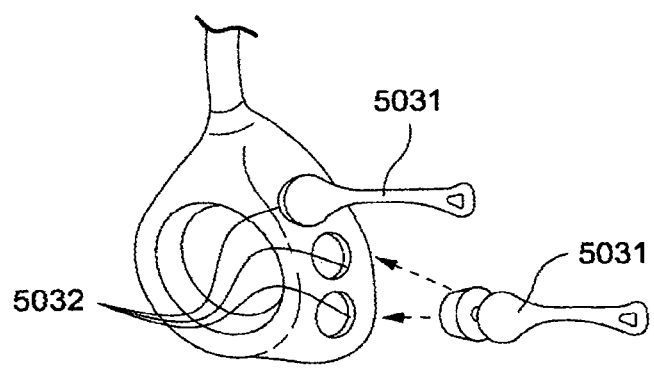
Figures 3, 4, 5, 6, 7, 8, 9, 10, 11, 12, 13, 14, 15, 16, 17, 18, 19, 20, 21, 22:
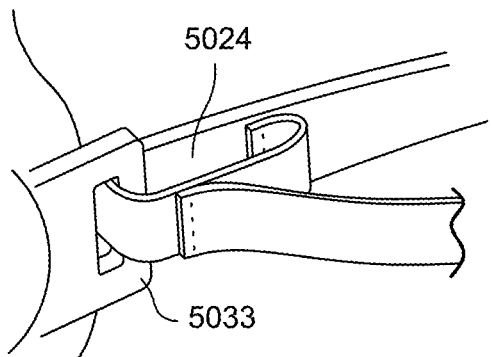
Figures 3, 4, 5, 6, 7, 8, 9, 10, 11, 12, 13, 14, 15, 16, 17, 18, 19, 20, 21, 22, 23:
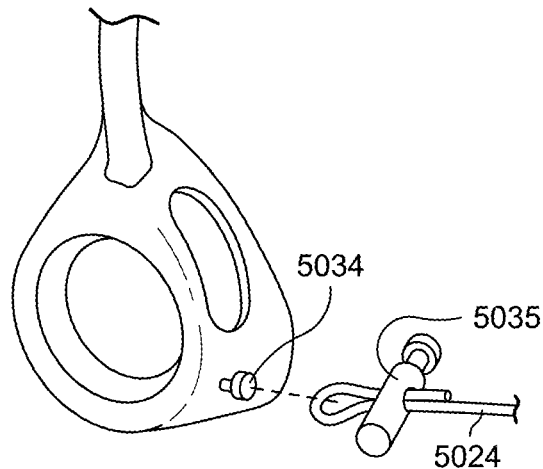
Figures 3, 4, 5, 6, 7, 8, 9, 10, 11, 12, 13, 14, 15, 16, 17, 18, 19, 20, 21, 22, 23, 24:
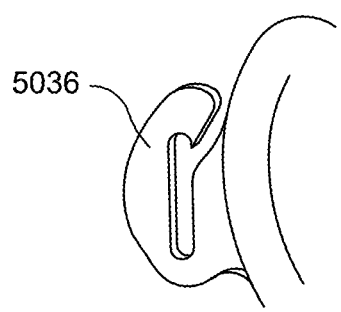
Figures 3, 4, 5, 6, 7, 8, 9, 10, 11, 12, 13, 14, 15, 16, 17, 18, 19, 20, 21, 22, 23, 24, 25, 26, 27, 28:
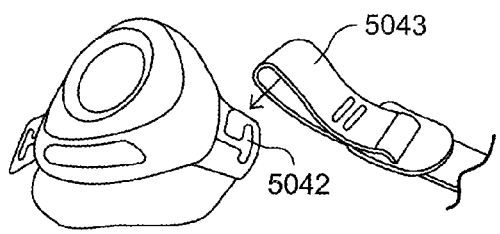
Figures 3, 4, 5, 6, 7, 8, 9, 10, 11, 12, 13, 14, 15, 16, 17, 18, 19, 20, 21, 22, 23, 24, 25, 26, 27, 28, 29:
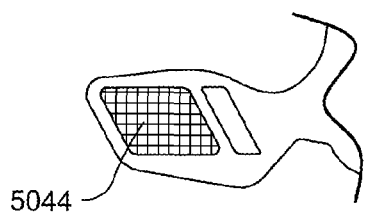
Figures 3, 4, 5, 6, 7, 8, 9, 10, 11, 12, 13, 14, 15, 16, 17, 18, 19, 20, 21, 22, 23, 24, 25, 26, 27, 28, 29, 30:
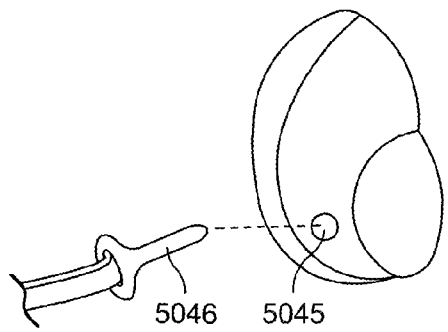
Figures 3, 4, 5, 6, 7, 8, 9, 10, 11, 12, 13, 14, 15, 16, 17, 18, 19, 20, 21, 22, 23, 24, 25, 26, 27, 28, 29, 30, 31, 31A:
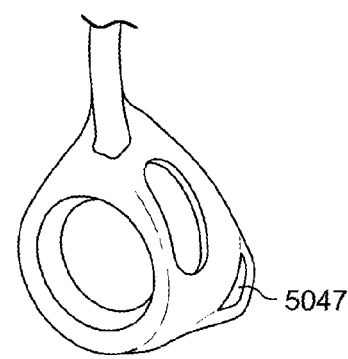
Figures 3, 4, 5, 6, 7, 8, 9, 10, 11, 12, 13, 14, 15, 16, 17, 18, 19, 20, 21, 22, 23, 24, 25, 26, 27, 28, 29, 30, 31, 31B:
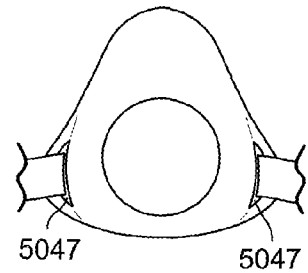
Figures 3, 4, 5, 6, 7, 8, 9, 10, 11, 12, 13, 14, 15, 16, 17, 18, 19, 20, 21, 22, 23, 24, 25, 26, 27, 28, 29, 30, 31, 32:
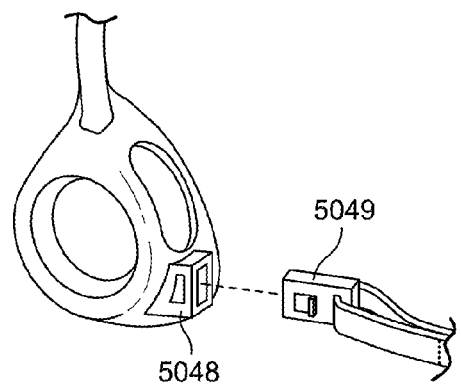
Figures 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33:
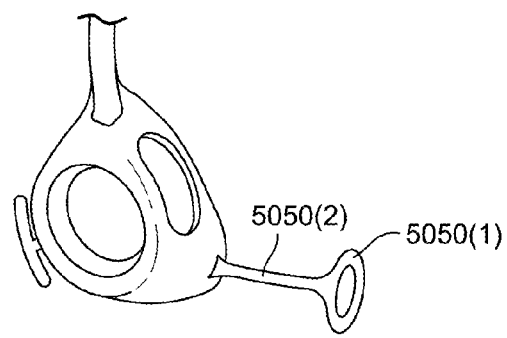
Figures 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34:
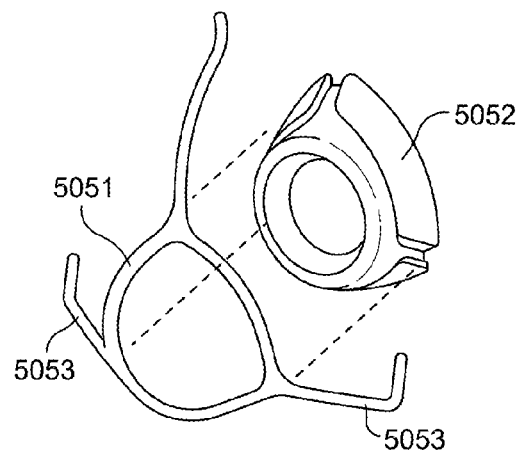
Figures 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35:
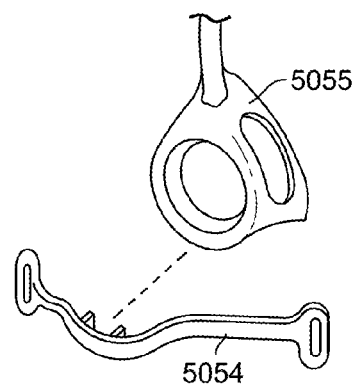
Figures 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 36A, 36B:
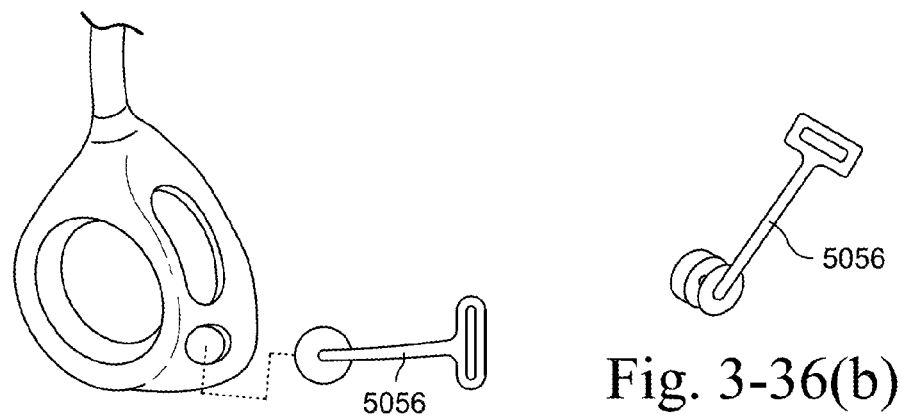
Figures 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37:
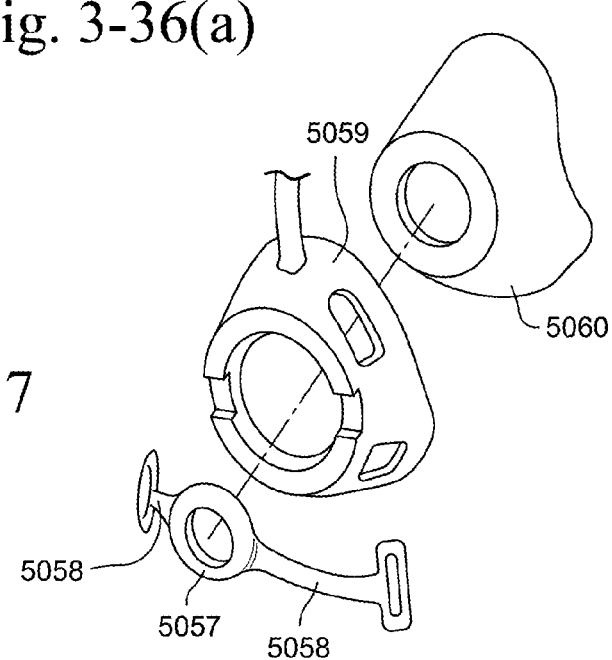
Figures 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38:
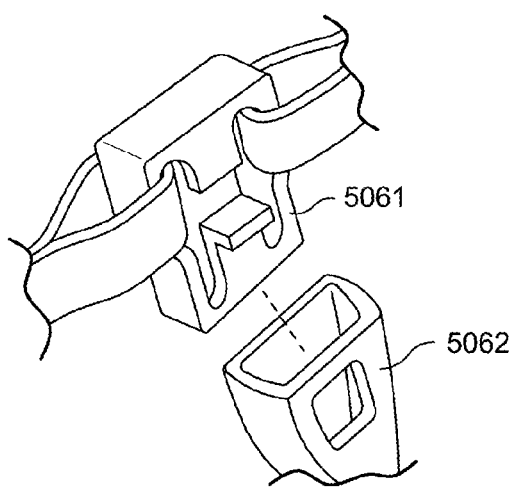
Figures 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39:
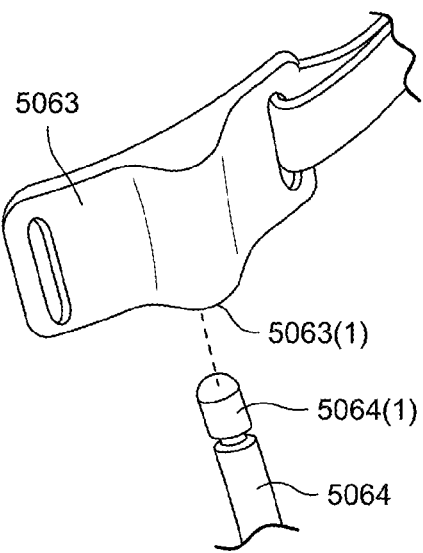
Figures 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40:
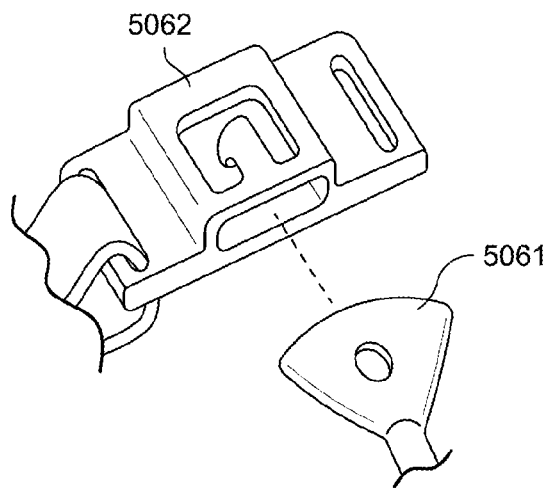
Figures 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41:
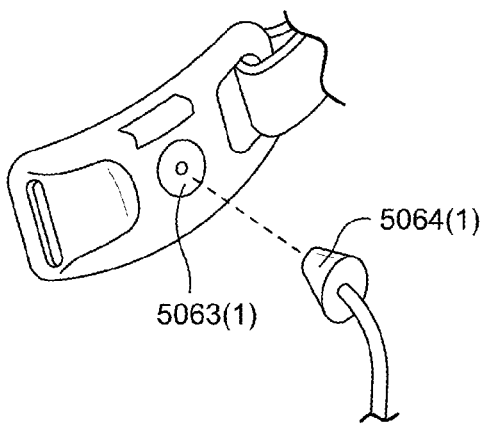
Figures 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42:
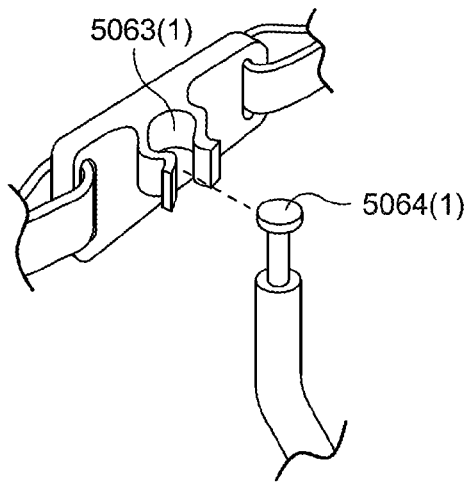

FIGS. 20-1(a) to 26 show alternative embodiments of the forehead support.

One of the advantages of the forehead support is that the forehead support provides a reasonable amount of adjustment without a lot of additional components. In a preferred example, the forehead support is all molded in one piece. Furthermore, pulling the headgear straps in the forehead region towards the back of the patient's head results in an intuitive movement of the cushion rotating it towards the nasal bridge and potentially reducing and eliminating leak in that region.

In accordance with an example of the present technology, a mask system is provided that includes a nasal cushion and a frame. The frame includes a forehead support having a T-bar. The T-bar includes a main shaft and a cross-bar. In one form, the cross-bar includes a left side and a right side.

A mask system in accordance with an aspect of the present technology includes headgear. In one form, the headgear includes a left forehead strap and a right forehead strap. The left and right forehead straps are constructed and arranged to engage with respective left and right sides of the cross-bar in use, at a location distal from the apex.

In one form, the left and right side are arranged at an angle with respect to one another that is less than about 180 degrees. In this form, the cross-bar may be V-shaped in a top view. An apex is defined between the left and right side. In one form, the left and right sides are constructed and arranged to bend or flex about the apex. In one form, bending or flexing the sides by pulling them at their distal ends causes the angle between them to increase and causes the point of contact between the cross-bar and the main shaft to move closer to the forehead and to rotate the cushion.

In an alternative form, the left and right sides of the cross-bar may be U-shaped. In this U-shape, the cross-bar may have similar functionality to the V-shaped form described above.

Figures 1A, 20:
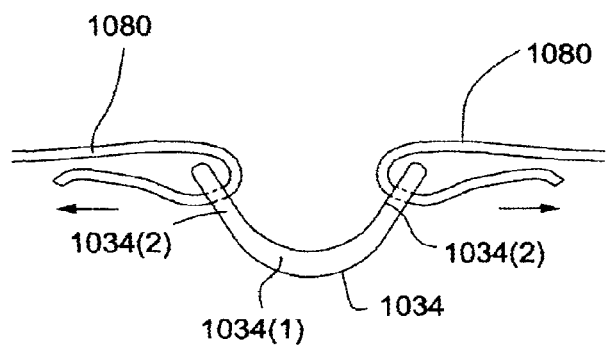
FIGS. 20-1(a), 20-1(b), and 20-1(c) are sequential top views of a bendable or flexible forehead support according to an embodiment of the invention.
Figures 1B, 20:
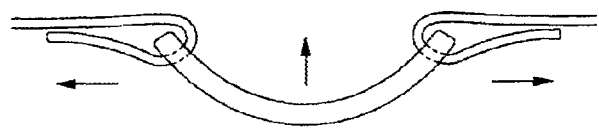
Figures 1C, 20:
Figures 2A, 20:
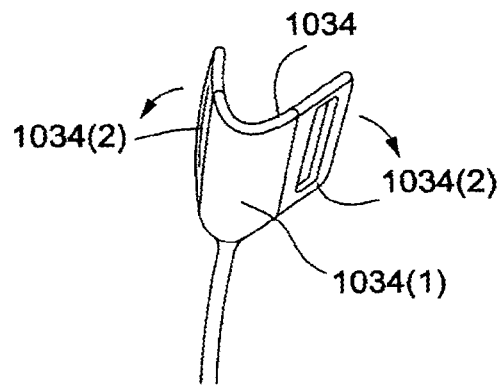
Figures 2B, 20:
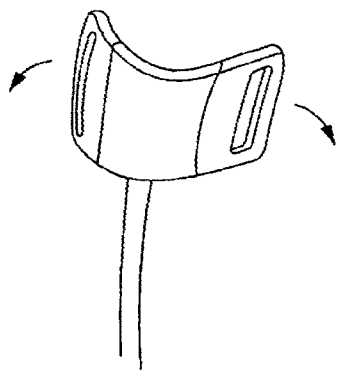
Figures 2C, 20:
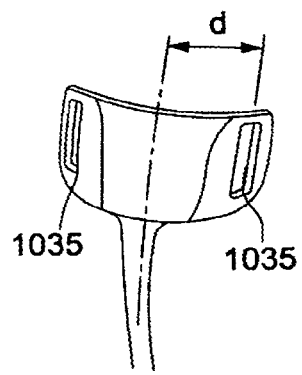
Figure 21A:
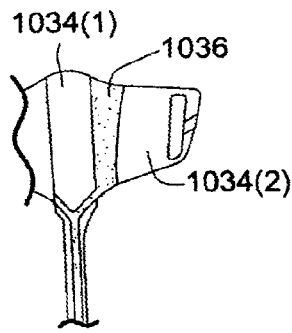
FIGS. 21(a), 21(b), 21(c), 21(d), 21(e), 21(f), and 21(g) are various views of a forehead support including flexible regions according to an embodiment of the invention.
Figure 21B:
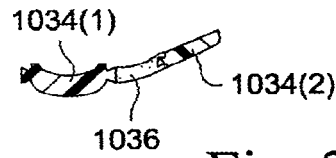
Figure 21C:
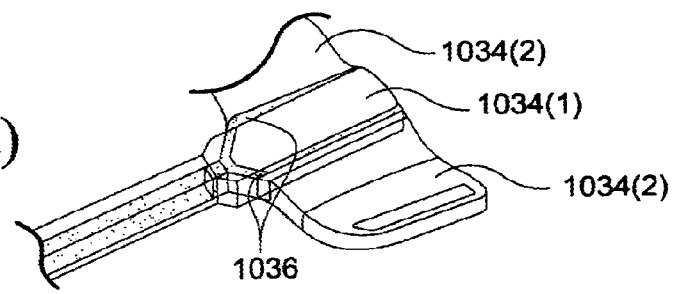
Figure 21D:
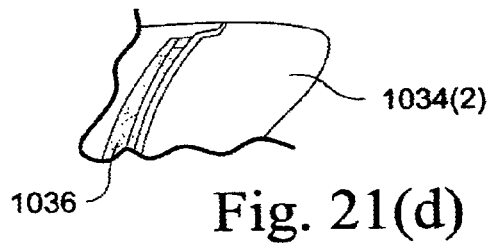
Figure 21E:
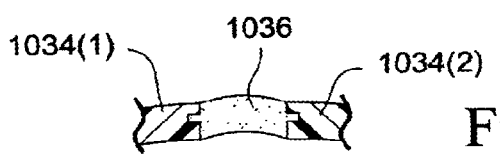
Figure 21F:
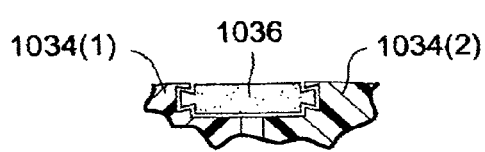
Figure 21G:
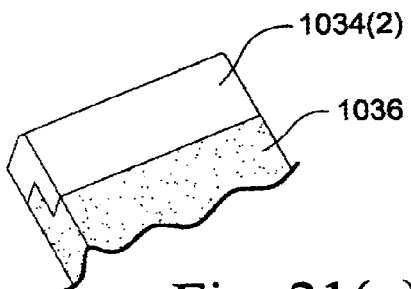
Figure 23A:
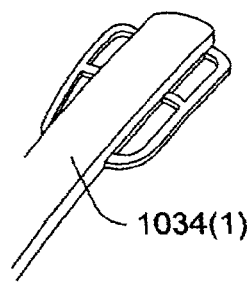
FIGS. 23(a), 23(b), 23(c), 23(d), and 23(e) are various views of a forehead support including flexible regions according to an embodiment of the invention.
Figure 23B:
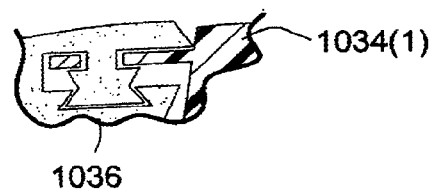
Figure 23C:
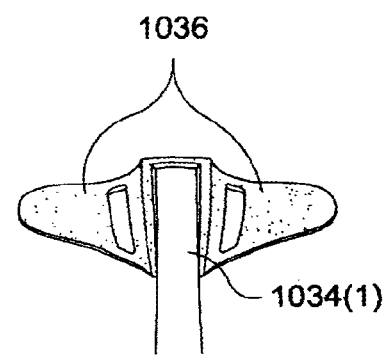
Figure 23D:
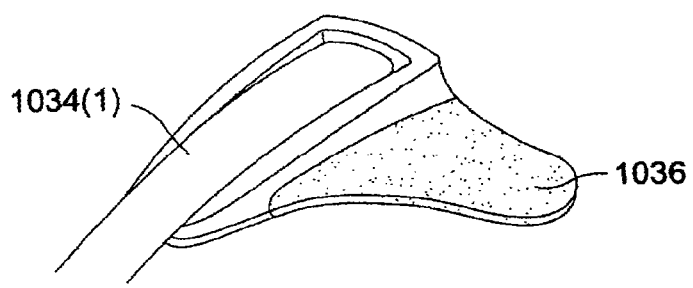
Figure 23E:
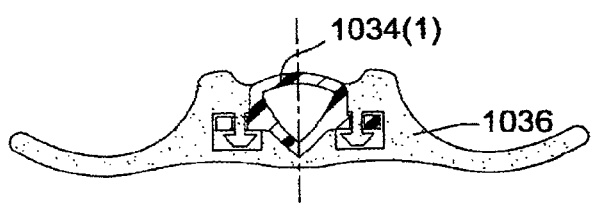

For example, FIGS. 20-1(a) to 20-1(c) and 20-2(a) to 20-2(c) each show sequential views of a generally U-shaped cross-bar 1034 structured to bend or flex about the apex as headgear tension from headgear straps 1080 is applied to respective sides of the cross-bar. As illustrated, the forehead support starts at an extended position forward of the patient's forehead. As the patient tightens the headgear (i.e., headgear straps pulled outwardly from the cross-bar as indicated by the arrows), the sides of the cross-bar splay open or flex outwardly and the cross-bar moves into a substantially flat position on the patient's forehead, which enables the cushion to be biased inwards towards the patient's face. The slots 1035 in the cross-bar for respective headgear straps may be positioned relatively far outward from the apex (e.g., by a distance d as shown in FIG. 20-2(c)) to improve vectors (e.g., less force required to pull forehead support toward the patient's head with effective force).

Bending or flexing may be achieved by molding a cross-bar from a material that has a thinner middle section. In this way, the cross-bar may be more flexible in the middle section than in ends thereof. Additionally or alternatively, a cross-bar may be formed by co-molding a more rigid material (e.g., such as nylon) with a more flexible material (e.g., such as a thermoplastic elastomer).

For example, as shown in FIGS. 20-1(a) to 20-1(c) and 20-2(a) to 20-2(c), the cross-bar may include an intermediate portion 1034(1) constructed of a more flexible material (e.g., flexible TPE or silicone) and end portions or sides 1034(2) constructed of a more rigid material (e.g., clear Nylon).

FIGS. 21(a) to 23(e) show alternative configurations of the forehead support and cross-bar thereof. For example, FIGS. 21(a) to 21(g) show a forehead support including flexible regions 1036 positioned between more rigid regions, i.e., an intermediate portion 1034(1) and respective sides 1034(2) of the cross-bar. The flexible regions 1036 are constructed of a more flexible material (e.g., Hytrel®) and the intermediate portion 1034(1) and sides 1034(2) are constructed of a more rigid material (e.g., nylon). As illustrated, the flexible regions may be embedded in the more rigid regions. Also, the flexible regions may interlocked with the more rigid regions by a retention feature, e.g., dovetail interlock. FIGS. 22(a) to 22(h) and 23(a) to 23(e) show alternative configurations for interlocking or coupling the flexible region 1036 with more rigid regions 1034(1), 1034(2). In FIGS. 23(a) to 23(e), the flexible region incorporates the sides of the cross-bar.

The forehead support and headgear are constructed and arranged so that tensioning the left and/or right forehead straps causes the main shaft to move and rotate the cushion. In this way, the mask fit may be adjusted to different facial shapes. For example, pulling the straps may rotate the cushion towards the face, reducing leak in the nasal bridge region.

Figure 24A:
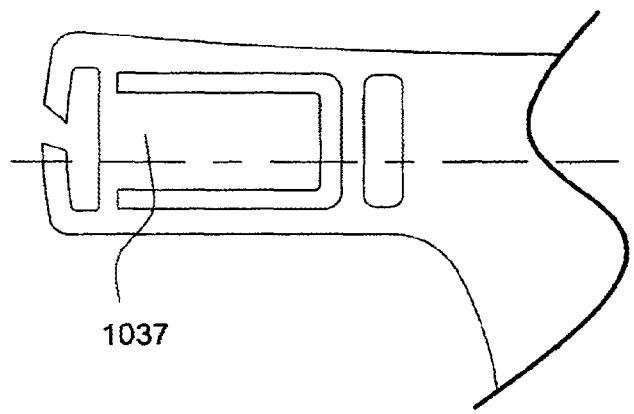
FIGS. 24(a) and 24(b) show a forehead support wherein each side of the cross-bar includes a resilient spring arm according to an embodiment of the invention.
Figure 24B:
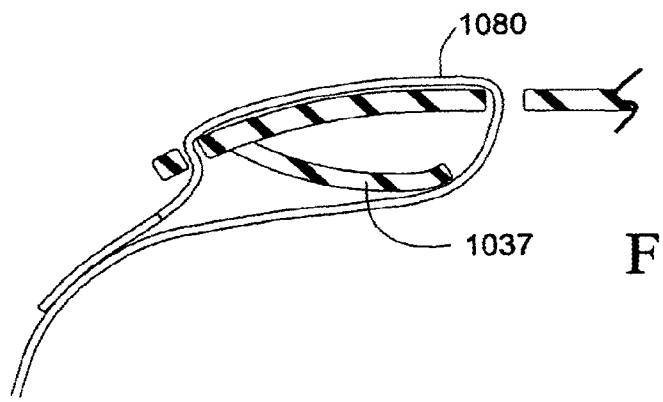
Figure 25:
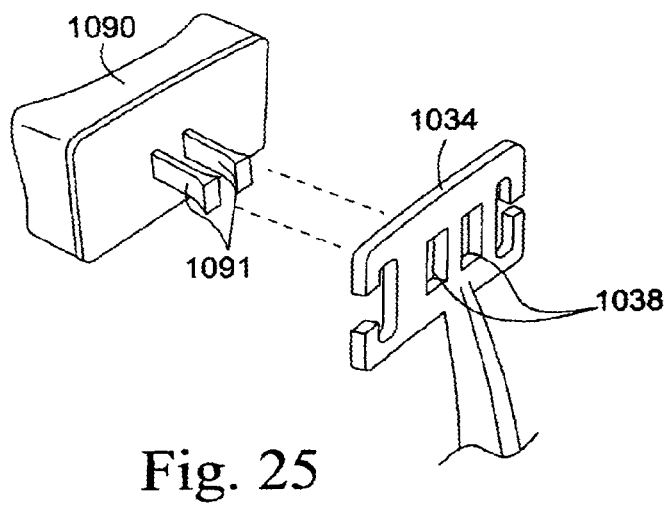
FIGS. 25 and 26 show a forehead support including a forehead pad constructed of a soft foam material according to an embodiment of the invention.
Figure 26:
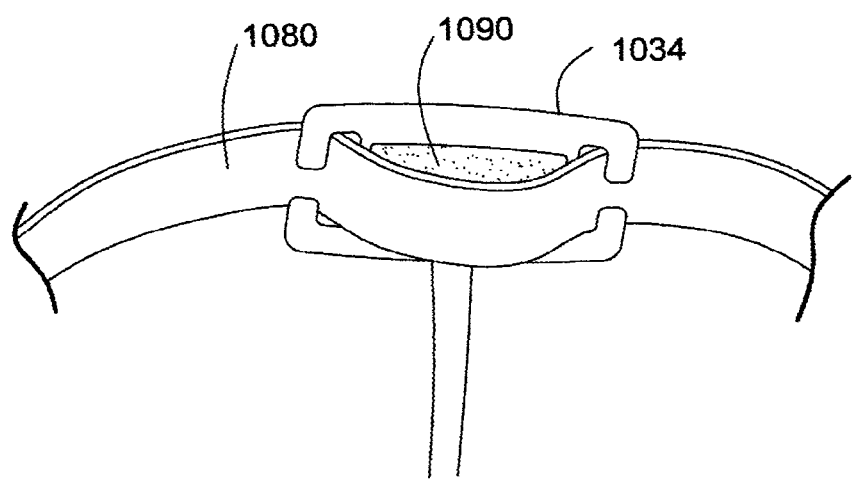
Figure 27:
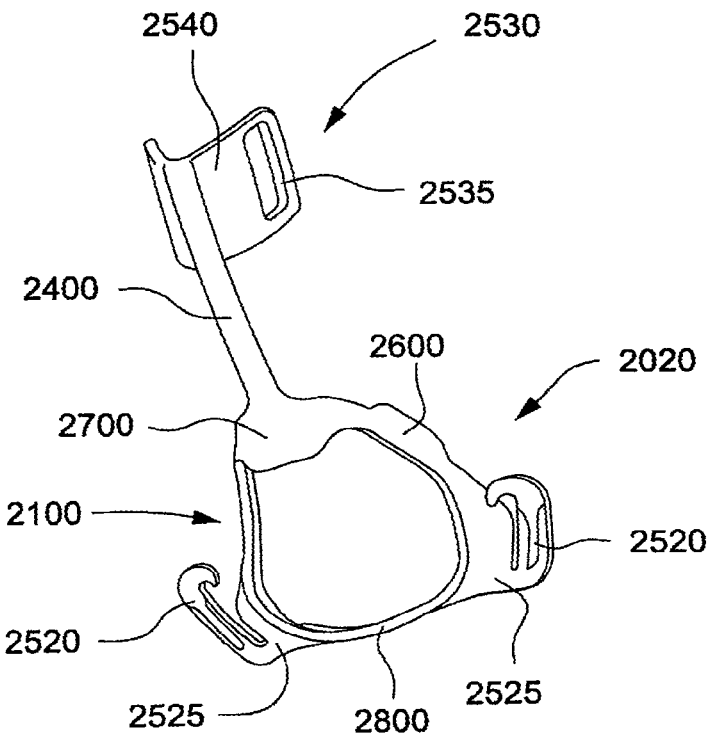
FIGS. 27 to 32 show various views of a frame for a mask system according to an embodiment of the invention.
Figure 28:
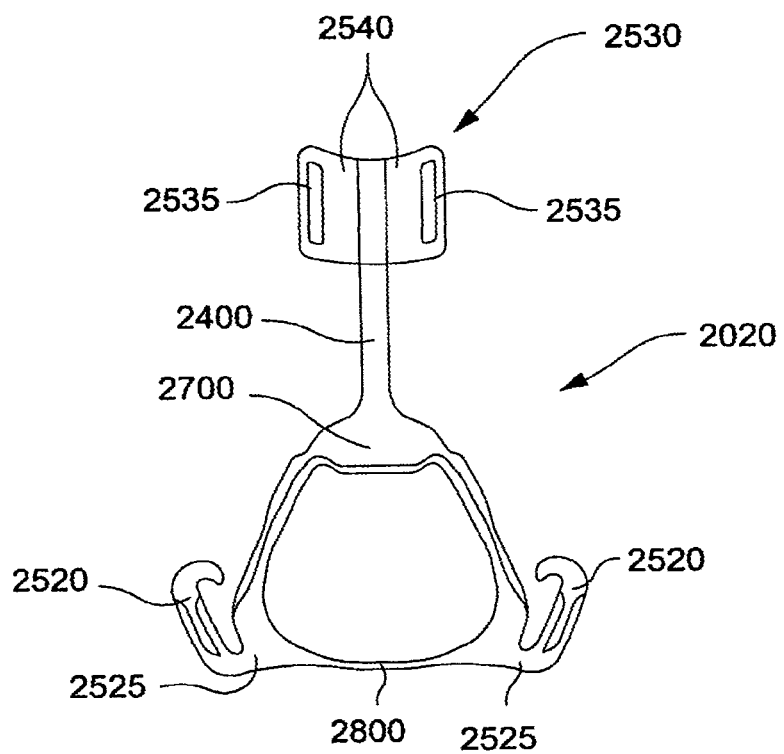
Figure 29:
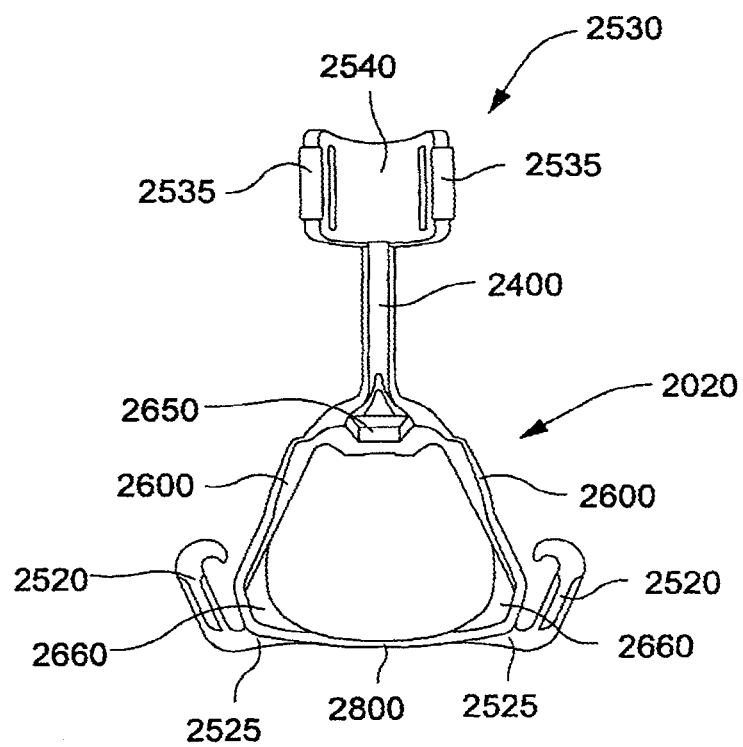
Figure 30:
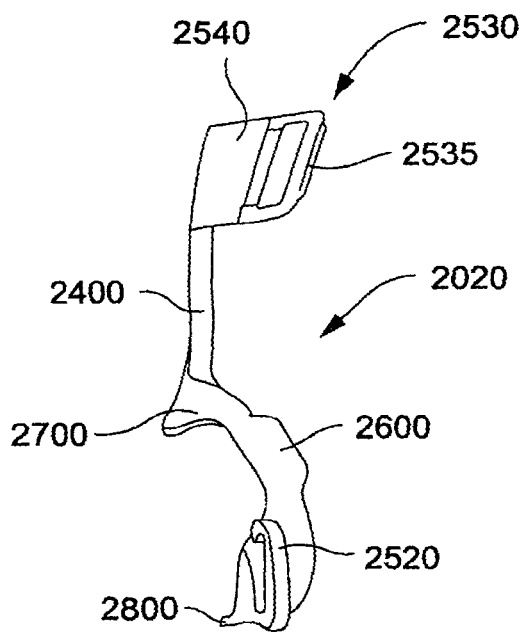
Figure 31:
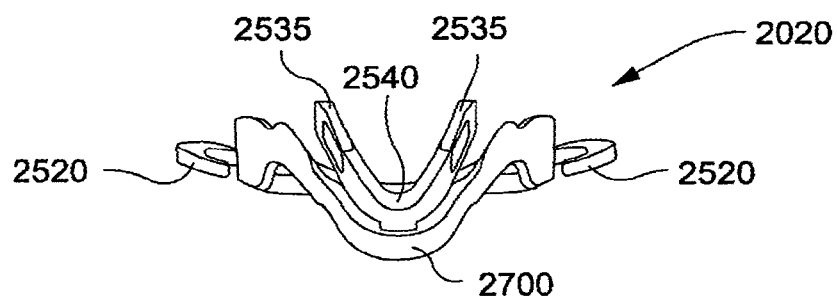
Figure 32:
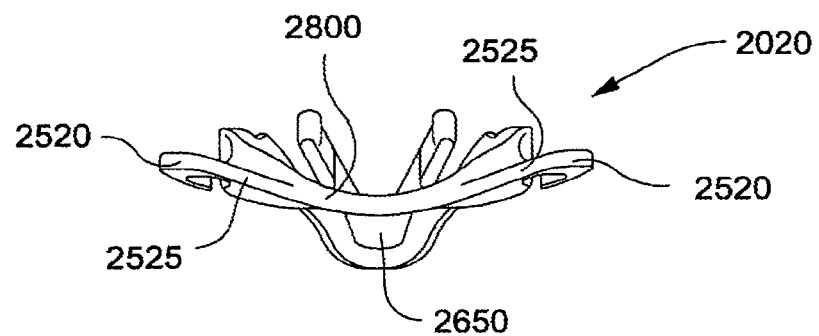
Figure 33:
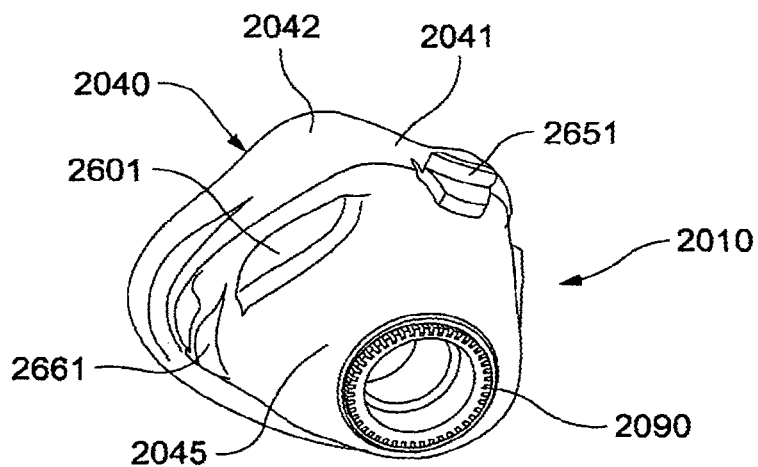
FIGS. 33 to 39 show various views of a cushion for a mask system according to an embodiment of the invention.
Figure 34:
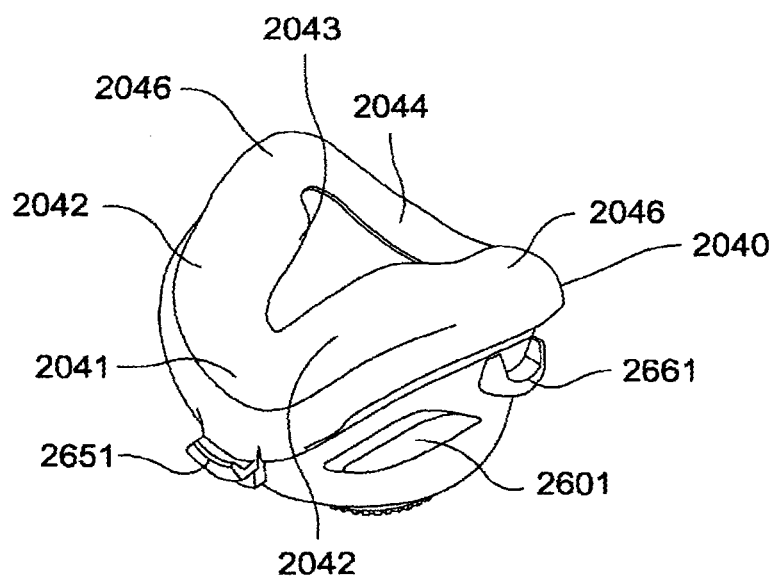
Figure 35:
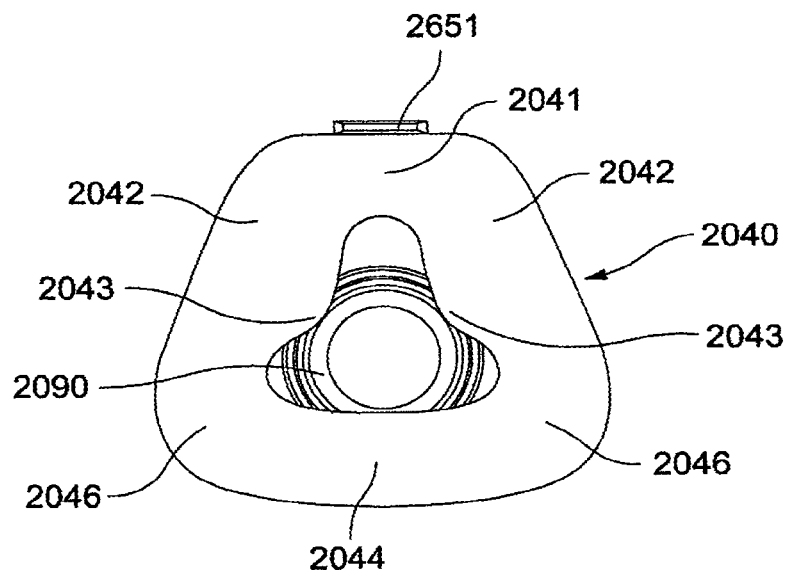
Figure 36:
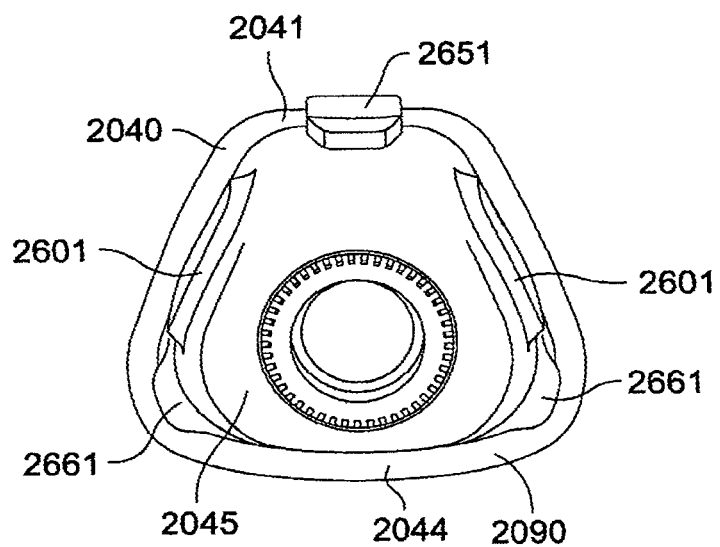
Figure 37:
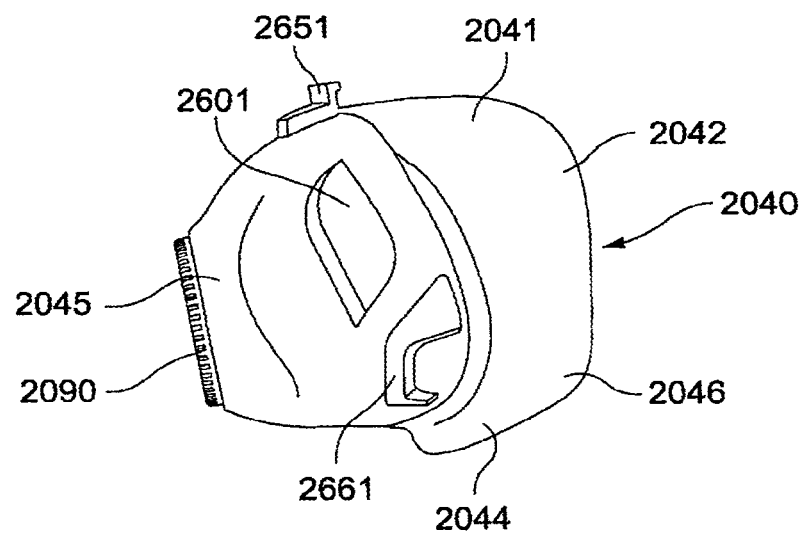
Figure 38:
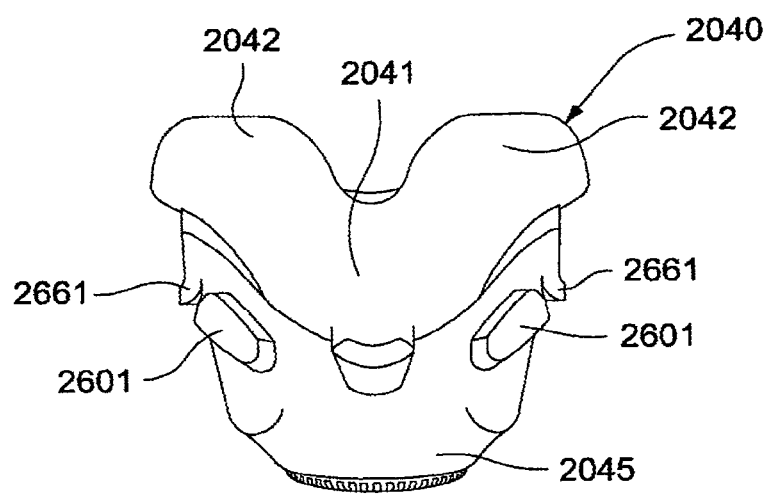
Figure 39:
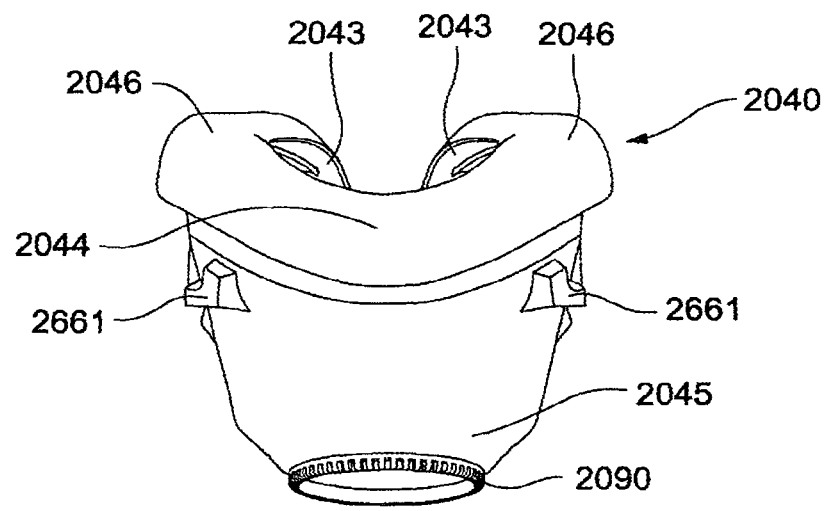
Figure 40:
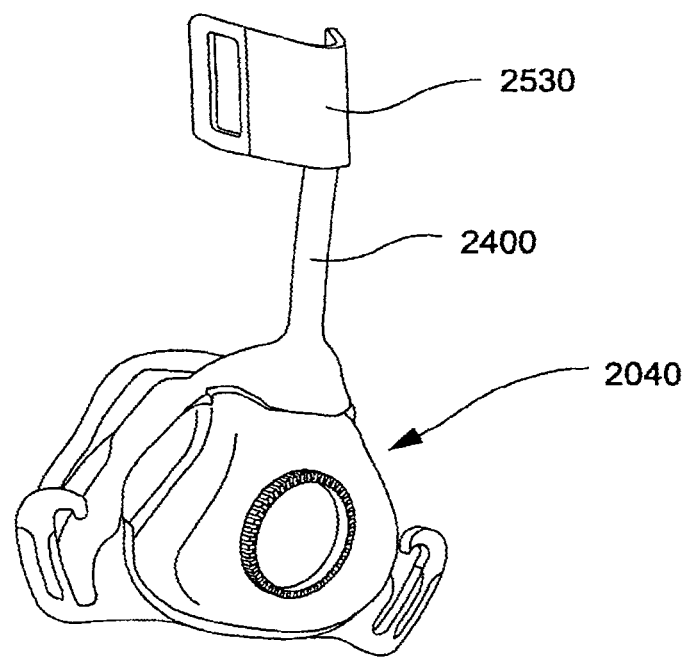
FIGS. 40 to 45 show various views of the cushion of FIGS. 33 to 39 and the frame of FIGS. 27 to 32 assembled to one another according to an embodiment of the invention.
Figure 41:
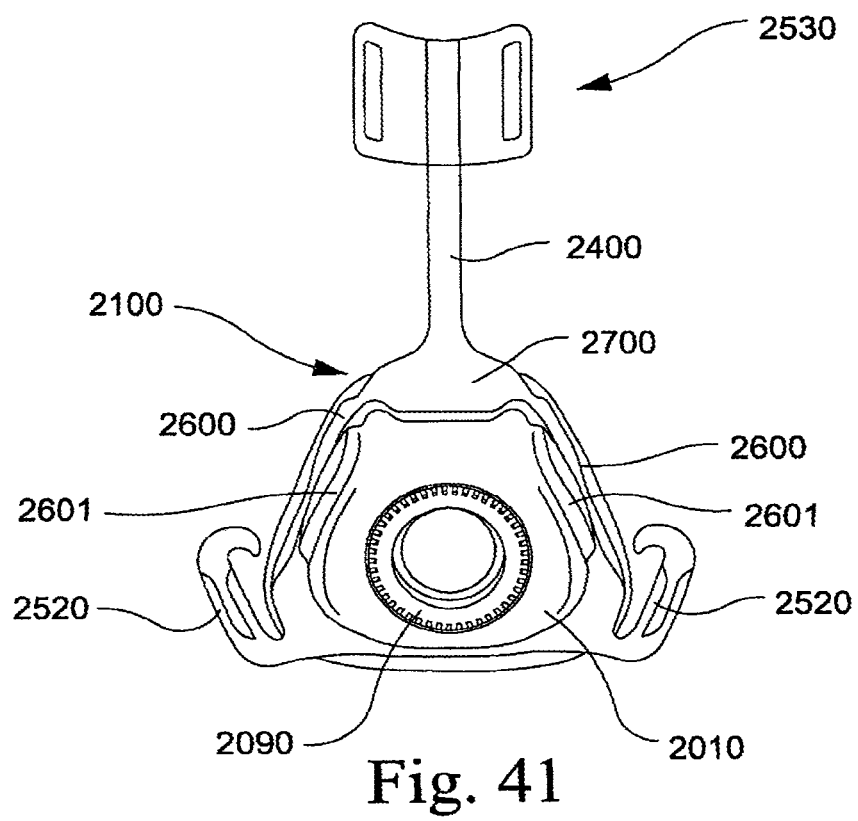
Figure 42:
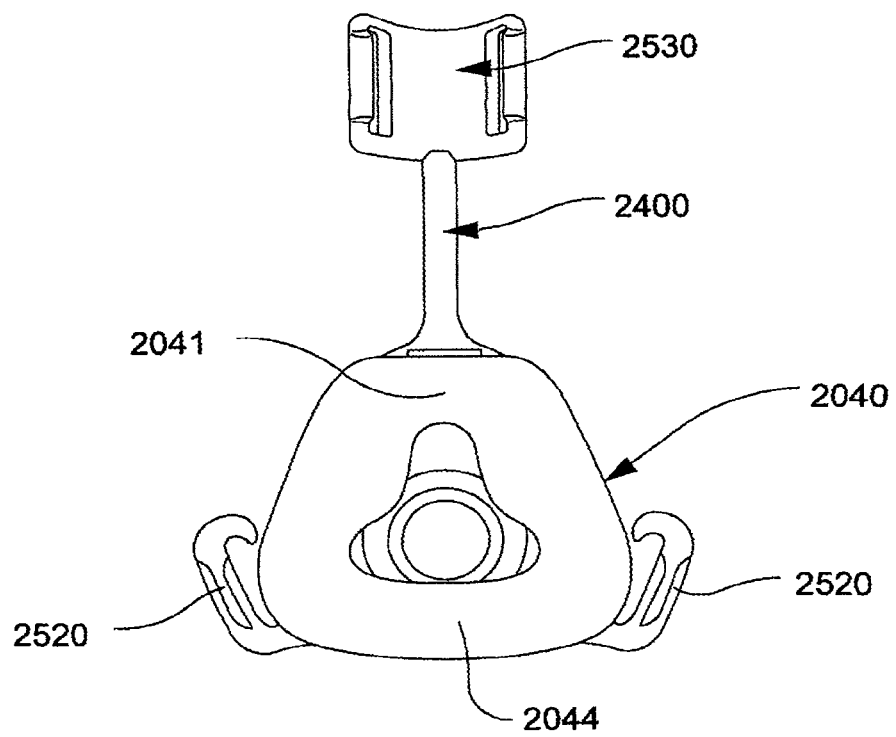
Figure 43:
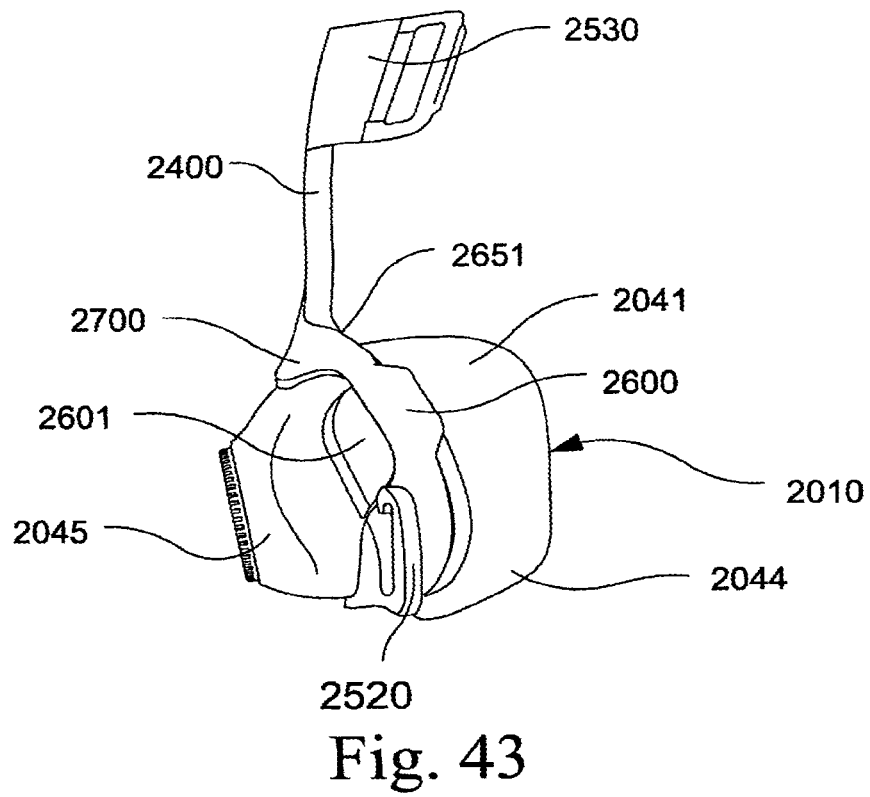
Figure 44:
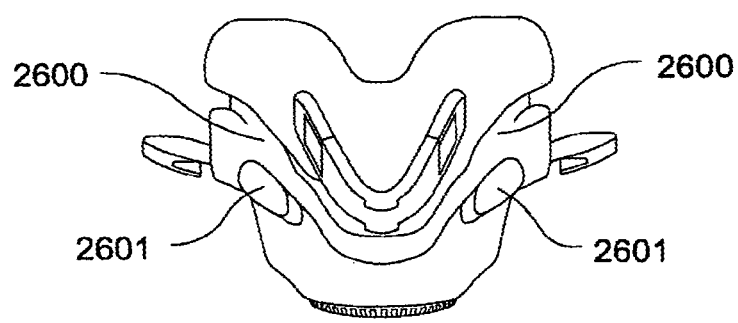
Figure 45:
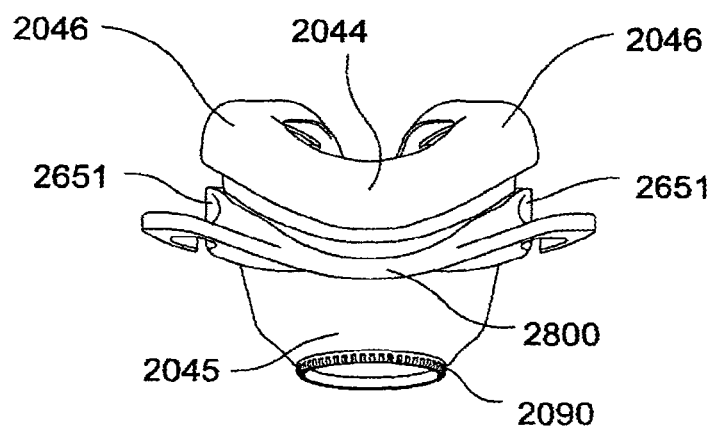
Figure 46:
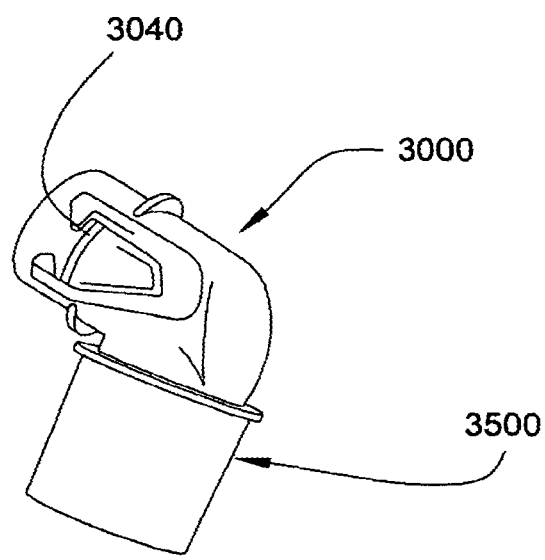
FIGS. 46 to 54 show various views of an elbow and swivel for a mask system according to an embodiment of the invention.
Figure 47:
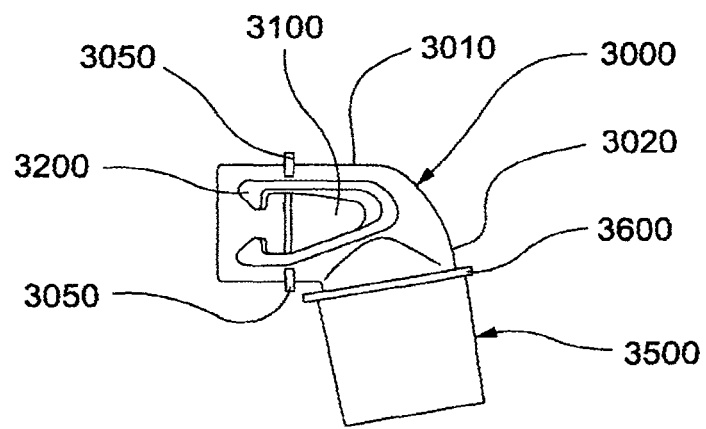
Figure 48:
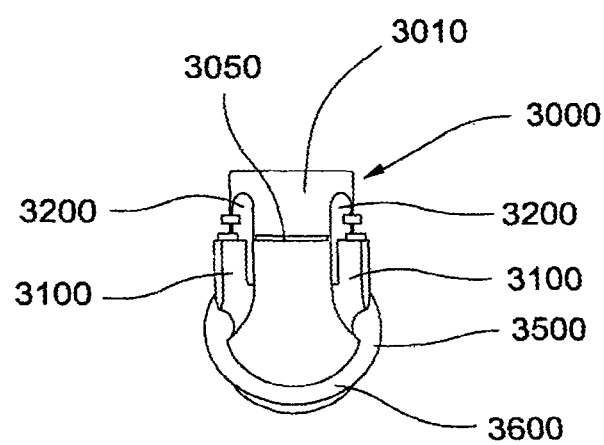
Figure 49:
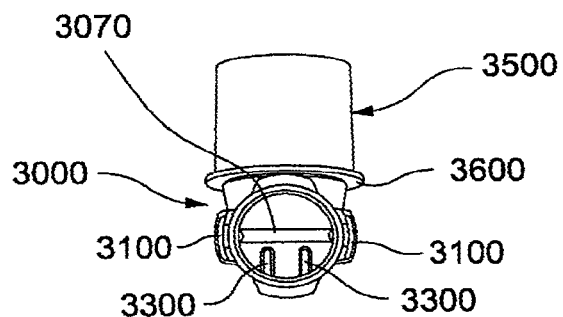
Figure 50:
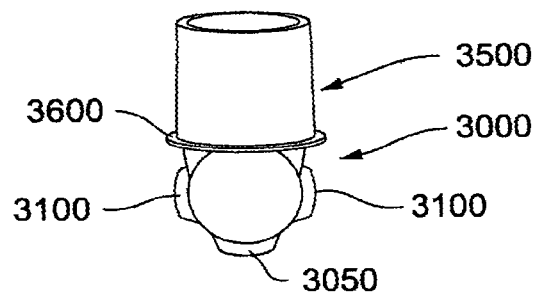
Figure 51:
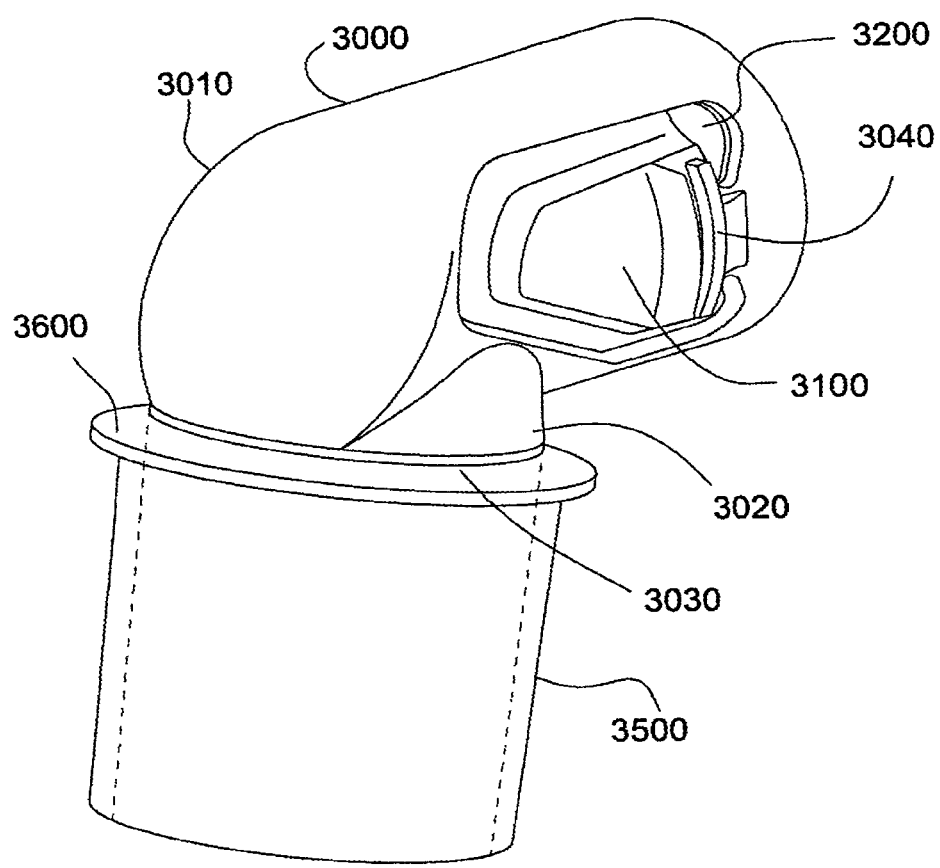
Figure 52:
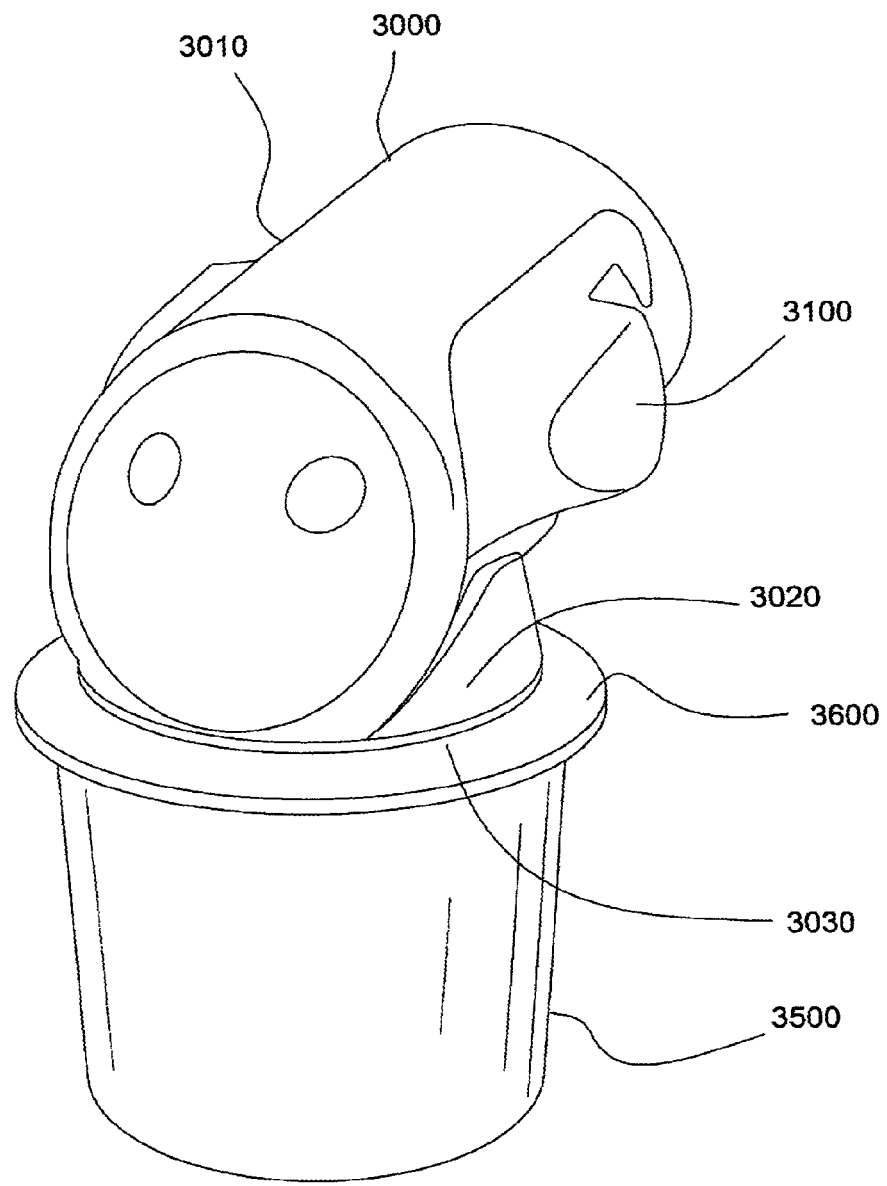
Figure 53:
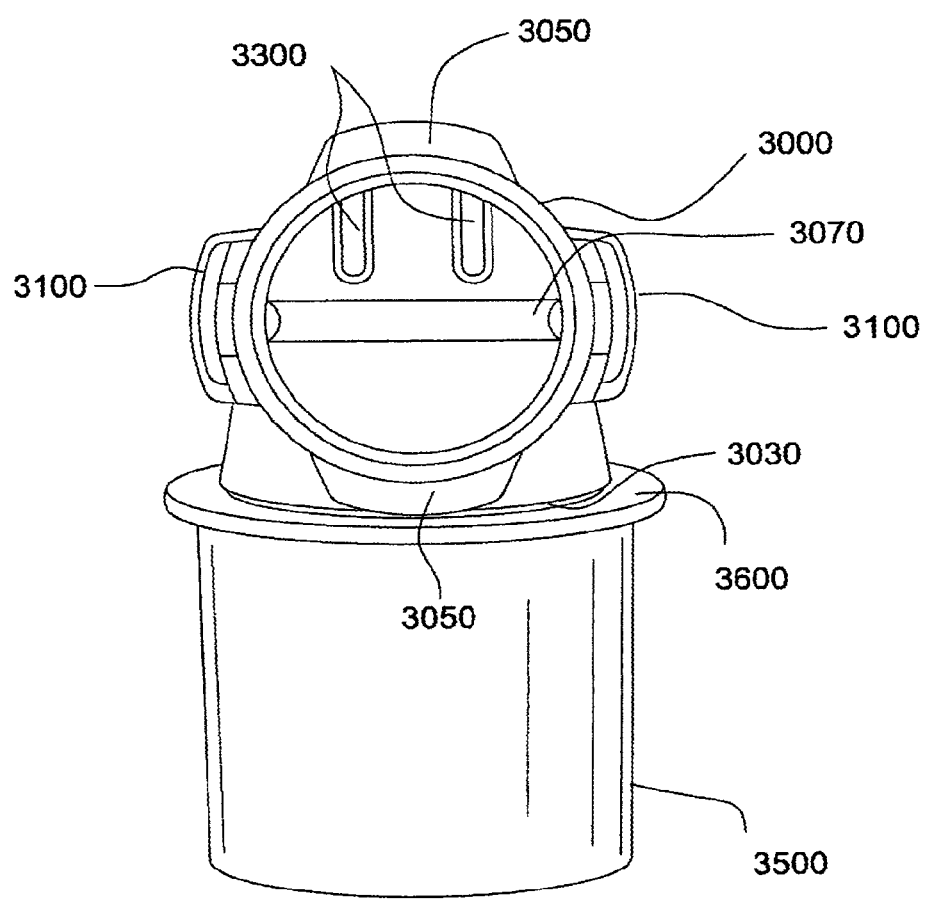
Figure 54:
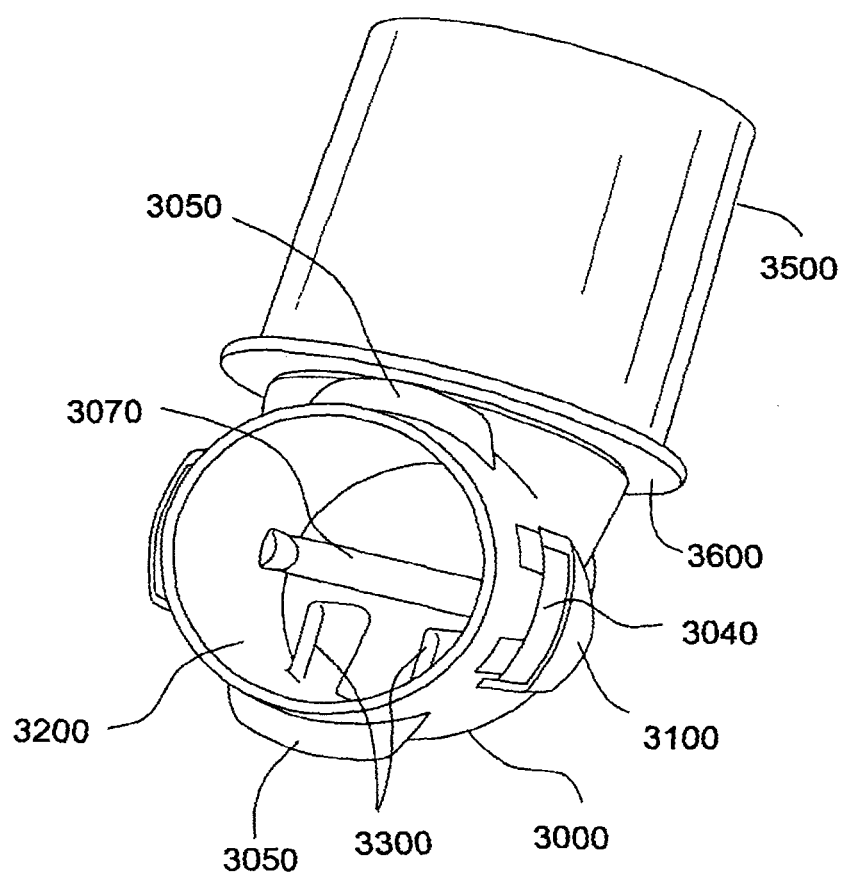
Figure 55:
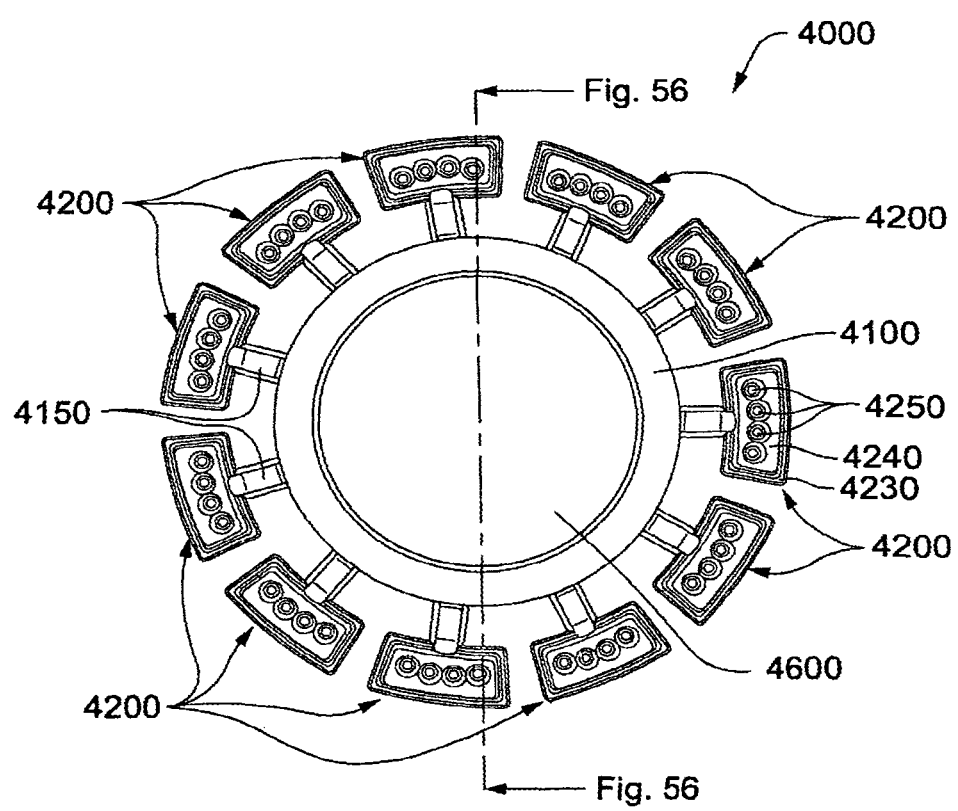
FIG. 55 shows a top view of a vent assembly according to another embodiment of the invention.
Figure 56:
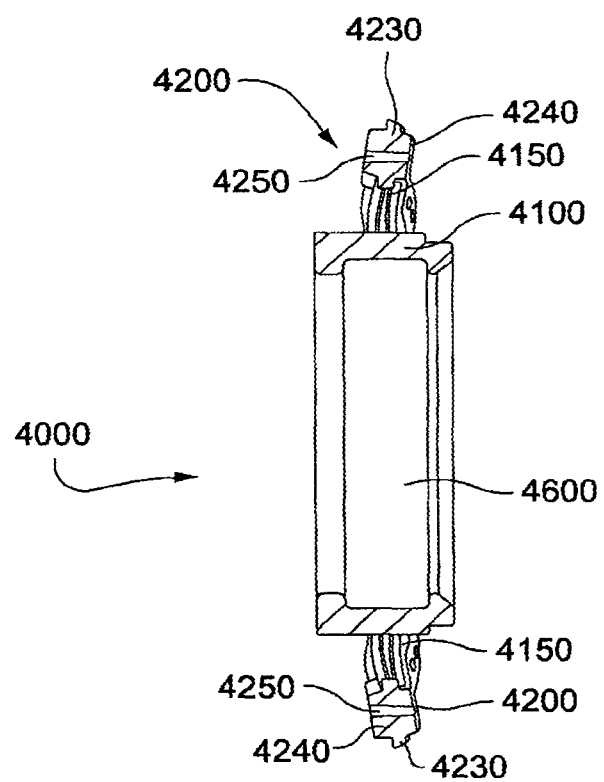
FIG. 56 is a cross-sectional view through line 56-56 of FIG. 55.

FIGS. 24(a) and 24(b) a forehead support wherein each side of the cross-bar includes a resilient spring arm 1037. As illustrated, a headgear strap 1080 is adapted to loop around the spring arm, such that the headgear strap engages the patient's forehead with the spring arm positioned between the cross-bar and the headgear strap. In use, headgear tension may bend or flex the spring arm and cause the point of contact of the forehead support to move closer to the patient's forehead.

FIGS. 25 and 26 show a forehead support including a forehead pad 1090 constructed of a compliant material such as foam or gel. As shown in FIG. 25, the forehead pad may be coupled to the cross-bar 1034 by a snap-fit, e.g., forehead pad 1090 includes snap fingers 1091 adapted to engage with respective openings 1038 in the cross-bar with a snap fit. Opposing sides of the cross-bar include open-ended slots adapted to engage a headgear strap. As shown in FIG. 26, the headgear strap 1080 may pass across the cross-bar 1034 and the forehead pad thereof 1090, such that the headgear strap engages the patient's forehead with the forehead pad positioned between the cross-bar and the headgear strap.

2.4 Further Alternative Frame Embodiment

A frame may be provided to the system to stabilise the cushion in position and anchor the headgear to hold the cushion in position. The frame may further add structure or support to the cushion.

The alternative frame 2020 shown in FIGS. 27 to 32 comprises a main body 2100, forehead support arm 2400 and forehead support pad 2530.

The main body 2100 may be structured to capture or engage the cushion and lower headgear straps. Upper region 2700 engages a top or apex region of a mask cushion. The upper region 2700 may be positioned at the superior or top portion of the main body 2100 on the non-patient side of the mask frame 2020. Upper region 2700 may also provide stability to the front or elbow engaging portion of the cushion by adding rigidity or support to this region of the cushion. Lower region 2800 may be positioned generally inferior to the upper region. The lower region 2800 may engage or otherwise interface with a bottom region of a mask cushion.

Rear connector or engagement portion 2650 (see FIGS. 29 and 32) may be structured to receive a tab or locking element on a mask cushion. Rear engagement 2650 may also assist location of the mask cushion within the mask frame 2020. Rear engagement 2650 may be a cut-out or aperture. Rear connector 2650 may be positioned on the patient side of the frame 2020.

Lower headgear connectors 2520 may be arranged to receive a loop of headgear. Lower headgear connectors 2520 may be generally hook or C shaped to receive the headgear strap and maintain it in position. Lower headgear connectors 2520 may be attached or otherwise formed with the main body 2100 by connection 2525. Connection 2525 may allow some flexibility or hinging to enable some freedom of movement of the lower headgear connections 2520.

Lower headgear connectors 2520 may be formed from a flexible material, including but not limited to silicone, TPE, or any other suitable material. Lower headgear connectors may be formed from a combination of materials such as a stiffer material to hold the shape and transmit headgear forces to the mask, and a more flexible material to allow easy engagement and disengagement of the headgear straps. This may include combinations of materials such as nylon and silicone. The flexible material may also have a tackiness or friction to the material to prevent the headgear from sliding within the connectors. This may include but not be limited to silicone. Preferably, assembly of the headgear to the lower headgear connectors requires less force than disassembling the headgear from the lower headgear connectors. Preferably, the disassembly force is less than 15N. Most preferably, the disassembly force is less than 10N.

Figure 70:
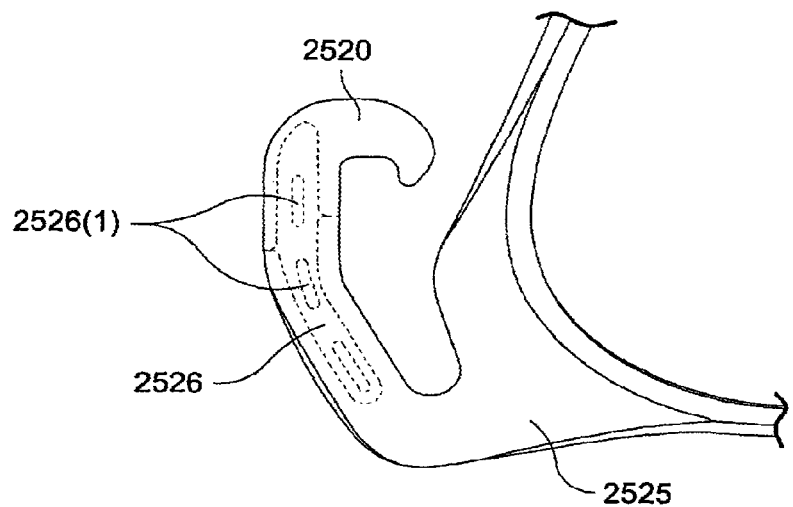
FIG. 70 shows an alternative view of a lower headgear connector according to an embodiment of the invention.
Figure 71:
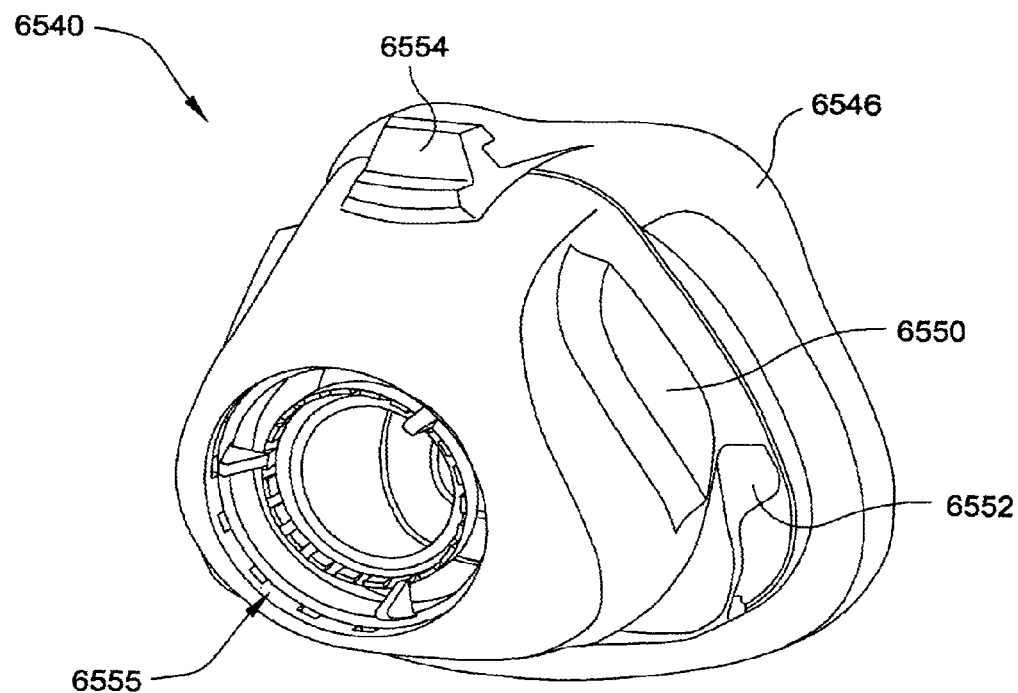
FIG. 71 is a front perspective view of a cushion according to an embodiment of the invention.
Figure 72:
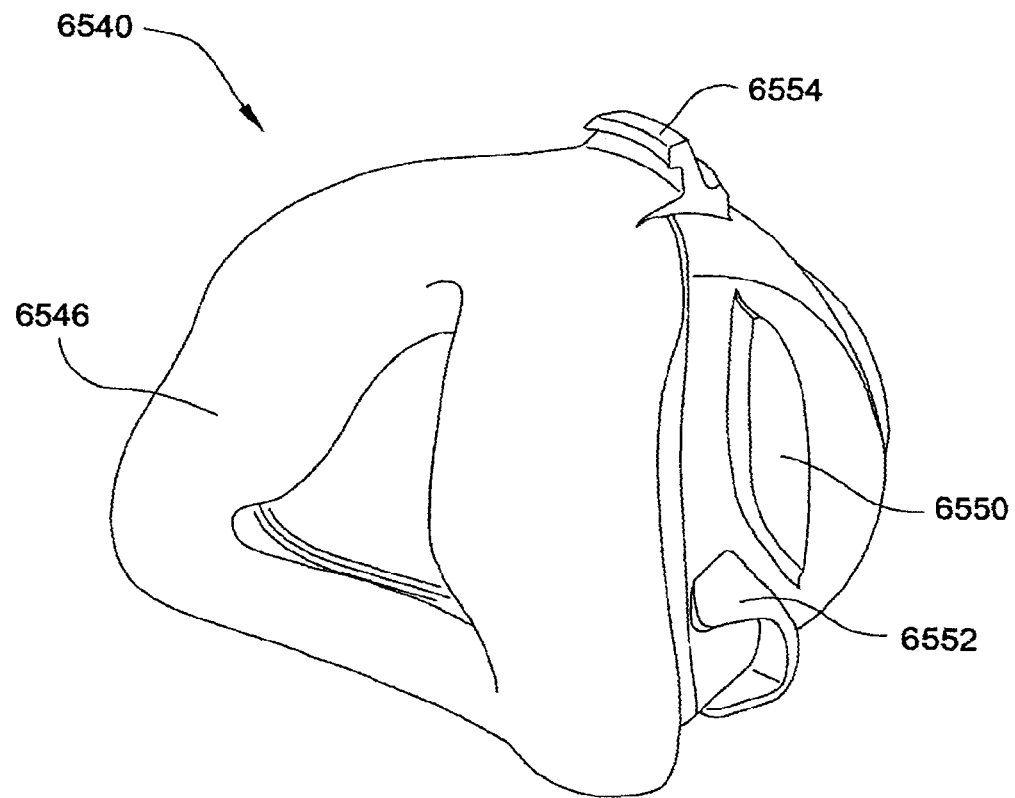
FIG. 72 is a rear perspective view of the cushion of FIG. 71.
Figure 73:
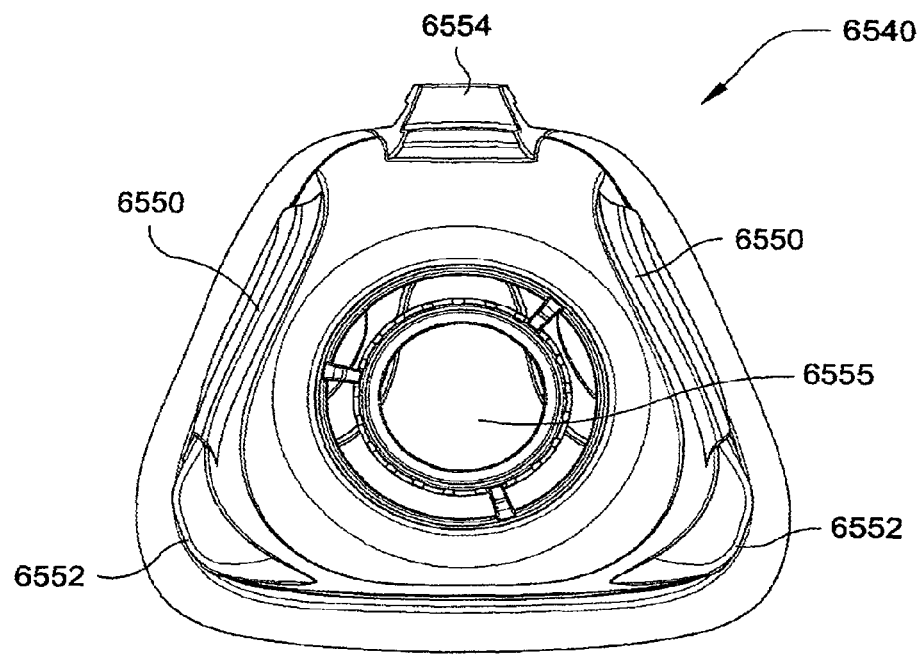
FIG. 73 is a front view of the cushion of FIG. 71.

FIG. 70 shows an alternative view of a lower headgear connector 2520. As illustrated, the generally hook or C shaped lower headgear connector 2520 (constructed of a more flexible material, e.g., silicone) is overmolded or comolded with the main body connection 2525 of the main body 2100 (e.g., constructed of a more rigid material, e.g., nylon). Preferably, the flexible material may be silicone. Preferably, the flexible material may have a Shore A durometer of about 20-80. Most preferably, the flexible material may have a Shore A durometer of about 40-60. Most preferably, the flexible material may have a Shore A durometer of about 60. The connection 2525 includes a connecting portion 2526 to assist in molding the connector 2520 to the connection 2525. The connecting portion 2526 includes retention slots 2526(1) to assist in the interlocking or mechanical locking of the overmolded flexible connector 2520 with the stiffer connection 2525. Also, the connecting portion 2526 extends substantially to the height or top of the connector 2520 to enhance headgear connection at the connector, i.e., stiffer material of connecting portion holds the shape of the connector to prevent headgear from sliding off the connector and transmits headgear forces to the mask. The flexible connector 2520 also allows easier removal of the strap from the connector and easier connection of the strap to the connector, e.g., connector deformable to facilitate removal and connection of strap.

Figure 89:
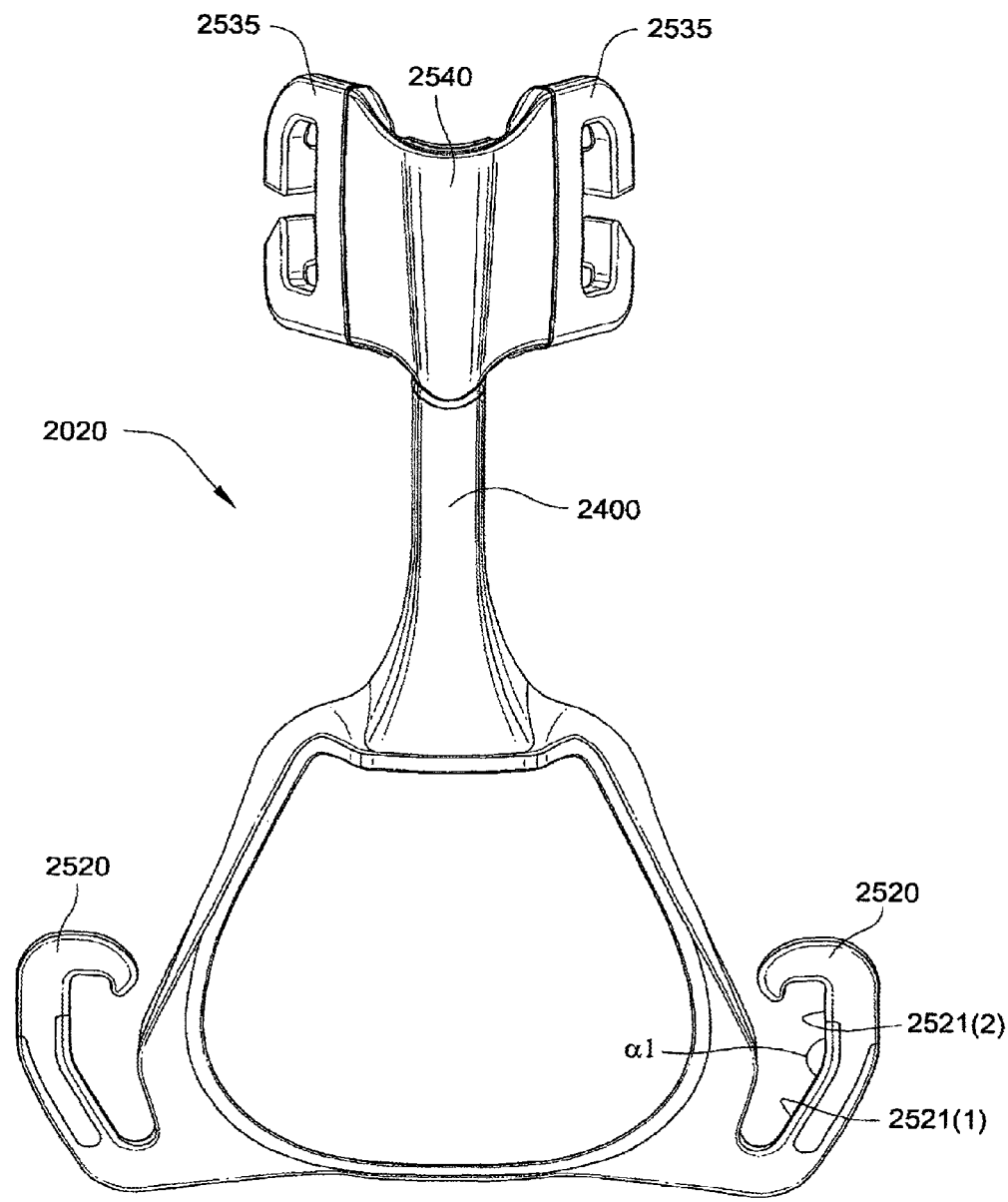
Figure 90:
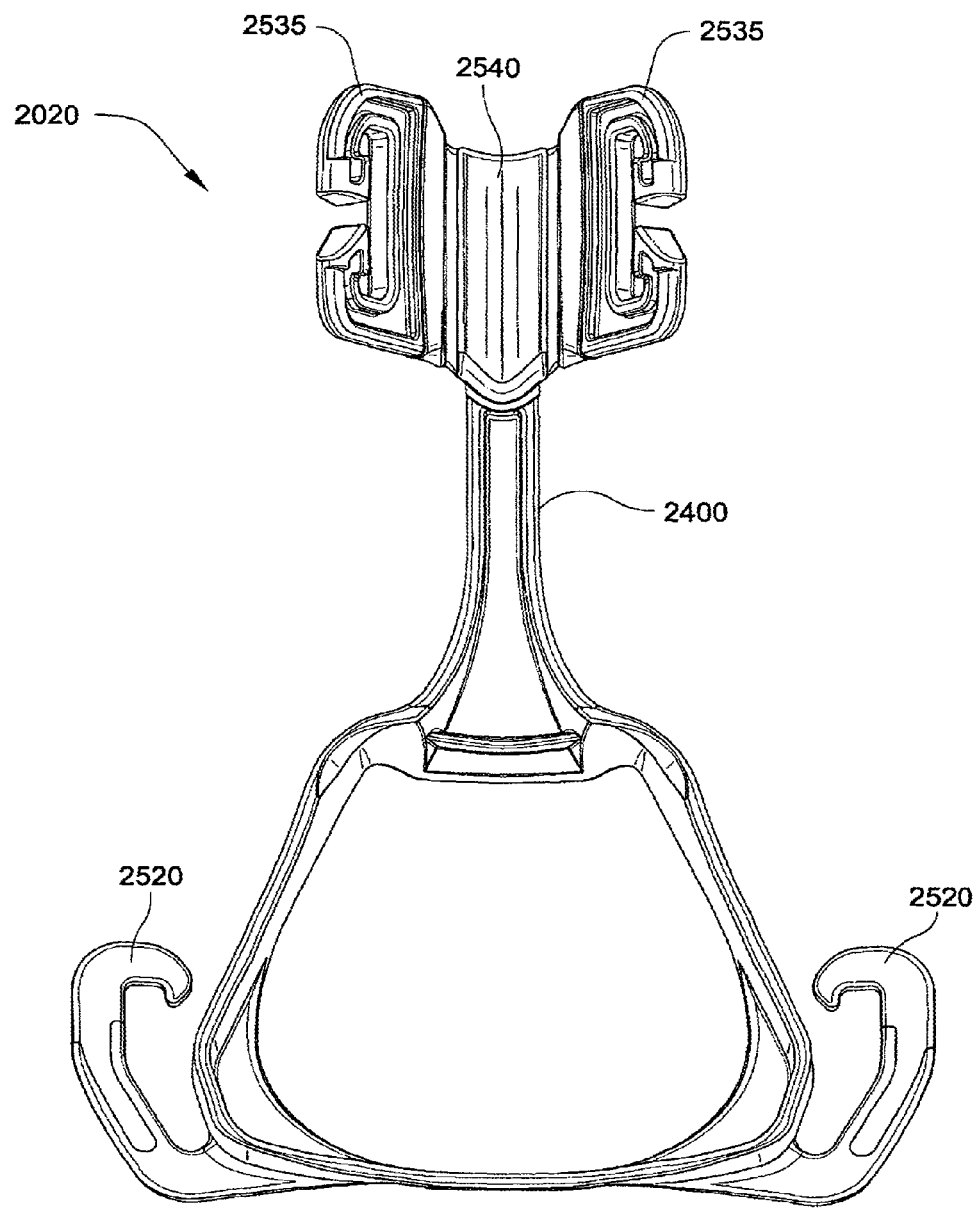

As shown in FIG. 89, the lower headgear connector may provide interior surfaces 2521(1), 2521(2) that are angled with respect to one another by an angle α1 to help retain the headgear strap and prevent inadvertent removal. Preferably, α1 may be less than 180°. Preferably, α1 may be about 110-160°. Most preferably, α1 may be about 120-150°. Also, the spacing of the connector from the main body of the frame also helps strap retention. Preferably, the spacing of the connector from the main body may vary along the length of the connector. Preferably, the widest gap between the connector and the main body may be less than 15 mm to aid in retention of the strap. Most preferably, the widest gap between the connector and the main body may be less than 10 mm to aid in retention of the strap.

Figures 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43:
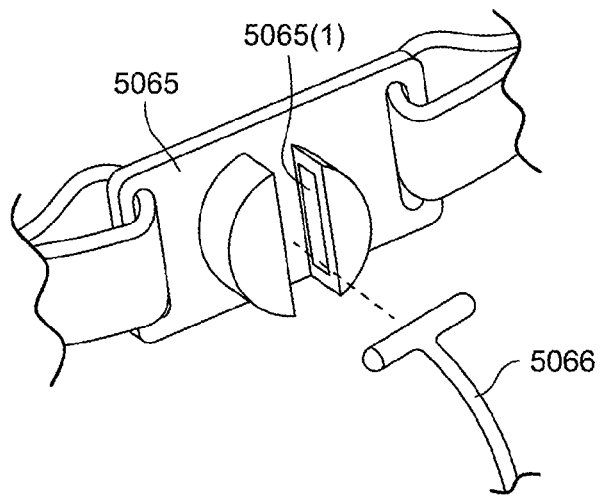
Figures 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 44A:
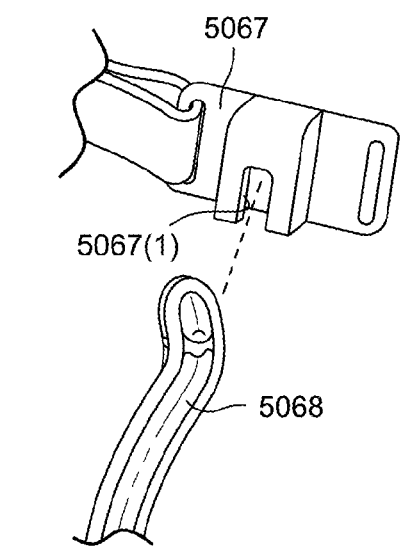
Figures 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 44B:
Figures 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45:
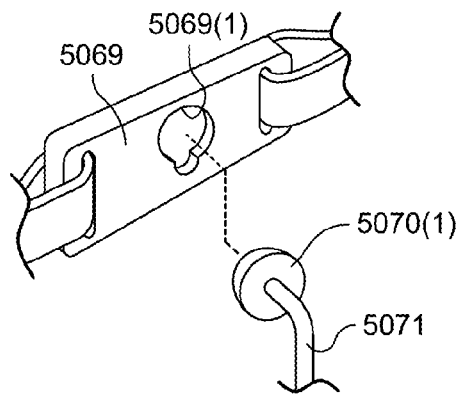
Figures 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 46A:
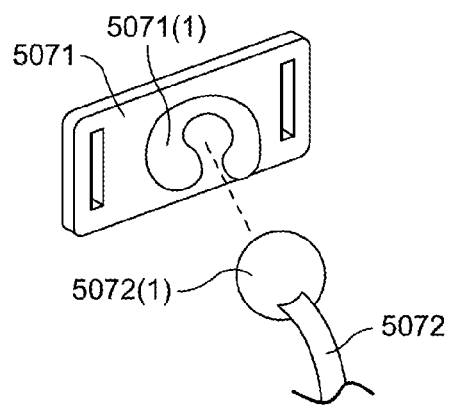
Figures 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 46B:
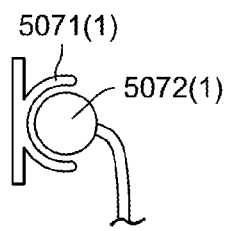
Figures 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47:
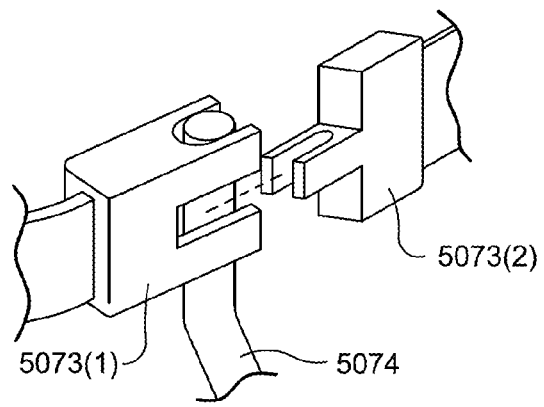
Figures 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 48A:
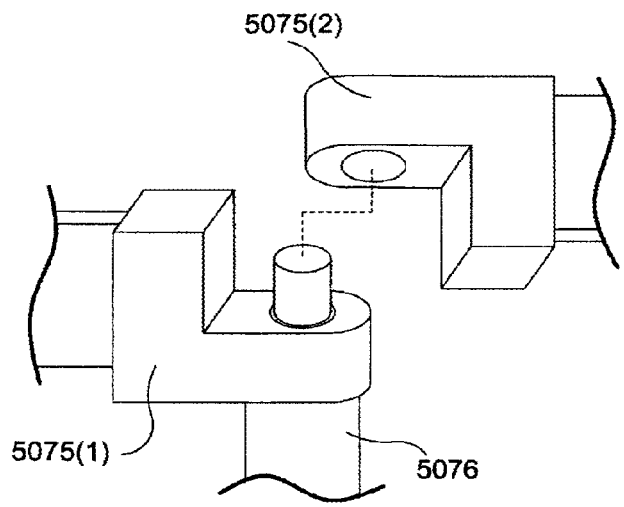
Figures 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 48B:
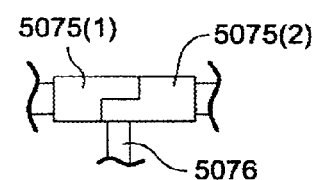

As shown in FIGS. 41-44, side engagement tabs 2600 may be positioned on the lateral flanges of the main portion 2100 and on the patient side of the mask frame for interfacing and supporting the mask cushion. In an embodiment, the tabs are positioned adjacent where the undercushion ends in the nasal bridge region. The tabs may form an interference fit with a portion of a cushion. The tabs may be thinner than remaining or surrounding part of the frame. The tabs may also support the cushion so that it is supported in sealing engagement with the sides of the patient's nose or cheek region. Tabs 2600 provide structural support to the flexible cushion so that it may not collapse away from the patient's face (e.g., blowout) and therefore break seal in use. The tabs 2600 may extend rearwardly from the arm 2400 as shown in FIG. 43.

Forehead support arm 2400 extends from the main body 2100 to the forehead pad 2530. Preferably, forehead support arm 2400 is thin (e.g., 1-5 mm, less than 10 mm, or about 1-5 mm) to avoid obstructing the patient's vision, and structurally stable or relatively inextensible so as to support the mask in position.

Forehead support pad 2530 may include upper headgear connectors 2535 for engagement with upper headgear straps. Forehead support pad may further include a flexible region 2540 for adjustment of the distance of the forehead support pad from the patient's forehead in use. By tightening or adjusting the upper headgear straps in the normal range of tension without causing discomfort, the flexible region 2540 may flatten to pull the forehead support pad closer to the patient's forehead. This will then in turn tilt the main body inwards towards the patient's nose bridge, thereby pushing the mask cushion further on to the patient's nasal bridge in use. In an embodiment, the force to flatten the flexible region may be in the range of about 1-8 N. Preferably, the force to flatten the flexible region may be in the range of about 2-6 N. Most preferably, the force to flatten the flexible region may be in the range of about 2-4 N.

FIGS. 66-69 show alternative views of the forehead support arm 2400 and forehead support pad 2530. As illustrated, the forehead support pad 2530 includes upper headgear connectors 2535 (e.g., constructed of a more rigid material, e.g., nylon) and a flexible region 2540 (constructed of a more flexible material, e.g., silicone). The flexible region is overmolded with the upper headgear connectors 2535 and the support arm 2400 (e.g., constructed of a more rigid material, e.g., nylon) so as to interconnect the headgear connectors and the support arm and provide flexibility to the forehead support for adjustment of the distance of the forehead support from the patient's forehead in use.

Figure 67:
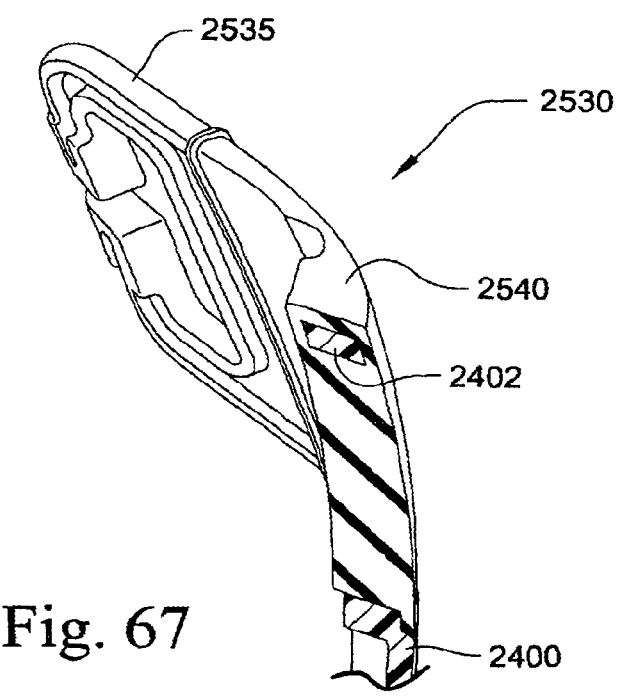

Each upper headgear connector 2535 includes a loop hole 2536 for attaching headgear and a connecting portion 2538 to assist in molding the flexible region to the headgear connector. As illustrated, a slot 2536-1 extends into the hole 2536 to provide a loop through arrangement. The support arm includes a connecting portion 2402 to assist in molding the flexible region to the support arm. The connecting portions 2538, 2402 each include respective retention slots 2538(1), 2402(2) to assist in the interlocking or mechanical locking of the overmolded silicone flexible region 2540 with the nylon headgear connectors 2535 and support arm 2400. Also, as shown in FIG. 67, the silicone flexible region 2540 is sufficiently thicker on each side of the nylon support arm 2400 (e.g., 0.5 mm or more thickness on each side, e.g., 0.8 mm thicker on each side) to enhance the interlock. In an embodiment, the flexible region may be thicker in the middle around the arm 2400 and taper towards the connector 2535.

Figure 66:
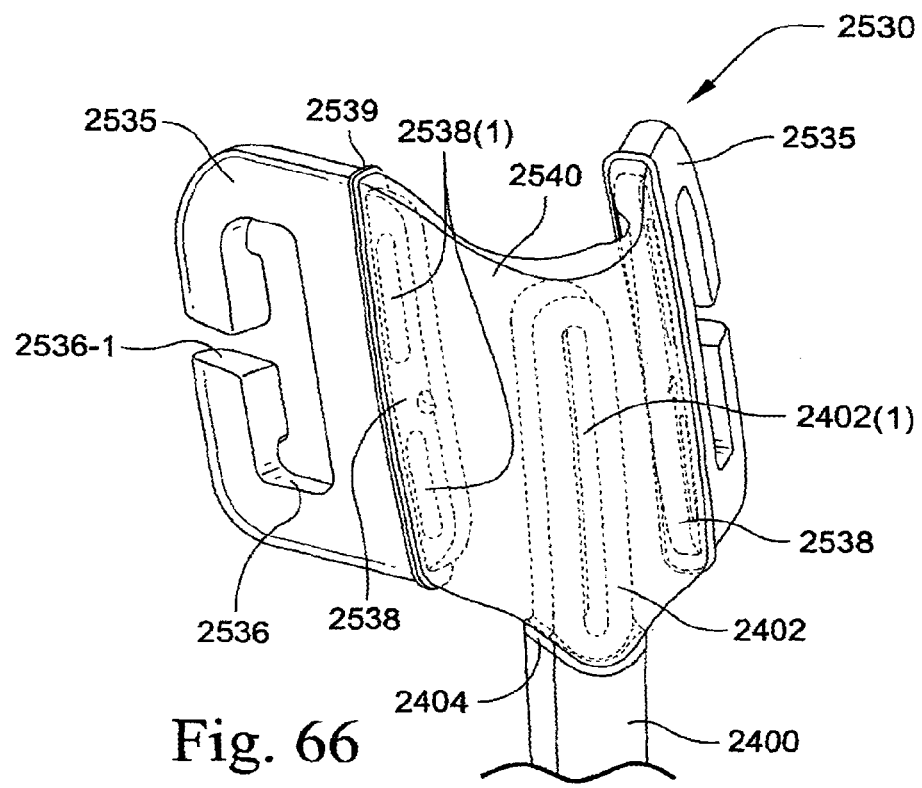
FIGS. 66 to 69 show alternative views of a forehead support arm and forehead support pad according to an embodiment of the invention.
Figure 68:
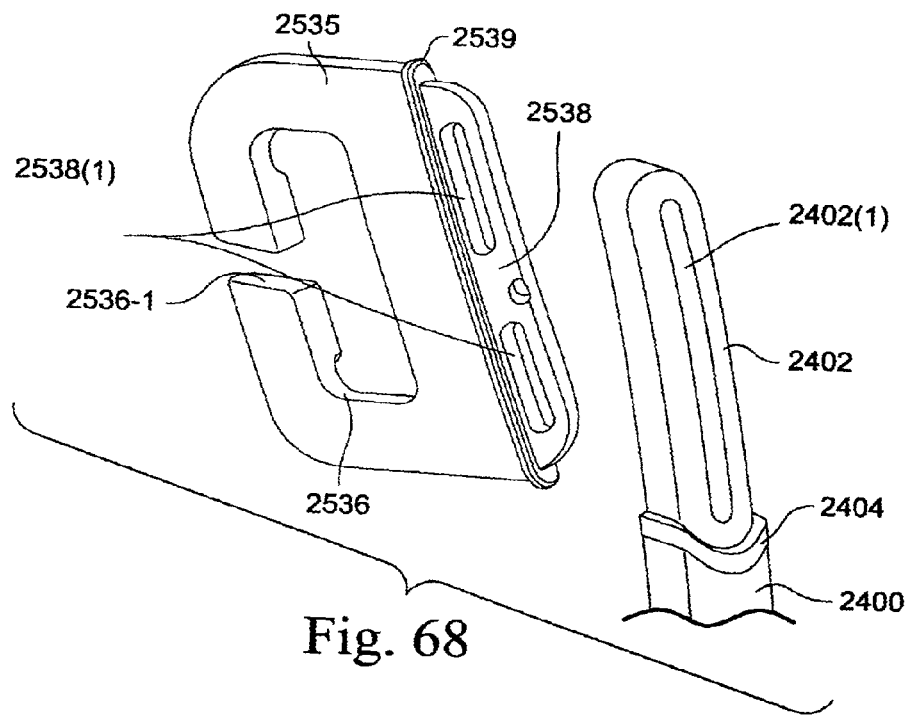
Figure 69:
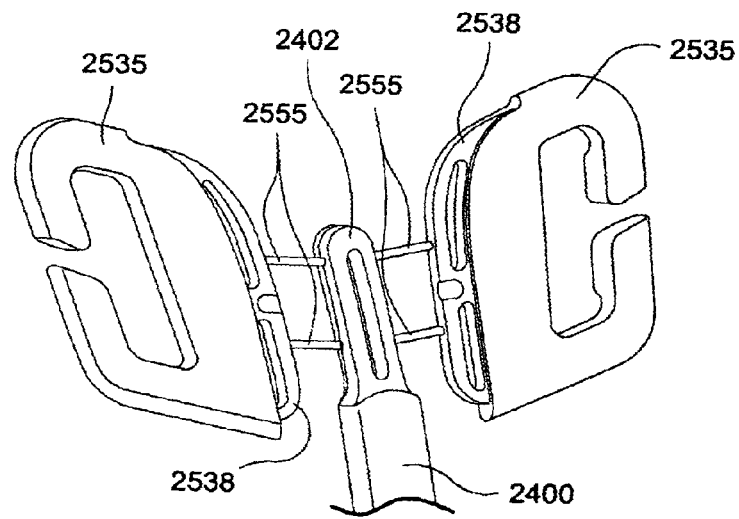

As shown in FIGS. 66 and 68, the headgear connectors 2535 and support arm 2400 may include features to assist in molding with the silicone flexible region 2540 and prevent flash and damage to the frame. For example, support arm 2400 may include a lip 2404 to aid molding of the silicone flexible region over the nylon arm. Also, each headgear connector 2535 may include a rounded wall 2539 (e.g., about 0.2 to 0.6 mm high, e.g., 0.4 mm high) to aid molding of the silicone flexible region over the nylon headgear connector. In an embodiment, the wall 2539 may be a crush bead that is crushed off the part when it is placed in the molding tool.

In a preferred embodiment, the headgear connectors 2535 and arm 2400 are formed separately from one another (e.g., 3 separate parts) and then connected to one another by the flexible region 2540. In an alternative embodiment, as show in FIG. 69, the headgear connectors 2535 may be connected to the arm 2400 by runners 2555 (e.g., headgear connectors and arm formed as one part) and then overmolded with the flexible region.

In an alternative embodiment, the headgear connectors 2535 may include silicone connectors such as the lower headgear connectors 2520 described above.

Figure 91:
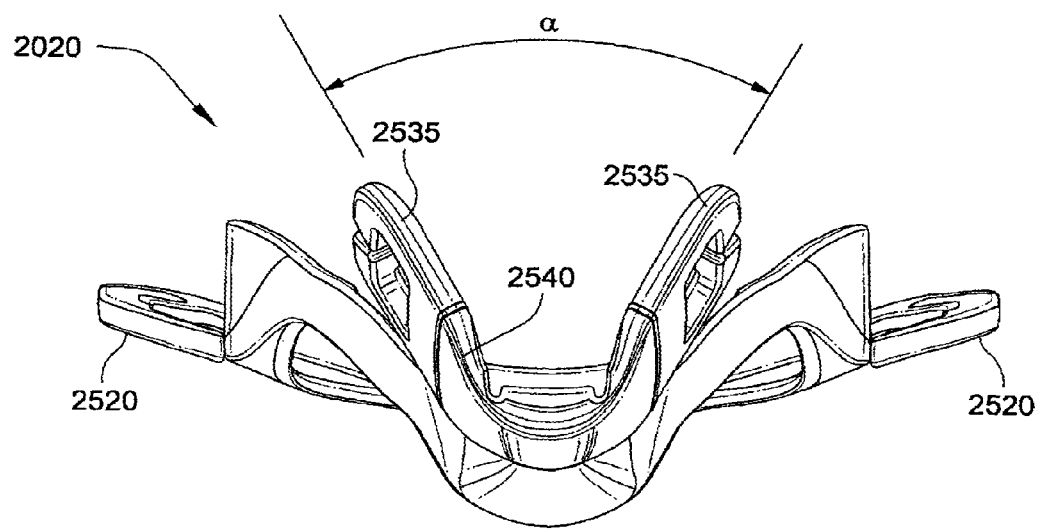
Figure 92:
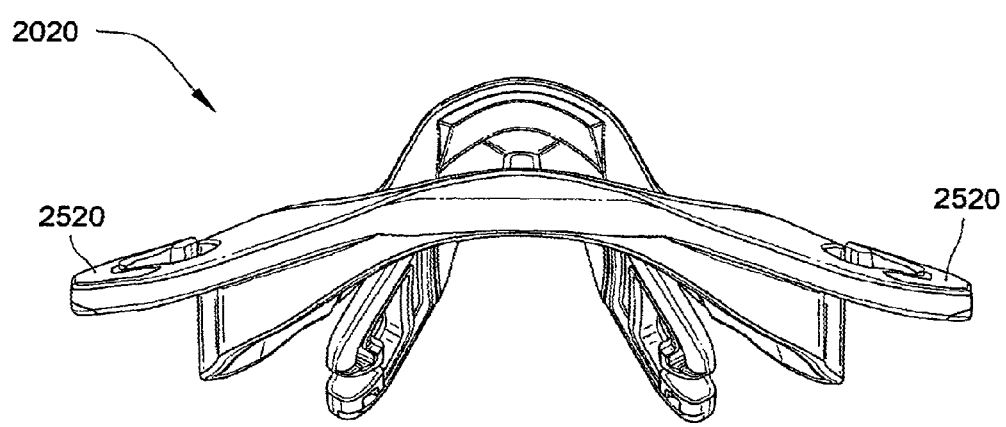
Figure 93:
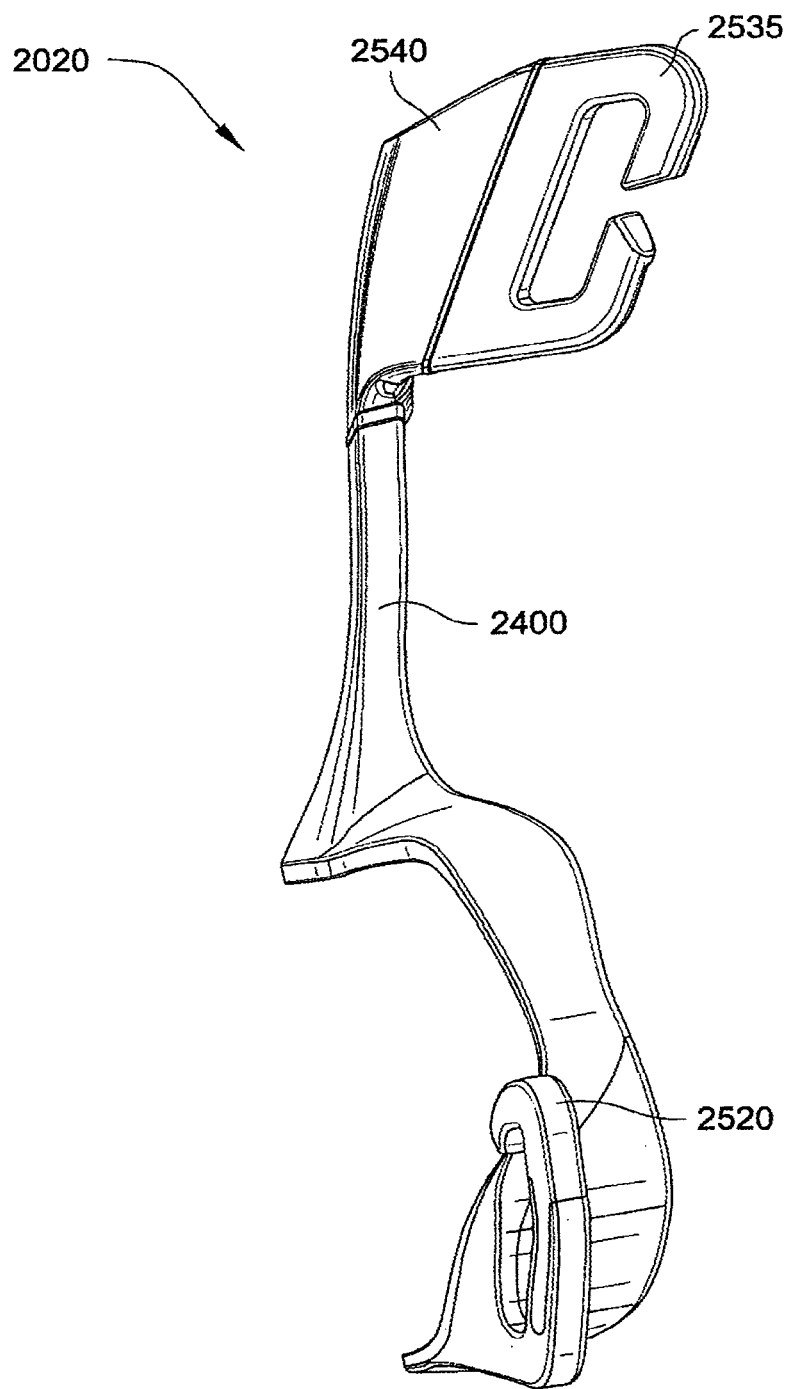
Figure 94:
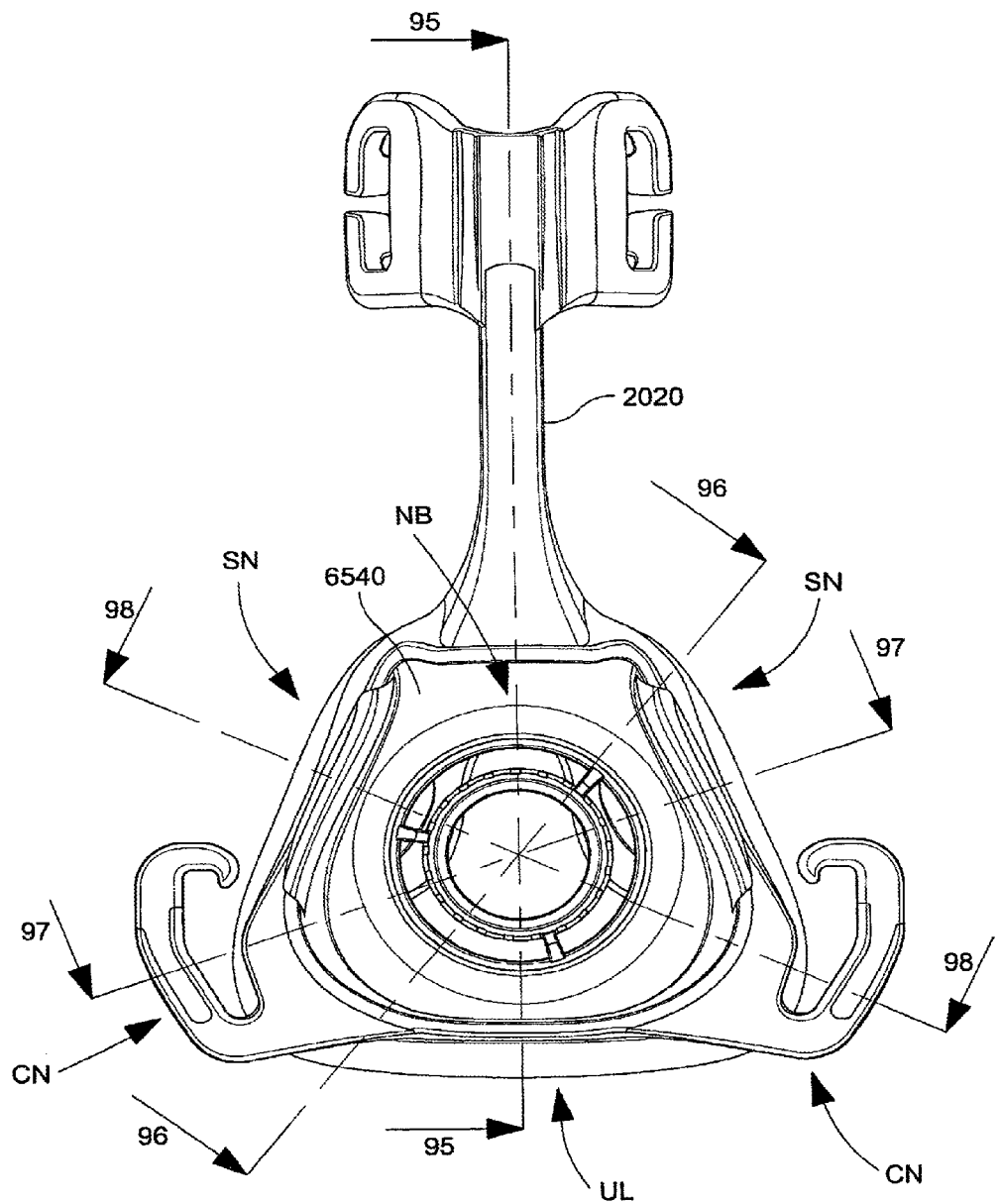
FIG. 94 is a front view of a frame and cushion according to an embodiment of the invention and showing section lines.

FIGS. 88 to 93 show various views of the frame 2020 and its forehead support arm 2400, upper headgear connectors 2535, flexible region 2540, and lower headgear connectors 2520. In an embodiment, as shown in FIG. 91, the angle between connectors 2535 may be about 100-170°, e.g., 125-145°. FIGS. 94 to 98 show the frame 2020 of FIGS. 88 to 93 engaged with the cushion 6540 of FIGS. 71 to 87.

3. Sealing Arrangement

The sealing arrangement 40 is structured to interface with the frame 20 and form a seal with the patient's nose in use. In this example, the sealing arrangement 40 provides a nasal interface adapted to engage the patient's face generally along nasal bridge, cheek, and upper lip regions of the patient's face. However, other interfaces are possible, e.g., full-face. The sealing arrangement provides a compliant arrangement adapted to seal relatively quickly and maintain seal in use. In an example, the sealing arrangement may be structured to seal with or without air pressure.

3.1 Silicone Cushion

In the example of FIGS. 1-1 to 1-4, the sealing arrangement 40 includes a cushion 42 constructed of a generally flexible material including but not limited to silicone, TPE, gel, or other material. The cushion may be moulded in a material having a Type A durometer of about 35 to about 45, for example, about 37 to about 42, preferably about 40. The cushion 42 defines a breathing chamber or cavity adapted to receive the patient's nose and provide air communication to the patient.

The face-contacting side of the cushion 42 includes a dual-wall configuration wherein the cushion includes an undercushion 44 and a membrane 46 that at least partially covers the undercushion 44 (e.g., see FIG. 1-4). The membrane is generally softer and less stiff than the undercushion and provides a seal against the patient's face in use. The undercushion is structured to generally support the membrane and prevent collapse of the membrane when the nasal mask system is attached and tightened using the headgear. In an example, the undercushion may only be provided in selected regions of the mask system, e.g., along the cheek regions, or not at all. Also, the cushion may be frosted, e.g., for easy fit and comfort, and/or tinted.

FIG. 1-4 shows a cross-section through cheek regions of the face-contacting side of the cushion 42. As illustrated, the cushion includes a sickle-shape or question-mark configuration with a base portion 60 and an upper portion 62 that is radially offset towards the outside of the base portion 60, e.g., to reduce size and perceived bulk, minimize dead space within the breathing chamber, and/or add more flexibility to the undercushion and membrane in use. Such cross-section may be provided around the entire perimeter of the cushion or may only be provided in selected regions of the cushion. In an example, the "question-mark"-shaped cross-section in the upper lip region may include less curvature, e.g., to avoid overhang of the cushion into the patient's mouth and prevent nostril occlusion.

In an example, the gap or spacing 45 between the membrane 46 and undercushion 44 (e.g., see FIG. 1-4) may be adjusted, e.g., to reduce wrinkling and leak. For example, the gap may be relatively small so that the membrane closely follows the geometry of the undercushion. In an example, the cushion may be molded so that the gap is larger, but the membrane is preloaded to hinge closer to the undercushion after molding. In another example, a bellows 64 (as indicated in dashed lines in FIG. 1-4) may be provided or molded with the membrane to bias the membrane closer to the undercushion.

The non-face-contacting or frame side of the cushion 42 includes one or more interfacing structures adapted to interface or otherwise removably connect to the frame 20. In the illustrated example, the cushion 42 includes one or more elongated and spaced protrusions 50, e.g., along the sides and bottom thereof adapted to engage or interlock with respective openings 27 along the side wall 26 of the frame 20. As shown in FIGS. 1-1 and 2-1, such arrangement provides positive reinforcement that the connection has been established as the user can visually see the connection and optionally a proper connection may result in an audible clicking noise. In addition, the cushion 42 includes a notch or detent 52 along the top thereof adapted to engage or interlock with a bead or catch along the inner side of the frame side wall 26 (not shown), e.g., to assist with alignment and even prevent misalignment. However, it should be appreciated that the cushion may be connected or interlocked with the frame in other suitable manners.

For example, a possible arrangement for connecting the cushion 42 to the frame 20 is disclosed in U.S. Pat. No. 7,000,614, which is incorporated herein by reference in its entirety.

The non-face-contacting side of the cushion 42 also includes an opening 55 adapted to receive or otherwise communicate with the elbow 70 as described below.

FIGS. 1-5 to 1-12 show a cushion substantially similar to the cushion 42 described above and indicated with similar reference numerals. In contrast, the cushion of FIGS. 1-5 to 1-12 does not include a notch or detent along the top thereof.

As illustrated, the face-contacting side of the cushion (i.e., including the membrane 46 and undercushion 44) may be co-molded with or formed separately and attached to the non-face-contacting side of the cushion (i.e., defining the opening 55 and breathing chamber). Preferably, the face contacting side of the cushion and the non-face-contacting side of the cushion are formed as a single component. Preferably, this single component may be made from a flexible sealing material that is relatively biocompatible when in contact with patient's skin, including but not limited to silicone.

FIGS. 1-9 to 1-12 show various cross-sections through the cushion. As shown in FIG. 1-9, the cushion may not include an undercushion in the nasal bridge region of the cushion. Also, as shown in FIG. 1-9, the curvature and/or length of the membrane and undercushion in the upper lip region membrane is selected for fit range, comfort, and to prevent occlusion of the nares. In contrast, the curvature and/or length of the membrane at the nasal bridge region may be flatter and longer than the upper lip region, e.g., to increase seal stability and fit range. This is because the cushion must accommodate for a variety of nasal bridge heights including high nose bridges and flatter nose bridges, and as such, a longer membrane at the nasal bridge region is required. There is no undercushion at the nose bridge region to allow greater flexibility and provide less force on the sensitive region that is the nose bridge. The anthropometric variation of the patients in the top lip region is less so the length of the membrane is less than the nose bridge region. The undercushion is provided in the top lip region to aid in stabilizing the cushion in position on the patient's face.

FIGS. 1-11 and 1-12 clearly illustrate the sickle-shape or question-mark configuration through cheek regions of the face-contacting side of the cushion, while FIGS. 1-9 and 1-10 show the upper lip region which is substantially devoid of such configuration. The sickle shape is required in the cheek regions to allow for greater flexibility of the cushion to accommodate anthropometric variation of a patient's faces. For example, some patients may have a generally flat face and hence require the cushion to flex from its substantially curved profile to a flatter profile. The cheek regions will be required to flex inwards or downwards. Alternatively, for patients with angular or swept back cheeks, they may not require as much flex of the cushion. In both scenarios, the patient's should have approximately the same level of comfort and hence force on their face from the cushion. The added flexibility of the sickle shape allows for a range of deflection of the cushion with approximately the same force feedback on the patient's face.

In addition, a lip seal 57 may be provided inwardly from the opening 55 to seal against the elbow in use.

3.2 Foam Cushion with Silicone Membrane

In an alternative example as shown in FIGS. 2-1, 2-2, and 2-4 to 2-8, the sealing arrangement 40 may include a foam cushion 241 and a silicone cushion or membrane 242.

The silicone cushion 242 defines the breathing chamber and is adapted to support or otherwise retain the foam cushion 241. As best shown in FIG. 2-6, the face-contacting side of the silicone cushion 242 provides a dual-wall configuration including an undercushion 244 and a membrane 246. The non-face-contacting side of the silicone cushion 242 includes an opening 255 adapted to receive or otherwise communicate with the elbow 70.

The undercushion 244 and adjacent side wall 247 extending from the undercushion 244 are structured to retain the foam cushion 241. The undercushion 244 curves outwards from the side wall 247 and away from the breathing cavity to provide a channel 248, which is opposite to the membrane 246 which curves inwards into the breathing cavity. As illustrated, at least the patient side of the foam cushion 241 is inserted into the channel 248 (e.g., see FIGS. 2-2 and 2-6) defined by the undercushion 244 with the interior surface of the foam cushion 241 supported by the side wall 247. The foam cushion 241 may be retained in position by an interference and/or friction fit with the silicone cushion 242. The foam cushion 241 is positioned under the membrane 246 and within the undercushion 244, but not in the air path or breathing chamber. In use, the foam cushion 241 may absorb forces applied to the undercushion 244, e.g., along cheek regions of the silicone membrane.

The non-patient side of the foam cushion 241 supports the foam cushion 241 and hence the silicone cushion 242 on the frame 20. As illustrated, the foam cushion 241 includes one or more interfacing structures adapted to interface or otherwise removably connect to the frame. In the illustrated example, the foam cushion 241 includes one or more spaced and elongated protrusions 250, e.g., along the sides thereof adapted to engage or interlock with respective openings 27 along the side wall of the frame 20. However, it should be appreciated that the foam cushion may be connected or interlocked with the frame in other suitable manners, or the frame may be connectable to the silicone cushion possibly in conjunction with the foam cushion.

In an example, the outer lip 249 (e.g., see FIG. 2-5) of the silicone cushion 242 (i.e., the joint between the membrane and the undercushion) may be structured to engage with an outer edge of the frame 20 so that the silicone cushion 242 and frame 20 encapsulate the foam cushion 241.

In an example, a concertina or bellows-type arrangement may be provided in a nasal bridge region of the silicone cushion, e.g., to provide a higher degree of flexibility or increased movement without compromising seal in use. For example, the silicone cushion may include a concertina section such as that described in PCT Application No. PCT/AU2009/000241, filed Feb. 27, 2009, which is incorporated herein by reference in its entirety.

In an example, corrugations may be provided in the upper lip region of the membrane and/or undercushion of the silicone cushion, e.g., to prevent occlusion of the nares.

The foam cushion 241 may include skinned or unskinned foam. The foam cushion 241 may be open cell, closed cell, or a combination of open and closed cells. The foam cushion 241 may be die cut, molded or compression cut. The foam cushion 241 may be made from a polyurethane foam, silicone foam, or any other suitable material. The foam cushion 241 may be made from the same material or a combination of materials, e.g., two foams with different properties. For example, protrusions 250 may be made from a denser or harder foam than the remainder of foam cushion 241.

The cushion 242 may also be made from materials other than silicone. For example, the cushion 242 may be made from a TPE, gel-filled, or any other suitable material.

3.3 One Size Fits Most Cushion

A cushion according to an embodiment of the present invention may be constructed to fit a wide variety of patient's faces with only one size, i.e., can fit a large variety of anthropometry.

The undercushion may include slits or may be constructed of multiple individual narrow portions or fingers that may be structured so that the fingers splay outwards when a force is applied by the user when applying the mask. The fingers are arranged to spread outwards thereby pressing or supporting the membrane over a greater area of the patient's face. In addition, the fingers may be structured to bend, flex and move into crevices and creases of the patient's face (e.g., due to wrinkling of the patient's skin or at the sides of the nose where the nostrils flare outwards), thus supporting the seal in these typically difficult to seal regions.

FIGS. 71-87 illustrate a cushion 6540 according to an embodiment of the invention. As described in greater detail below, the cushion 6540 provides a nasal interface adapted to engage the patient's face generally along the nasal bridge region NB, side of nose region SN (including upper side of nose and lower side of nose), nasal-labial crease or corner of nose region CN, and upper or top lip region UL of the patient's face (e.g., see FIGS. 74, 78-82, and 94-98).

Figures 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 49A:
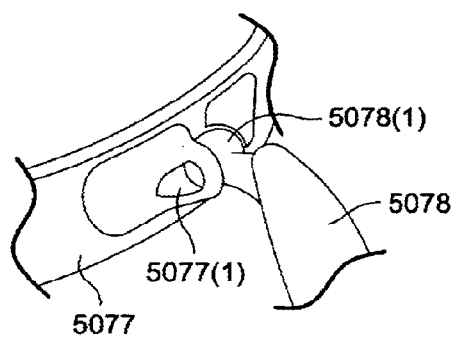
Figures 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 49B:
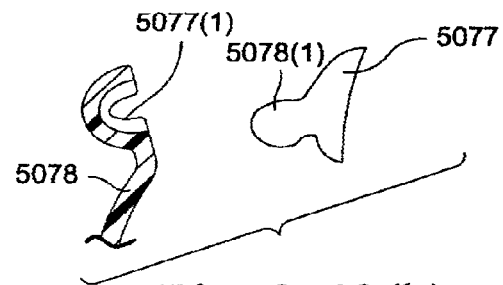
Figures 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 50A:
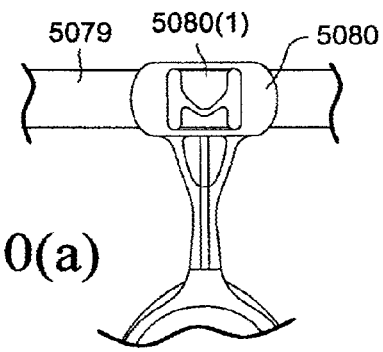
Figures 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 50B:
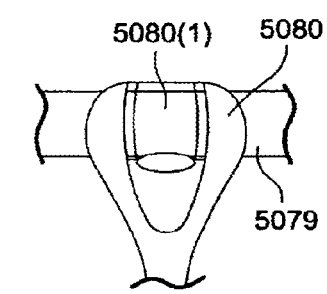
Figures 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51:
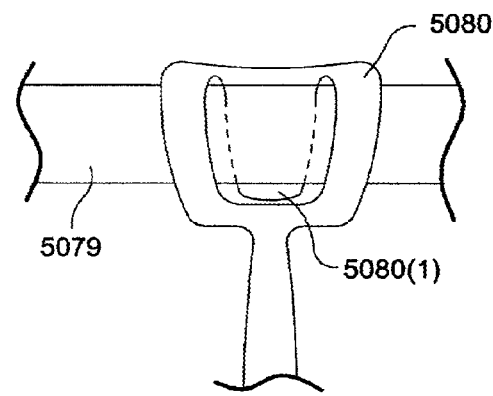
Figures 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 52A:
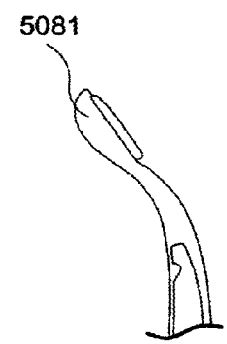
Figures 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 52B:
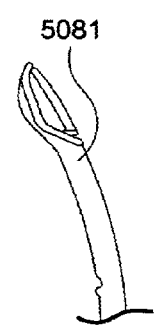
Figures 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 52C:
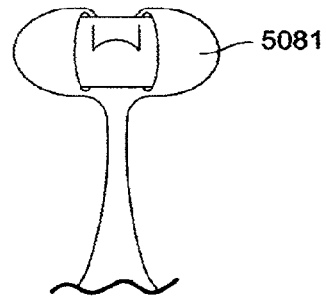
Figures 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 53A:
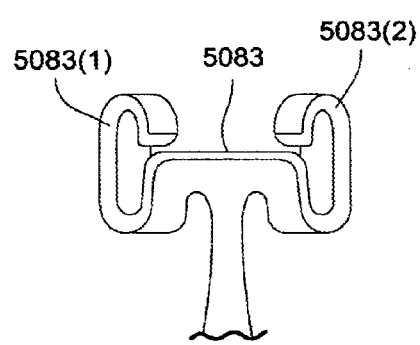
Figures 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 53B:
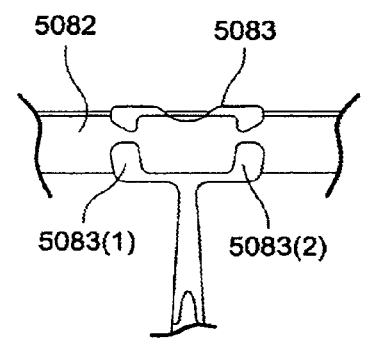
Figures 3, 54:
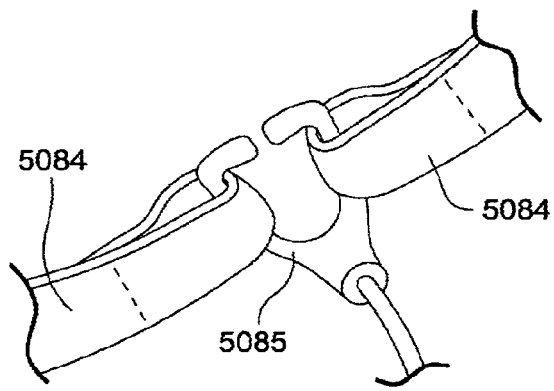

The face-contacting side of the cushion 6540 includes a dual-wall configuration wherein the cushion includes an undercushion 6544 and a membrane 6546 that at least partially covers the undercushion 6544. In the illustrated embodiment, the undercushion is not provided in the nasal bridge region NB, e.g., see FIGS. 79 and 95. As shown in FIG. 79 for example, the free end of the membrane 6546 may include a bead 6546(1). The inclusion of the bead may allow the orifice defined by the membrane to be molded into the cushion, so that no additional cutting is required to form such orifice. In the illustrated embodiment, the membrane includes a relatively thin thickness, e.g., about 0.2 mm to about 0.35 mm.

The cushion may include a sickle shape in one or more regions of the cushion, e.g., see upper lip, side of nose, and corner of nose regions in FIGS. 79-82. In use, the sickle shape of the cushion provides a hinge or flex point 6567 (e.g., see FIG. 98) to facilitate controlled deformation of the cushion in use. Also, such sickle shape of the cushion allows one or more portions of the cushion to overhang the frame 2020 (e.g., see FIGS. 95-98), which may allow the frame to support one or more portions of the cushion as it is deformed in use. In one form, this arrangement provides a less stiff undercushion which reduces the likelihood of the cushion bottoming out over the range of displacements used, hence making the cushion more comfortable.

Figure 117:
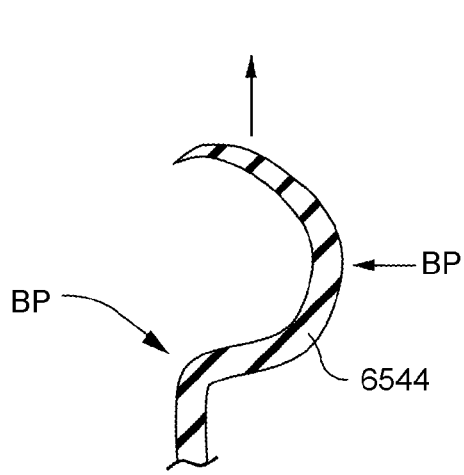
FIGS. 117 to 120 illustrate bending points or bending regions of the undercushion according to different aspects of the present technology.
Figure 118:
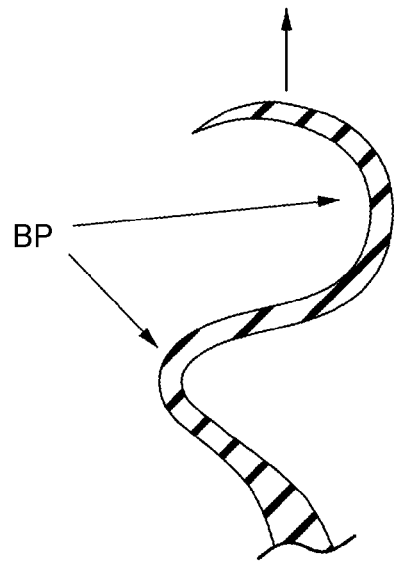
Figure 119:
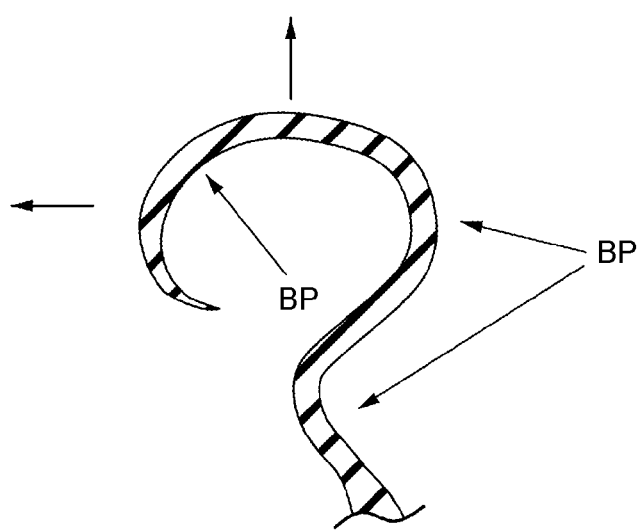
Figure 120:
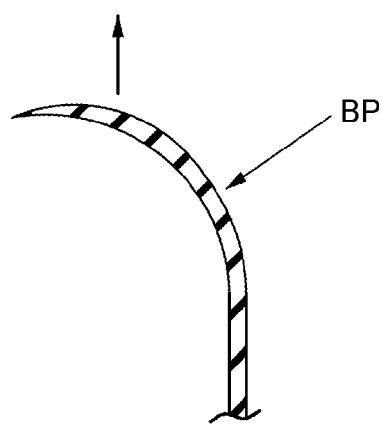

FIG. 117 shows bending points or bending regions BP of the undercushion or backup band 6544 according to an embodiment invention, and FIGS. 118, 119, and 120 show bending points BP for undercushions of other arrangements. Different cross-sections may be used in different regions.

Preferably the arrangement illustrated in FIG. 117 is used in a top lip region of an undercushion or a backup band. This arrangement may be described as a double cantilever, depending on the relative thickness of the different sections. Increasing the thickness increases the stiffness. The shape of the cross-section may be arranged to extend laterally or radially outward of the adjacent sidewall, or in another version such as shown in FIG. 118 may be more in line with an adjacent sidewall, and have a similar radial outer extent by arranging folds or bends inwardly of the adjacent sidewall.

Preferably the cross-section shown in FIG. 119 is suitable for use along the sides of the nose. This arrangement can lead to improved lateral force being exerted to seal a difficult region of the face. This arrangement may be described as a triple cantilever, depending on the relative stiffnesses of the different sections.

An alternative arrangement is shown in FIG. 120 which may be described as a single cantilever.

Figure 95:
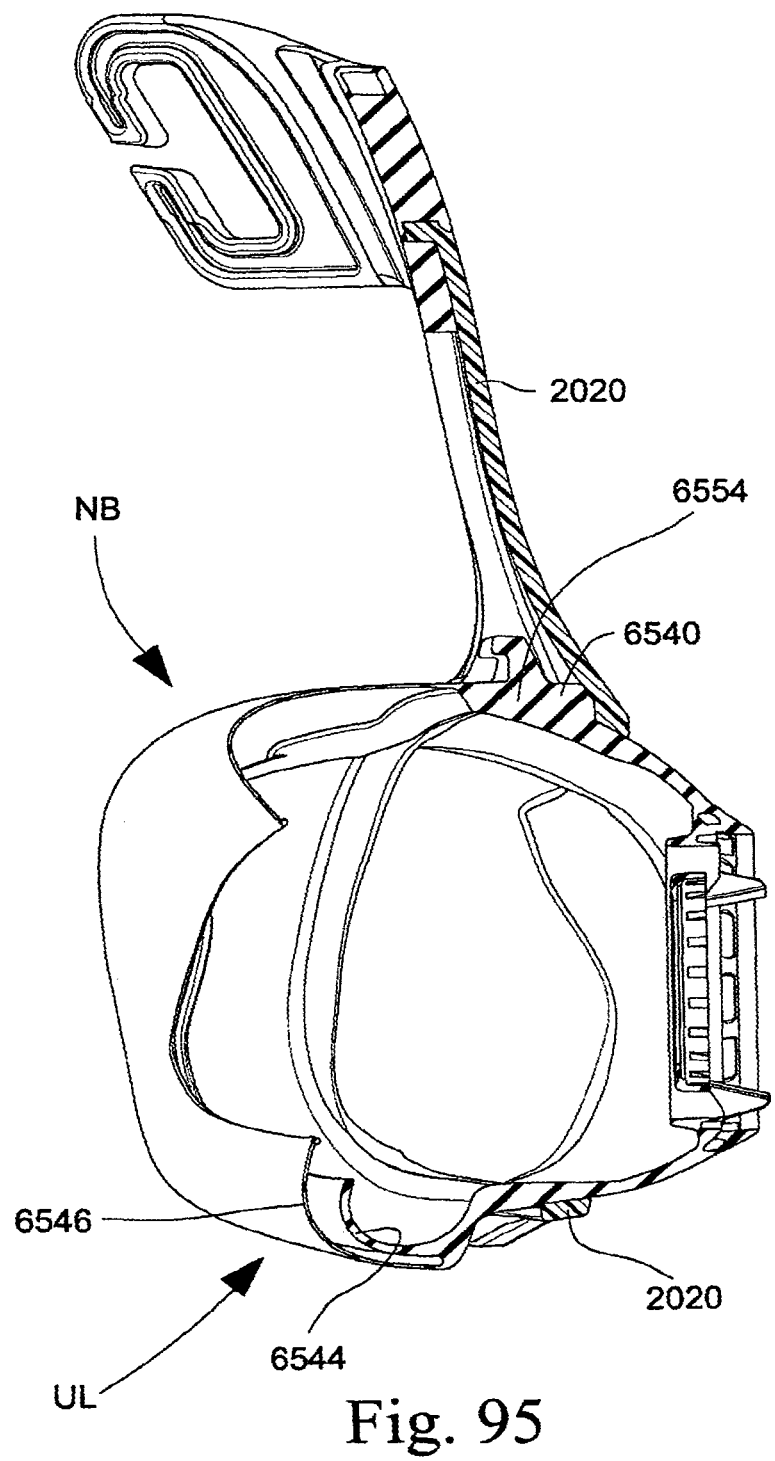
FIG. 95 is a cross-sectional view through line 95-95 of FIG. 94.
Figure 97:
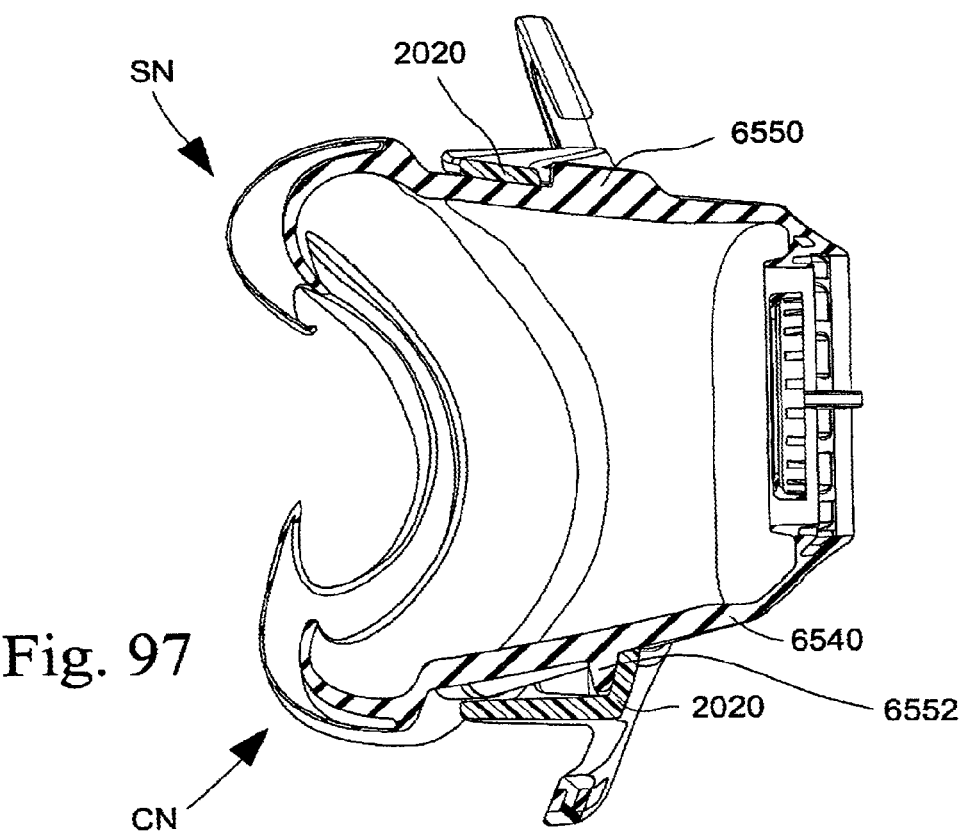
FIG. 97 is a cross-sectional view through line 97-97 of FIG. 94.
Figure 98:
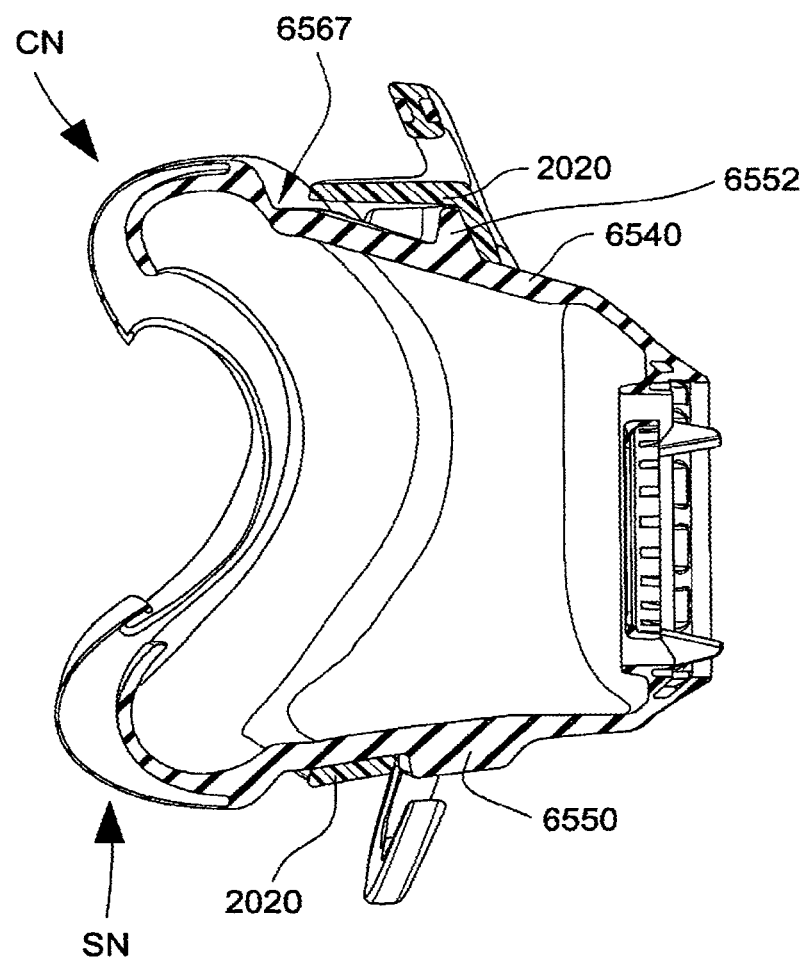
FIG. 98 is a cross-sectional view through line 98-98 of FIG. 94.
Figure 99:
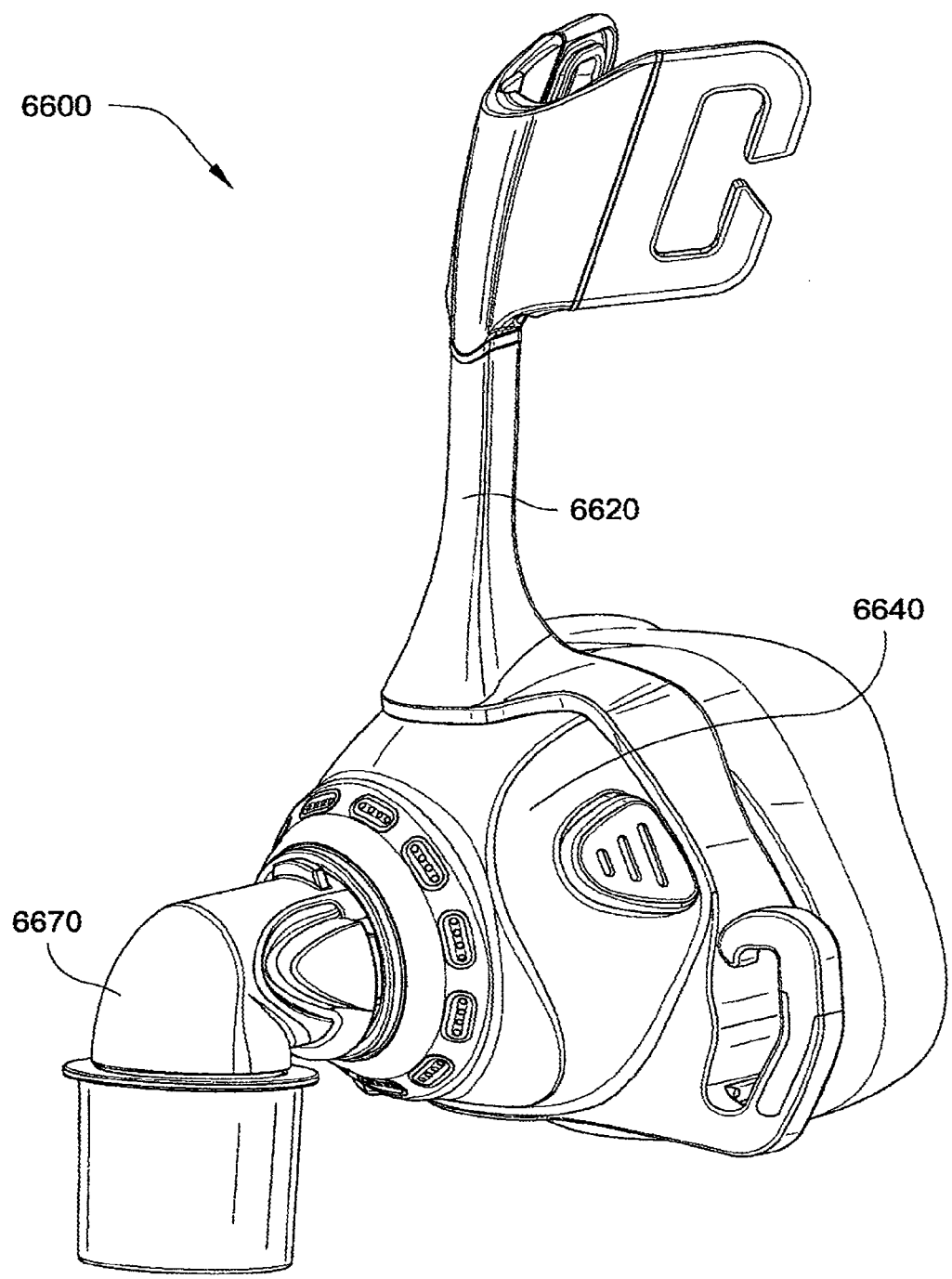
FIGS. 99 to 105 are various views of a mask system according to an embodiment of the invention.
Figure 100:
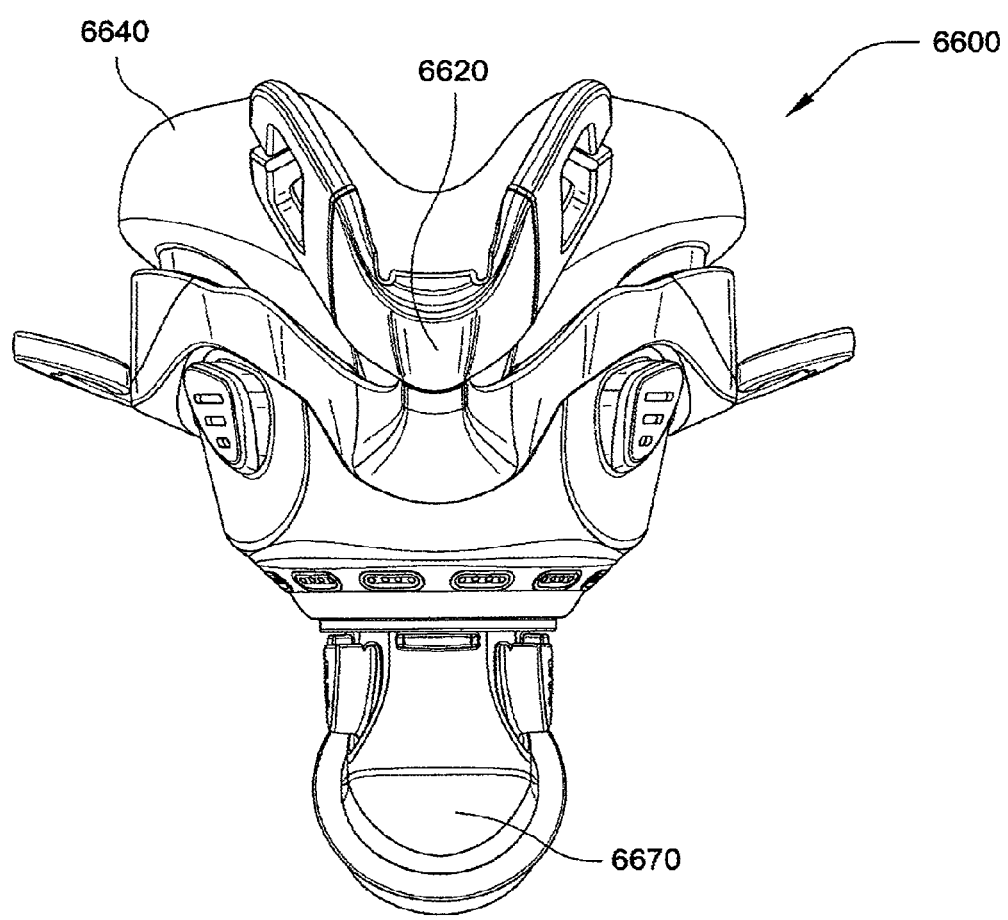
Figure 101:
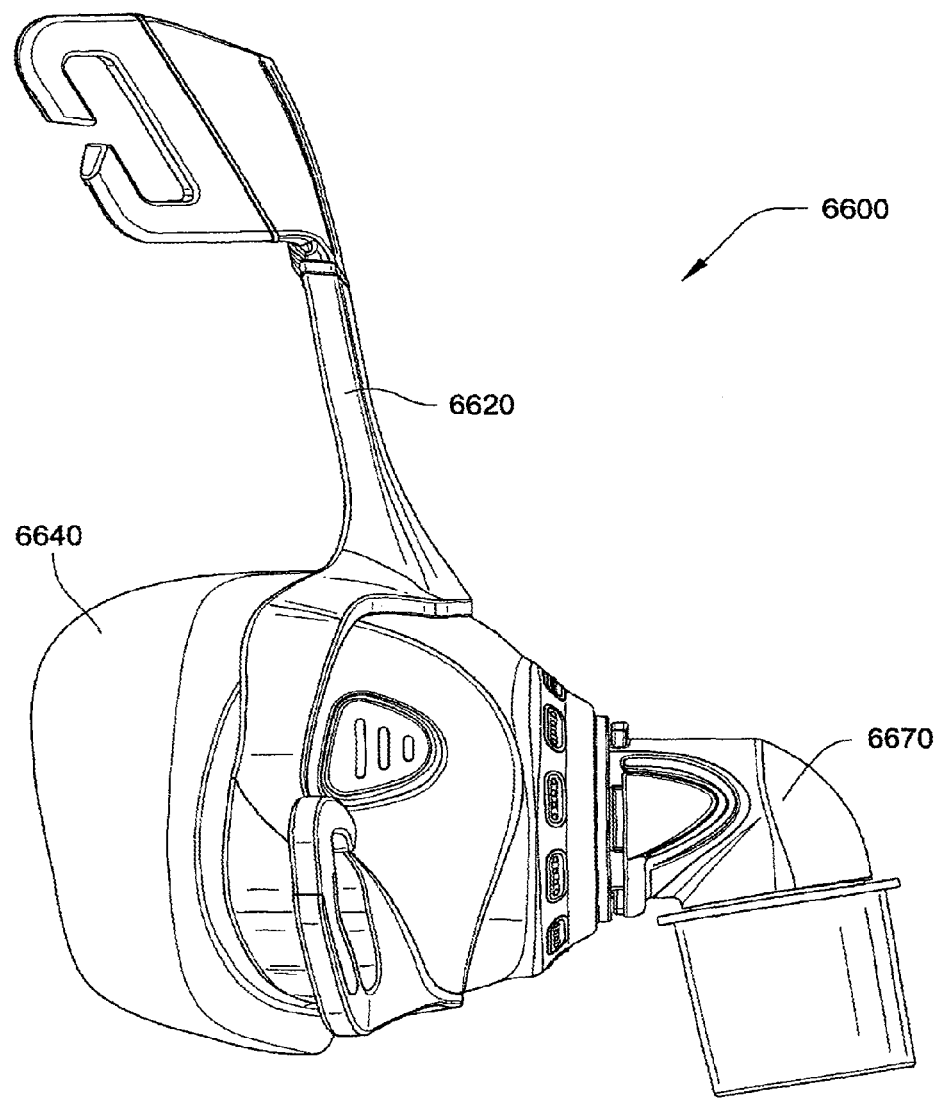
Figure 102:
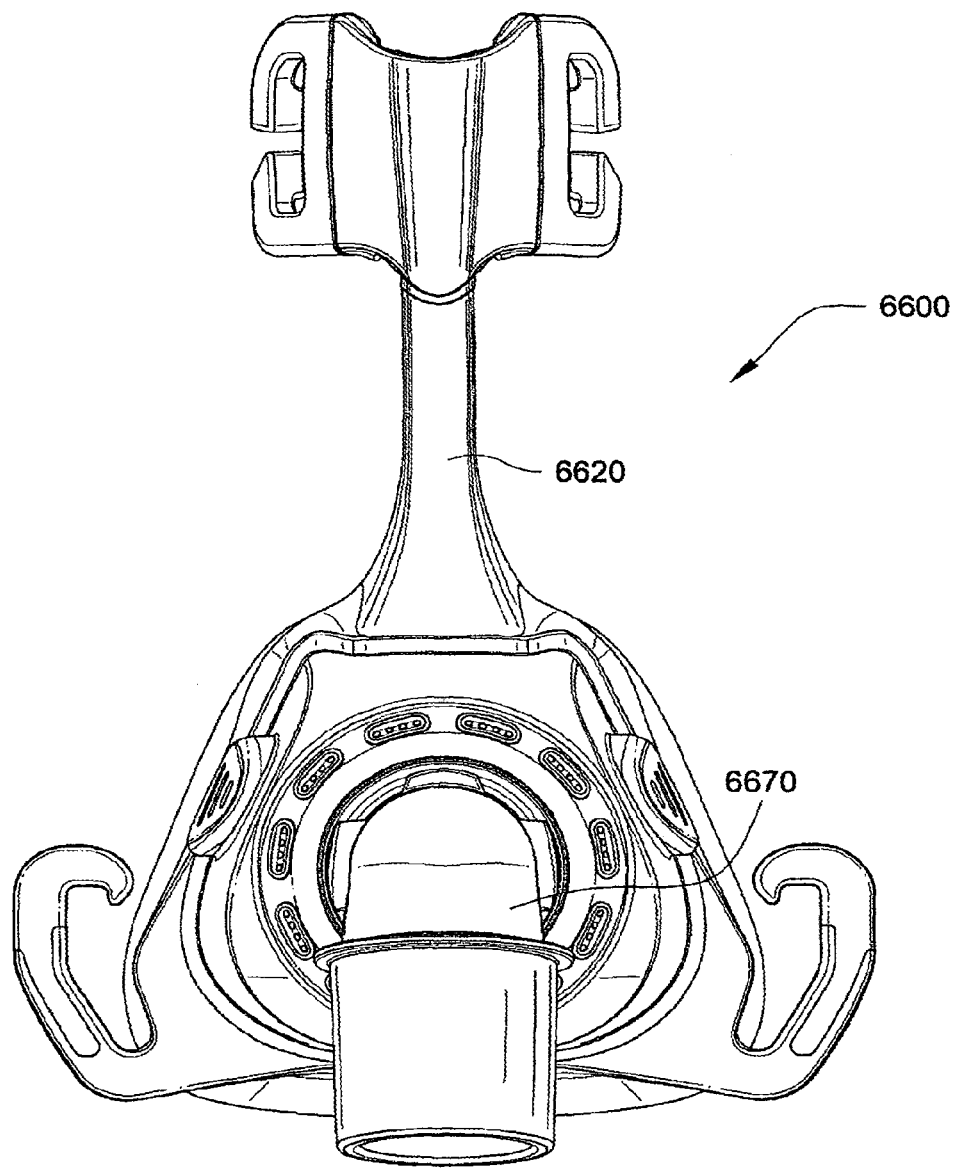
Figure 103:
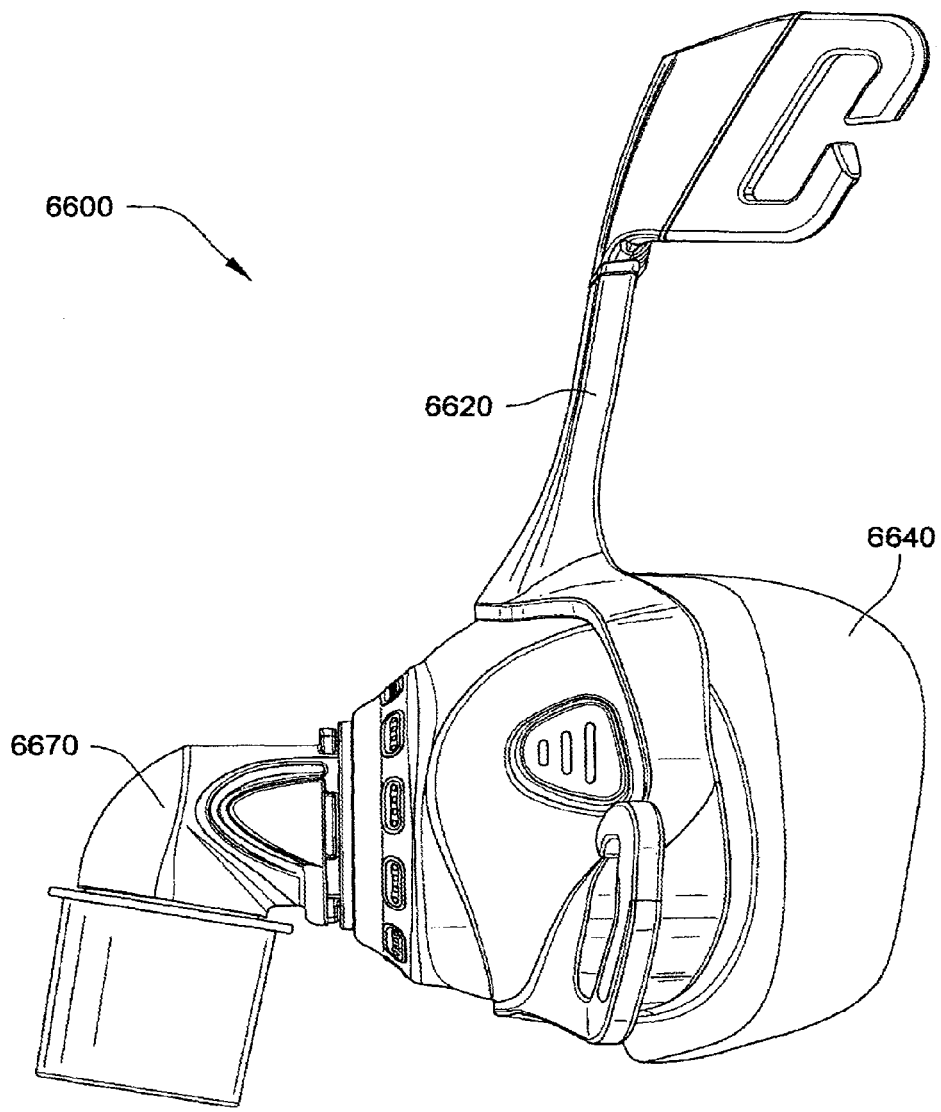
Figure 104:
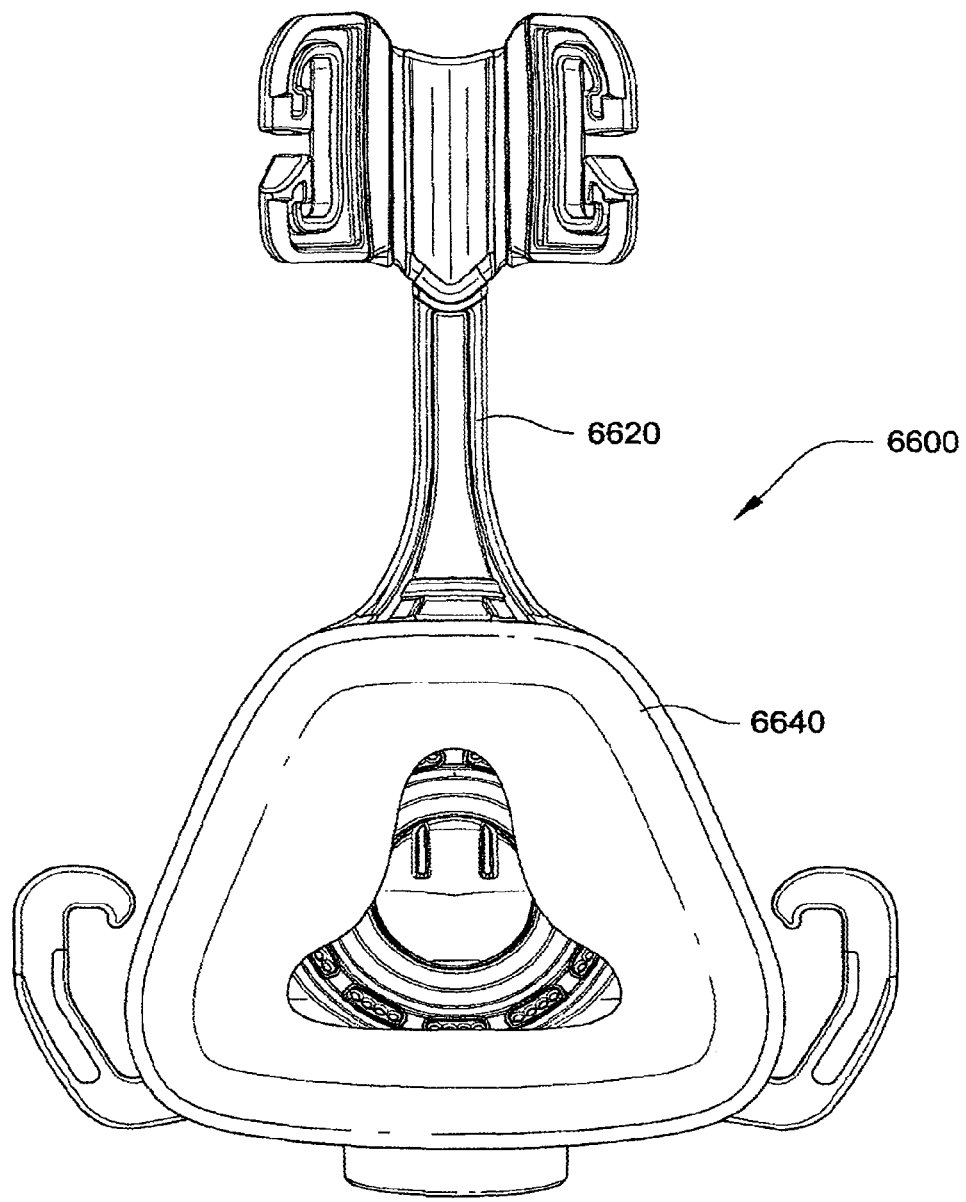
Figure 105:
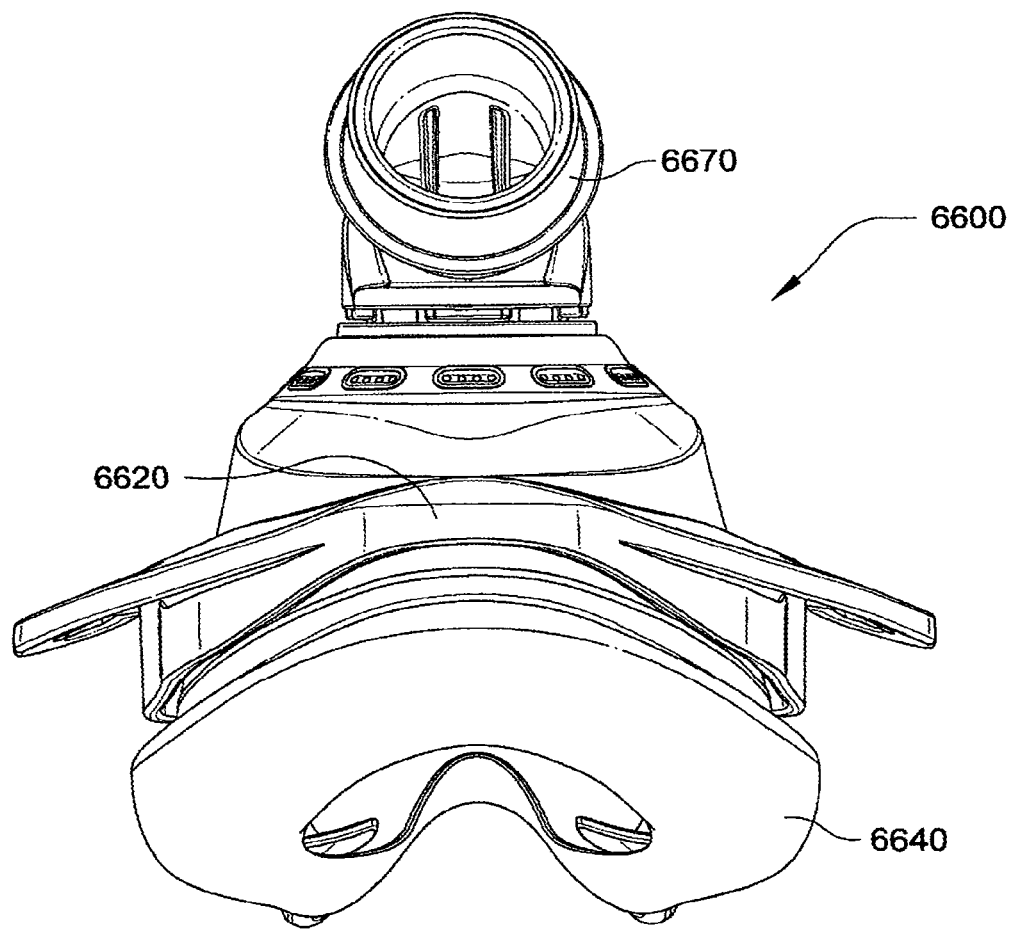

The non-face-contacting or frame side of the cushion 6540 includes elongated protrusions or locking tabs 6550 along the sides thereof to engage or interlock with the frame 2020 to secure the cushion in position, e.g., see FIGS. 97 and 98. The cushion 6540 also includes raised securing tabs 6552 along lower sides thereof to interface or engage with the frame (e.g., see FIGS. 97 and 98), and a raised top tab 6554 at the apex of the cushion to interface or engage with the frame. FIG. 95 shows the tab 6554 engaged with the frame 2020 to help retain the cushion to the frame. The raised top tab 6554 may also provide aid to robotic demolding of the cushion from the mold. However, it should be appreciated that the cushion may be connected, interlocked, and/or aligned with the frame in other suitable manners.

The non-face-contacting side of the cushion also includes an opening 6555 adapted to receive or otherwise communicate with the elbow. As illustrated, the opening may provide a vent arrangement such as that shown in FIGS. 13-1 and 13-2. However, it should be appreciated that the cushion may have alternative vent configurations, e.g., such as that shown in FIGS. 55-59.

Nasal Bridge Region

As best shown in FIG. 79, the length or depth d1 of the membrane 6546 in the nasal bridge region is in the range of about 10-30 mm, e.g., 15-25 mm, e.g., 19-20 mm, e.g., 19.58 mm. As illustrated, the depth d1 extends from about the start of the membrane (i.e., where the thin sealing portion is able to flex/hinge from the connecting portion 6547) to the tangent of the patient contacting portion. The depth d1 of the membrane in the nasal bridge region is relatively larger than those in the art and has been optimized to suit variations in anthropometry. For example, relatively high nasal bridges may extend further into the membrane, whereas relatively shallow nasal bridges may rest on the membrane with little or no flex of the membrane.

Figure 75:
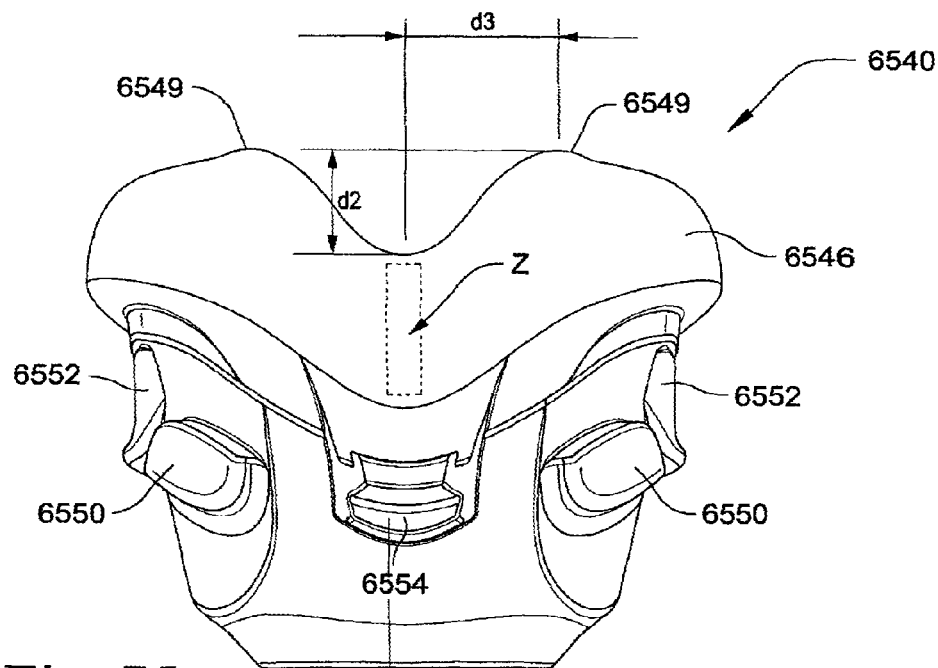
FIG. 75 is a top view of the cushion of FIG. 71.

The geometry or curvature of the membrane 6546 in the nasal bridge region when viewed from the top is also configured to fit a wide variety of patient's faces. As best shown in FIG. 75 (which shows the scallop or curvature at the nasal bridge region and raised portions 6549 at side of nose region), the depth d2 in the nasal bridge region is in the range of about 10-15 mm, e.g., 11-12 mm, e.g., 11.52 mm, and the width d3 in the nasal bridge region is in the range of about 10-20 mm, e.g., 15-16 mm, e.g., 15.35 mm.

The depth d2 is sufficient to accommodate the flattest noses, such that the edge of the membrane will sit on the nasal bridge and the raised portions 6549 will sit on respective sides of the nose. A higher nasal bridge will anchor on the sides of the nose at the raised portions and the membrane at the nasal bridge region will flex to allow the nasal bridge to move into the membrane at the nasal bridge region and stop somewhere within the zone z.

The width d3 is sufficient to accommodate wide nasal bridges. The raised portions 6549 will anchor at the sides of the nose and then the membrane will flex or stretch to accommodate the nasal bridge. The width d3 is selected to suit the widest nose, so that the raised portion always lies on the harder, boney tissue under the eye socket so as to anchor, stabilize, and position the cushion in the desired location.

In use, in one preferred form, as the membrane or sealing flap is substantially unsupported by undercushion in the nasal bridge region, when a nose moves into sealing position, the membrane is in tension on the highest portion of the nasal bridge. Furthermore, it is preferably "pinched in" on the sides of the nose in the region adjacent the highest point of the nasal bridge. The lateral force on the sides of the nose may be arranged to vary with height of nasal bridge. A deeper nasal bridge pushes further into the membrane, increasing the tension in that region, and drawing the sides of the cushion to bend, or cantilever inwards and to increase the lateral force and improving the seal on the sides of the nose. On a face with a relatively low nasal bridge, and with high cheekbones, the region of the cushion adjacent the nasal bridge may be splayed outwards, increasing a tension force in the membrane and leading it to increase a sealing force on the relatively low nasal bridge. In the preferred form of the present invention, the backup-band or undercushion is relatively free to flex inwardly and outwardly compared to prior art cushions in a region adjacent the nasal bridge. See FIGS. 116-1 to 116-3.

Side of the Nose

The undercushion 6544 at the side of the nose has been constructed so as to anchor the cushion, and position and stabilize the membrane, particularly due to curvature on the face as the nose transitions to the cheeks. This curvature can vary across patients. The undercushion positions the membrane and maintains the profile of the membrane so that it does not crinkle.

There is a flap or extending portion 6545 of the undercushion 6544 that is wider than other regions of the undercushion such as the corner of the nose region or top lip region. This arrangement ensures that very thin noses may contact the membrane in a region where the membrane is supported by the undercushion and ensure the smooth transition of the membrane from the nose to the cheeks. Wider noses will contact a wider area of the membrane and a larger portion of the undercushion will support the membrane.

Figure 74:
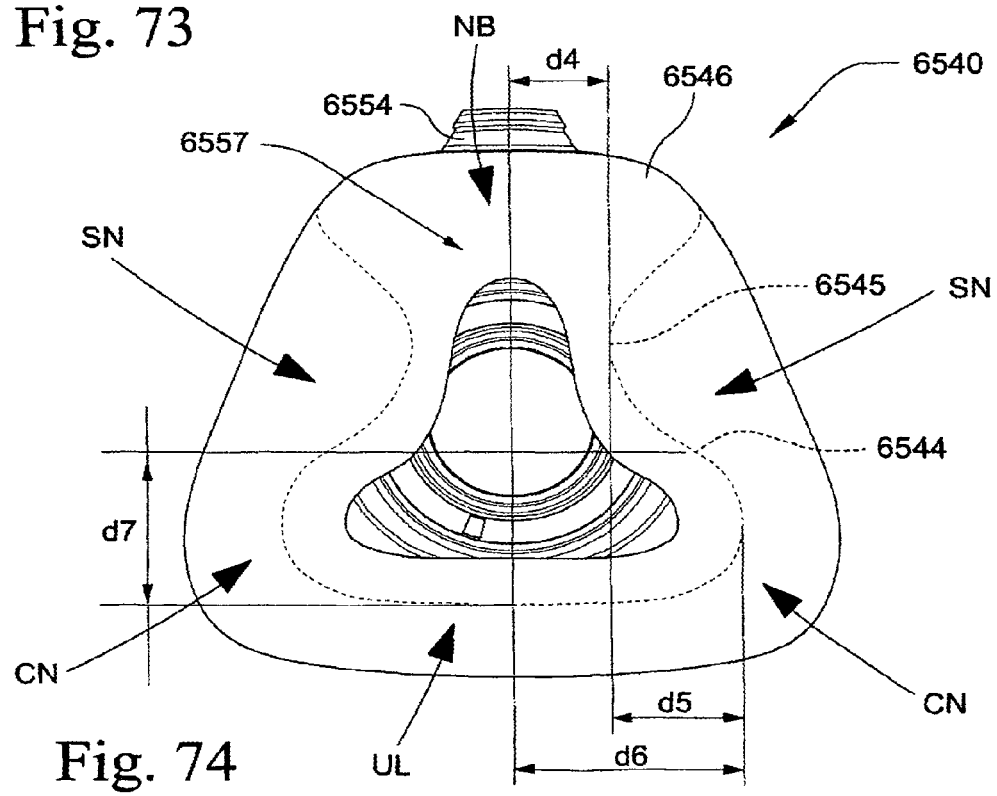
FIG. 74 is a rear view of the cushion of FIG. 71.

FIG. 74 shows various exemplary dimensions to provide an indication of the approximate location of the flap 6545 of the undercushion. In an embodiment, d4 is about 5-15 mm, e.g., 9-10 mm, e.g., 9.26 mm, d5 is about 10-15 mm, e.g., 12-13 mm, e.g., 12.80 mm, d6 is about 20-25 mm, e.g., 22-23 mm, e.g., 22.10 mm, and d7 (e.g., distance from the bottom of the flap to the top lip region) is about 10-20 mm, e.g., 15-16 mm, e.g., 15.58 mm. FIG. 75 also shows an exemplary distance d8 from the top of the flap 6546 to the approximate contact point of the cushion in the top lip region. The cushion typically sits on the patient's top lip in about the same place, but the place where the cushion is likely to sit on the nasal bridge may vary. Accordingly, the flaps are spaced a sufficient distance from the top lip region to sit on the sides of the nose.

Figure 83:
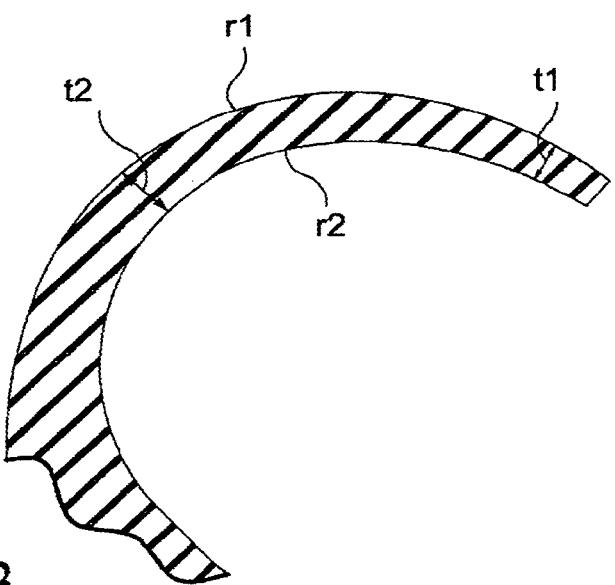
FIG. 83 is an enlarged cross-sectional view of a flap of the undercushion in the side of nose region of the cushion of FIG. 71.

FIG. 83 is a cross-sectional view through the widest portion of the flap 6545 of the undercushion 6544. As illustrated, the flap has a relatively large radius so that the undercushion may roll or flex inwards easily so that undue pressure is not exerted on the sides of the nose (e.g., such pressure may occlude the nares or cause a pinching sensation). In an embodiment, the radius r1 of the outer face is about 12-20 mm, e.g., 16 mm, and the radius r2 of the inner face is about 8-16 mm, e.g., 12 mm. Also, the thickness t1 towards the free end of the flap is about 0.5-1.5 mm, e.g., 0.9 mm, to enable easy flexing, and the thickness t2 inwards from the free end of the flap is about 1.0-1.5 mm, e.g., 1.2 mm, to encourage hinging rather than collapse of the undercushion.

The length of the flap 6545 is measured from the tip to the connection of the flap to the frame or front of the cushion. The length of the flap is about 10-30 mm. Preferably, the length of the flap is about 15 to 25 mm. Most preferably, the length of the flap is about 18-23 mm. Most preferably, the length of the flap is about 20 mm.

Crease or Corner of the Nose

Figure 81:
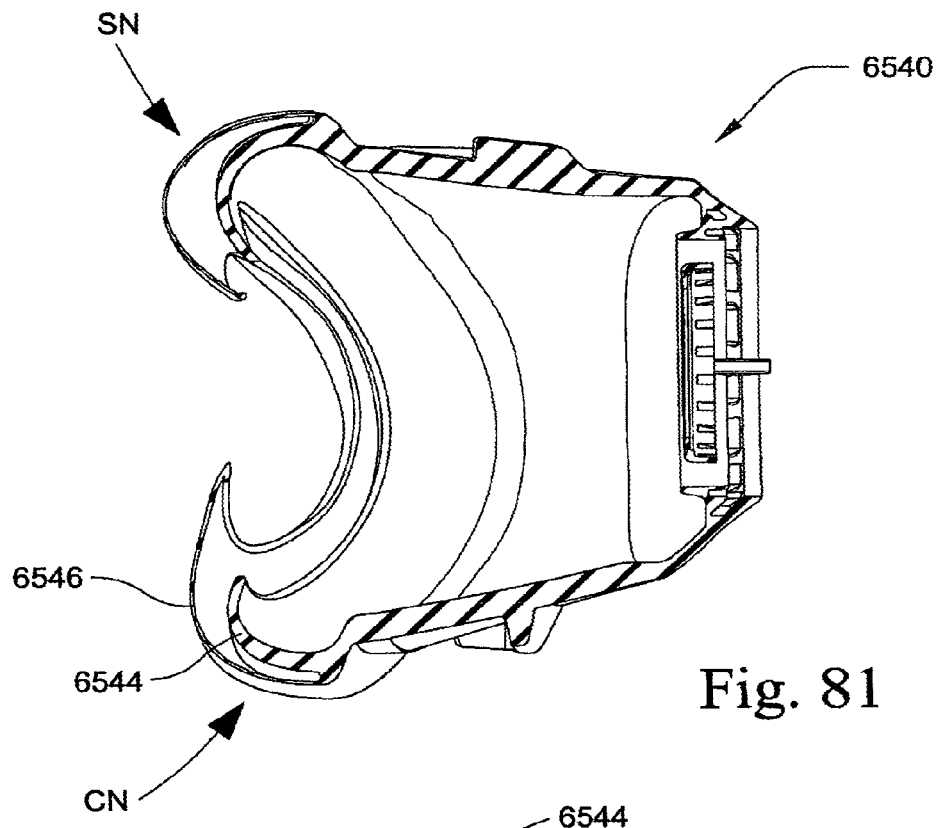
FIG. 81 is a cross-sectional view through line 81-81 of FIG. 78.
Figure 82:
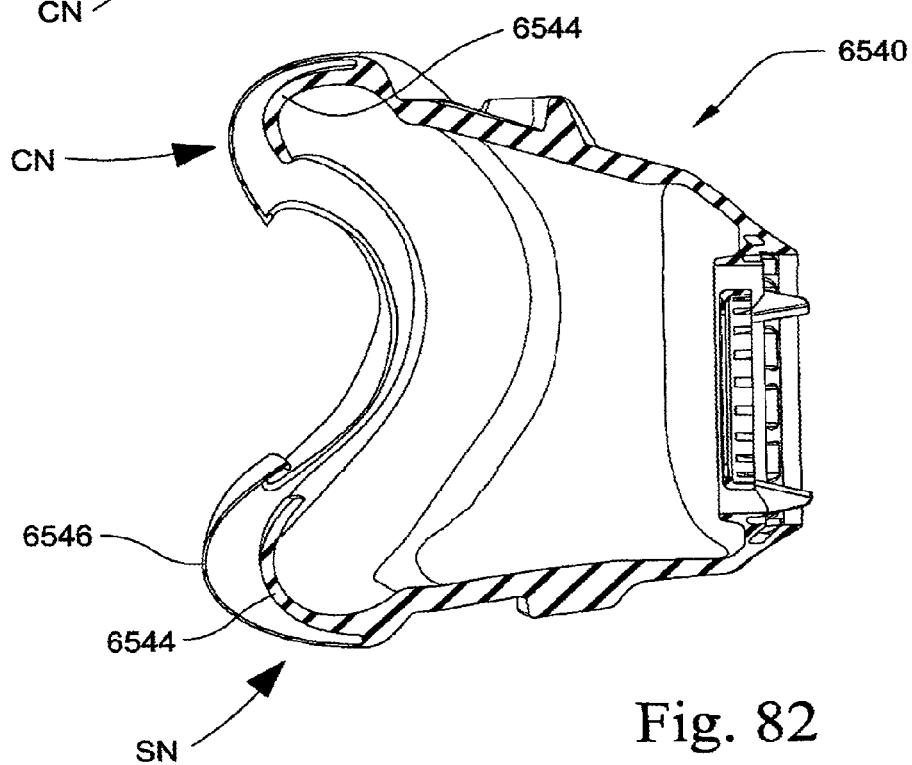
FIG. 82 is a cross-sectional view through line 82-82 of FIG. 78.
Figure 84:
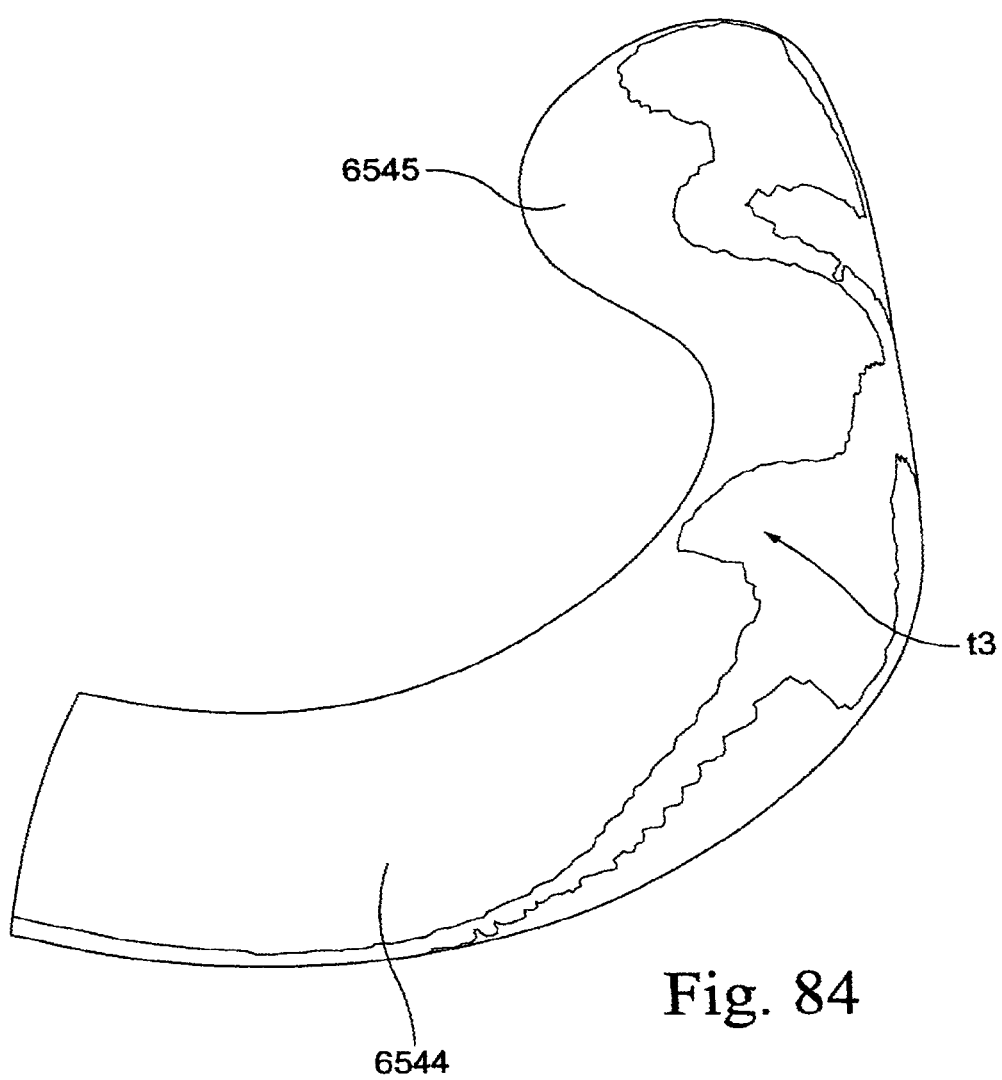
FIG. 84 is a schematic view showing localized thickening of the undercushion of the cushion of FIG. 71.

The undercushion at the crease or corner of the nose has been structured so as to stabilize or anchor the mask in this region. Also, the crease or corners of the nose are inherently difficult to seal on as the geometry of this region of the face can be complex, i.e., flares of the nostrils, top lip, and cheek regions come together in a depression and/or crease of the skin. The undercushion is stiffer in this region so as to sufficiently support the membrane such that it can be positioned to abut or conform to this more complex geometry. As shown in FIG. 84 (which shows the undercushion for half the cushion), the undercushion in the corner of nose region includes localized thickening to increase its stiffness. In an embodiment, the localized thickness t3 may be about 1-2 mm thick, e.g., 1.4 mm thick. Also, FIGS. 81 and 82 show the undercushion in the corner of nose region CN, and its relatively thicker thickness and tighter radius.

Figure 85:
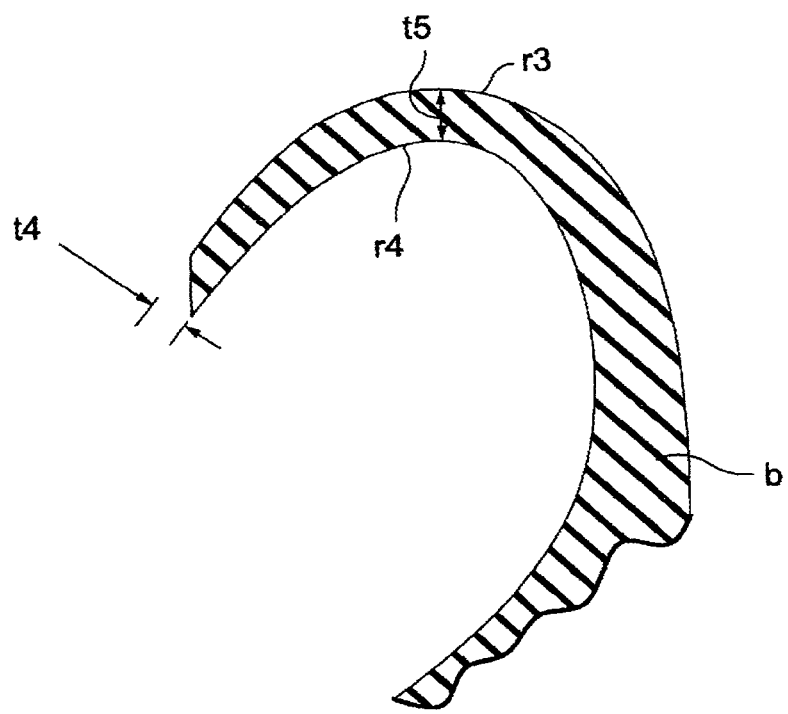
FIG. 85 is an enlarged cross-sectional view of the undercushion in the corner of nose region of the cushion of FIG. 71.
Figure 88:
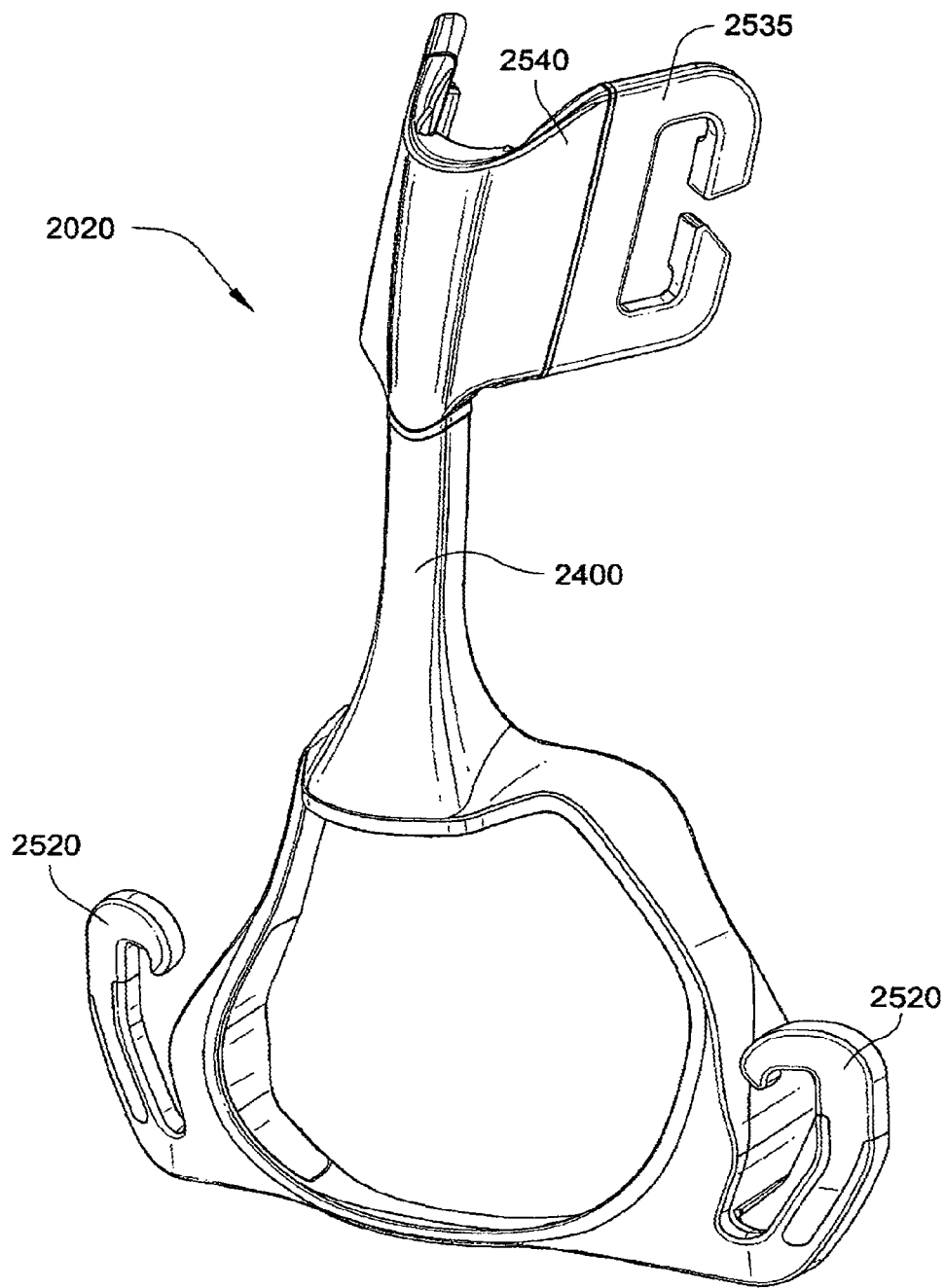
FIGS. 88 to 93 are various views of a frame according to an embodiment of the invention.

FIG. 85 is a cross-sectional view through the corner of nose region of the undercushion 6544. In an embodiment, the radius r3 of the outer face is about 5-15 mm, e.g., 8 mm, and the radius r4 of the inner face is about 2-8 mm, e.g., 4.85 mm. Also, the thickness t4 at the tip of the undercushion is about 0.5-1.5 mm, e.g., 0.85 mm, and the thickness t5 at the peak of the undercushion is about 1-2 mm, e.g., 1.4 mm. The thickness t5 at the peak is relatively thicker to stabilize the membrane and cause hinging about this point rather than at the base b of the undercushion.

Upper or Top Lip Region

As best shown in FIGS. 79 and 95, the undercushion at the upper or top lip region UL has been configured to accommodate the sensitive mouth gum tissue. Therefore, the thickness of the undercushion in this region is about 0.5-1.0 mm, e.g., 0.7 mm. The thickness of the undercushion in the top lip region may be the thinnest with respect to the other regions of the undercushion. The radius of the undercushion in the top lip region is relatively large with the intention that the cushion rests on the top lip region rather than anchoring. In an embodiment, the radius of the top lip region may not be constant, e.g., radius r5 at its center is about 65-75 mm, e.g., 72.71 mm, and radius r6 towards the corner of the nose region is about 30-40 mm, e.g., 36.85 mm.

A mask in accordance with the present technology is able to adapt the sealing forces dependent upon the size and shape of the face and nose of the wearer. For example, in the top lip region, the sealing forces may be the result of both compression forces through the undercushion or backup-band, and a tension force of the membrane or facial flap. A wider nose may splay the corners of the cushion outwards and increase the amount of tension force which is applied to the face to effect a seal. Such an arrangement may be suitable for a flatter shape of face in this region.

Relationship Between Membrane and Undercushion

In the illustrated embodiment, the membrane may vary in its distance from the undercushion in different regions of the cushion, i.e., the gap between the membrane and the undercushion may vary in different regions in the cushion. In regions of the facial topography where there is more diversity (e.g., such as the top and sides of the nose), a larger gap may be provided to allow additional area for the membrane to flex.

Figure 76:
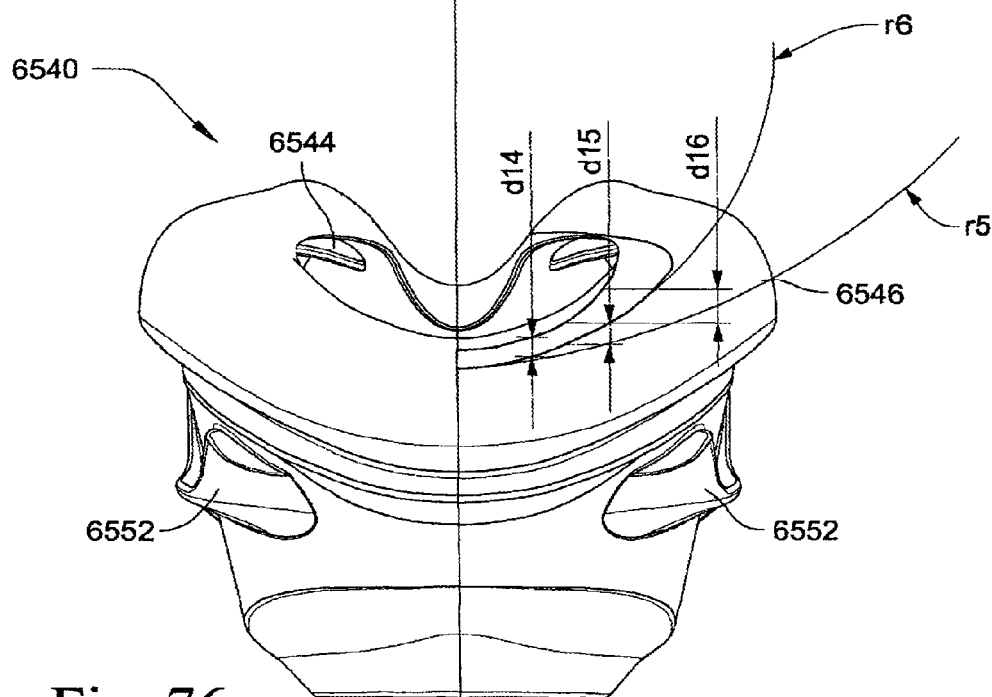
FIG. 76 is a bottom view of the cushion of FIG. 71.
Figure 77:
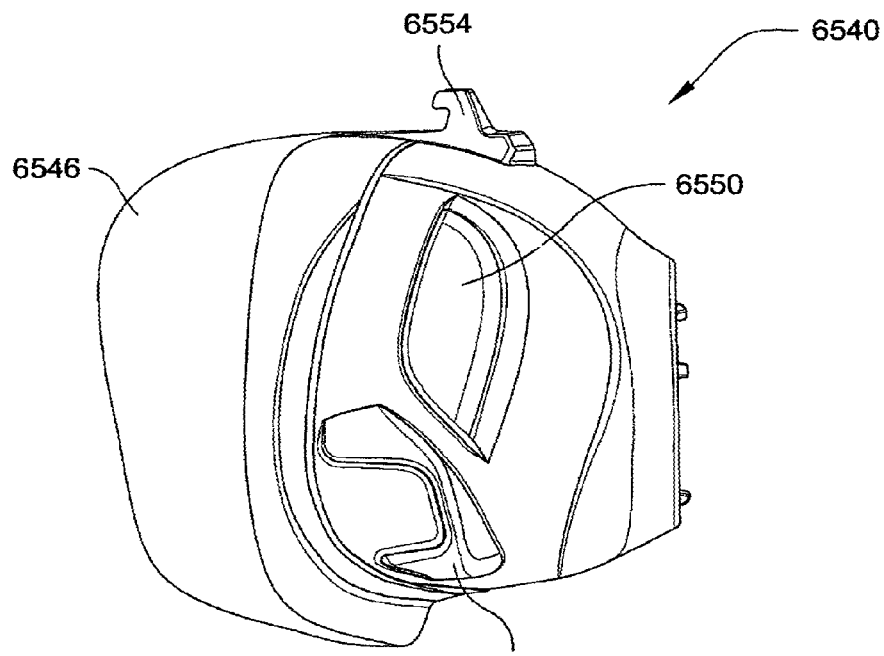
FIG. 77 is a side view of the cushion of FIG. 71.
Figure 78:
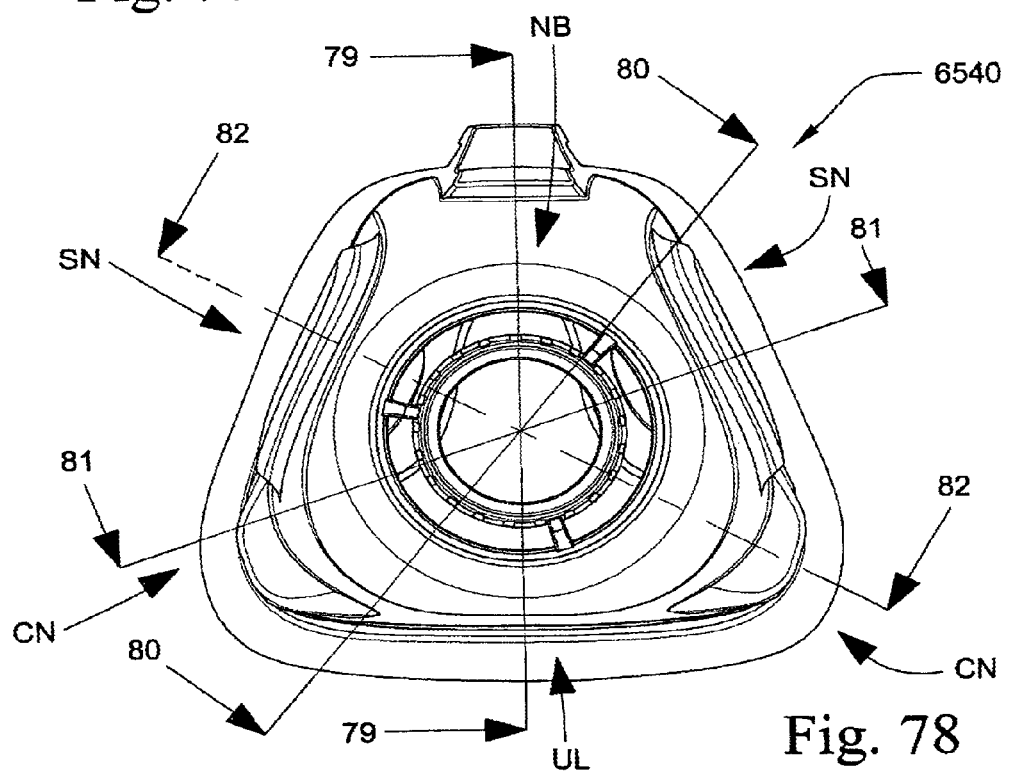
FIG. 78 is a front view of the cushion of FIG. 71 showing section lines.
Figure 79:
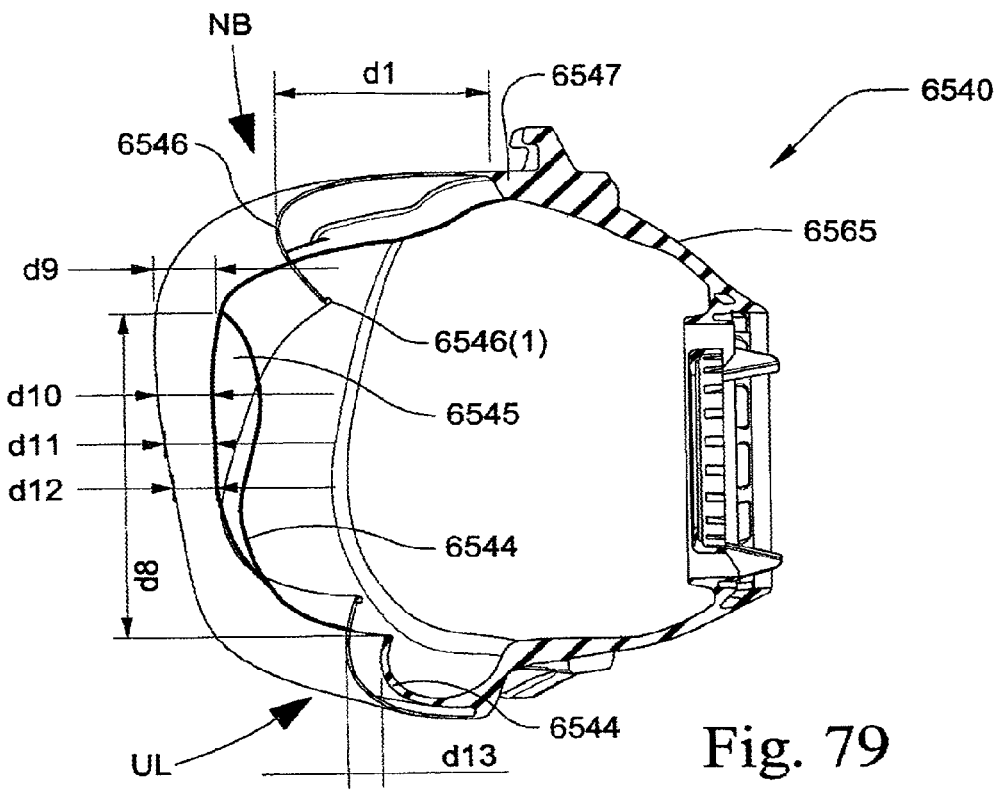
Figure 80:
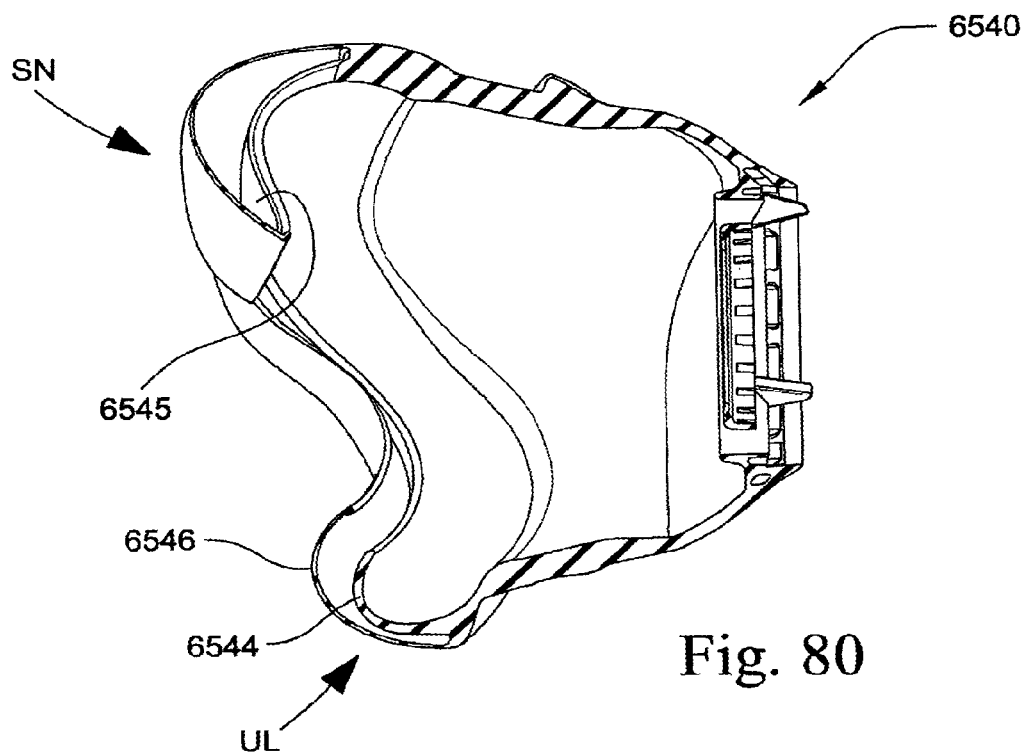
FIG. 80 is a cross-sectional view through line 80-80 of FIG. 78.

Also, in regions such as the top lip region where there is a tendency for the membrane to stretch or exert a tensile force on the top lip, a smaller gap may be provided to allow less flexibility and thus more support of the membrane. FIGS. 76 and 79 show exemplary distances of the gap between the undercushion and membrane in different regions of the cushion. In an embodiment, the distance d9 is about 5.8-6.0 mm, e.g., 5.89 mm, d10 is about 4.8-5.0 mm, e.g., 4.93 mm, d11 is about 4.2-4.4 mm, e.g., 4.29 mm, d12 is about 4.0-4.2 mm, e.g., 4.06 mm, d13 is about 3.2-3.4 mm, e.g., 3.3 mm, d14 is about 3.4-3.6 mm, e.g., 3.49 mm, d15 is about 3.7-3.9 mm, e.g., 3.76 mm, and d16 is about 3.7-3.9 mm, e.g., 3.76 mm.

Sealing Forces

FIGS. 86 and 87 are schematic views showing exemplary sealing forces of the cushion as viewed from the side and front of the patient's nose in use.

As shown in FIG. 86, the cushion in the nasal bridge region does not seal along the sellion or dip of nose indicated at A. Rather, the cushion in the nasal bridge region seals along a lower region of the nasal bridge indicated at B. Since the cushion seals lower down the nose, a relatively large cutout of the undercushion in the nasal bridge region is provided (e.g., see cutout 6557 in FIG. 74). That is, the nose is wider lower down the nose, so the cutout is sufficiently wide to accommodate a wide range of patients.

The membrane in the nasal bridge region includes a stretching effect to apply force in the patient's nasal bridge, i.e., the stretch or elasticity of the membrane is used to apply force in the nasal bridge rather than the undercushion as in other regions of the cushion. For example, the cushion is pushed onto the patient's face until no spacing or gap is provided between the membrane and the undercushion. Because no undercushion is provided in the nasal bridge region, the membrane stretches as the cushion is pushed onto the patient's face, i.e., membrane stretches across the raised portions 6549 shown in FIG. 75. The stretched or expanded membrane provides a taut, trampoline-like membrane portion to apply force in the nasal bridge.

Figures 1, 116:
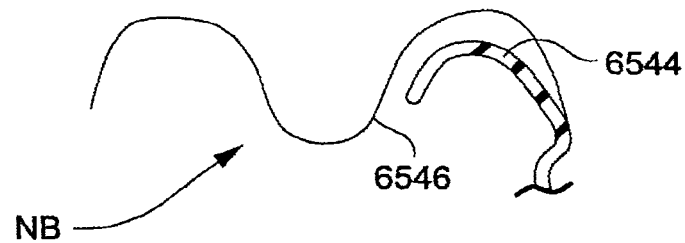
Figures 2, 116:
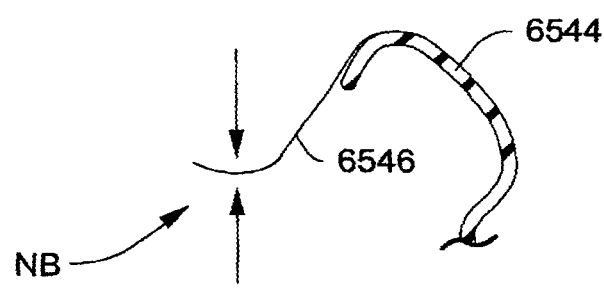
Figures 3, 116:
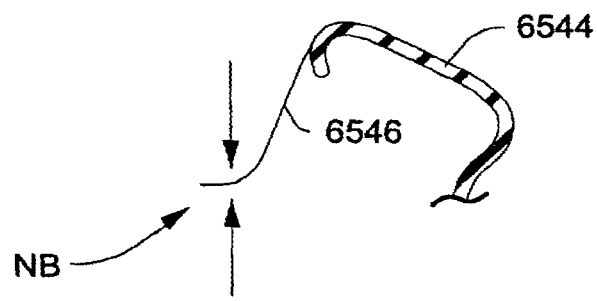

For example, FIGS. 116-1, 116-2, and 116-3 illustrate sealing in the nasal bridge region NB with stretch and tension. FIG. 116-1 shows the cushion before contact with the patient's nose. As illustrated, the membrane or facial flap 6546 is spaced from the undercushion or backup band 6544. FIG. 116-2 shows the nose contacting the membrane 6546 so that the membrane engages the undercushion, which places the membrane in tension (illustrated in this figure as a point load) across the gap defined by the undercushion in the nasal bridge region. As the nose is pushed further into the cushion as shown in FIG. 116-3, the undercushion acts as a cantilever spring and starts to bend (illustrated in this figure as a point load).

The surface of the membrane may be frosted or polished to create friction and enhance the seal. Polishing the surface of the tool may give rise to a more sticky or tacky feel and increase friction. A frosted sealing surface may be provided by increasing the roughness of the surface of the tool. A frosted surface may be preferable in some regions.

As shown in FIGS. 87 and 87-2, the curved flaps 6545 of the undercushion are configured to provide a sealing force into the sides of the nose and above the nasal vents indicated at C. The curved flaps push and/or roll in on the sides of the nose, as well as surround the nose (except in the nasal bridge region). There is no undercushion above the flaps to the apex. The gap G between the flaps is sized to fit the smallest nose population, i.e., gap is sufficient narrow to ensure that the flaps contact the sides of the nose for a wide range of patients. In an embodiment, the gap G is about 10-30 mm, e.g., 15-25 mm, e.g., 18.5 mm.

As a result of the preferred relatively large radius of the flaps 6545, each flap defines a bending point for low nose bridge-type noses that is sufficiently spaced from the stiff portion of the side wall. In use, each flap bends or rolls without the low nose bridge encountering the stiff portion of the side wall. FIG. 87-1(*a*) shows exemplary deformation of the flap for a nose low bridge, and FIG. 87-1(*b*) shows exemplary deformation of the flap for a high low bridge. This arrangement is in contrast to undercushions known in the art which have a smaller radius which may allow a wider/low nose to encounter a stiffer region of the side wall.

As shown in FIG. 87, the thickened undercushion in the corner of nose region provides a sealing force into the plane of the patient's face at the crease of the nose indicated at D. This region of the face is less sensitive and able to bear more force to stabilize the mask on the patient's face. The seal at the crease of the nose is important for nasal cushions, in contrast to a full-face cushion which passes over this region. Thus, the undercushion is relatively stiff in the corner of nose or crease region to dig in at the crease and force the cushion into the plane of the patient's face to seal and stabilize. Also, the cushion in the crease region includes a sickle shape (e.g., see FIG. 82) to provide controlled deformation in use.

The undercushion in the lip region for providing sealing force at the patient's upper lip (indicated at E in FIG. 86) is relatively less stiff (e.g., compared to the crease region) for comfort.

The shape, size, curl, and/or thickness of the undercushion may be varied to vary the force in different regions of the face.

3.4 Alternative Sealing Arrangement

FIGS. 5-1 to 5-6 show an alternative embodiment of a sealing arrangement 440. The sealing arrangement 440 may include a protrusion or protrusions 450 that are configured to be received in openings in the main body 422 of the frame 420 in a manner similar to that described above. The sealing arrangement 440 may also include a cushion as described above. For example, the sealing arrangement 440 may include an undercushion and a membrane, or a foam cushion and a silicone cushion as described above.

The cushion may have a dual wall seal, with the under cushion at the nose bridge cut out or removed. The under cushion at the upper cheeks or sides of nose may be raised to stabilize the cushion on the face of the user. The cushion may have a polished outer surface and matte inner surface. The cushion may be made from silicone or any other suitable material.

3.5 Alternative Cushion

Figures 1, 2, 3, 4, 5, 6, 7, 8, 9, 10, 11:
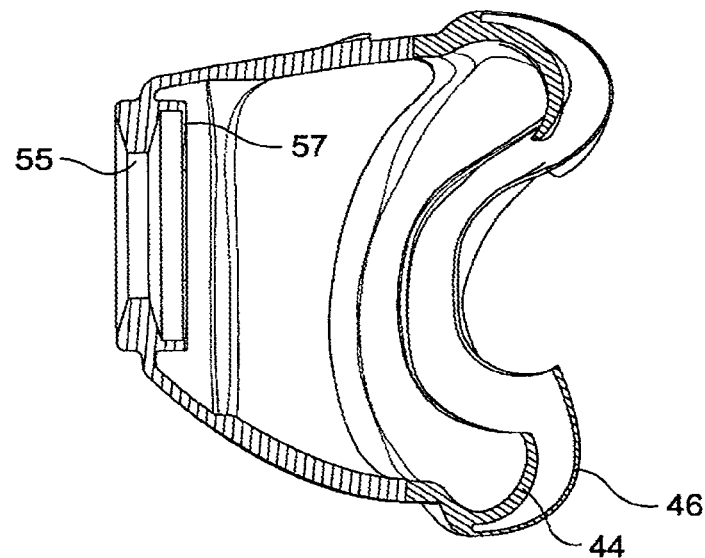

In FIG. 11-1, each side of the cushion 540 includes a protrusion 550 which provides a retention feature adapted to interlock with the frame in a manner to that described above. The top end of the frame includes a landing 541 for branding and cushion retention, and each side of the frame includes a cupped section 543 to assist with retention and tie in aesthetically with the landing at the top end of the frame.

FIGS. 11-2 to 11-9 show various views of a cushion 540-1 according to another embodiment. As best shown in FIGS. 11-8 and 11-9, the face-contacting portion of the cushion (e.g., membrane 546, undercushion 544, and side wall 542) provides a sickle-shape or question-mark configuration to enhance comfort and flexibility.

As best shown in FIGS. 11-6 to 11-9, the cushion 540-1 includes a shock absorbing portion 545 at the front of the cushion, i.e., portion between seal and elbow. The shock absorbing portion is a thinned region, e.g., 1 mm thick compared to other parts of the cushion that are 2 to 3 mm thick.

FIGS. 15-1 to 15-3 are various views of the cushion 540-1 engaged with a frame. Similar to arrangements described above, the cushion includes protrusions 550 adapted to engage or interlock with respective openings along the side wall of the frame 520.

In an embodiment, the undercushion at the top lip region may be removed so as to prevent discomfort due to pressure on the patient's top lip when cushion is in use.

In an embodiment, the patient side of the cushion may include a frosted finish and the non-patient side of the cushion may include a polished finish.

3.6 Further Alternative Cushion

An embodiment of a cushion 2010 is shown in FIGS. 33 to 39. The cushion 2010 may be designed to fit a range of patient's in a single size. In order to achieve this, various regions of the cushion 2010 may be tailored to flex and adjust to comfortably fit larger noses and smaller noses.

Membrane 2040 contacts and seals with the patient's face in use. Nasal bridge region 2041 is structured to abut the nasal bridge or top portion of a patient's nose in use. Nasal bridge region 2041 may be elastically deformable such that it may stretch over the patient's nose in use. Raised side portions 2042 may engage and compress on the sides of the patient's nose proximal to the patient's eyes in use. This compression force may stabilize the cushion into engagement at the sides of the patient's nose. The compression force may also mean that on wider noses, the nasal bridge region 2041 will stretch over the patient's nasal bridge. Alternatively, nasal bridge region 2041 may rest or abut the patient's nose without stretching. Furthermore, the nasal bridge region 2041 is deeper or longer so that patient's with high nasal bridges can position their nose on the membrane and flex the nasal bridge region 2041 of the membrane over their longer nasal bridge in use.

Side flaps 2043 are longer or extend further into the mask cushion so that the cushion may seal with a flatter or shallow nose in use. Side flaps 2043 may be flexible so that they can flex into the cushion if the patient has a higher nose bridge.

Peaks 2046 on the membrane may be raised portions or points of greater height when compared to other regions of the membrane. This may be to secure the cushion in the corners of the user's nose proximal to the nostrils or flares of the nares in use.

Upper lip region 2044 is positioned on the lower portion of the membrane and may engage or rest on the user's top lip in use. The curvature may be swept to conform to various top lip geometries of patients.

Flexible portion 2045 may be positioned proximal to the connection of the elbow or swivel ring on the cushion 2040. Flexible portion 2045 may be a region of thinned material or more flexible material to allow decoupling of the tube from the cushion.

Locking tabs 2601 may be positioned on at least one portion of the front region of the cushion. Locking tabs 2601 may have raised profile or peaks that secure the cushion in position when assembled with a frame.

Securing tabs 2661 may also be positioned on at least one portion of the front region of the cushion. Securing tabs 2661 may also be higher than other portions of the cushion to interface other otherwise engage with a frame.

Top tab 2651 may be a raised portion positioned at the apex of the cushion. Top tab 2651 may be positioned to allow for easier robot demolding of the cushion and also to engage with a frame.

Vent or swivel ring 2090 may be positioned at an orifice of the cushion to receive an elbow or supply of breathable gas. Vent ring 2090 may be molded or otherwise permanently attached with the cushion 2010. Vent ring 2090 may have vent holes around at least a portion of the perimeter to permit the exhaust of gases from the mask system.

FIGS. 40 to 45 show the cushion 2100 and the frame 2020 described above assembled to one another according to an embodiment of the present invention.

4. Elbow

The elbow 70 includes a first end portion 72 and a second end portion 74, e.g., see FIGS. 1-2, 2-2, and 2-5. The first end portion 72 provides an interfacing structure structured to interface or otherwise attach to the sealing arrangement 40. The second end portion 74 is adapted to be connected to an air delivery tube. The first portion is angled about 135° with respect to the second portion. However, the first and second portions of the elbow may have other suitable angles with respect to one another, e.g., 0°, 90°, 120°, etc.

In an embodiment, the elbow may be similar to that disclosed in PCT Application No. PCT/AU2008/001557, filed Oct. 22, 2008, which is incorporated herein by reference in its entirety.

4.1 Elbow Connection to Sealing Arrangement

The sealing arrangement 40 is structured to maintain the elbow 70 in an operative position with respect to the patient's face. That is, the sealing arrangement may act as a carrier and bearing surface for the elbow 70. The sealing arrangement and elbow may connect with a friction fit, snap-fit, mechanical interlock, or other suitable attachment mechanism. However, other suitable arrangements for attaching the elbow to the sealing arrangement are possible.

In the illustrated example, a swivel ring 90 is provided to couple the elbow 70 to the sealing arrangement 40. Such swivel ring 90 is an optional component, and it should be appreciated that the elbow 70 may be directly coupled to the sealing arrangement 40 without the swivel ring.

As best shown in FIG. 2-5, the swivel ring 90 includes an annular groove 92 along its outer circumference adapted to interlock with the annular flange 256 defining the opening 255 of the silicone cushion 242 (or opening 55 in the cushion 42 of FIGS. 1-1 to 1-4). The inner circumference of the swivel ring 90 provides a relatively smooth annular surface 94 adapted to engage the exterior surface of the first end portion 72 of the elbow 70. The free end of the first end portion 72 provides an annular bead 73 to engage the interior shoulder of the swivel ring 90, e.g., with a snap fit. Such connection holds the elbow in place (e.g., preferably a relatively airtight connection) and permits rotation or swiveling of the elbow with respect to the sealing arrangement.

The swivel ring is constructed from a more rigid material than the sealing arrangement (e.g., made of plastic, silicone, foam). This arrangement may facilitate connection of the elbow, e.g., hard elbow to hard swivel ring rather than hard elbow to soft sealing arrangement. In an example, the swivel ring may be co-molded, mechanically overmolded, and/or chemical bond overmolded with the sealing membrane or cushion, e.g., to reduce parts. Alternatively, the swivel ring may be provided as a separate part, e.g., to allow disassembly.

Figure 96:
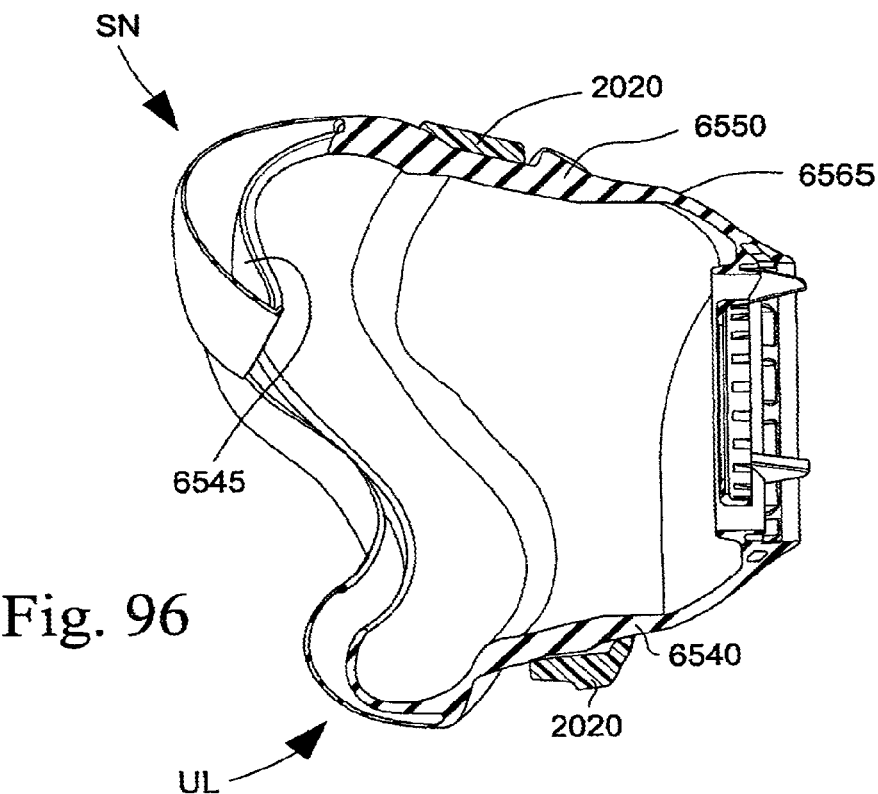
FIG. 96 is a cross-sectional view through line 96-96 of FIG. 94.

Also, the region of the cushion surrounding the opening 55, 255 may include some flexibility to allow decoupling of the elbow from the remainder of the mask system, e.g., to reduce tube drag. For example, a decoupling mechanism between the cushion opening 55 and the elbow 70 may include a flexible gimble or membrane on the cushion 42 in the region of the opening 55. A similar decoupling mechanism is described in U.S. patent application Ser. No. 12/379,940, filed Mar. 4, 2009, which is incorporated herein by reference in its entirety. The thickness of the gimble region may be ⅓ the thickness of the cushion adjacent the gimble region. Preferably, the thickness of the gimble may be less than ⅓ the thickness of the cushion adjacent the gimble region. Most preferably, the thickness of the gimble region is less than ½ the thickness of the cushion adjacent the gimble region. FIGS. 79, 96, and 98 show another exemplary gimble region 6565 at the front of cushion 6540 between the seal and elbow opening. As illustrated, the gimble region is includes thicker and thinner regions with the thinner region towards the elbow opening.

The sealing mechanism between the cushion and the elbow may be similar to that described in U.S. Patent Publication No. US 2006/0201514, which is incorporated herein by reference in its entirety.

FIGS. 4-1 to 4-4 show alternative arrangements for coupling the elbow 70 to the cushion 42. In FIG. 4-1, the cushion 42 includes an interference lip seal 57 inwardly from the opening 55 adapted to seal against an end of the elbow 70 in use. FIG. 4-2 illustrates alternative sealing arrangements for the lip seal 57 of FIG. 4-1. As illustrated, the lip seal 57(1) may seal against the end of the elbow 70, e.g., like the arrangement of FIG. 4-1. Alternatively, the lip seal 57(2) may be arranged to seal around the perimeter of the elbow 70. FIG. 4-3 shows the elbow 70 attached to the cushion 42 via a swivel ring 90 as described above. In this embodiment, the cushion provides an inwardly extending, interference lip seal 57 adapted to seal against an end of the elbow 70 in use. FIG. 4-4 shows an arrangement in which the swivel ring 90 provides an inwardly extending lip seal 91 adapted to retain the elbow 70 and/or seal around the perimeter of the elbow 70 in use.

In examples, a swivel may be provided to the second end portion of the elbow and adapted to be connected to the air delivery tube. FIG. 4-5 shows one example of a swivel 95. FIGS. 4-6 to 4-9 show alternative arrangements for forming a seal between the elbow 70 and the swivel 95. As shown in FIG. 4-6, a lip seal 96 may be provided (e.g., overmolded) to an interior surface of the swivel 95 for sealing with the elbow. As shown in FIG. 4-7, the swivel 95 may include flange portions 97(1), 97(2) adapted to overhang respective ends of the elbow 70. In this embodiment, the elbow 70 defines a channel 71 for receiving and retaining an end of the swivel 85. In FIG. 4-8, the end of the swivel 95 includes a resilient clip portion 98 adapted to clip onto a flange 73 of the elbow 70. Also, a lip seal 96 may be provided to an interior surface of the swivel 95 for sealing with the elbow 70. The lip seal 96 may be structured such that is biased into engagement with the elbow 70 in use. FIG. 4-9 shows a swivel 95 in which an internal lip seal 96 is formed separately from the swivel 95 and attached thereto, e.g., by spin weld or glue.

4.2 Vent Arrangement

As shown in FIGS. 1-1 and 1-2, the elbow 70 includes a vent arrangement 75 for gas washout. The vent arrangement 75 includes a plurality of holes (e.g., 5-100 holes, e.g., 20-50 holes, or about 45 holes). As shown in FIG. 2-5, each hole may include a contour or taper along its length. However, it should be appreciated that the vent arrangement may include other suitable arrangements, e.g., different number of holes, hole arrangement, vent insert with one or more vent holes, etc.

The vent may also, for example, be a diffuse vent as disclosed in U.S. Patent Publication No. US 2009/0050156, which is incorporated herein by reference in its entirety.

4.3 Alternative Elbow

Figures 1, 2, 3, 4, 5, 6, 7, 8, 9, 10, 11, 12:
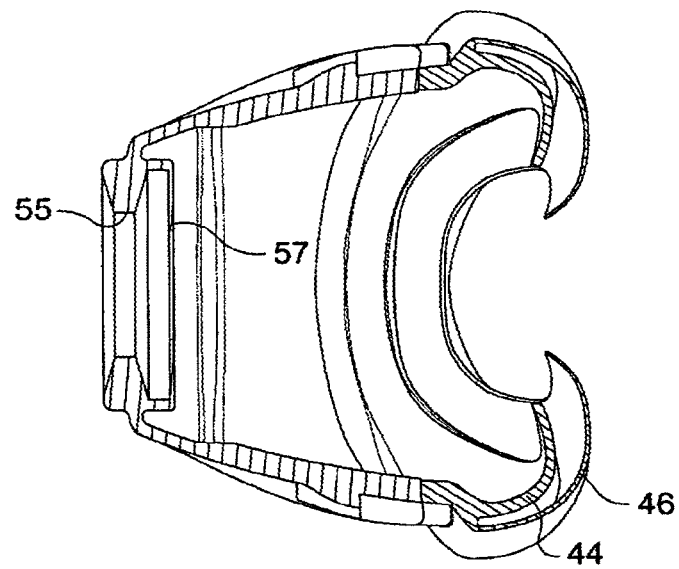
Figures 1, 2:
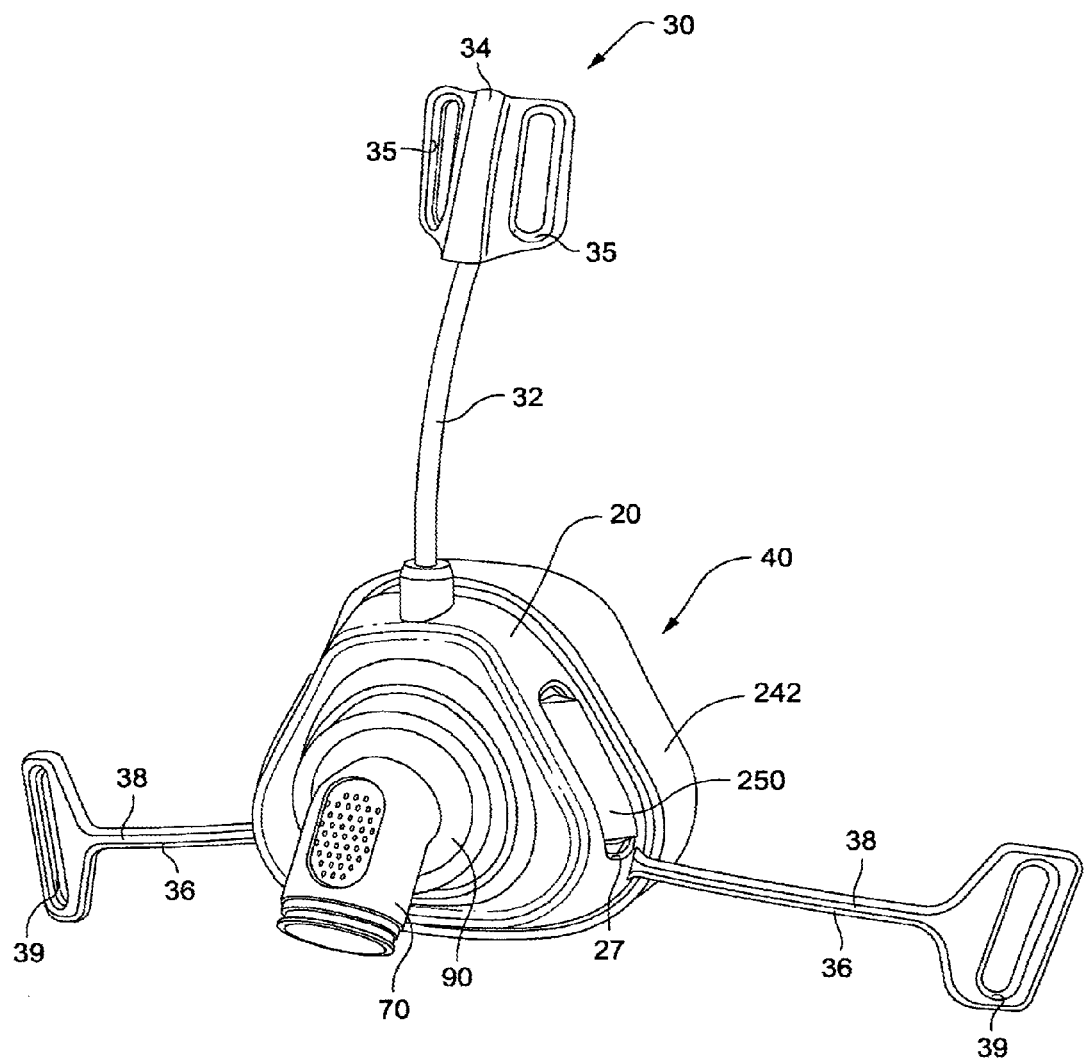
Figure 2:
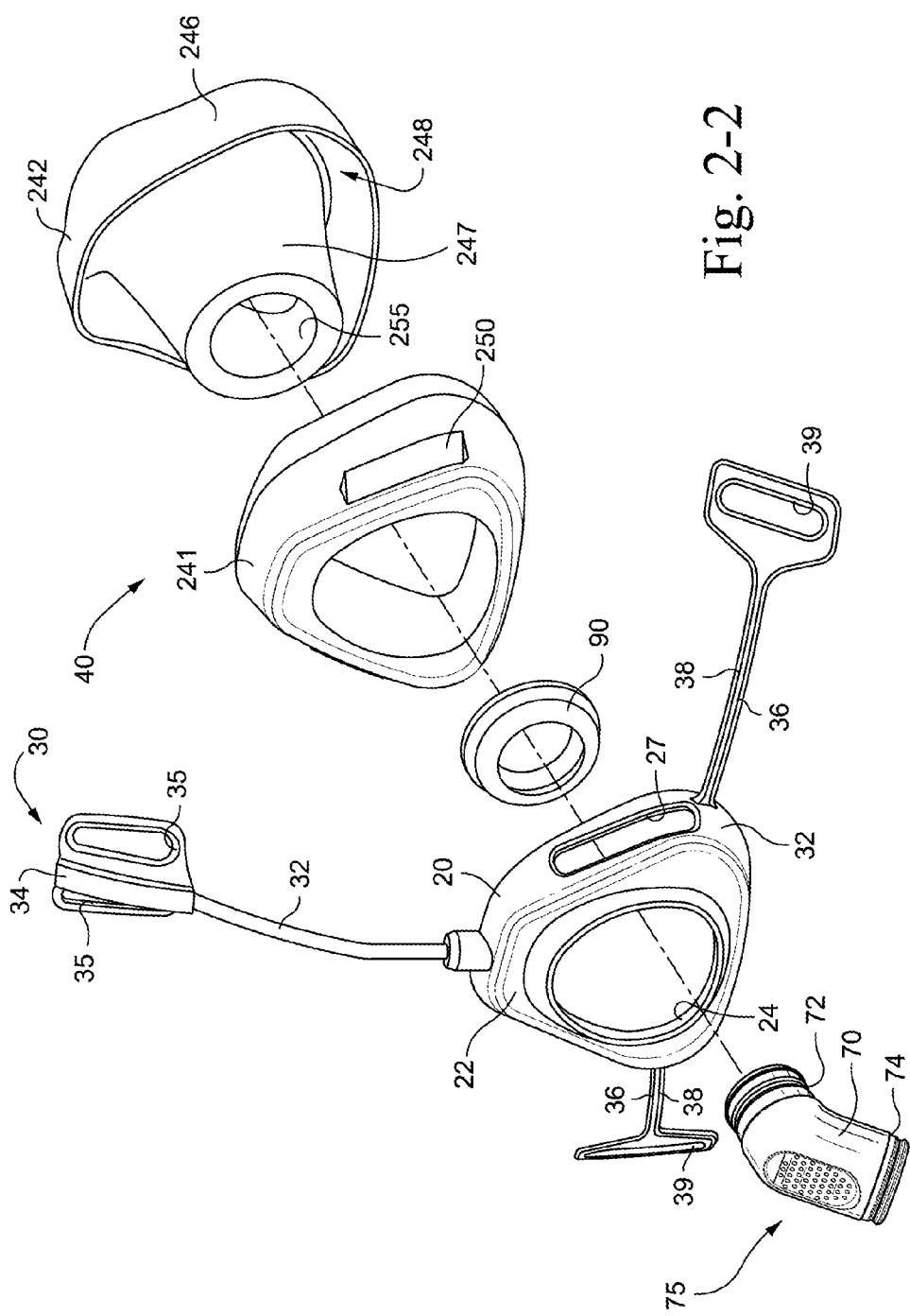
Figures 2, 3:
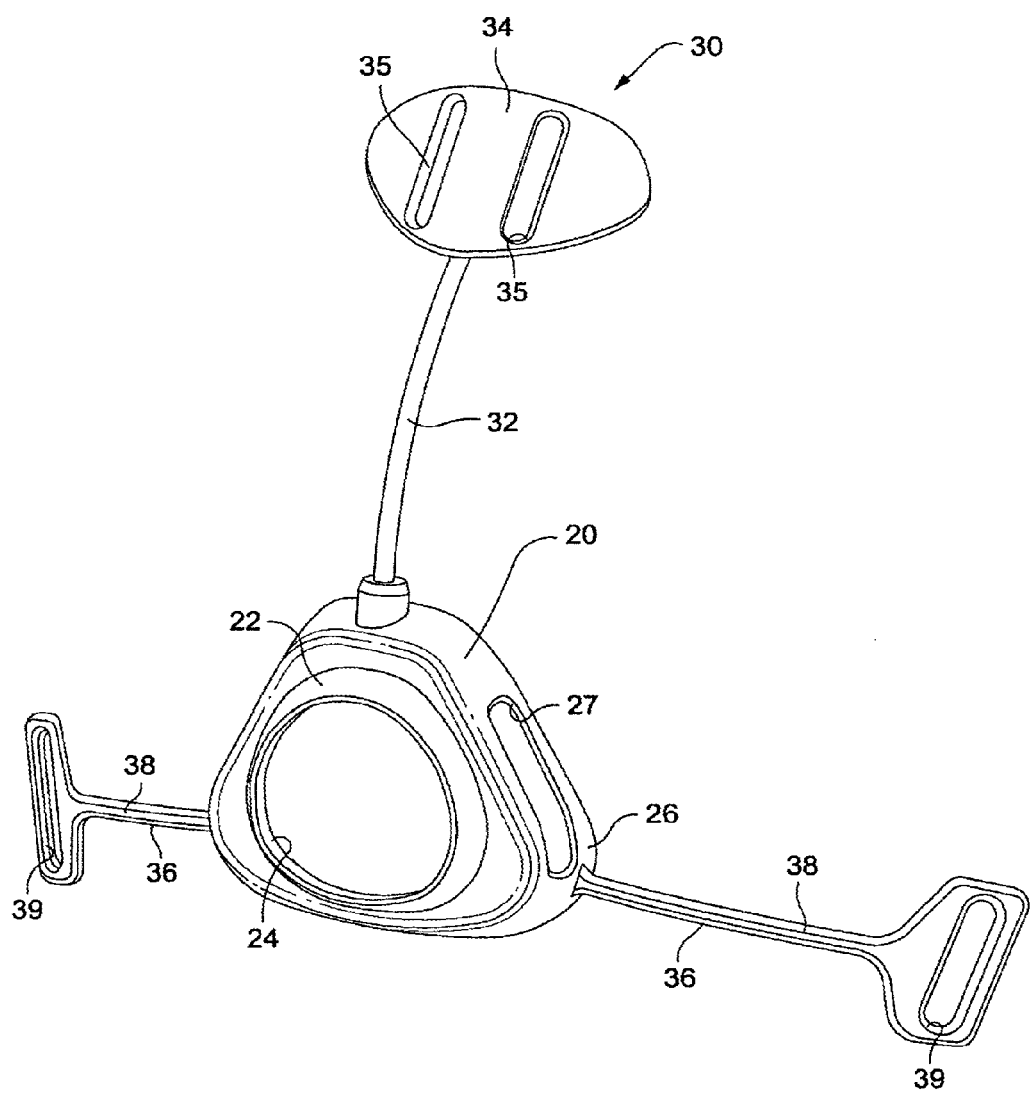
Figures 2, 3, 4:
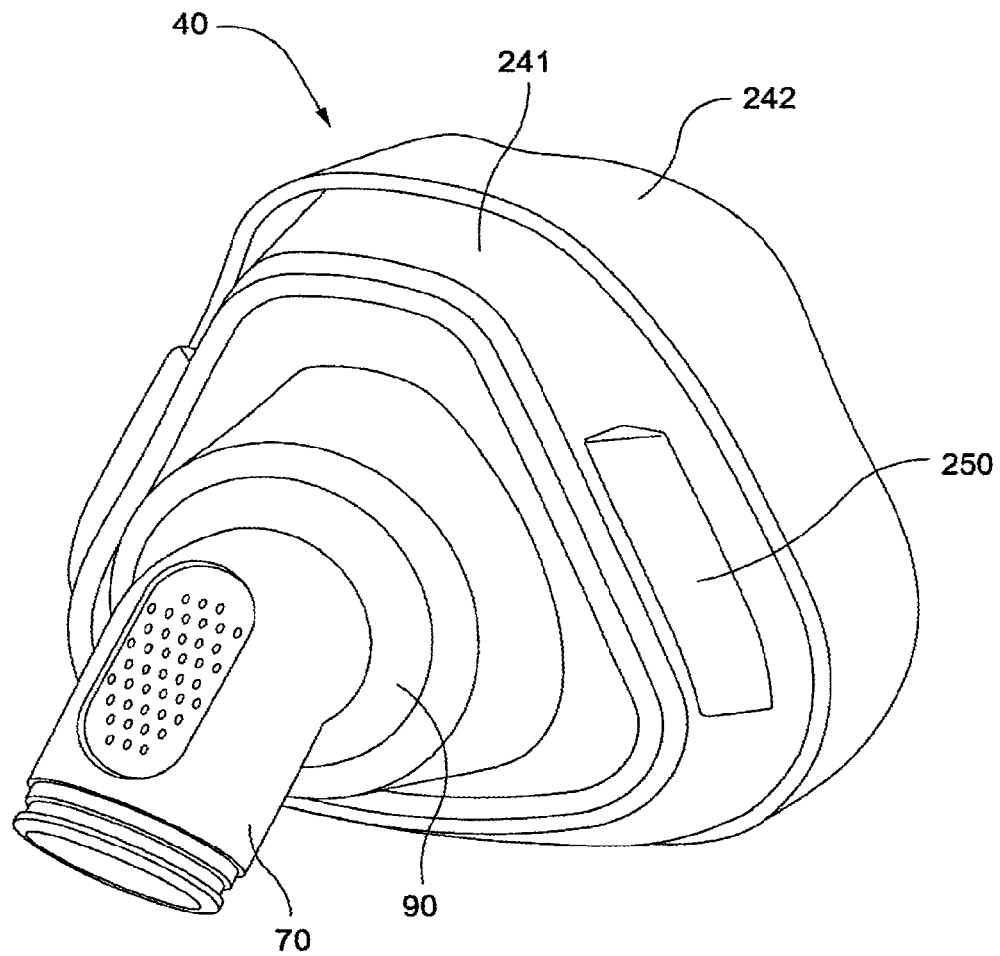
Figures 2, 3, 4, 5:
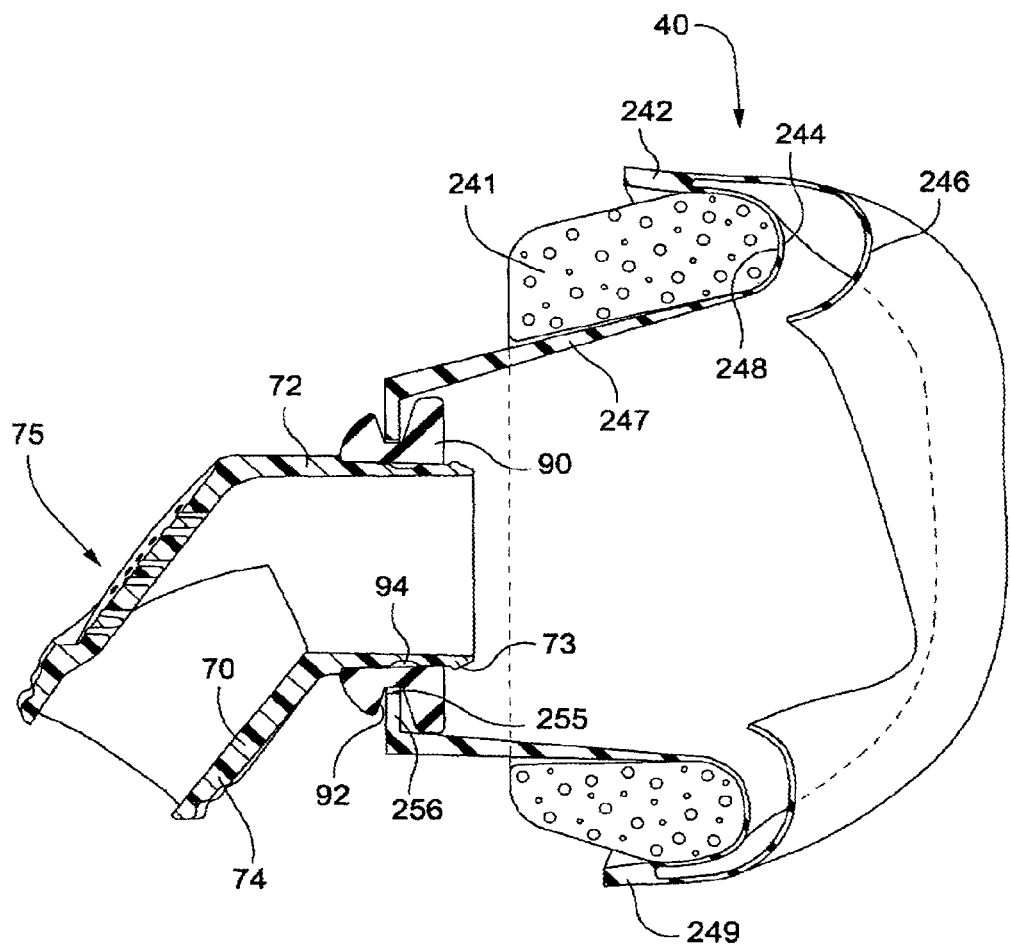

FIGS. 12-1 to 12-3 show various views of an embodiment of a non-vented elbow and FIGS. 12-4 to 12-8 show various views of another embodiment of a non-vented elbow. Each elbow 570 includes a cushion connection end 570(1) adapted to connect to the cushion and a tube connection end 570(2) adapted to connect to the air delivery tube. In FIGS. 12-4 to 12-8, sides of the elbow provide "button" points or flexible fingers 573 for the user to grab and quick release the elbow from the cushion.

As best shown in FIGS. 12-4 to 12-8, the elbow includes a flexible region 571 (constructed of soft and tactile TPE or flexible polymer) that may be co-molded with a more rigid region (constructed of polymer such as polypropylene or polycarbonate). The flexible region allows portions of the elbow to flex inwards when the patient pinches or squeezes these regions, enabling disengagement of the cushion connection end from the mask.

The arrangement also enables sealing of the elbow, a soft touch feature that adds value, some color to the part to make it more appealing, and easy assembly.

As shown in FIG. 12-9, there may be stoppers 575(1) within the elbow to prevent the flexible regions from occluding the air path in use. A support beam 575(2) may also be provided to the inside of the elbow to provide strength to the annulus of the elbow, and also to maintain the stoppers in position.

In an embodiment, a TPE portion may be molded onto the cushion connection end of the elbow to enable better seal and ease of rotation of the elbow when connected to the cushion.

The use of a vent ring as described below enables the elbow to be non-vented.

In an embodiment, the elbow may include a frosted finish.

4.4 Swivel/Vent Ring

The swivel/vent ring is provided to provide an interface between the cushion and elbow, i.e., allow elbow to connect to the cushion. As shown in FIG. 13-1, the ring 590 provides an interface 591 for cushion connection, an interface 593 for elbow connection, and vent holes 595 along the perimeter of the ring to provided diffused venting. In an embodiment, the ring may be co-molded (by either chemical or mechanical retention) with the cushion.

The ring provides ease of flow tuning (i.e., possible to add or remove vent holes), improved $CO_2$ washout, control of humidification requirements, greater diffusivity, unobtrusiveness, ease of elbow manufacture since no vent holes in elbow, and/or facilitates aesthetic freedom in the elbow.

In an embodiment, a lip seal may be provided (e.g., co-molded) with the ring. For example, as shown in FIG. 13-2, the ring may be molded with channels 596 between the vent holes 595 on the patient side, and then the vent ring may be placed in the tool for making the cushion and as the material to create the cushion is filled into the tool, some of the cushion material will flow through the channels between the vent holes to form a lip seal 597. The lip seal 597 may provide a more effective seal between the cushion 540 and the elbow 570. Molding the lip seal in the vent ring is beneficial to reduce parts for the patient to handle.

In an embodiment, the ring may be non-venting (i.e., no vent holes) for use with non-vented mask embodiments or vented elbows.

4.5 Alternative Elbow and Swivel

FIGS. 46 to 50 show an embodiment of an elbow 3000 and swivel 3500.

The elbow 3000 includes a first portion 3010 adapted to connect to a mask (e.g., vent ring 2090 of cushion 2010 described above) and a second portion 3020 provided to the swivel 3500 adapted to connect to an air delivery tube. In an embodiment, the swivel (e.g., constructed of nylon) may be overmolded to the elbow (e.g., constructed of polypropylene), e.g., second portion of elbow includes stepped shoulder 3030 for swivel overmolding and tooling shut off. However, the swivel may be connected to the elbow in other suitable manners, e.g., snap-fit. An annular ring 3600 is provided to the swivel, which provides a stop for connecting the air delivery tube.

The first portion includes a flexible quick release mechanism for attaching the elbow to the mask, e.g., vent ring 2090 of cushion 2010. The mechanism includes a button 3100 on one or both sides of the first portion and a groove 3200 surrounding each button that allows the button to flex with respect to the first portion. The button is raised for ease of use and pinch travel. The profile shape of the button may change, e.g., for function and/or tooling. Also, each button includes a tab or catch 3040 adapted to engage the vent ring 2090, e.g., with a snap-fit, to releasably secure the elbow to the cushion 2010.

Moreover, at least a portion of the button is constructed of a soft, tactile material (e.g., TPE), e.g., to aid ease of use. As best shown in FIGS. 49, 53, and 54, a channel 3070 is provided between the buttons to allow flow of TPE or soft tactile material. Also, interior stops 3300 are provided to prevent the buttons from being pressed too far into the elbow cavity and possibly breaking.

As illustrated, upper and lower tabs 3050 are provided to the first portion to interface with the vent ring 2090 and prevent the elbow from pushing too far into the vent ring.

Figure 108:
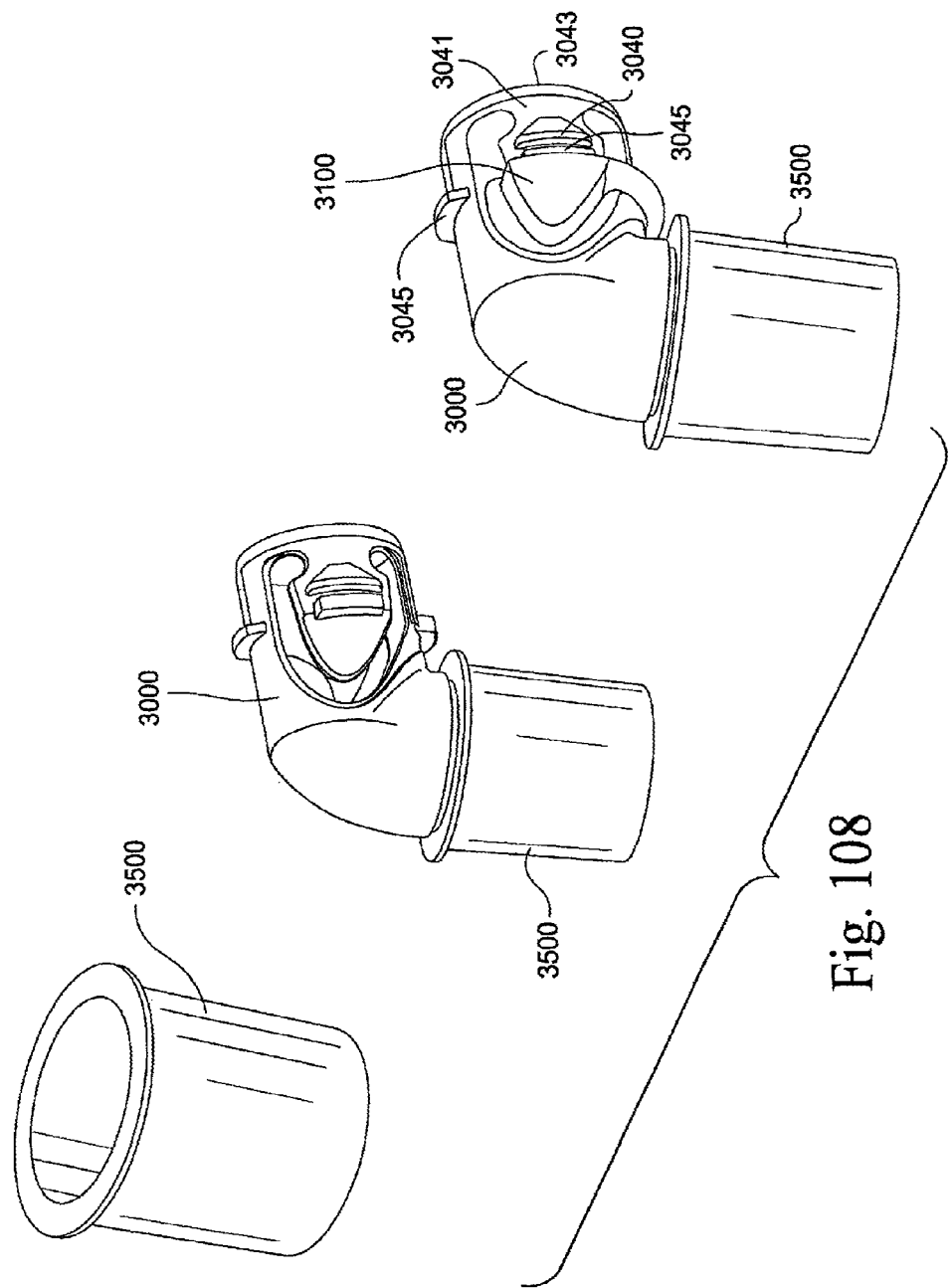
FIG. 108 is an assembly view of an elbow according to an embodiment of the invention.
Figure 109:
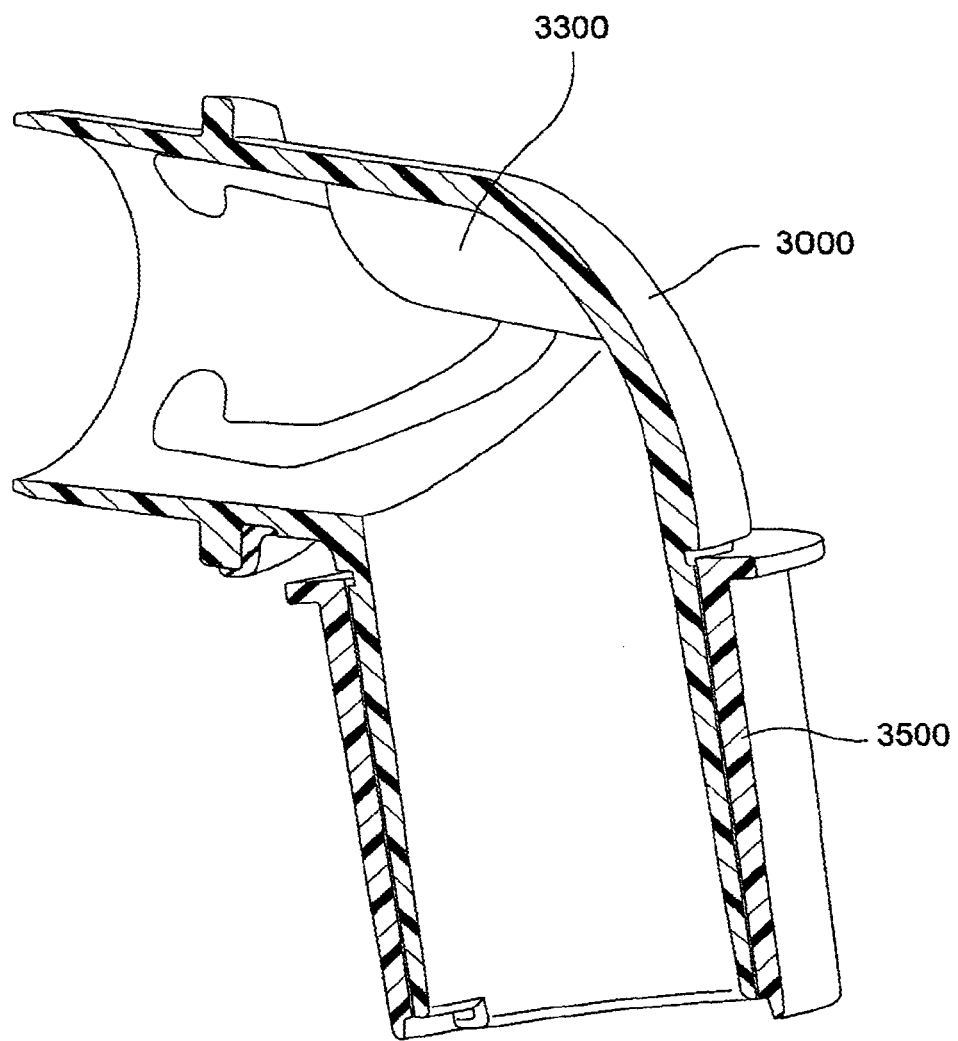
FIG. 109 is a cross-section view of the elbow of FIG. 108.
Figure 110:
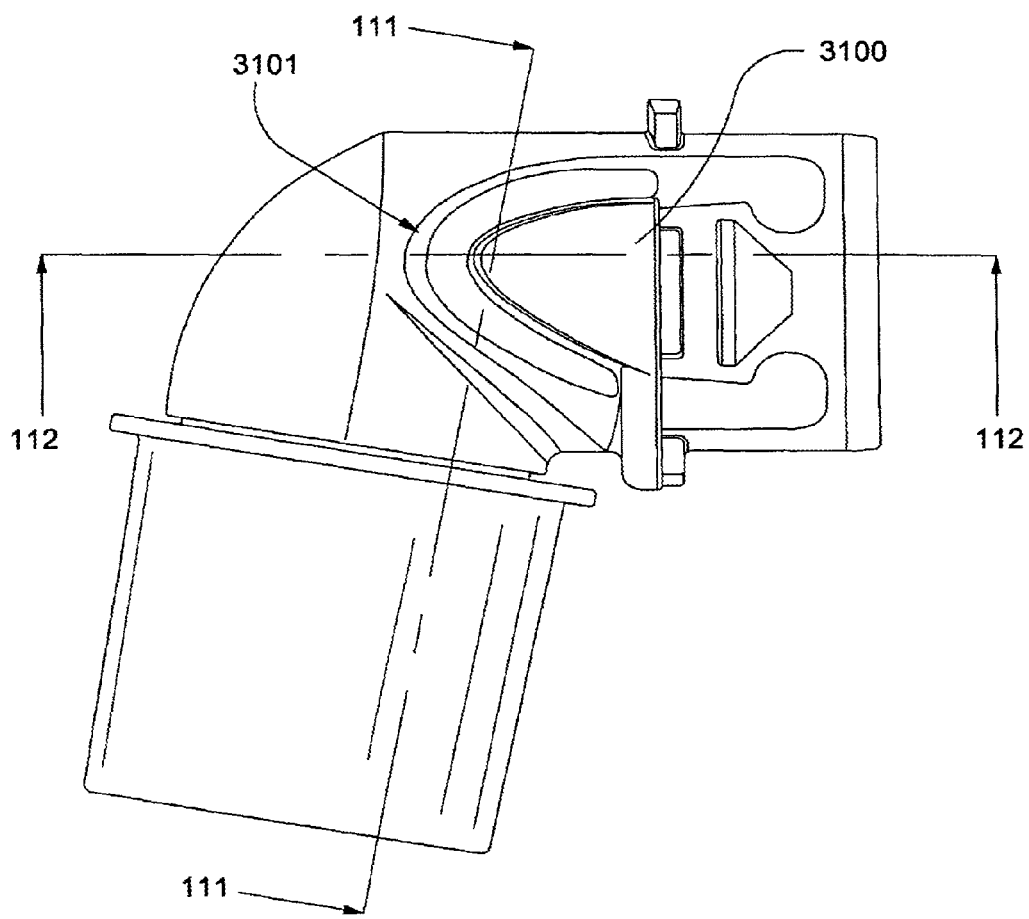
FIG. 110 is a side view of the elbow of FIG. 108.
Figure 111:
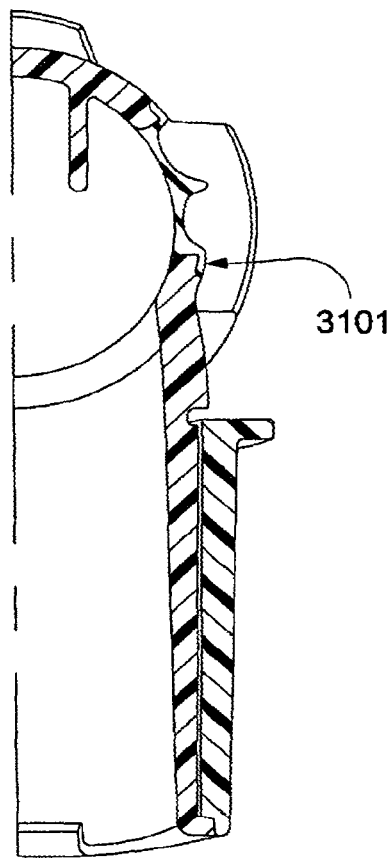
FIG. 111 is a cross-sectional view through line 111-111 of FIG. 110.
Figure 112:
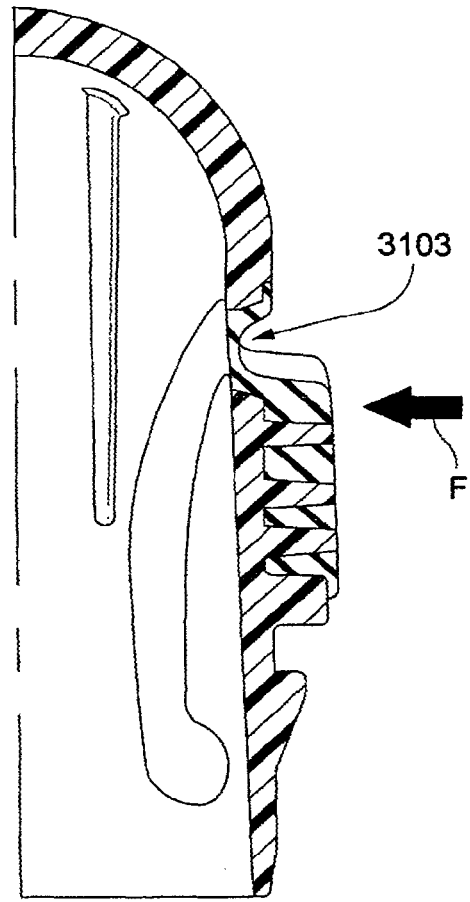
FIG. 112 is a cross-sectional view through line 112-112 of FIG. 110.
Figure 113:
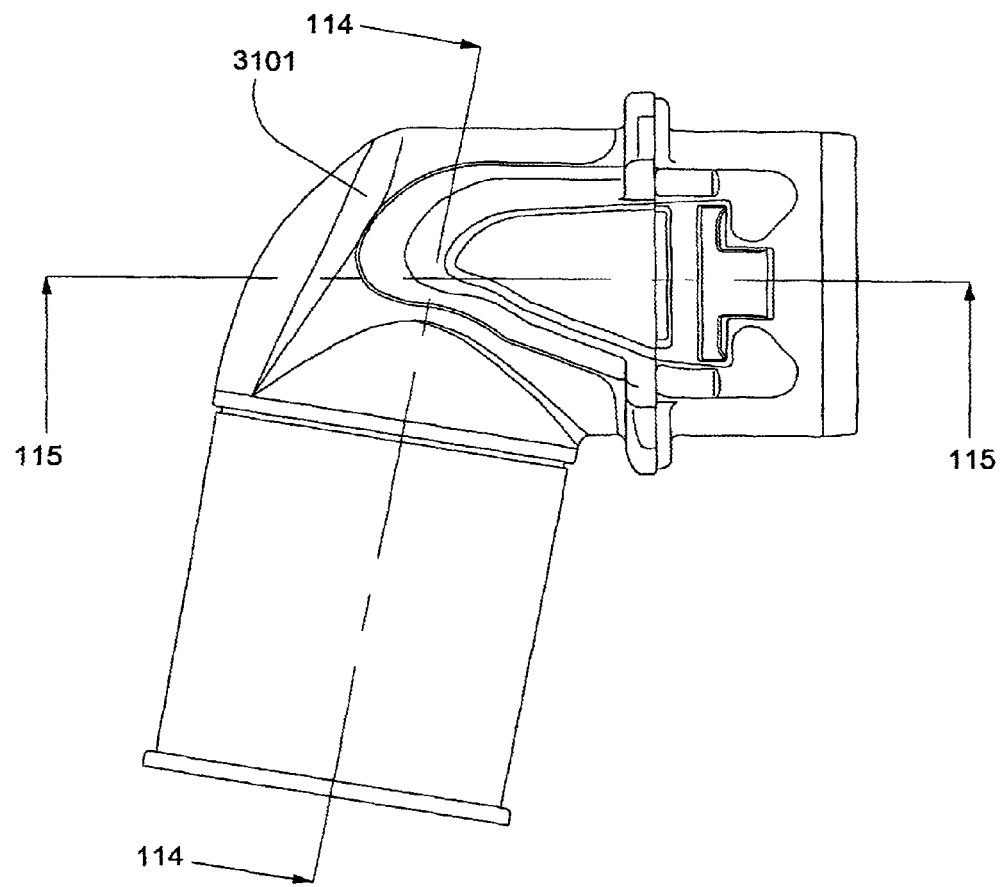
FIG. 113 is a side view of an elbow according to an embodiment of the invention.
Figure 114:
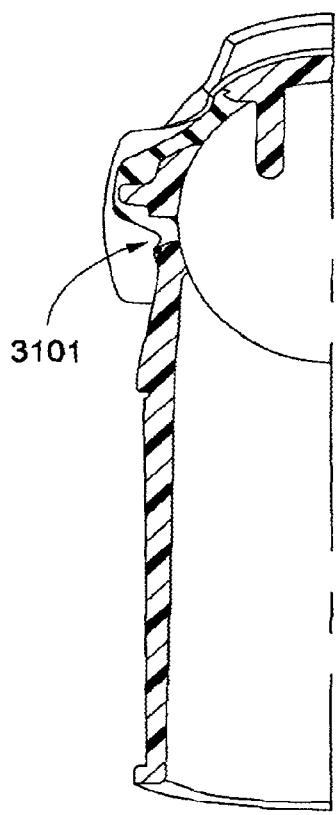
FIG. 114 is a cross-sectional view through line 114-114 of FIG. 113.
Figure 115:
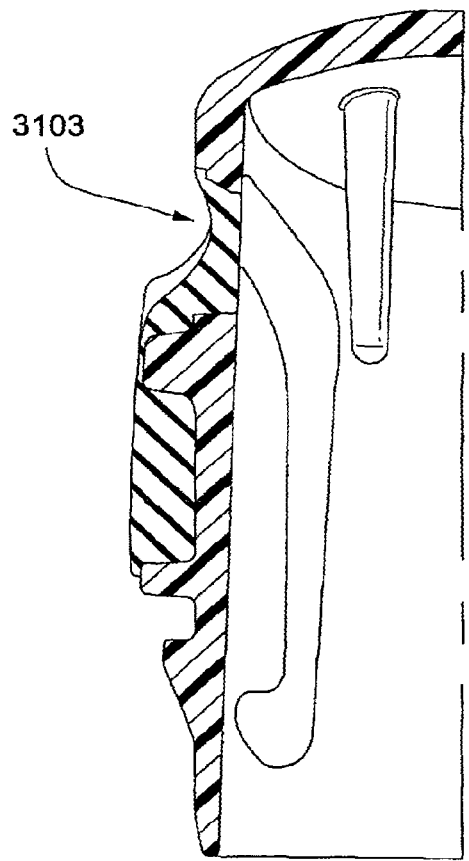
FIG. 115 is a cross-sectional view through line 115-115 of FIG. 113.

FIGS. 108-112 show alternative views of the elbow. FIG. 108 shows the overmolding of the swivel 3500 to the elbow 3000, and then the overmolding of the buttons 3100 to the elbow. As illustrated, the elbow includes a retention catch 3040, a bearing surface 3041 to facilitate rotation relative to the cushion, a sealing edge 3043 for sealing with the cushion, and an insertion stop 3045 (provided on top, bottom, and sides of the first portion of the elbow) that provides a stop for connecting the cushion. FIG. 109 shows an interior stop 3300 to prevent a respective button from being pressed too far. As shown in FIGS. 110 and 111, the button 3100 may include a step 3101 (e.g., 0.85 mm or greater) along its perimeter that overhangs the elbow. Such step provides a flat even section for button movement in use. In an alternative embodiment, as shown in FIGS. 113 and 114, the step may be thinner (e.g., 0.35 mm). As shown in FIG. 112, the button may include a generally thin (e.g., about 0.4 mm thick) and concave section 3103 along its perimeter to facilitate button depression. Section 3103 may be formed from an elastomer such as TPE or silicone. Section 3103 may seal the buttons to the elbow body so as to seal the air path through the elbow. In an embodiment, the depression force F may be less than about 10 N. In an alternative embodiment, as shown in FIG. 115, the concave section 3103 may be thicker 3103 (e.g., about 1.3 mm) which may increase the depression force. It should be appreciated that the thickness of the concave section may be tuned to adjust the force.

As noted above, venting for the mask is provided by the vent ring 2090. This arrangement provides several advantages, e.g., ease of flow tuning, improved $CO_2$ washout, control of humidification requirements, greater diffusivity, unobtrusive, ease of elbow manufacture, and/or facilitates aesthetic freedom in the elbow.

5. Alternative Vent Assembly

FIGS. 55 to 59 show an alternative vent 4000 that may be molded into or with another part of the mask assembly. An embodiment of the present invention relates to an assembly of interconnected vent structures joined together by element or structure in a first position that can be deformed to cause the vent structures to move to a second position.

An embodiment of the present embodiment relates to a vent 4000 being molded into a cushion 4500, however it is possible for vent 4000 to be molded into any other part of the mask assembly in the air path, for example a tube, an elbow or a frame.

Vent 4000 may comprise a first structure to interconnect the vent arrays, where if the shape of the first structure is changed the arrangement or position of the vent arrays is also changed.

Figures 3, 55:
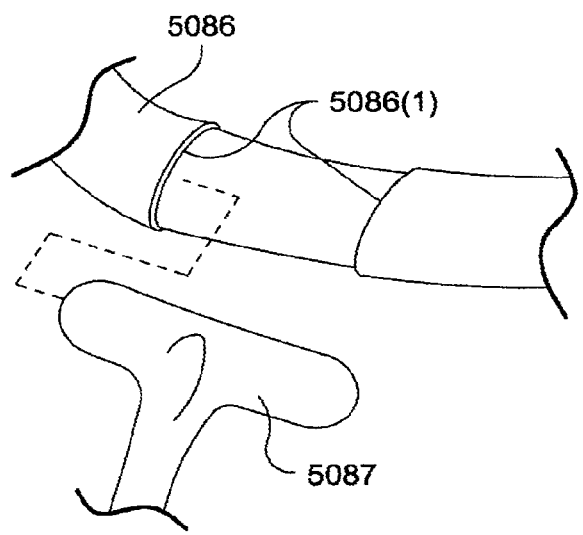

FIG. 55 shows an embodiment of vent 4000. The first structure may comprise a stem 4100 and/or at least one branch 4150. Stem 4100 may support the array of vent branches 4200. Stem 4100 may be central to the branches 4150. Stem 4100 may position and/or maintain branches 4150 in a defined spacing or array. Stem 4100 may also be structured to aid alignment of the vent 4000 with respect to the cushion 4500 or other mask system element (e.g., elbow, frame, etc.).

The embodiment of stem 4100 shown in FIG. 55 has a ring or circular structure. It should be appreciated that stem 4100 may have an alternative configuration such as a rectangle, triangle or any other shape that meets the desired outcomes of positioning and aligning the vent 4000 in the mask system and spacing the branches 4150.

Figure 58:
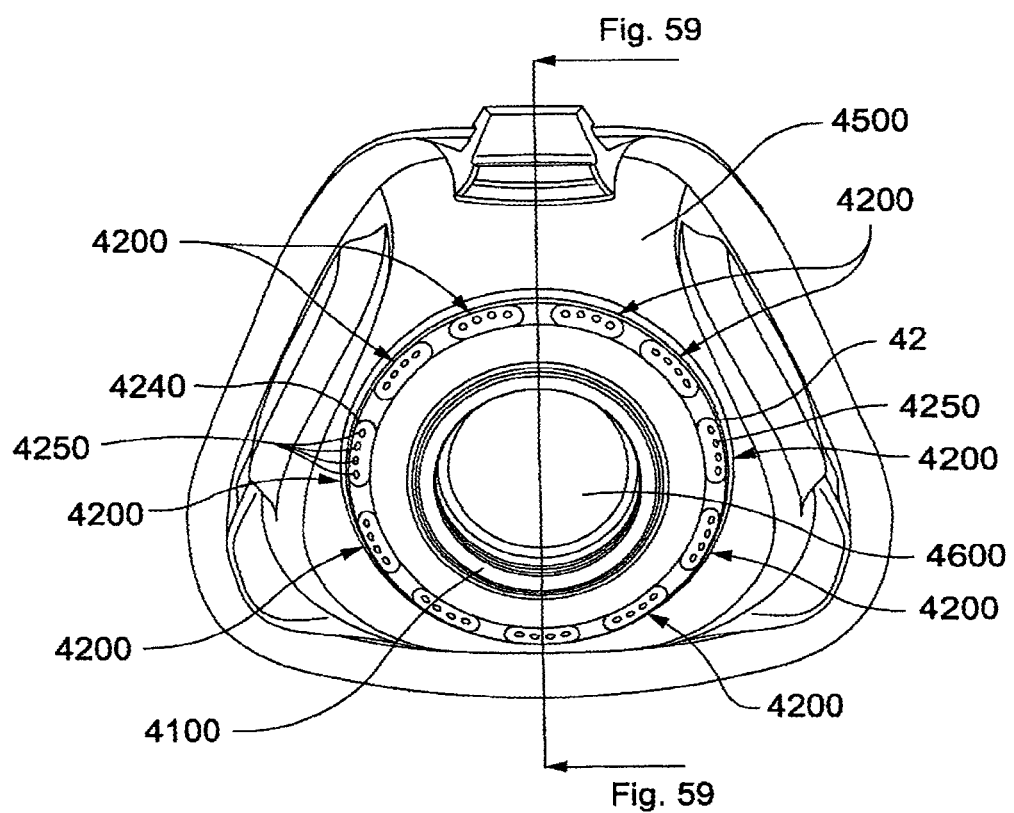
FIG. 58 shows a mask cushion provided with the vent assembly of FIG. 55 according to an embodiment of the invention.
Figure 59:
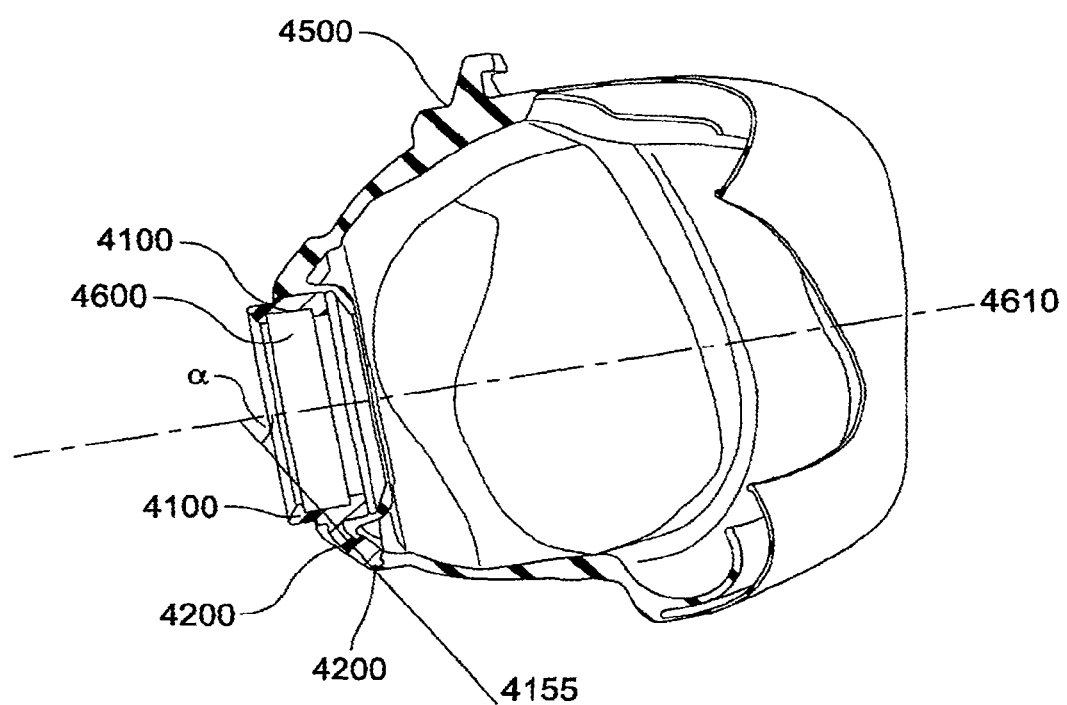
FIG. 59 is a cross-sectional view through line 59-59 of FIG. 58.
Figure 60:
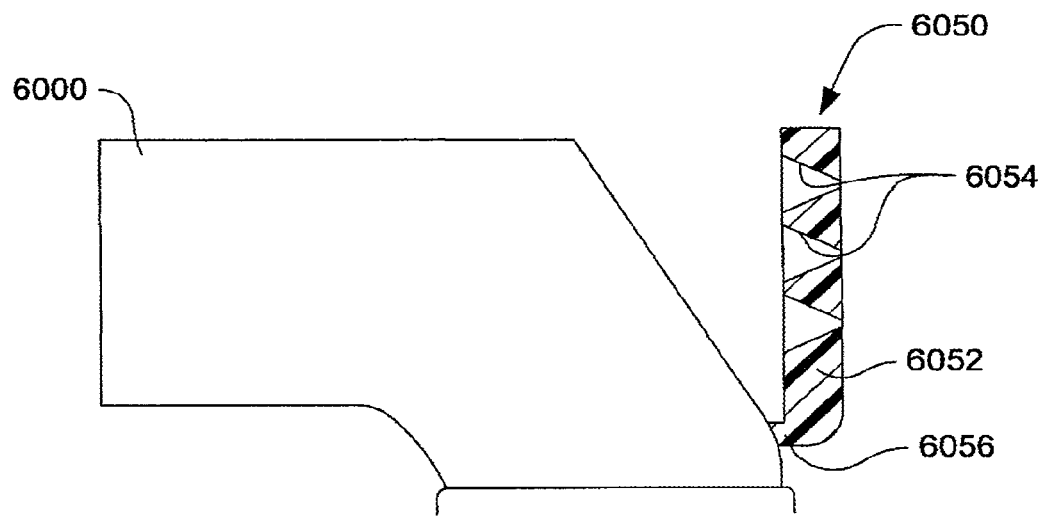
FIGS. 60 and 61 illustrate an elbow with a vent according to another embodiment of the invention.
Figure 61:
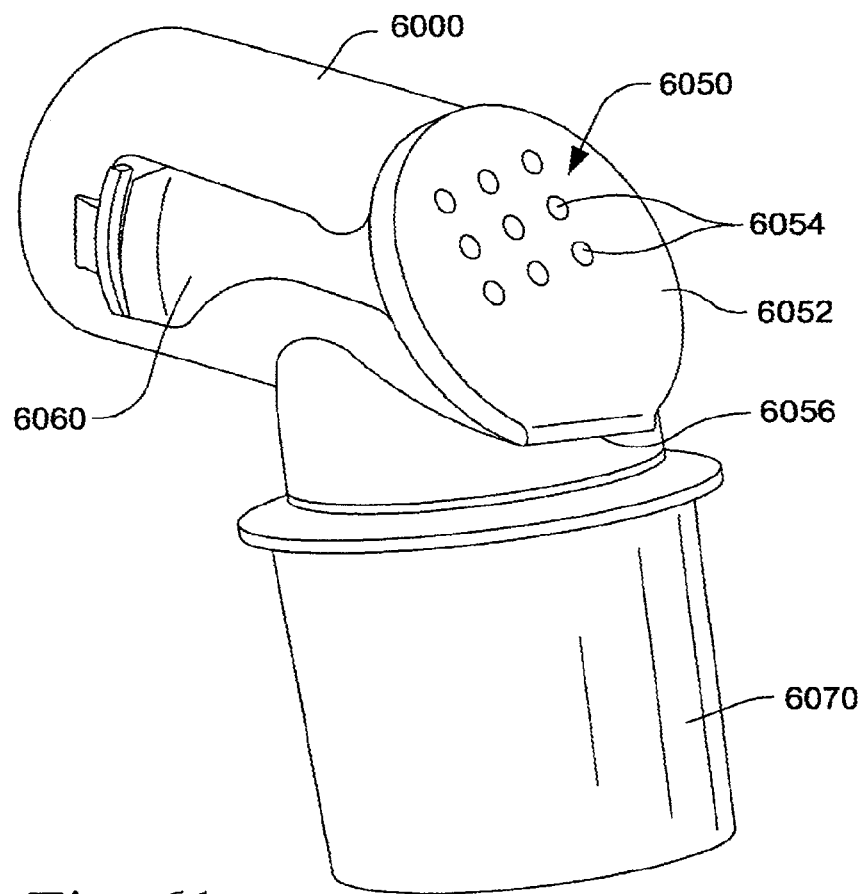
Figure 62:
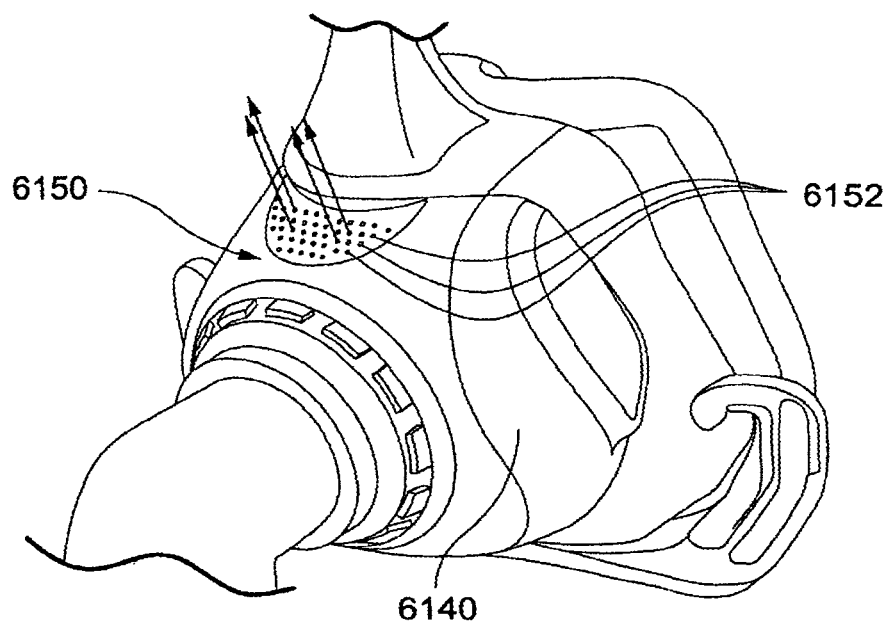
FIGS. 62 and 63 illustrate a cushion with a vent according to another embodiment of the invention.

Stem 4100 may have an aperture 4600. Aperture 4600 may be constructed and arranged to receive a portion of the mask system. For example, as best shown in FIGS. 58 and 59, aperture 4600 is located to receive an elbow of a mask system.

Branches 4150 may connect the stem 4100 to the vent arrays 4200. Branches 4150 may be evenly spaced about stem 4100 or may have an alternative configuration. The spacing of branches 4150 may be constructed to position vent arrays 4200 such that they achieve diffuse exiting air flow streams.

In another embodiment, branches 4150 may be selectively deformable. Branches 4150 may be formed into a first position by molding, cutting or any other forming method. Branches 4150 may then be deformed by heating, cooling, force, or other method into a second position. In an embodiment, branches 4150 may be deformed by placing vent 4000 into a tool for a mask component, closing the tool such that shape of the tool force the branches to bend or otherwise deform, and injecting or otherwise adding a second material into the tool and allowing this second material to set or stabilize around the vent 4000 so as to maintain branches 4150 in their deformed position.

In an embodiment, the second position or deformed position of the branches may be 0-120° from the first position. In an embodiment, the second position or deformed position of the branches may be 30-90° from the first position. In an embodiment, the second position or deformed position of the branches may be 40-60° from the first position. In an embodiment, the second position or deformed position of the branches may be 45° from the first position.

In another embodiment, stem 4100 may be selectively deformable. Stem 4100 may be formed into a first position by molding, cutting or any other forming method. Stem 4100 may then be deformed by heating, cooling, force, or other method into a second position. In an embodiment, stem 4100 may be deformed by placing vent 4000 into a tool for a mask component, closing the tool such that shape of the tool forces the stem to bend or otherwise deform, and injecting or otherwise adding a second material into the tool and allowing this second material to set or stabilize around the vent 4000 so as to maintain stem 4100 in its deformed position.

In an embodiment, the second position or deformed position of the branches may be 0-120° from the first position. In an embodiment, the second position or deformed position of the branches may be 30-90° from the first position. In an embodiment, the second position or deformed position of the branches may be 40-60° from the first position. In an embodiment, the second position or deformed position of the branches may be 45° from the first position.

Figures 3, 56:
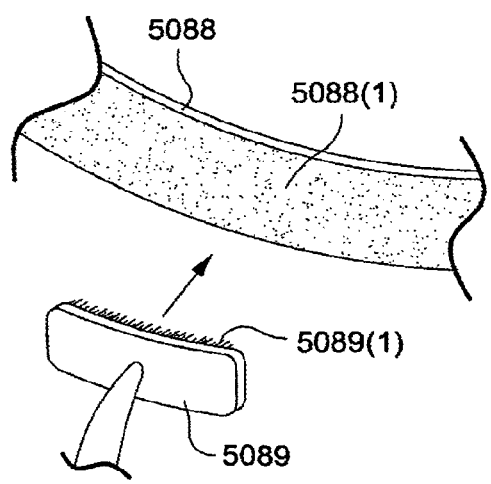
Figure 57:
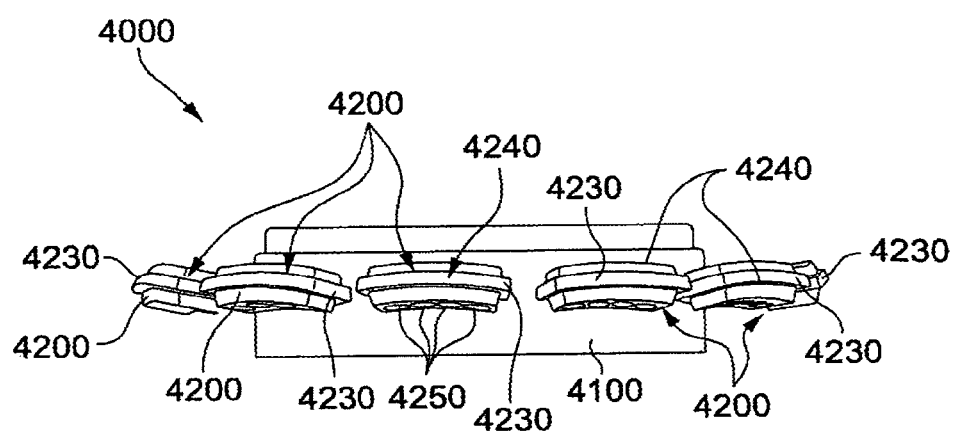
FIG. 57 is a side view of the vent assembly shown in FIG. 55.

As best shown in FIGS. 55 to 57, branches may connect to at least one vent array 4200. Vent array 4200 may comprise a body 4240 and at least one vent hole 4250.

As best shown in FIGS. 56 and 57, body 4240 may be generally rectangular or any other shape that may accommodate the at least one vent hole 4250. Body 4240 may also comprise a ledge or protrusion 4230 that may assist in mechanically bonding or locking the vent 4000 in position when formed with the mask component, such as cushion 4500.

In an embodiment, there is at least one vent hole 4250 on each body 4240. In the illustrated embodiment, as shown in FIG. 55, four vent holes 4250 are arranged on each body 4240. However, any number of holes is possible, for example, 1, 5, 10, 11, or more holes.

In an embodiment, vent holes 4250 may be convergent, that is, their entrance may have a greater diameter than their exit. In an embodiment, their exit diameter is about 0.1-2 mm. In an embodiment, the exit diameter is about 0.3-0.8 mm. In an embodiment, the exit diameter is about 0.7 mm. In an embodiment, the vent holes have an aspect ratio of approximately 1:3.

FIGS. 58 and 59 show the vent 4000 arranged in cushion 4500. Vent arrays 4200 are distributed around aperture 4600. FIG. 59 shows the longitudinal axis 4155 of branch 4150 disposed at an angle $\alpha$ to the axis 4610 of aperture 4600. Hence, vent holes 4250 on body 4240 are arranged to position exiting air flow streams from vent holes 4250 at an angle $\alpha$ with respect to the aperture 4600, hence splaying or dispersing the individual air stream exiting each vent hole. This diffuses the air flow paths and thus reduces the jetting of air streams onto a bed partner or bed clothes. This arrangement may also reduce vent noise.

In alternative embodiments, a similar vent 4000 may be arranged in an elbow, whereby the vent 4000 is formed in a first position, then placed in the mold for an elbow. In the mold for the elbow, the branches and vent arrays are deformed approximately 90° from their first position, thereby being positioned around the circumference of a portion of an elbow. The material for the elbow component is then injected into the mold and set, thereby maintaining the vent 4000 in the desired position.

The vent 4000 may be constructed of a material that is flexible and/or extensible. The vent 4000 may be constructed of nylon, polypropylene, thermoplastic elastomer, silicone, polycarbonate, polyurethane or any other moldable, selectively deformable polymer.

The mask component into which the vent is formed may be made from a material with a lower melting point than the material used for the vent. This is so that when the vent is inserted into the mold for the mask component, and the second material for the mask component is injected or otherwise inserted into the mold, the vent does not melt.

Figure 64:
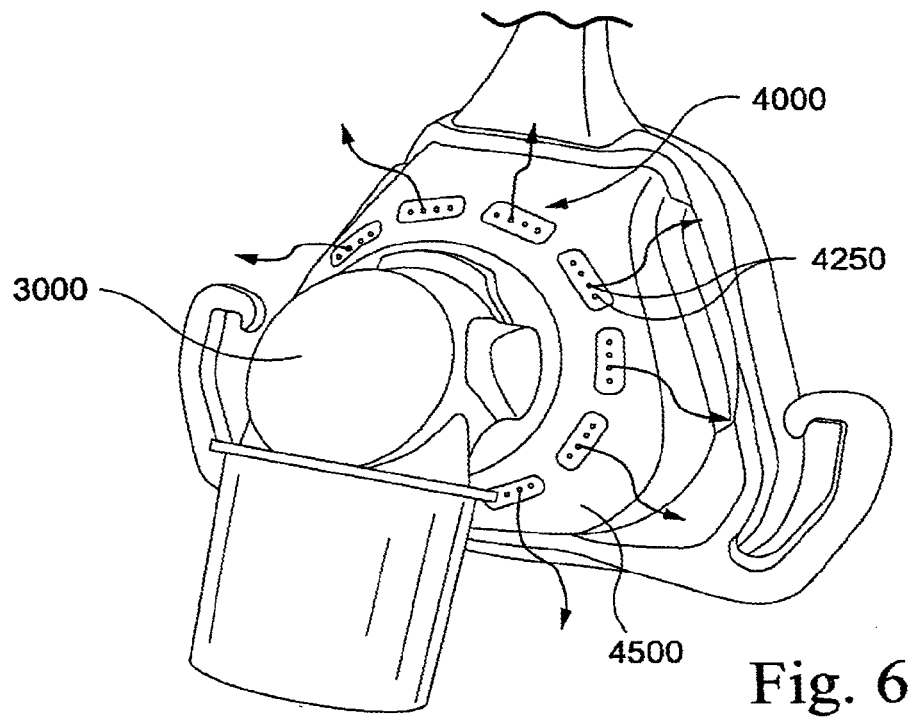
FIGS. 64 and 65 are alternative views of the vent assembly of FIGS. 55-59.
Figure 65:
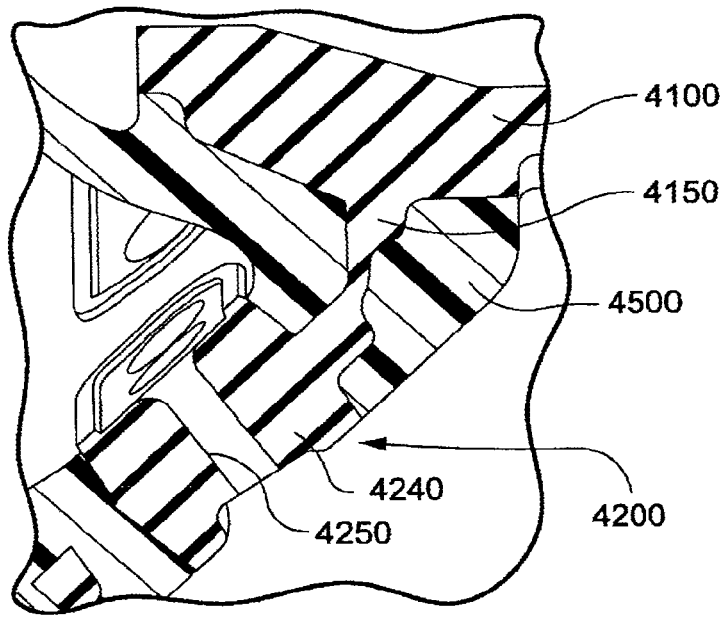

FIGS. 64 and 65 show alternative views of the vent 4000 arranged in cushion 4500. As illustrated, the vent arrangement allows multiple vent holes 4250 to be molded in the line of draw on a plastic cushion ring, and then bent during an over-moulding process to create a very diffuse and quiet vent array about the elbow 3000. This array is encapsulated and suspended in the silicone material of the cushion 4500.

Figure 106:
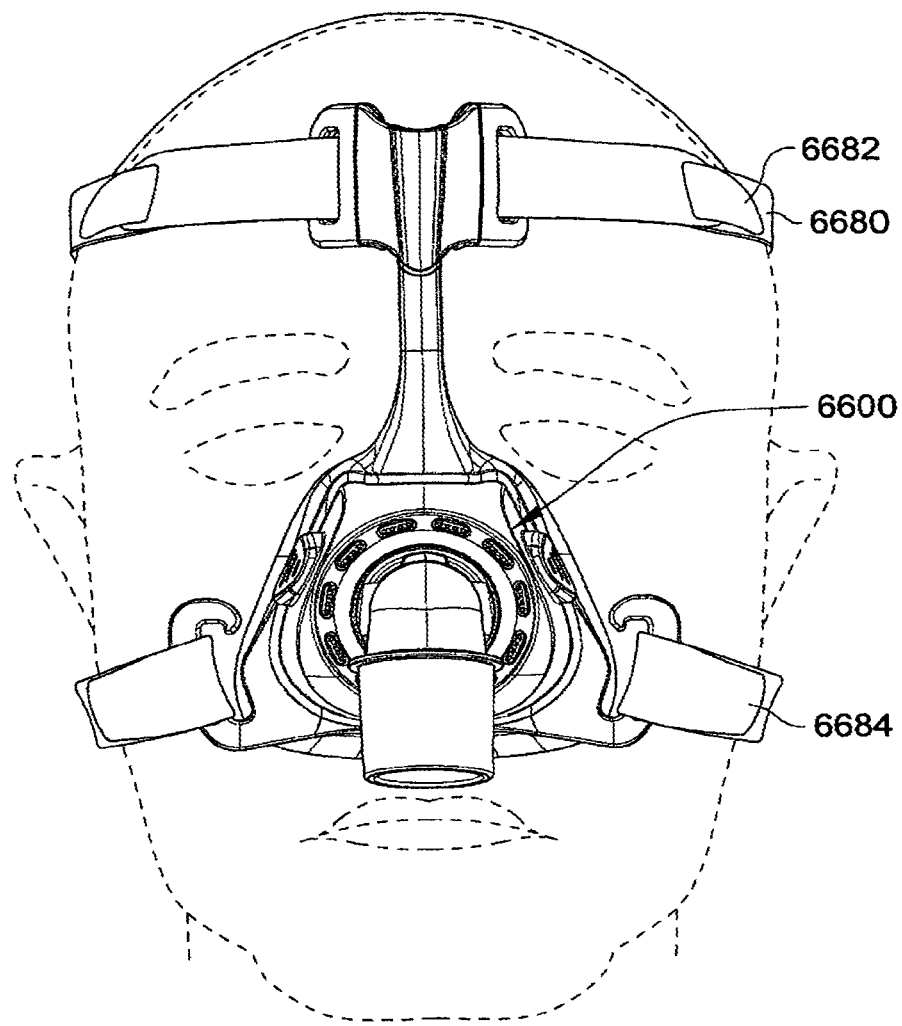
FIGS. 106 and 107 show the mask system of FIGS. 99-105 with headgear on a patient's face in use according to an embodiment of the invention.
Figure 107:
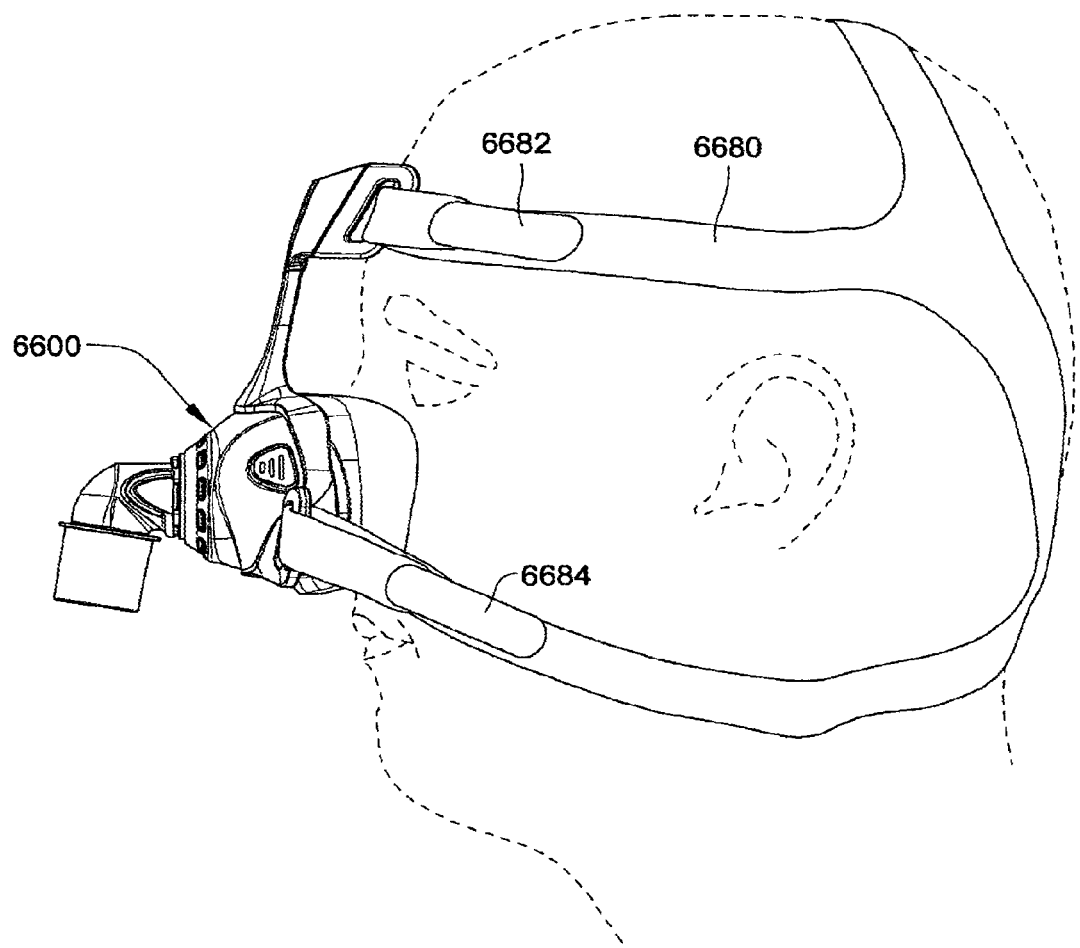

FIGS. 99 to 105 show various views of a nasal mask system 6600 including a frame 6620 (e.g., like that shown in FIGS. 88 to 93), cushion 6640 (e.g., like that shown in FIGS. 71-87 with the vent of 55-59 and 64-65), and elbow 6670 (e.g., like that shown in FIGS. 46-50) according to an embodiment of the invention. FIGS. 106 and 107 show the mask system 6600 with headgear 6680 on the patient's head in use, e.g., headgear including upper side straps 6682 routed over the ears and lower side straps 6684 routed under the ears. In an embodiment, the mask system may be used with headgear described in U.S. Pat. No. 7,509,958 and PCT Application No. PCT/AU2009/001605, each of which is incorporated herein by reference in its entirety.

Alternative Vents

Figures 3, 60:
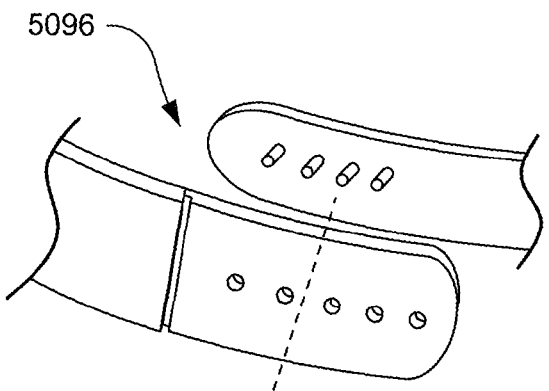
Figures 3, 61:
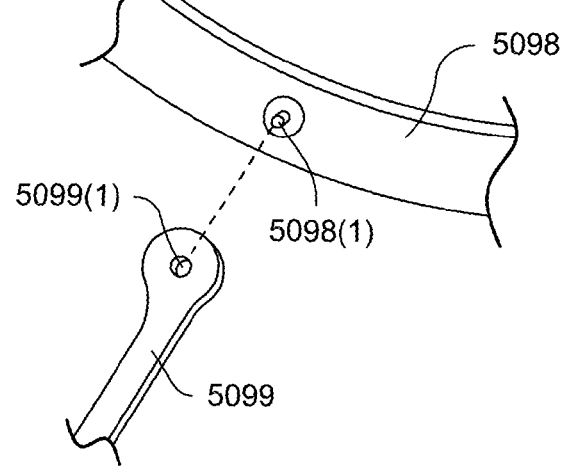

FIGS. 60 and 61 illustrate an elbow 6000 with a vent 6050 according to another embodiment of the invention. In the illustrated embodiment, the vent 6050 includes a vent plate 6052 having one or more vent holes 6054 formed within it. The vent plate also includes a weakened or bendable region 6056 (i.e., hinge). A swivel 6070 may be provided to the elbow for attachment to an air delivery tube. Each vent hole may include a contour or taper along its length. However, it should be appreciated that the vent may include other suitable arrangements, e.g., different number of holes, hole arrangement, etc.

In an embodiment, the vent plate 6052 may be molded with the vent holes 6054 and the hinge 6056. Then, the vent plate may be placed in the mold for the elbow 6000. As the mold for the elbow closes, the hinge of the vent plate allows the vent plate to bend from a first position (as shown in FIG. 60 which shows the vent plate in a generally upright position in the elbow mold) to a second, in use position (as shown in FIG. 61 which shows the vent plate bent into engagement with the elbow). Once the mold for the elbow is closed, the material for the elbow is injected into the mold and the vent plate remains in its second, in use position by the molded elbow. Also, additional components may be molded onto the elbow (e.g., elbow buttons 6060 as shown in FIG. 61).

Figures 3, 62:
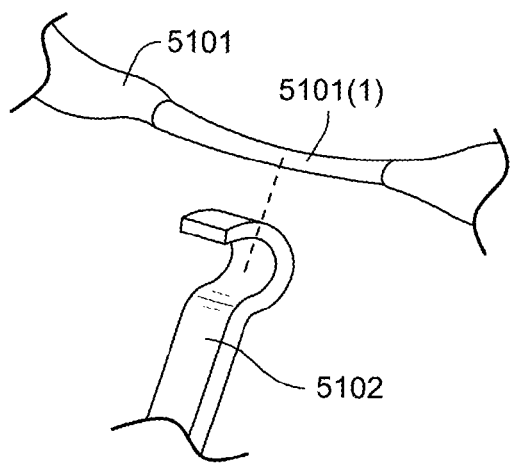
Figure 63:
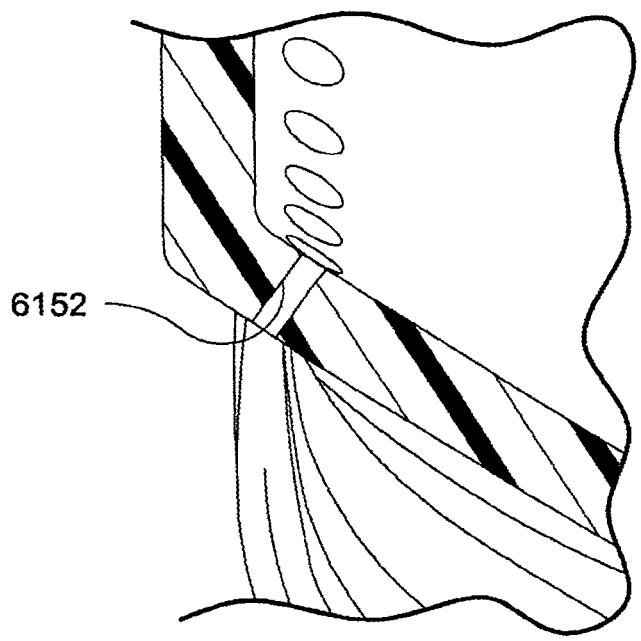

FIGS. 62 and 63 show a vent 6150 according to another embodiment of the invention. In this embodiment, the vent 6150 is in the form a vent insert that is molded (e.g., overmolded) with the cushion 6140. The vent insert is positioned along a top portion of the cushion above the opening adapted to receive the elbow. As illustrated, the vent insert includes a plurality of vent holes 6152 that are oriented to direct exhausted gas away from the patient's face in use. In addition, the vent holes may be arranged to diffuse exiting air flow streams. It should be appreciated that the vent may include other suitable arrangements, e.g., contoured vent holes, different number of holes, hole arrangement, etc.

6. Headgear

Headgear may be removably attached to the headgear connectors 34, 36 of the frame 20 to maintain the nasal mask system in a desired position on the patient's face. In the illustrated example, the frame provides a four-point connection for a pair of upper headgear straps and a pair of lower headgear straps. However, the frame may provide other arrangements, e.g., two-point connection or three-point connection. Rigidizers or reinforcing materials may be provided to one or more of the straps.

Headgear may be constructed of an elastic or flexible material such as woven and non-woven fabric, TPE, polypropylene, nylon, or any other suitable material. The headgear may also be reinforced with stiffening members that may add stability.

In an example, the nasal mask system may be used with headgear such as that described in Australian Provisional Application Nos. AU 2008906390, filed Dec. 10, 2008, and AU 2009900327, filed Jan. 29, 2009, each of which is incorporated herein by reference in its entirety. In an example, attachment/adjustment of such headgear may be provided by buckles or hook and loop material. For example, the headgear straps may be constructed of a nylon elastic material with strap adjustment provided by buckles without any hook and loop material.

However, the nasal mask system may be used with alternative headgear arrangements. For example, FIGS. 3-1 to 3-79 illustrate headgear strap arrangements and headgear connection arrangements according to alternative examples of the present invention.

FIGS. 3-1 to 3-4 illustrate alternative arrangements for sizing the headgear straps. FIG. 3-1 shows a headgear with two part top strap adjustment. Each side of the top strap 5001(1), 5001(2) may be adjusted by a ladder lock or buckle connected at the mask, or Velcro™ adjustment, or any other suitable means. This arrangement provides central adjustment, can be evenly tensioned, and provides a greater fit range. In addition, the rear portion of the headgear straps may be narrowed or widened by sliding the rear straps 5003 (shown generally vertical, but may be otherwise angled) over the lower headgear straps 5004. FIG. 3-2 shows a headgear with a single top strap 5001 and a single lower strap 5004. The top and lower straps may preferably be constructed from an elastic or other suitable stretchy material, so as to provide a wide range of fit. This arrangement may also provide minimal to no adjustment and no requirement of a buckle or extraneous parts on the mask system. FIG. 3-3 shows a headgear with an adjustable top strap with sides 5001(1), 5001(2) where a buckle 5002 is provided to one side of the top strap, such that the adjustment of the top strap length is independent of the mask (i.e., forehead support). This may provide advantages such as one adjustment point, and low profile. FIG. 3-4 shows a headgear with one piece top strap 5001 with adjustment and an alternative buckle 5002. This buckle may be hinged at one end (e.g., hinge 5002(1)), such that when it is positioned perpendicular to the headgear strap, the buckle teeth 5002(2) are disengaged from the strap 5001 thereby allowing the strap to pass through the buckle and adjust the length in use. When the buckle 5002 is positioned parallel to the headgear strap, the buckle teeth 5002(2) engage with the strap 5001 and prevent it from sliding through the buckle, thus locking or fixing the length of the top strap. Such an arrangement may provide advantages such as one adjustment point and simple clasp mechanism.

FIGS. 3-5 to 3-7(*b*) illustrate alternative arrangements for sizing the bottom or lower headgear straps. FIG. 3-5 shows a lower strap 5004 overlapping such that at its end, the overlapped end 5004(1) would slidably engage with a lower headgear connector. The lower strap end may be threaded through an adjustment buckle 5005, such that sliding of the buckle along the length of the lower headgear strap may adjust the amount of overlapping of the lower strap hence adjusting its length in use. Such an arrangement may advantageously provide a simple adjustment mechanism and no requirement for traditional adjustment means such as hook and loop. FIG. 3-6 shows a lower strap 5004 overlapping such that at its end, the overlapped end would slidably engage with a lower headgear connector. The lower strap end may be attached along the length of the lower strap material using hook and loop attachment (e.g., the lower strap headgear material is loop material, and a portion 5004(2) at the end of the lower strap is hook material). Such an arrangement advantageously provides a simple hook and loop connection and slim line. FIGS. 3-7(*a*) and 3-7(*b*) show an adjustment arrangement that could be utilized anywhere on the headgear, however more preferably at the top or lower headgear straps. The adjustment arrangement may include a push through mushroom shaped connector 5010 that resides on one portion of the headgear, that may engage with a selected hole 5012 in another portion of the headgear so as to prevent sliding adjustment of the headgear portions. Advantageously, this arrangement may still allow the headgear portions to rotate over one another. Additionally, this arrangement may have a positive feedback (e.g., a clicking noise) when the adjustment arrangement is locked in position, meaning the patient will know when their headgear is adjusted. One or more holes and/or one or more mushroom shaped connectors may be provided to the headgear. The adjustment arrangement may be constructed from a flexible and sufficiently hard material, such that the arrangement maintains its connection once in use, for example TPE, silicone, polycarbonate or any other suitable materials.

FIGS. 3-8 to 3-13(*b*) show alternative fixed or adjustable headgear arrangements. FIG. 3-8 shows a headgear strap size adjustment, where a loop of material 5014 with a hole 5014(1) is provided to allow sliding engagement with a headgear strap 5004 (e.g., lower strap). The headgear strap may be provided with one or more mushroom shaped connectors 5016 to interface or engage with the hole 5014(1) provided to the loop of material. Preferably, size indicators (e.g., S, M, L or 1, 2, 3, 4, 5, etc.) may be provided on or near the mushroom shaped connectors to specify the size that the headgear has been adjusted to. This arrangement may be advantageous since it provides a simple, known adjustment mechanism and an ability to know what size the headgear has been adjusted to. FIG. 3-9 shows back strap size adjustment (that may be adapted for use with a top strap, rear strap, or any other headgear strap) where the back strap 5006 may be provided with markings 5007 to indicate size (e.g., S, M, L, XL, etc). The manufacturer, patient or other suitable person may choose which size to adjust the headgear strap to, align the adjustment markers (for example, by folding or cutting the strap to align the markers) such that the headgear is positioned to match the chosen size, and then the headgear strap may be permanently fixed in this position using stitching, ultrasonic welding, or other suitable technique. Such an arrangement provides no adjustment once permanently fixed, and a low profile connection. FIG. 3-10 shows a centre back strap 5008 constructed from an elastic or other suitably flexible material, with adjustable arms similar to those shown in FIGS. 3-7(*a*) and 3-7(*b*), i.e., mushroom shaped connector 5010 and hole 5012 arrangement. FIG. 3-11 shows headgear with two positions for top strap adjustment, i.e., a hook and loop connection 5015 and a mushroom shaped connector and hole arrangement 5016 (e.g., like that shown in FIGS. 3-7(*a*) and 3-7(*b*)). This arrangement allows for greater adjustability and may thus accommodate varying sizes of patient's heads. FIG. 3-12 shows a headgear connection where a first headgear strap 5004 (such as a lower strap) may be slidably engaged with a second headgear strap 5003 (such as a rear strap). The second headgear strap 5003 may be provided with a loop or additional layer of material 5003(1) that is ultrasonically welded, stitched, or otherwise attached to the second headgear strap. The first headgear strap is positioned in the spacing or channel between the second headgear strap and the additional layer of material. The ultrasonic weld or stitch or other attachment means may include bumps or projections that provide more friction in the channel between the second headgear strap and the additional layer of material, to prevent excessive sliding of the first headgear strap through the channel. The additional layer of material may be the same as the headgear material, or a more durable component such as a TPE or silicone. FIGS. 3-13(*a*) and 3-13(*b*) show sliding clip adjustment, where the headgear strap 5018 is looped through the clip 5020 and may be adjusted by engaging or disengaging an internal spring by pressing the button 5020(1) on the clip. The end of the headgear strap may be provided with a hole 5018(1) for attachment to a frame or forehead support. This hole may be reinforced (e.g., with laminate, stitching, or other reinforcing means) whereby the reinforcement 5018(2) prevents the hole from propagating and may also prevent the sliding clip from sliding off the headgear material.

FIGS. 3-14(*a*) to 3-14(*h*) show alternative arrangements for sizing of the headgear straps. In embodiment, the strap may be ultrasonically welded, may include ultrasonically cut holes, or may be ultrasonically modified.

FIG. 3-15 shows a similar arrangement to FIG. 3-8, with a different shape mushroom connector 5016 to interface with a hole 5014 (i.e., generally square shaped).

FIGS. 3-16(*a*) and 3-16(*b*) show alternative arrangements to FIGS. 3-8 and 3-15, whereby a similar sizing indicator is used, however the headgear straps are routed differently. A first end 5021(1) of a first headgear strap is looped through a first side of a second headgear strap 5022. A second end 5021(2) of a first headgear strap is looped through a second side of a second headgear strap 5022. Either the first or second end of the first headgear strap may have a size indicator on it. The second headgear strap may have a hole 5023 or other means to display the size indicator on the first headgear strap.

FIGS. 3-17 to 3-24 show alternative arrangements of headgear connections to the frame or forehead support. FIG. 3-17 shows a bottom strap 5024 that may wrap around an arm or hole 5025 in the frame and then re-connects to the bottom strap with button or hook and loop material. This arrangement may provide a simple, intuitive connection, with the potential for multiple adjustment positions should multiple connections be provided, slim line design, and easy to manufacture. FIG. 3-18 shows a bottom strap 5024 that may have a hook shaped clip 5025 (e.g., made from plastic or other suitable material) welded, sewn or laminated at one or both ends of the bottom strap material. The hook may snap into a receptacle 5026, slot or hole on the frame. Such a connecting means may provide a simpler drop in connection, slim line, and be easy to manufacture. FIG. 3-19 shows a headgear strap 5024 with a series of fingers 5027 positioned at the end of a strap, that may be welded or sewn or otherwise attached. The frame may also be supplied with similar fingers 5028 such that when the fingers on the headgear strap are interlocked or overlaid onto the fingers on the frame, lateral movement and hence sliding of the headgear strap away or towards the frame is prevented or minimized. Disengagement of the fingers in the direction of the fingers may be relatively simple when compared to disengagement of typical headgear clips (for example, headgear clips provided to a ResMed Mirage Quattro™). FIGS. 3-20(*a*) and 3-20(*b*) show a headgear strap 5024 that may have a T-bar 5029 provided at its end(s). The T-bar may be constructed from a flexible material such as a TPE, silicone, polycarbonate, or any other suitable material. The T-bar may be attached by looping the headgear strap through a hole provided to a T-bar connecting rod. Alternatively, the T-bar may be welded, sewn, ultrasonically welded or attached by any other suitable means. The T-bar may loop over or around a receptacle or catch 5030 provided on the frame. FIG. 3-21 shows headgear strap with a push-fit connection means 5031 attached at its end(s). The push-fit connection means may be constructed from a generally flexible material such as silicone or TPE. The push-fit connected means may be attached to the headgear strap by similar means described for the T-bar shown in FIGS. 3-20(*a*) and 3-20(*b*). The push-fit connection means may be a bulbous shaped rod that may engage with holes or slots 5032 on the frame. Multiple holes or slots may be provided to the frame. FIG. 3-22 shows a headgear strap 5024 looped over at its end and sewn or otherwise re-attached to itself along its length. The looped section is slidably engaged around a receptacle 5033 in the frame. Hook material may be provided on the looped section of the headgear strap to enable adjustment and then fixation of the headgear strap. The headgear material may need to be constructed of a looped material to enable engagement of the hook material. FIG. 3-23 shows a headgear strap 5024 that loops over a notch or barb 5034 on the frame. The headgear strap may be adjusted by a sliding sprung clip 5035 whereby a spring mechanism within the clip enables engagement and disengagement with the headgear strap. FIG. 3-24 shows headgear connection hook 5036 with slotted receptacle to allow for the headgear strap to feed into it.

FIGS. 3-25(*a*) to 3-30 show alternative arrangements of headgear connections to the frame. FIGS. 3-25(*a*) and 3-25(*b*) show a headgear strap with an 'R' shaped clip 5037 attached at its end(s). The 'R' shaped clip may be sprung or biased such that it preferably remains in its locked position. A loop 5038 may be provided to the frame (for example, a lower headgear connector as shown in FIGS. 3-25(*a*) and 3-25(*b*)) that engages with the 'R' shaped clip (cross section shown). FIGS. 3-26(*a*) and 3-26(*b*) show a headgear strap with a slot or cylinder 5039 provided at its end(s), that slots over a frame extension or finger 5040. FIG. 3-27 shows open ended headgear strap receptacle 5041 that may be provided to a frame that enables a loop of headgear strap to be wound or looped vertically, however the slit provided at the front of the receptacle. FIG. 3-28 shows a generally shaped headgear connection receptacle 5042 on the frame. Such an arrangement may be preferable for vertical insertion of the headgear strap loop 5043 (as indicated by the drawing). Once the headgear strap loop is inserted into the headgear connection receptacle, the headgear strap loop may pass from one side of the 'U' shaped receptacle to the other and as such, may prevent accidental disassembly of the headgear strap loop from the headgear connection receptacle since the headgear strap loop is anchored in the 'U' shape. FIG. 3-29 shows hook or loop material 5044 attached directly on the frame to interface with opposing hook or loop from a headgear strap. FIG. 3-30 shows a magnetic attachment where a magnet 5045 is provided to the frame and a magnet 5046 is provided to the headgear strap. FIGS. 3-31(*a*) and 3-31(*b*) and FIG. 3-32 show alternative arrangements for headgear attachment positions on the frame. FIGS. 3-31(*a*) and 3-31(*b*) show headgear attachment receptacles or slots 5047 located on the perimeter of the frame, which reduces the visual bulk of the mask. FIG. 3-32 shows headgear mount receptacles 5048 located on the frame and adapted to receive headgear clips 5049 associated with the headgear strap, similar to that disclosed in U.S. Pat. No. 6,374,826, which is incorporated herein by reference in its entirety.

FIGS. 3-33 and 3-37 show alternative arrangements for attaching the cushion to the frame or the lower headgear straps to the frame. FIG. 3-33 shows headgear connection loops 5050(1) located at the end of headgear connection arms 5050(2). This arrangement may space the connection of the headgear away from the frame, thereby allowing a more streamlined look. FIG. 3-34 shows a skeleton frame 5051 that is positioned along or within grooves in the cushion 5052, i.e., connects to the cushion with an interference fit or snap fit. The skeleton frame may have headgear connection arms 5053 with a generally perpendicular post at its end to enable a looped connection with a headgear strap. It may be preferable to create the skeleton frame from a more rigid material than the cushion. FIG. 3-35 shows a lower headgear connecting portion 5054 positioned to snap or otherwise interface with the cushion 5055 underneath or below the aperture where the elbow connects. FIGS. 3-36(*a*) and 3-36(*b*) show snap fit lower headgear connection assembly 5056; a variation of that shown in FIG. 3-21. FIG. 3-37 shows elbow seal ring 5057 with combined headgear attachment arms 5058 that snaps or otherwise interfaces with a frame 5059 and/or cushion 5060.

FIGS. 3-38 to 3-49(*b*) show alternative arrangements for connecting a headgear to a forehead support or a forehead support arm to a forehead support cushion. FIG. 3-38 shows a male buckle 5061 that may snap fit to a female buckle 5062 mounted on a forehead support arm (push to release). Headgear may be looped or otherwise connected to the male buckle. Alternatively, the male and female buckle positions may be reversed. The buckle may be made from a suitably rigid material so as to allow for a snap fit, for example polycarbonate, polypropylene, nylon, etc. FIG. 3-39 shows a forehead support cushion 5063 with a slot or female connector 5063(1), that may be engaged or interfaced with a rod or male connector 5064(1) attached to a forehead support arm 5064. This arrangement may allow for some horizontal rotation that may be preferable or desirable to patients. There may also be a permanent or removable retention feature for connection of the male and female components. FIG. 3-40 shows an alternative buckle arrangement including a male buckle 5061 and a female buckle 5062 to that shown in FIG. 3-38. FIG. 3-41 shows an alternative arrangement of male and female connectors 5064(1), 5063(1) to that shown in FIG. 3-39. FIG. 3-42 shows another alternative arrangement of male and female connectors 5064(1), 5063(1) to that shown in FIG. 3-39. FIG. 3-43 shows a forehead support cushion 5065 for attachment with upper headgear straps. The forehead support cushion may have a slot or cavity 5065(1) to receive a T shaped forehead support arm 5066. Such an arrangement may allow rotation of the forehead support arm vertically and thus greater flexibility to adjust the mask in use. FIGS. 3-44(*a*) and 3-44(*b*) show a forehead support cushion 5067 with a slot 5067(1) to receive a sliding engagement with a forehead support arm 5068. The forehead support arm may vertically slide into the slot, and may be provided with retention tabs to prevent accidental disengagement of the connection. The forehead support arm may have a generally T-shaped cross section that may prevent horizontal rotation of the forehead support arm when connected to the forehead support cushion. It may also act to strengthen the forehead support arm. FIG. 3-45 shows a forehead support cushion 5069 with a keyhole shaped aperture 5069(1) that may receive a forehead support arm 5070. The forehead support arm may have a generally round disk 5070(1) attached at its end for communication with the aperture on the forehead support cushion. Such an arrangement may allow for horizontal rotation of the forehead support arm in use. FIGS. 3-46(*a*) and 3-46(*b*) show a forehead support cushion 5071 that may have generally C-shaped pocket 5071(1) that may capture a ball 5072(1) attached to the end of forehead support arm 5072. FIG. 3-47 shows two piece forehead support cushion including first and second pieces 5073(1), 5073(2) that may snap around a generally cylindrical forehead support arm 5074. FIGS. 3-48(*a*) and 3-48(*b*) show two piece forehead support cushion that may have a first side 5075(1) that slidably engages with a generally cylindrical forehead support arm 5076, and a second side 5075(2) that receives the end of the forehead support arm and first side. FIGS. 3-49(*a*) and 3-49(*b*) show a forehead support cushion 5077 that may have a two piece construction, where each forehead support cushion is permanently or removably attached to the upper headgear straps. The forehead support cushions 5077 may also have apertures 5077(1) to receive a ball 5078(1) attached to the end of the forehead support arm 5078 to rotatably engage with the forehead support arm.

Alternatively, the ball/aperture arrangement may be reversed as shown in the related cross-sectional view.

FIGS. 3-50(a) to 3-69(b) show alternative arrangements for connecting headgear to the forehead support with no buckle. FIGS. 3-50(a) and 3-50(b) show an upper headgear strap 5079 that may be threaded through an aperture in a forehead support 5080. In addition, the aperture may be provided with a lip or engagement tab 5080(1) on the outer or non-patient contacting side of the forehead support to maintain the upper headgear strap in position. FIG. 3-51 shows an upper headgear strap 5079 that may thread through the forehead support 5080 with an engaging tab or hook 5080(1) to anchor the upper headgear strap within the forehead support. The forehead support may have an aperture for the upper headgear strap to rest within. FIGS. 3-52(a) to 3-52(c) show a flexible forehead support 5081 that can flex vertically away from the forehead of the patient to allow for a greater range of fit. FIGS. 3-53(a) and 3-53(b) show an upper headgear strap 5082 that may be thread through a forehead support 5083 which may have two engagement arms 5083(1), 5083(2) to encompass and maintain the position of the upper headgear strap. These two arms may be generally C-shaped when viewed from the side. FIG. 3-54 shows upper headgear straps 5084 that may be threaded through a generally Y-shaped forehead support 5085. The slot or gap in the top of the forehead support may be provided for disengagement of the headgear straps. FIG. 3-55 shows an upper headgear strap 5086 that may be provided with a pocket or gap 5086(1) such that the forehead support 5087 may be inserted within the pocket of the upper headgear strap. FIG. 3-56 shows an upper headgear strap 5088 that may have loop material 5088(1) on its outer or non-patient contacting side. The forehead support 5089 may have a facing of hook material 5089(1) that may interface with the upper headgear strap, thereby engaging the forehead support with the upper headgear strap. FIG. 3-57 shows an upper headgear strap 5090 that may have a receptacle 5090(1) in its structure. The receptacle may be a gap in the fabric or an inserted reinforcing such as a small tube. A forehead support 5091 may be generally cylindrical and may push fit or slide into the receptacle for engagement of the forehead support with the upper headgear strap. FIGS. 3-58(a) and 3-58(b) show a forehead support 5092 with a hinged region 5092(1) that may enclose over an upper headgear strap 5093, gripping said upper headgear strap and retaining it within the clamp. FIG. 3-59 shows forehead support 5094 that may be ultrasonically welded to an upper headgear strap 5095. The forehead support may be permanently attached to the upper headgear strap by other reasonable means such as gluing. FIG. 3-60 shows a two piece upper headgear strap 5096 in a baseball cap style that may thread through a forehead support 5097. FIG. 3-61 shows an upper headgear strap 5098 with button or push pin 5098(1) that engages with a slot or receiving portion 5099(1) on the forehead support 5099. FIG. 3-62 shows an upper headgear strap 5101 with a cylindrical section 5101(1) that may engage with a forehead support 5102 that may be shaped like a cradle or hook, such that the forehead support anchors over the cylindrical section of the upper headgear strap. FIG. 3-63 shows an upper headgear strap 5103 with a cylindrical section 5103(1) that may engage with a Y-shaped forehead support 5104. The Y-shaped forehead support may wrap around the cylindrical region of the upper headgear strap and may include pins adapted to engage within respective openings in the cylindrical region. FIG. 3-64 shows an upper headgear strap 5105 with the end region of each end of the upper headgear strap folded into a T-shape. This T-shaped fold 5105(1) may then be slid into a buckle or receiving portion 5106(1) attached to the forehead support 5106. FIG. 3-65 shows an upper headgear strap 5107 with a two piece sliding adjusting channel that may have an aperture or hole 5107(1) for receiving a projection 5108(1) on the forehead support 5108. FIGS. 3-66(a) and 3-66(b) show an upper headgear strap 5109 that may be slid or otherwise engaged with a channel 5110(1) formed on the top of a forehead support 5110. Alternatively, the forehead support 5111 may be slid or otherwise engaged within receiving channels in the ends of the headgear 5112. FIG. 3-67 shows forehead support 5113 attached to an upper headgear strap 5114, with the arm of the forehead support including a portion for snapping or otherwise attaching onto the frame 5115. FIG. 3-68 shows forehead support 5116 sewn into a loop at the end of upper headgear strap 5117, and the forehead support then snaps or otherwise connects onto the frame 5118. FIGS. 3-69(a) and 3-69(b) show a forehead support with separatable arms 5119. In an embodiment, the arms may be connected by an elastic strap 5120.

Figures 3, 72:
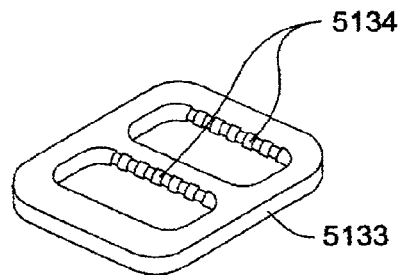
Figures 3, 73:
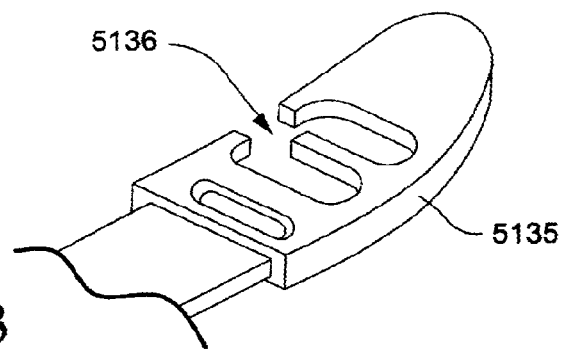
Figures 3, 74A:
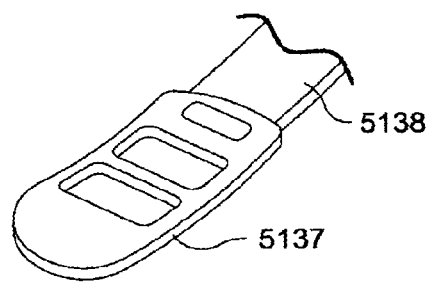
Figures 3, 74B:
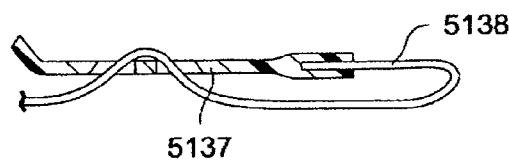

FIGS. 3-70(a) to 3-76 show alternative arrangements of buckle arrangements to be used to attach the upper headgear connectors to the straps of the headgear. Preferably, the buckles (shown in FIGS. 3-70(a) to 3-76) are adapted to form ladder-type locking clips. In these examples, the strap of the headgear is weaved through a first and second aperture in the buckles. The apertures are adapted to be in parallel and are generally aligned with the orientation of the strap, to be received. The weaving of the strap through this series of apertures allows the strap to be secured or locked in position so as to prevent or limit slipping. The straps may also include a contoured or rippled surface to facilitate better engagement with the buckle. Further, FIGS. 3-70(a) and 3-70(b) show an example of a buckle 5130 wherein the series of parallel apertures (also named a ladder lock) includes a series teeth or ripples 5131 on an extended end of the buckle. In an example, the extended end is kinked away from the horizontal plane to allow for or facilitate better access by a patient's fingers which may be necessary to disengage to the buckle, when the strap is secured. FIGS. 3-71(a) and 3-71(b) show a further example of a buckle 5132 wherein the length of a buckle has been configured into a curved or arcuate shape (when viewed from the side). This also improves the ability of a user to remove or engage the strap, depending on the circumstances. FIG. 3-72 shows a further example of a buckle 5133 that may be used with any of the above-described examples. This example of a buckle includes a further series of teeth or engagement means 5134 positioned so as to come into frictional contact with the strap, when in use. These second series of teeth are generally aligned with the general orientation of the engagement of the strap. This second series of teeth are generally adapted to prevent or limit slippage of the strap, when engaged. FIG. 3-73 shows a further buckle 5135 wherein the series of apertures, referred to in FIGS. 3-70(a) and 3-70(b) and 3-71(a) and 3-71(b) and 3-72, are joined to form a single aperture 5136. The single aperture is adapted to receive a strap and allow it to be weaved around the buckle to prevent or limit slippage. Further, the aperture is opened or broken at the upper surface to permit easier threading or weaving of the strap. FIGS. 3-74(a) and 3-74(b) show a further example of a buckle 5137 wherein the buckle is ultrasonically welded to one end of a headgear strap 5138. The other end of the strap or another strap may be threaded or weaved through the apertures of this buckle. It is noted that other means of fixing the buckle to an end of the strap may achieve the same or similar result, including frictional locks, gluing, or other kinds of suitable welding. FIGS. 3-75(a) and 3-75(b) show a further buckle 5139 wherein the piece 5139(1) of the buckle positioned between the two apertures is slightly raised. This feature of raising the centre of the buckle may further prevent or limit slippage by increasing the frictional forces impacted on the strap 5140, when in use. FIG. 3-76 shows a further buckle 5141 wherein the buckle is attached to an end of a first strap 5142(1) through a first set of two apertures. The first strap is weaved through the first set of apertures and looped back onto itself. The first strap may then be secured against itself by stitching. This buckle also includes a second set of two apertures positioned on the opposed end and this second set may be used to engage a second strap 5142(2). In an example, the second set of apertures is adapted to releasably secure the second strap wherein the first set of apertures is relatively more permanent and may generally prevent releasability of the first strap.

Figures 3, 77:
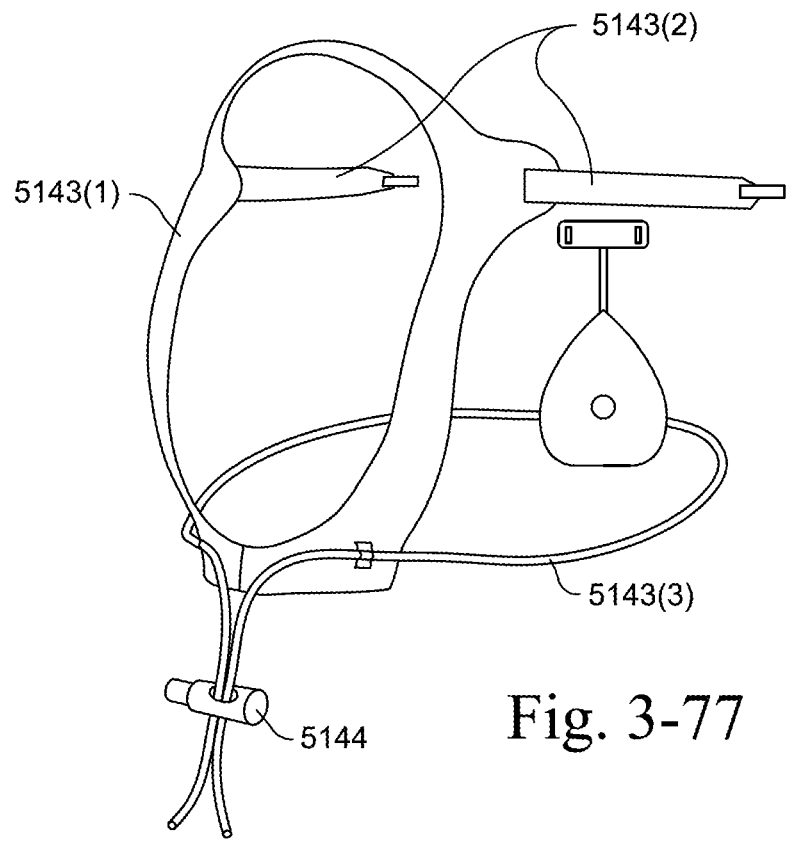
Figures 3, 78:
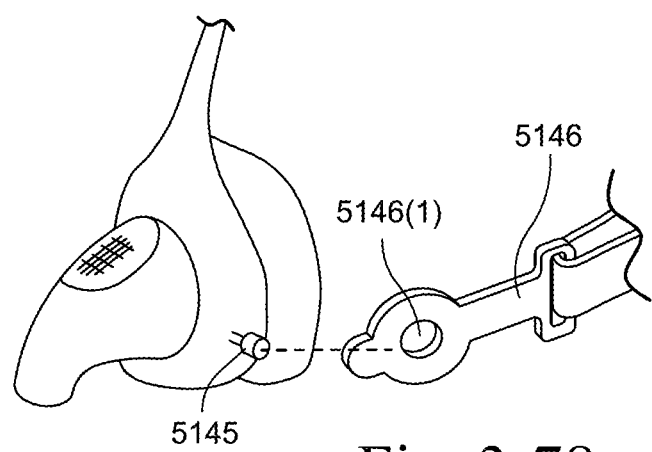
Figures 3, 79:
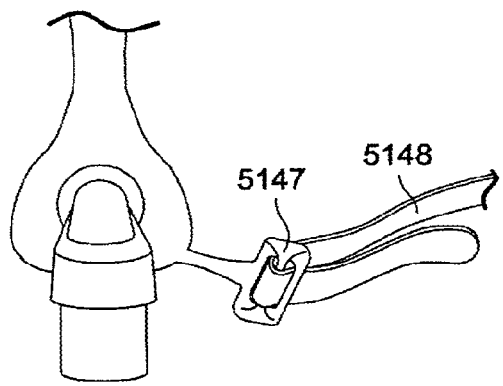
Figures 1, 4:
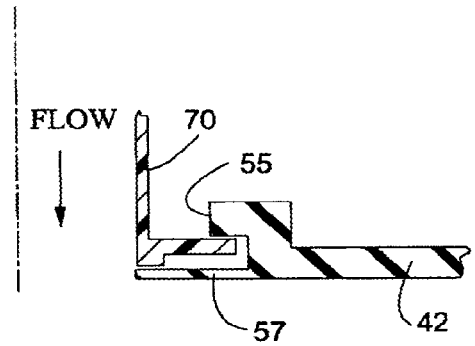
Figures 2, 4:
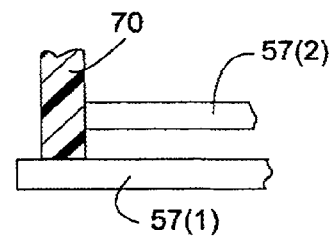
Figures 3, 4:
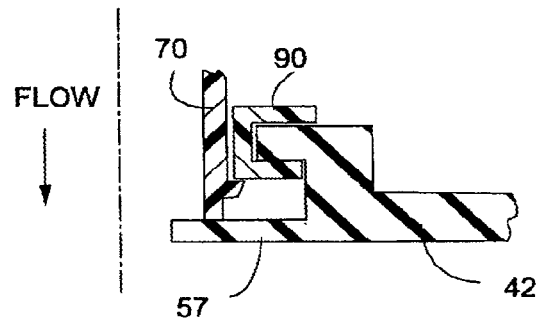
Figure 4:
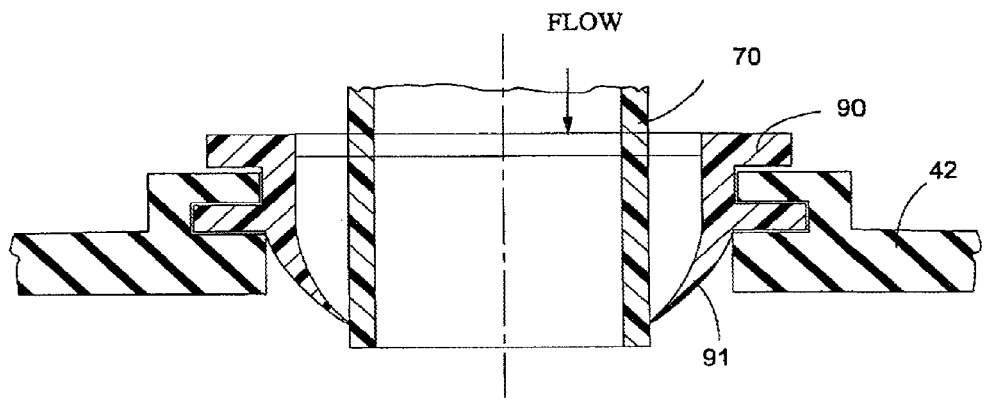
Figures 4, 5:
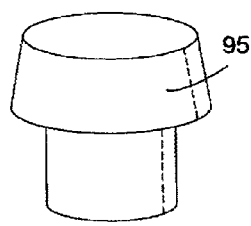
Figures 4, 5, 6:
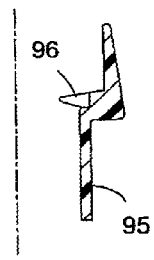
Figures 4, 5, 6, 7:
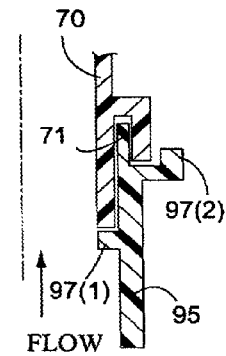
Figures 4, 5, 6, 7, 8:
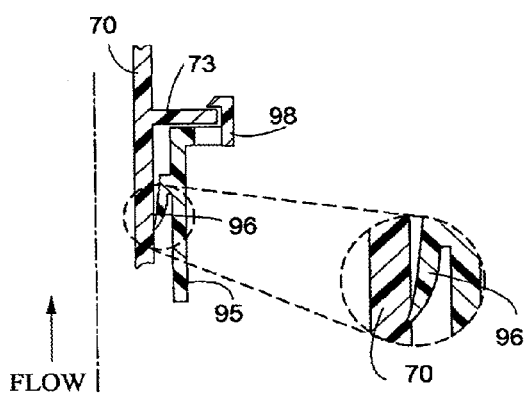
Figures 4, 5, 6, 7, 8, 9:
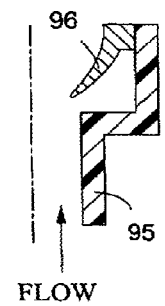
Figures 1, 5:
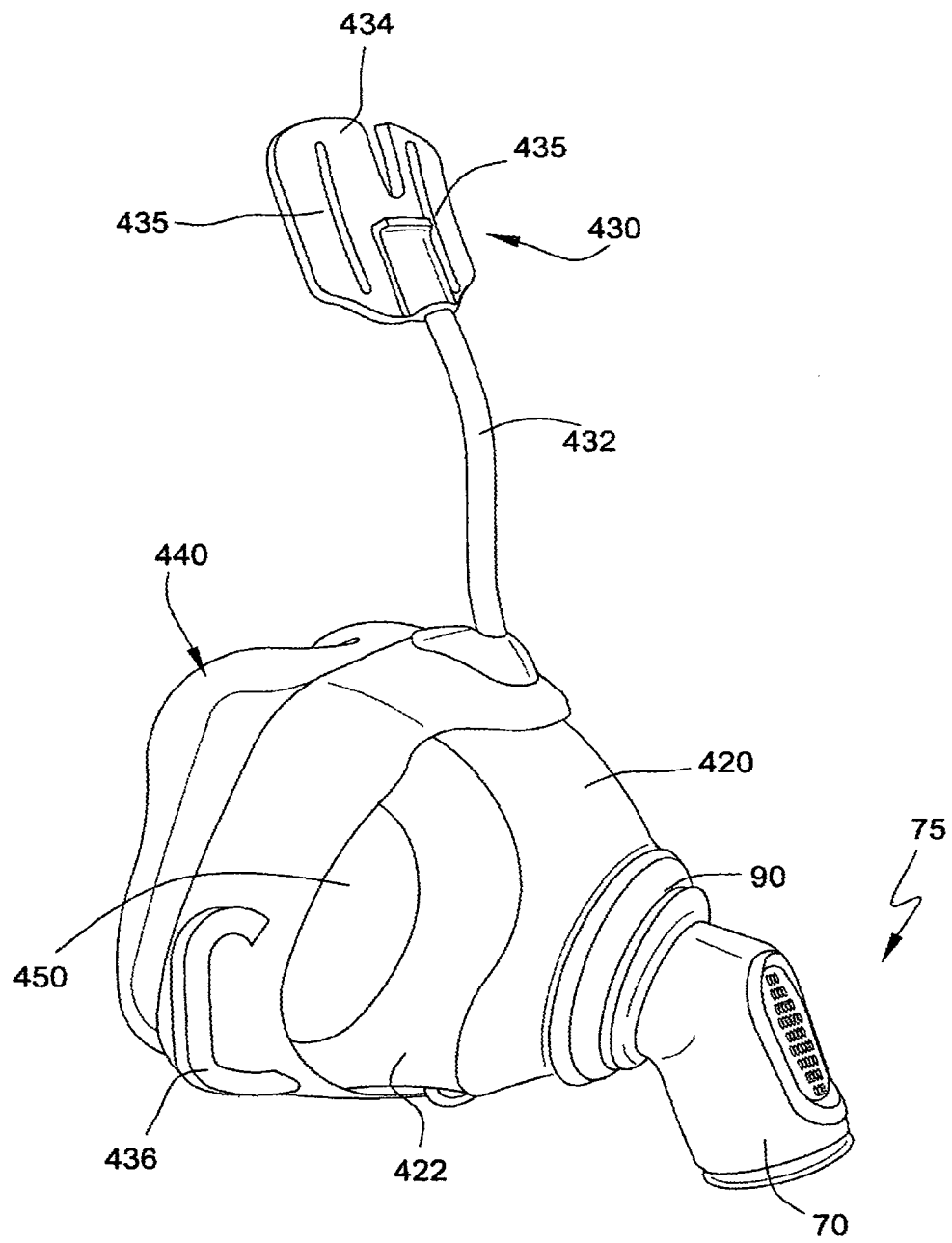
Figures 2, 5:
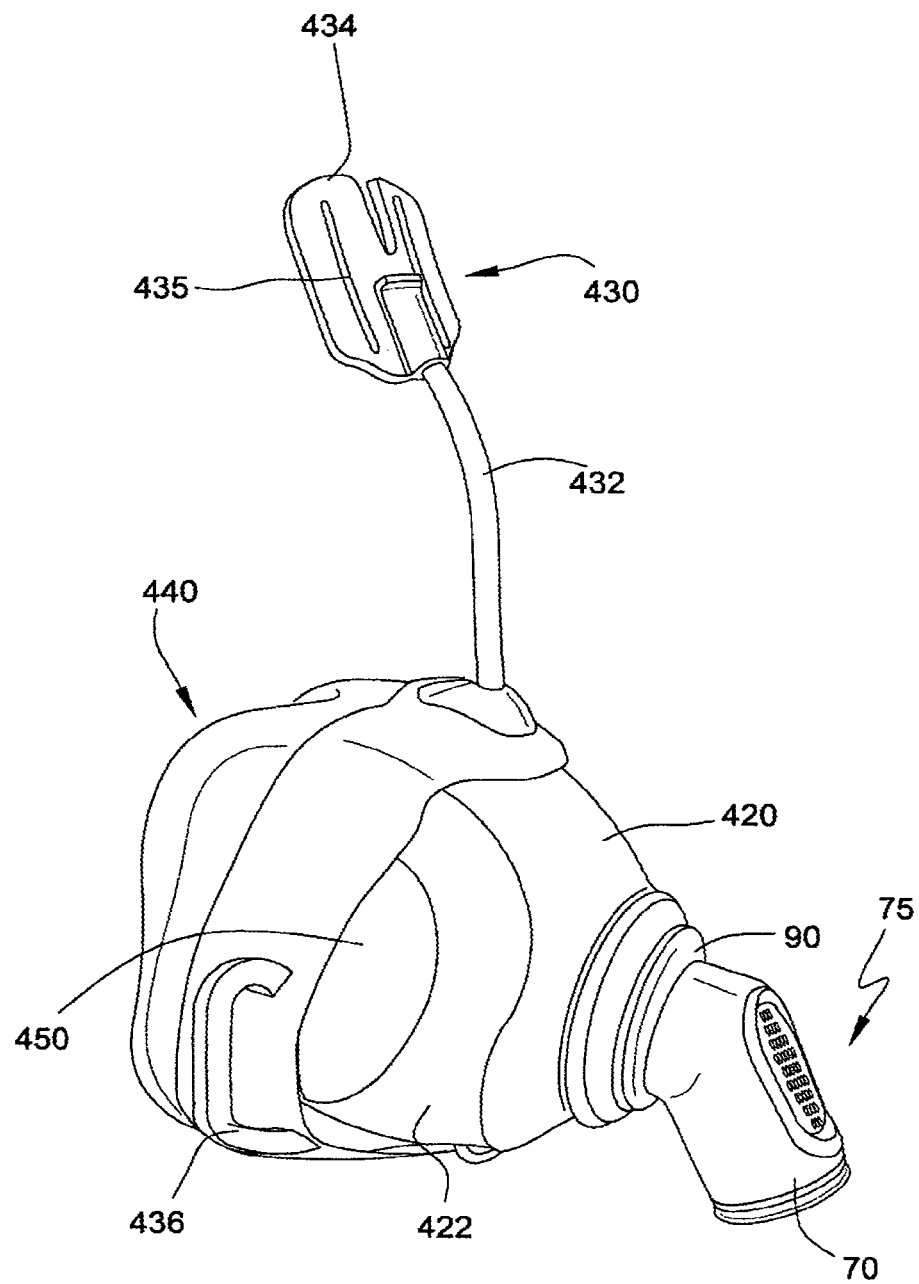
Figures 3, 5:
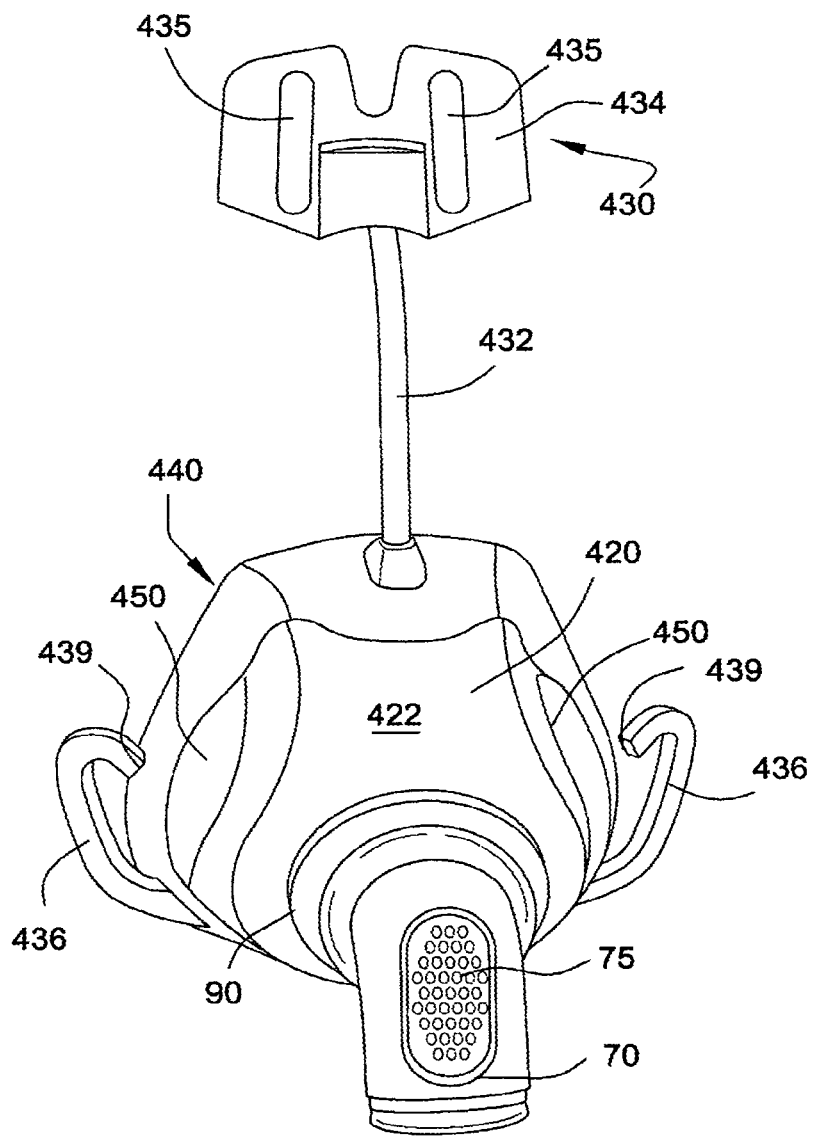
Figures 4, 5:
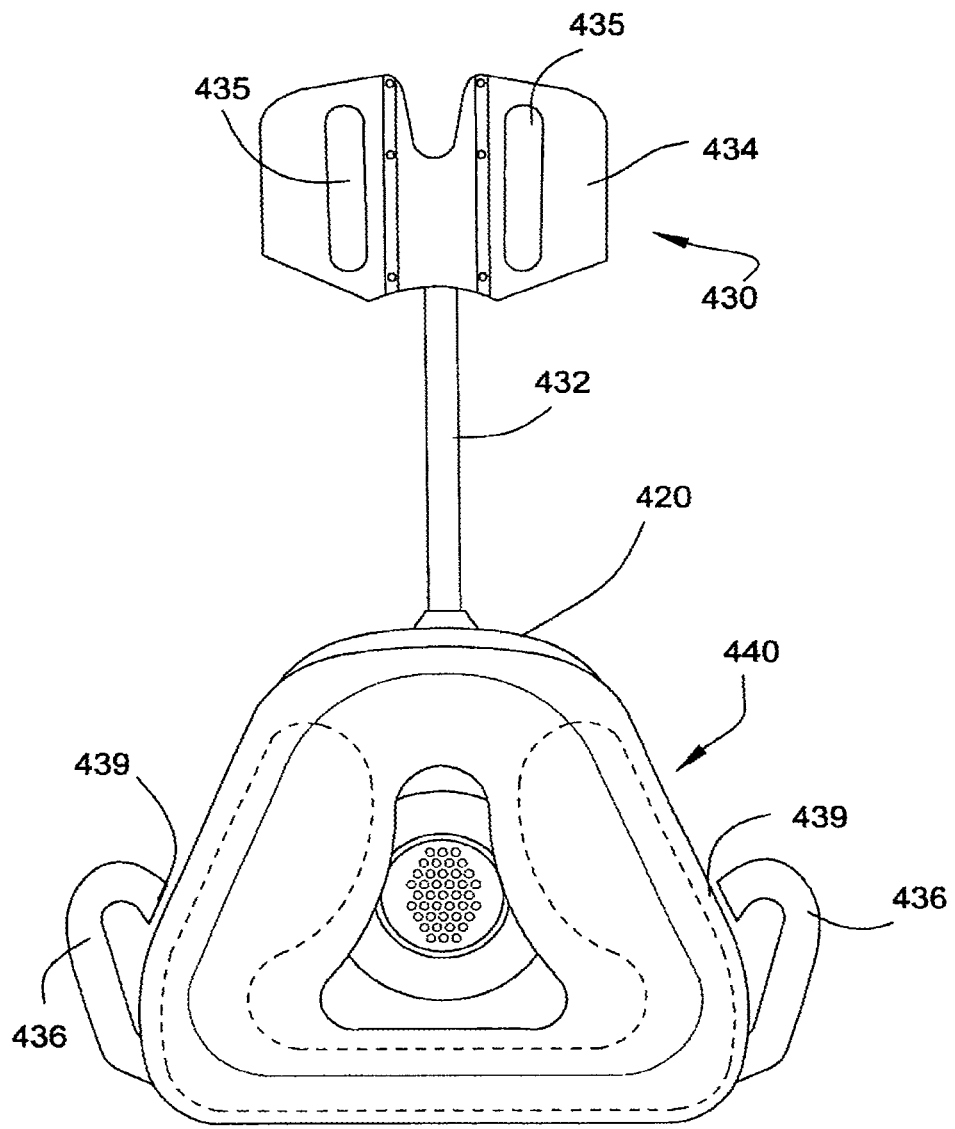
Figure 5:
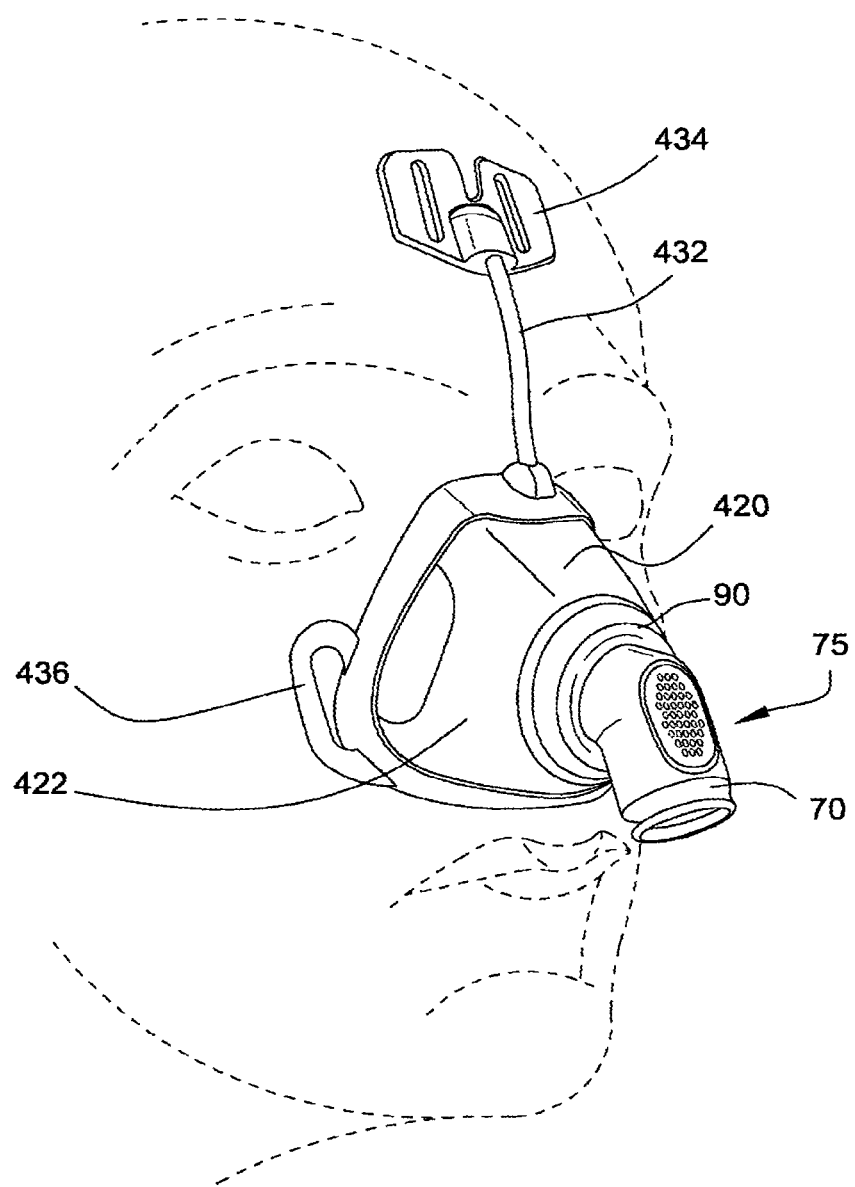
Figures 5, 6:
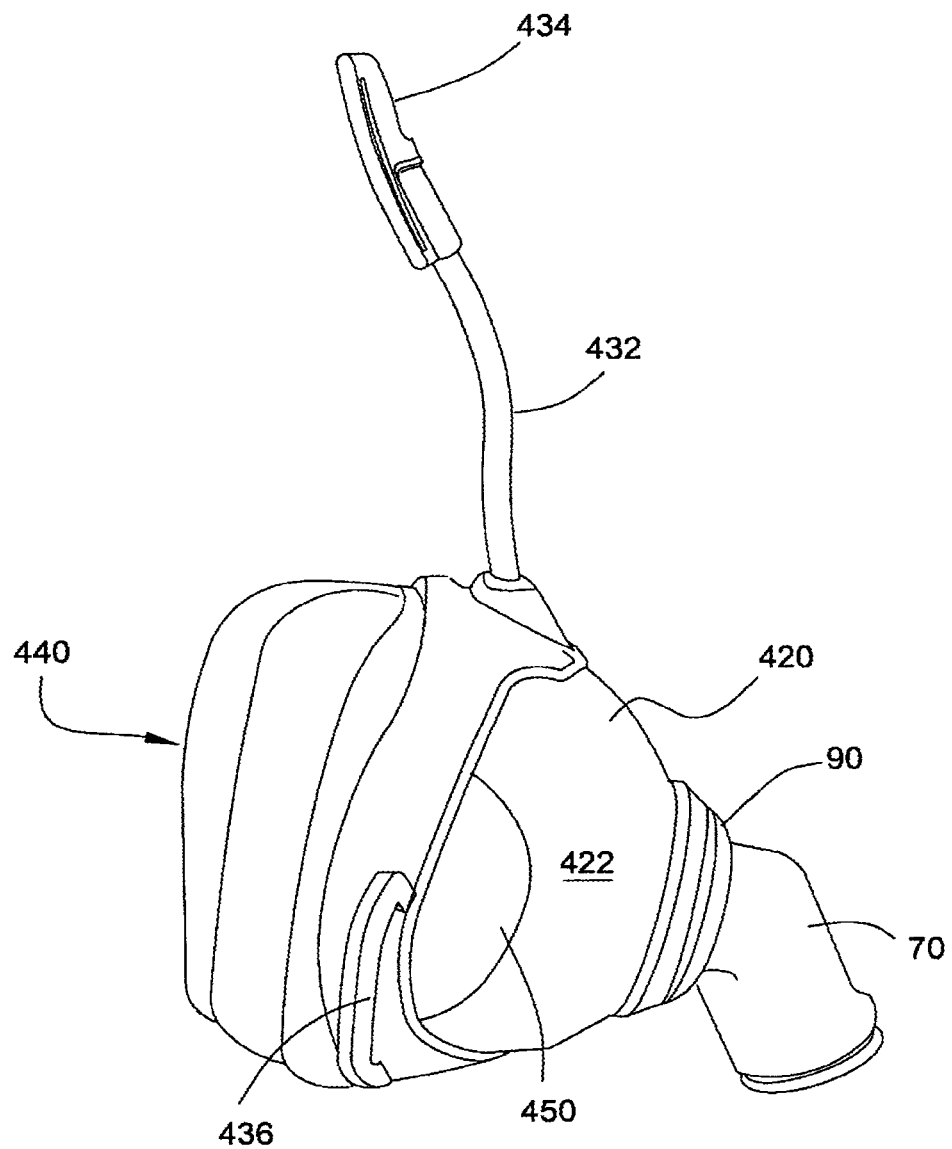
Figures 1, 6:
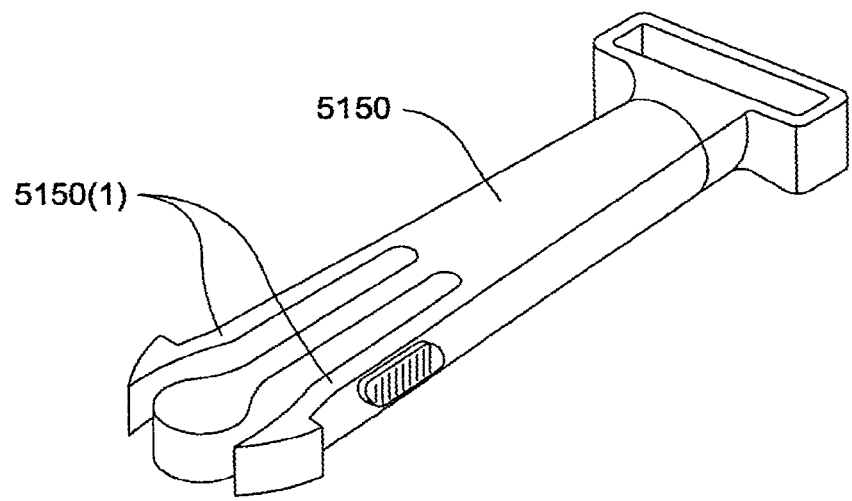
Figures 2, 6:
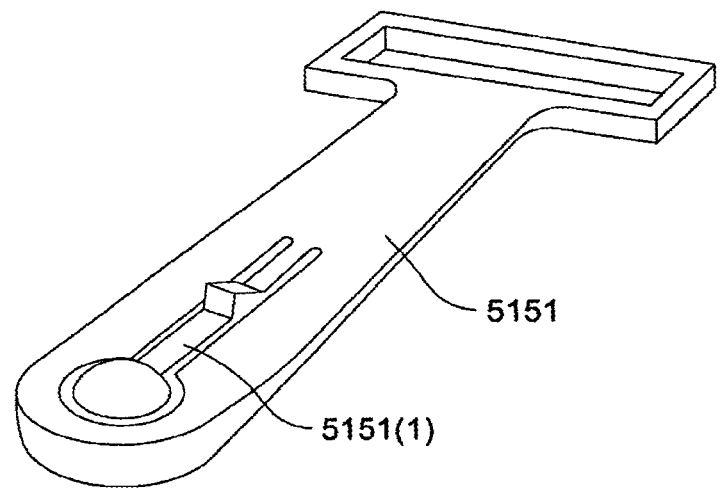
Figures 3, 6:
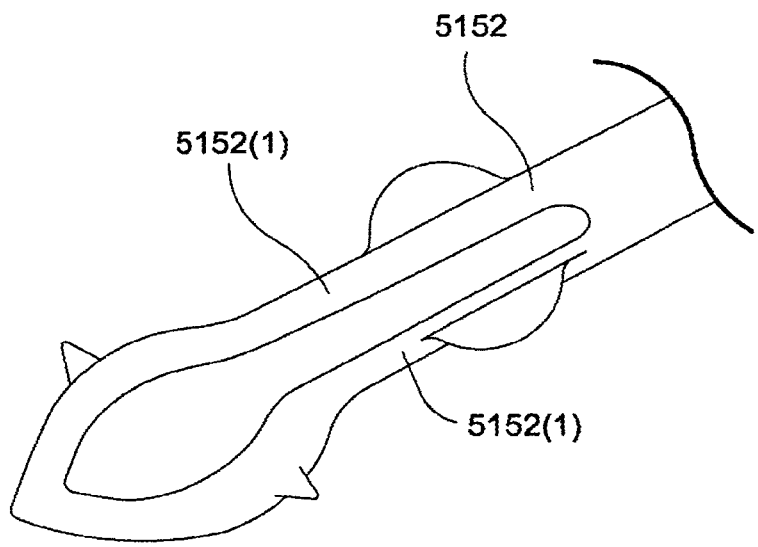
Figures 4, 6:
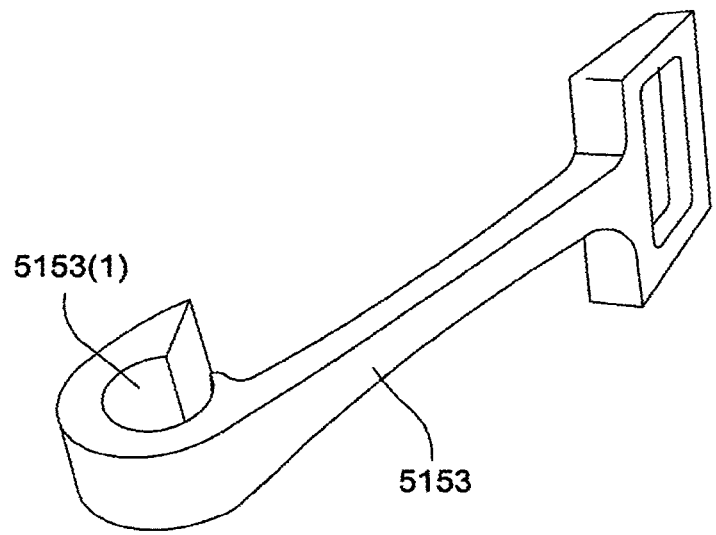
Figures 5, 6:
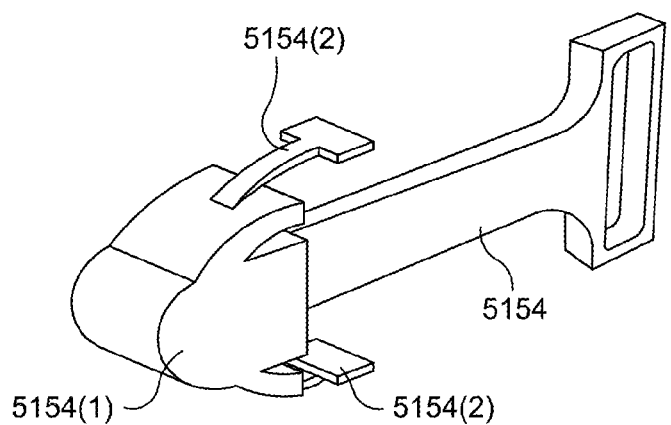
Figure 6:
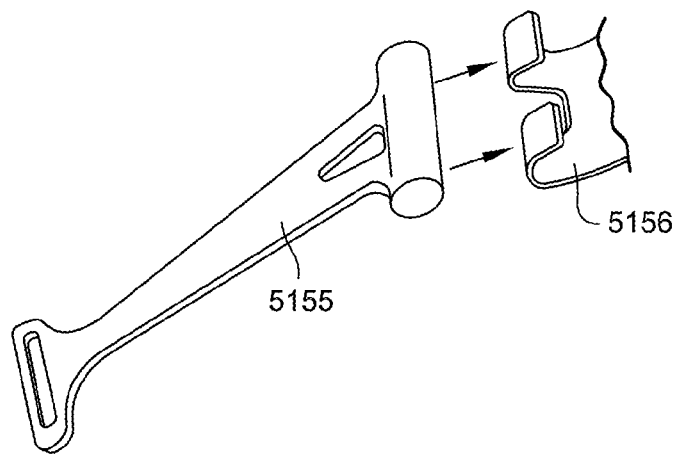
Figures 6, 7:
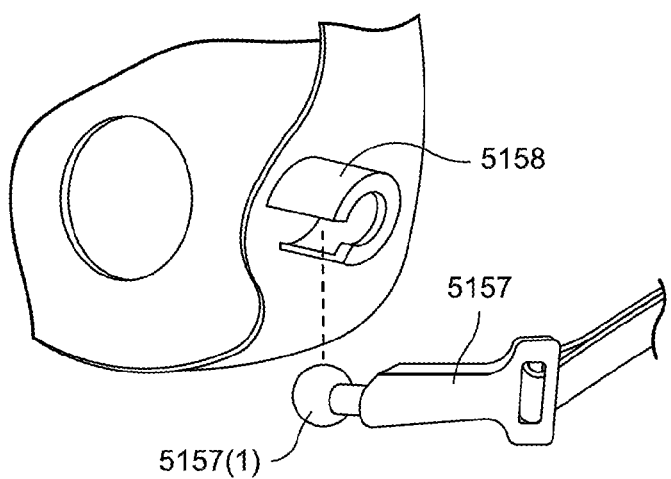
Figures 6, 7, 8:
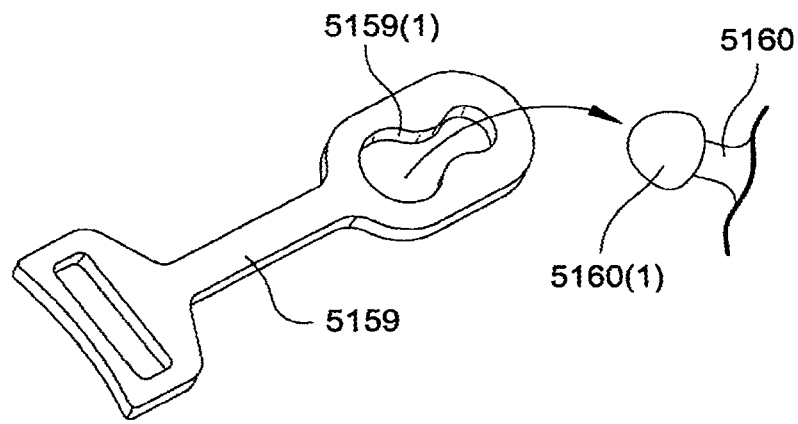
Figures 6, 7, 8, 9:
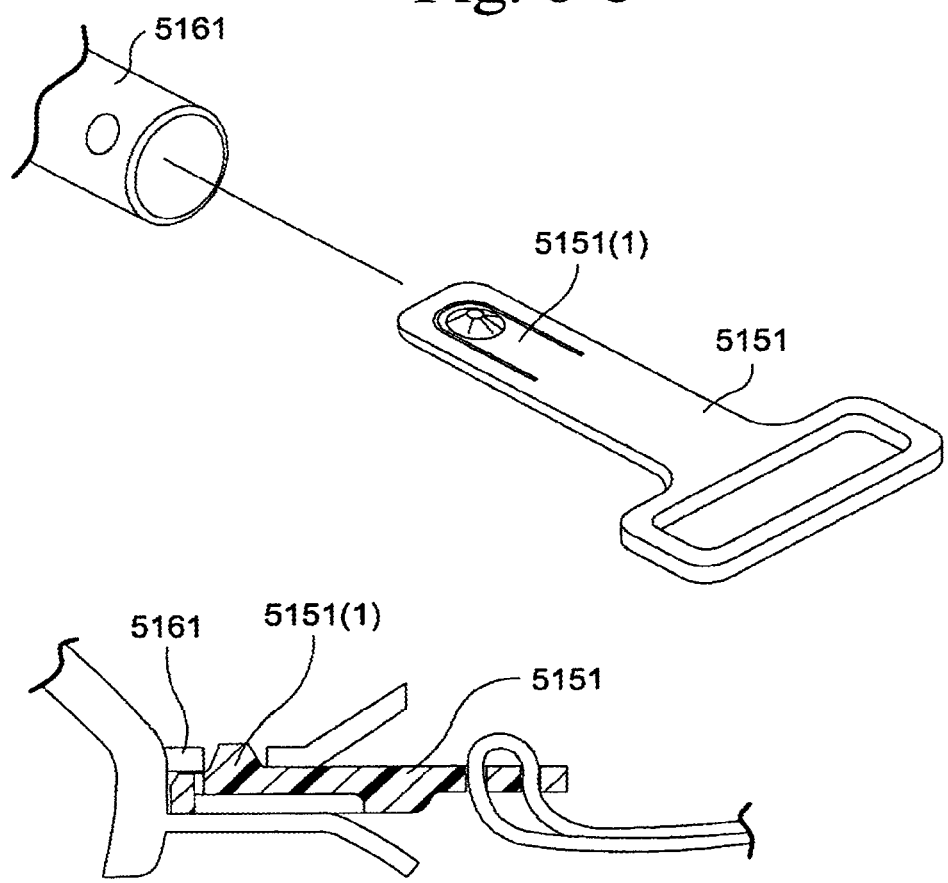
Figures 6, 7, 8, 9, 10, 10A:
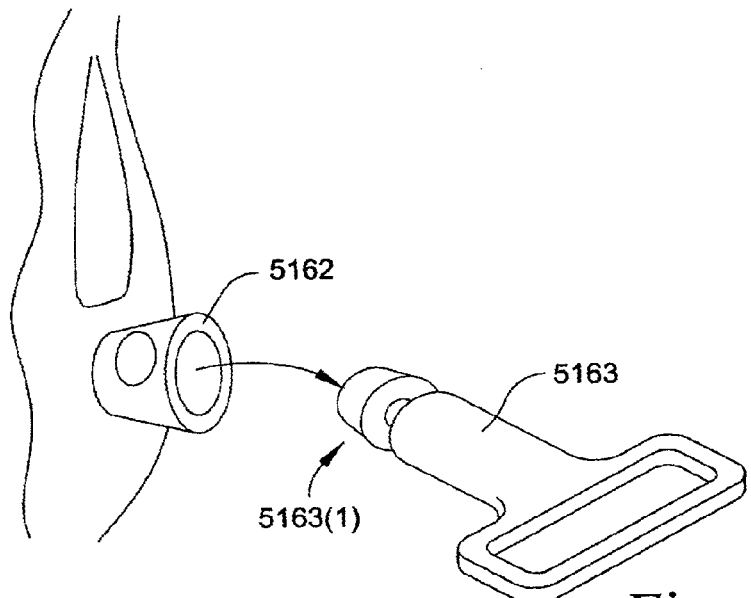
Figures 6, 7, 8, 9, 10, 10B:
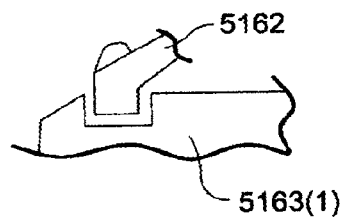
Figures 6, 7, 8, 9, 10, 11:
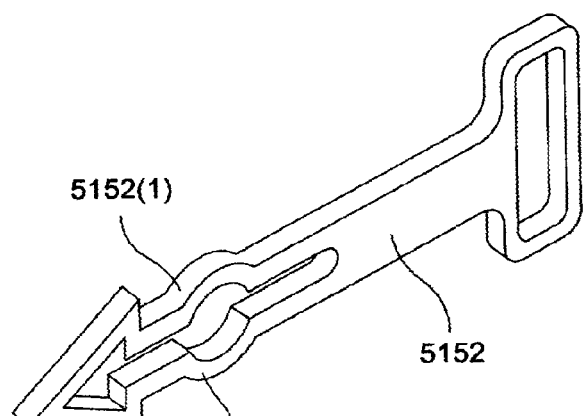
Figures 6, 7, 8, 9, 10, 11, 12, 12A:
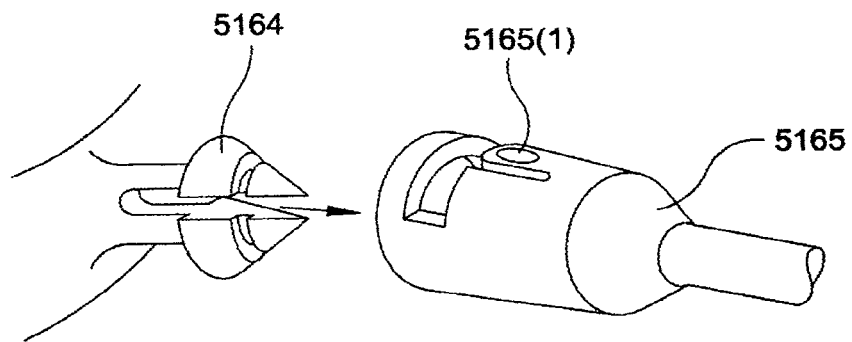
Figures 6, 7, 8, 9, 10, 11, 12, 12B:
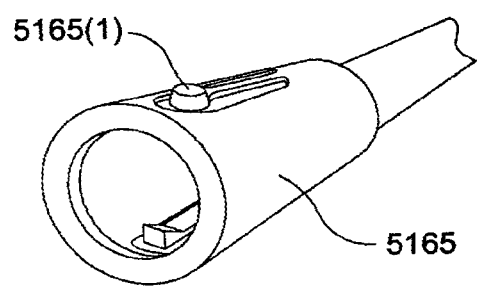
Figures 1, 7:
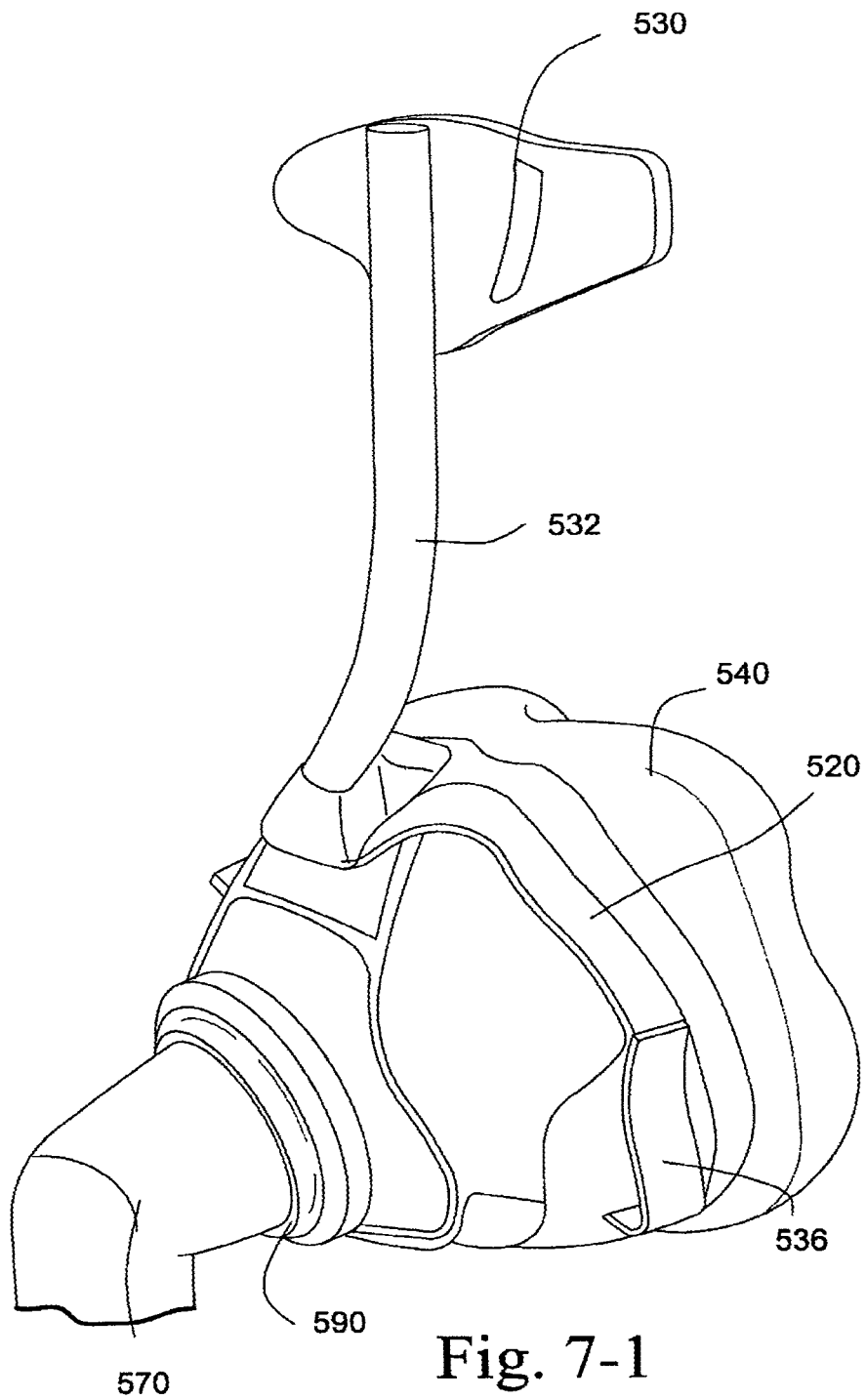
Figures 2, 7:
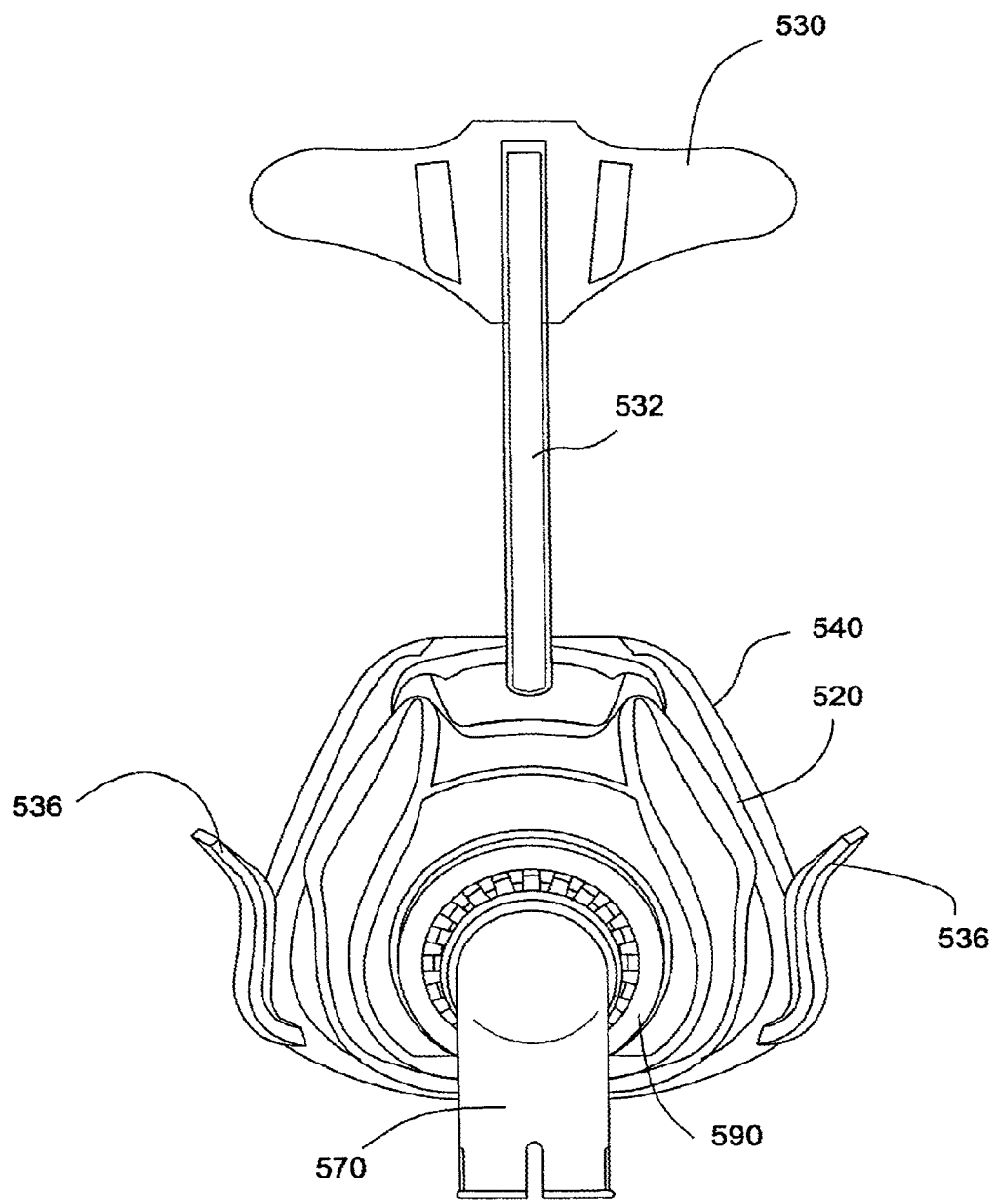
Figures 3, 7:
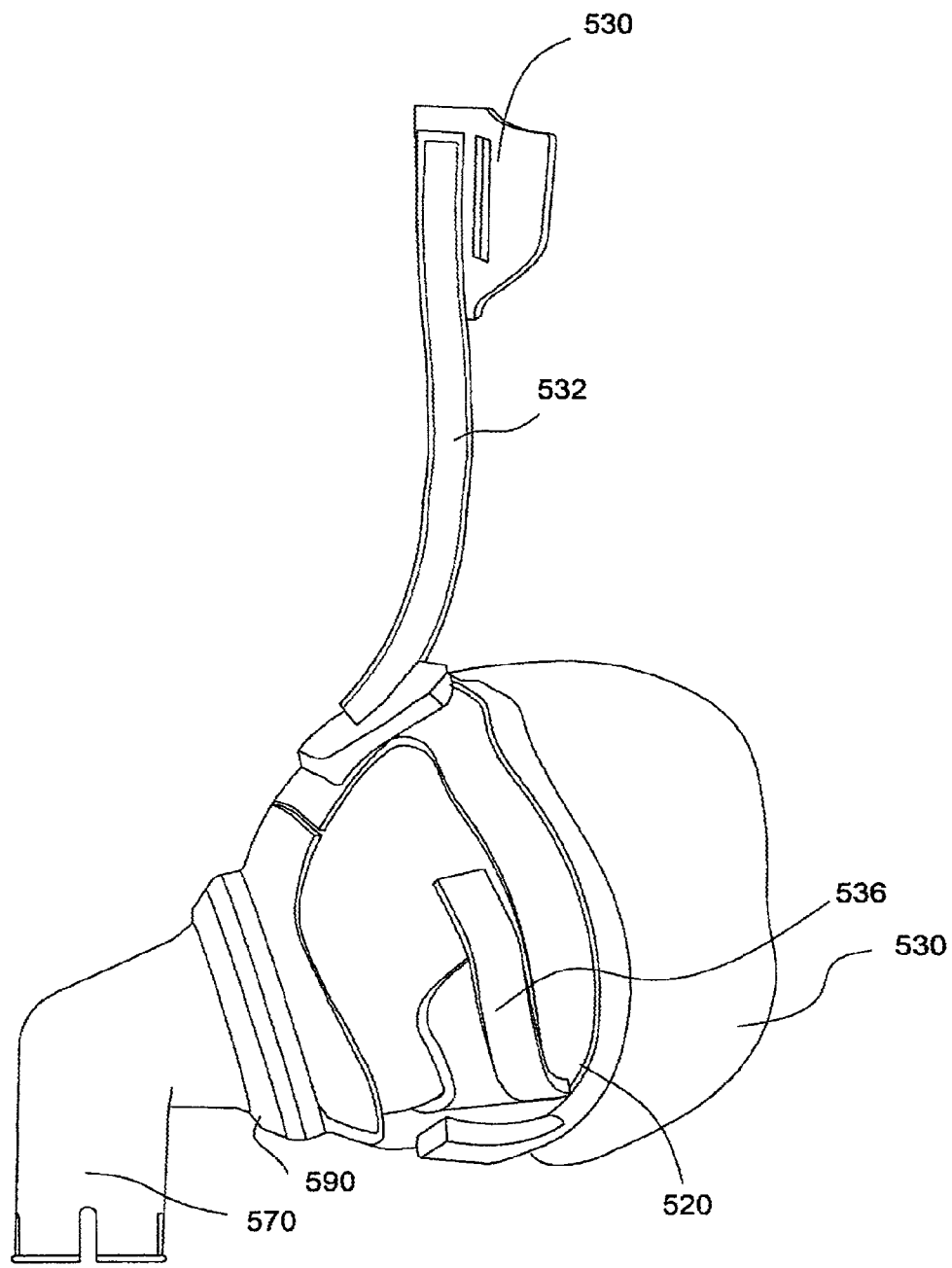
Figures 1, 8:
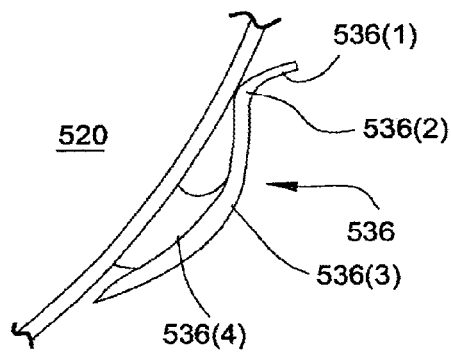
Figures 2, 8:
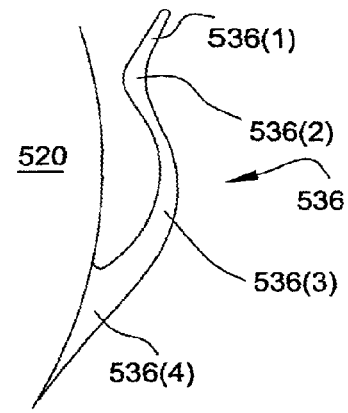
Figures 3, 8:
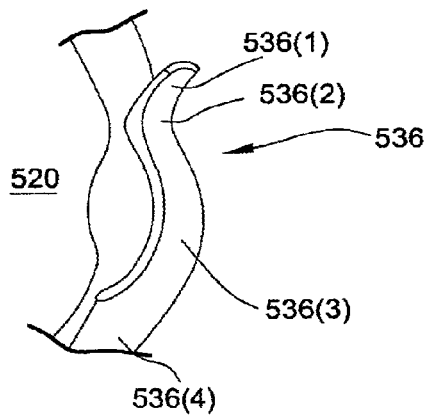
Figures 4, 8:
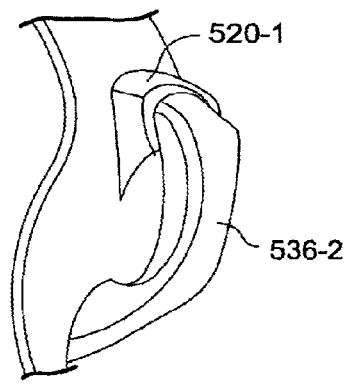
Figures 5, 8:
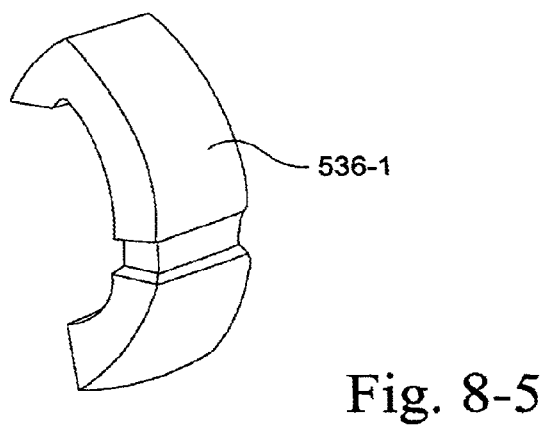

FIG. 3-77 shows headgear including a rear strap loop 5143 (1), upper straps 5143(2) extending from a top of the rear strap loop, and a lower strap loop 5143(3) that wraps around the mask and a bottom of the rear strap loop. The length of the lower strap loop may be adjusted by a spring loaded clip 5144. FIG. 3-78 shows an adjustment arrangement including a mushroom shaped connector 5145 provided to the mask that is adapted to engage with a hole 5146(1) provided to a headgear clip 5146 for a headgear strap. FIG. 3-79 shows an adjustment arrangement including a ladder-lock buckle 5147 provided to the mask that allows a headgear strap 5148 to loop therethrough.

FIGS. 6-1 to 6-12(b) illustrate headgear connection arrangements (e.g., buckle clip designs) according to alternative examples of the present invention. FIG. 6-1 shows an outrigger-type clip 5150 having a narrow configuration with clip arms 5150(1) adapted to be pushed along the sides to release. The neck of the clip may be flexible. FIG. 6-2 shows an outrigger-type clip 5151 including a clip arm 5151(1) adapted to be pushed down from the top to release. The neck of the clip may be flexible. The clip provides a relatively flat, low profile design. FIG. 6-3 shows a continuous clip 5152 with a flexible neck. The clip includes clip arms 5152(1) adapted to be pushed along the sides to release. The clip includes no gaps to jam into the clip receptacle. FIG. 6-4 shows a clip 5153 with a hook-like attachment portion 5153 (1) adapted to engage a bar-like receptacle on the frame. FIG. 6-5 shows a clip 5154 with a flexible neck ball or tapper lead in 5154(1) and clip arms 5154(2) adapted to be pushed along the sides to release. FIG. 6-6 shows a T-bar type clip 5155 adapted to engage a hook-like receptacle 5156. The neck of the clip may be flexible. FIG. 6-7 shows a ball in socket arrangement in which the ball 5157(1) on the end of the outrigger 5157 is adapted to engage a c-cup receptacle 5158 provided to the frame, e.g., with a snap fit. In an embodiment, the receptacle (e.g., plastic) may be constructed of a harder material than the ball in socket arrangement (e.g., silicone). FIG. 6-8 shows a loop over arrangement in which an opening 5159(1) on the end of an outrigger 5159 is adapted to engage a bar-like receptacle 5160 with an enlarged head 5160(1). FIG. 6-9 shows further details and alternatives of the clip 5151 shown in FIG. 6-2 described above, e.g., receptacle 5161 on frame to receive clip. FIGS. 6-10(a) and 6-10(b) show an arrangement wherein the frame includes a release mechanism 5162 and the outrigger 5163 has a ball and catch detail 5163(1) for retention. The tension of the straps may be used for release. FIG. 6-11 shows further details and alternatives of the clip 5152 shown in FIG. 6-3 described above. FIGS. 6-12(a) and 6-12(b) show an arrangement wherein the frame includes a flexible receptacle 5164 and the outrigger 5165 includes a push button release 5165(1).

6.1 Alternative Headgear

As shown in FIGS. 14-1 and 14-2, headgear 580 may include a two tone color combination (e.g., blue and grey) to assist ease of use in indicating which orientation the headgear should be when fitting the mask (e.g., two tone color provides intuitive ease of use indicating when headgear is correctly aligned and where hook and loop tabs are positioned). For example, the grey or lighter color may be arranged on the inside of the headgear so that when the headgear straps are threaded through the mask and fold over on itself, the grey faces the outside to be visually less unobtrusive on the face.

The headgear provides an arrangement that looks easy to use (inherent stability structure, two-tone alignment indication), looks comfortable (no hard ridgidized parts visible, soft fabric finish, 'soft' greys), does not look obtrusive (soft gender neutral greys, greys sympathetic to metal and silicone colours in system, provides a high quality look and increased value perception (two-tone colors, premium heat transfer branding, new manufacturing methods), and looks unique (departure from traditional breathe-o-prene style, high quality edge treatment, greys help emphasize branding).

FIGS. 18-1 to 18-2 and 19-1 to 19-2 show alternative arrangements for routing the headgear straps on the patient's head in use, e.g., upper side straps 5560 routed over the ears and lower side straps 5570 routed under the ears.

While the invention has been described in connection with what are presently considered to be the most practical and preferred embodiments, it is to be understood that the invention is not to be limited to the disclosed embodiments, but on the contrary, is intended to cover various modifications and equivalent arrangements included within the spirit and scope of the invention. Also, the various embodiments described above may be implemented in conjunction with other embodiments, e.g., aspects of one embodiment may be combined with aspects of another embodiment to realize yet other embodiments. Further, each independent feature or component of any given assembly may constitute an additional embodiment. In addition, while the invention has particular application to patients who suffer from OSA, it is to be appreciated that patients who suffer from other illnesses (e.g., congestive heart failure, diabetes, morbid obesity, stroke, bariatric surgery, etc.) can derive benefit from the above teachings. Moreover, the above teachings have applicability with patients and non-patients alike in non-medical applications.

What is claimed is:

1. A nasal cushion for a mask system, the nasal cushion comprising:
   a side wall defining a breathing chamber;
   an undercushion extending from the side wall; and
   a membrane at least partially covering the undercushion, the membrane being adapted to seal along the nasal bridge, sides of nose, corners of nose, and upper lip of the patient's face in use;
   wherein the undercushion is only provided along the side of nose, corner of nose, and upper lip regions of the cushion, and
   wherein the undercushion includes a flap or extending portion in each side of nose region, each flap or extending portion having a length measured from a tip or free end thereof to a connection of the flap or extending portion to the side wall, and the length of the flap or extending portion is longer than a corresponding length of the undercushion in the corner of nose and upper lip regions, the flap or extending portion being adapted to engage and provide a force into the sides of the patient's nose in use.

2. The nasal cushion according to claim 1, wherein the cushion includes a lower region to provide a sealing force into the plane of the patient's face, and an upper region that is stretchable to accommodate the patient's nasal bridge region.

3. The nasal cushion according to claim 1, wherein the length of each flap or extending portion is about 10-30 mm.

4. The nasal cushion according to claim 1, wherein the length of each flap or extending portion is about 15-25 mm.

5. The nasal cushion according to claim 1, wherein the length of each flap or extending portion is about 18-23 mm.

6. The nasal cushion according to claim 1, wherein the length of each flap or extending portion is about 20 mm.

7. The nasal cushion according to claim 1, wherein the length is a distance along a path on an outer surface of the undercushion from the free end thereof to its connection to the side wall.

8. The nasal cushion according to claim 1, wherein the undercushion includes a gap therein to leave a portion of the membrane unsupported, and the gap is provided in a nasal bridge region of the cushion only.

9. The nasal cushion according to claim 1, wherein the flap or extending portion includes an outer face having a radius of about 12-20 mm and an inner face having a radius of about 8-16 mm.

10. The nasal cushion according to claim 1, wherein a gap between flaps or extending portions in the side of nose regions is about 10-30 mm.

11. The nasal cushion according to claim 1, wherein the flap or extending portion in each side of nose region projects further inwardly into the breathing chamber than the undercushion in the corner of nose and upper lip regions.

12. The nasal cushion according to claim 1, wherein the undercushion includes a sickle-shaped cross-section in one or more regions of the cushion.

13. The nasal cushion according to claim 12, wherein the sickle-shaped cross-section is provided in the upper lip, side of nose, and corner of nose regions of the cushion.

14. The nasal cushion according to claim 12, wherein the sickle-shaped cross-section includes a base portion and an upper portion that is radially offset towards the outside of the base portion.

15. The nasal cushion according to claim 1, wherein the cushion includes no undercushion above each flap or extending portion to the apex of the cushion.

16. The nasal cushion according to claim 1, wherein the membrane and the undercushion include a gap therebetween that varies in different regions of the cushion.

17. The nasal cushion according to claim 1, wherein the side wall, the undercushion and the membrane provide a face-contacting portion of the cushion, and the cushion further comprises a non-face contacting portion providing a breathing chamber forming portion defining the breathing chamber.

18. The nasal cushion according to claim 17, wherein the breathing chamber forming portion defines at least a portion of a front side of the mask system and the face-contacting portion defines at least a portion of a rear side of the mask system, the breathing chamber forming portion, when provided to a frame, forms an exterior surface exposed at the front side of the mask system.

19. The nasal cushion according to claim 17, wherein face-contacting portion and the non-face contacting portion are formed as a single component.

20. The nasal cushion according to claim 17, wherein the breathing chamber forming portion includes an opening adapted to receive an elbow.

21. A nasal mask system for the delivery of a supply of gas at positive pressure to an airway of a patient for treatment of sleep disordered breathing, the nasal mask system comprising the nasal cushion according to claim 1 and a frame to support the nasal cushion.

22. A nasal cushion for a mask system, the nasal cushion comprising:
a side wall defining a breathing chamber;
an undercushion extending from the side wall; and
a membrane at least partially covering the undercushion,
the membrane being adapted to seal along the nasal bridge, sides of nose, corners of nose, and upper lip of the patient's face in use;
wherein the undercushion is only provided along the side of nose, corner of nose, and upper lip regions of the cushion,
wherein the undercushion includes a flap or extending portion in each side of nose region, wherein the undercushion includes a gap measured from a free end of the flap or extending portion in one side of nose region to a free end of the flap of extending portion in the opposing side of nose region, and
wherein the gap between said opposing flaps or extending portions increases at points superior and inferior its narrowest point.

23. The nasal cushion according to claim 22, wherein the gap at its narrowest point is about 15-25 mm.

24. The nasal cushion according to claim 22, wherein the gap at its narrowest point is about 18-20 mm.

25. The nasal cushion according to claim 22, wherein the gap at its narrowest point is about 18.5 mm.

26. The nasal cushion according to claim 22, wherein the flap or extending portion in each side of nose region projects further inwardly with respect to the side wall into the breathing chamber than the undercushion in the corner of nose and upper lip regions.

27. The nasal cushion according to claim 22, wherein the undercushion includes a sickle-shaped cross-section in one or more regions of the cushion, the sickle-shaped cross-section including a base portion and an upper portion that is radially offset towards the outside of the base portion.

28. The nasal cushion according to claim 22, wherein the membrane and the undercushion include a gap therebetween that varies in different regions of the cushion.

29. The nasal cushion according to claim 22, wherein the side wall, the undercushion and the membrane provide a face-contacting portion of the cushion, and the cushion further comprises a non-face contacting portion providing a breathing chamber forming portion defining the breathing chamber.

30. A nasal mask system for the delivery of a supply of gas at positive pressure to an airway of a patient for treatment of sleep disordered breathing, the nasal mask system comprising the nasal cushion according to claim 22 and a frame to support the nasal cushion.

31. The nasal cushion according to claim 22, wherein a free end of the undercushion is continuously curved from the side of nose region to the corner of nose region.

32. The nasal cushion according to claim 22, wherein the gap at its narrowest point is about 10-30 mm.

* * * * *